United States Patent
Frey et al.

(10) Patent No.: US 9,328,112 B2
(45) Date of Patent: May 3, 2016

(54) TETRACYCLIC CDK9 KINASE INHIBITORS

(71) Applicant: AbbVie Inc., North Chicago, IL (US)

(72) Inventors: Robin Frey, Libertyville, IL (US); Jane Gong, Deerfield, IL (US); Zhiqin Ji, Libertyville, IL (US); Chunqiu Lai, Libertyville, IL (US); Thomas Penning, Elmhurst, IL (US); Xiaohong Song, Grayslake, IL (US); Andrew Souers, Libertyville, IL (US); Yunsong Tong, Libertyville, IL (US); Gui-Dong Zhu, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/568,153

(22) Filed: Dec. 12, 2014

(65) Prior Publication Data

US 2015/0218165 A1    Aug. 6, 2015

(30) Foreign Application Priority Data

Feb. 6, 2014    (WO) ................ PCT/CN2014/071865

(51) Int. Cl.
 *A61K 31/437*   (2006.01)
 *A61K 31/55*    (2006.01)
 *C07D 471/16*   (2006.01)
 *C07D 498/16*   (2006.01)
 *C07D 519/00*   (2006.01)

(52) U.S. Cl.
 CPC ............ *C07D 471/16* (2013.01); *A61K 31/437* (2013.01); *A61K 31/55* (2013.01); *C07D 498/16* (2013.01); *C07D 519/00* (2013.01)

(58) Field of Classification Search
 USPC .................. 514/210.21, 287; 546/64
 See application file for complete search history.

(56) References Cited

U.S. PATENT DOCUMENTS

| | | | |
|---|---|---|---|
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2009/0082471 A1 | 3/2009 | Czarnik | |
| 2009/0088416 A1 | 4/2009 | Czarnik | |
| 2009/0093422 A1 | 4/2009 | Tung | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| WO | 2008049856 A2 | 5/2008 |
| WO | 2008079521 A2 | 7/2008 |
| WO | 2009047359 A1 | 4/2009 |
| WO | 2010003133 A2 | 1/2010 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23(3), pp. 251-257.
Blagojevic N., et al., In "Dosimetry & Treatment Planning for Neutron Capture Therapy", Zamenhof R, et al., Edition, 1994, Advanced Medical Publishing, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Coley W., et al., "Novel HIV-1 Therapeutics Through Targeting Altered Host Cell Pathways.," Expert Opinion on Therapy, 2009, vol. 9 (11), pp. 1369-1382.
Czajka D. M., et al., "Effect of Deuterium Oxide on the Reproductive Potential of Mice," Annals of the New York Academy of Sciences, 1960, vol. 84, pp. 770-779.

(Continued)

*Primary Examiner* — Kristin Vajda
(74) *Attorney, Agent, or Firm* — Changxia Sun

(57) ABSTRACT

Disclosed are compounds of Formula (Ia), and pharmaceutically acceptable salts thereof,

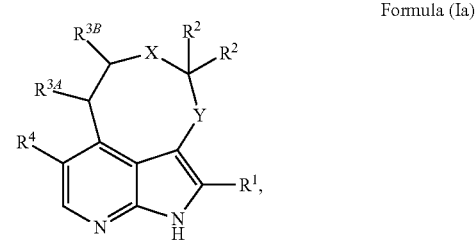

Formula (Ia)

wherein X, Y, $R^1$, $R^2$, $R^{3A}$, $R^{3B}$, and $R^4$ are as described herein. The compounds may be used as agents in the treatment of diseases, including cancer. Also disclosed are pharmaceutical compositions comprising one or more compounds of Formula (Ia).

9 Claims, No Drawings

(56) References Cited

OTHER PUBLICATIONS

Czajka, D. M. et al., "Physiological Effects of Deuterium on Dogs," American Journal of Physiology, 1961, vol. 201 (2), pp. 357-362.
Foster, A. B. et al., "Deuterium isotope Effects in the Metabolism of Drugs and Xenobiotics: Implications for Drug Design," Advances in Drug Research, 1985, vol. 14, pp. 2-36.
International Search Report for Application No. PCT/US2014/070008, mailed on Feb. 5, 2015, 4 pages.
"IUPAC 1974 Recommendations for Section E, Fundamental Stereochemistry," Pure and Applied Chemistry, 1976, vol. 45, pp. 10-13.
Kato, S. et al., "Synthesis of Deuterated Mosapride Citrate," Journal of Labelled Compounds and Radiopharmaceuticals, 1995, vol. 36 (10), pp. 927-932.
Krystof V., et al., "Pharmacological Targeting of CDK9 in Cardiac Hypertrophy.," Medicinal Research Reviews, 2010, vol. 30 (4), pp. 646-666.
Kushner D.J., et al., "Pharmacological Uses andPerspectives of Heavy Water and Deuterated Compounds.," Canadian Journal of Physiology and Pharmacology, 1999, vol. 77 (2), pp. 79-88.
Lizondo, J. et al., "Linezolid: Oxazolidinone antibacterial," Drugs of the Future, 1996, vol. 21 (11), pp. 1116-1123.
Mallesham, B. et al., "Highly E-fficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Malumbres M., et al., "Cell Cycle, CDKs and Cancer: a Changing Paradigm.," Nature Reviews Cancer, 2009, vol. 9 (3), pp. 153-166.
Miyaura N., et al., "Palladium-Catalyzed Cross-Coupling Reactions of Oganoboron Compounds," Chemical Reviews, 1995, vol. 95 (7), pp. 2457-2483.
Prescott, Ed., Methods in Cell Biology, vol. XIV, Academic Press, New York, 1976, pp. 33.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Suzuki A., "Recent Advances in the Cross-Coupling Reactions of Organoboron Derivates with Organic Electrophiles, 1995-1998," Journal of Organometallic Chemistry, 1999, vol. 576, pp. 147-168.
Thomson J.F. "Physiological Effects of D20 in Mammals," Annals of the New York Academy of Sciences, 1960, vol. 84, pp. 736-744.
Wang S., et al., "Cyclin-dependent kinase 9: a key Transcriptional Regulator and Potential Drug Target in Oncology, Virology and Cardiology.," Trends in Pharmacological Sciences, 2009, vol. 29 (6), pp. 302-312.

* cited by examiner

TETRACYCLIC CDK9 KINASE INHIBITORS

CROSS-REFERENCE TO RELATED APPLICATION

This application claims the benefit of the PCT Application No. PCT/CN2014/071865 filed Feb. 6, 2014, which is incorporated by reference herein in its entirety.

FIELD OF THE INVENTION

This invention pertains to compounds which inhibit the activity of CDK9 kinase, compositions containing the compounds, and methods of treating diseases during which CDK9 kinase is expressed.

BACKGROUND OF THE INVENTION

Cyclin-dependent kinases (CDKs) are serine/threonine protein kinases whose activity depends on binding and activation by cyclin partners. These heterodimeric complexes can phosphorylate various substrates involved in the control of transcription and cell-cycle progression in response to different stimuli. CDK8 and CDK9 have key roles in the control of transcription by RNA polymerase II. CDK9 responds specifically to several cytokines, including tumor necrosis factor and interleukin-6, indicating that it might have special roles in the regulation of a variety of physiological processes, especially immune responses, inflammation, cell activation, and differentiation.

Deregulated CDK activity is a hallmark of human cancer, and a variety of genetic and epigenetic events, such as over expression of cyclins, diminished levels of CDK inhibiting proteins or gain-of function mutations in CDK, have been described to cause increased activity of these enzymes and provide a selective growth advantage in tumor cells. CDK9 inhibition causes rapid depletion of short-lived mRNA transcripts and their associated protein products. Many genes encoding proteins involved in cell growth, proliferation, and tumor development (Myc, Cyclin D1, and Mcl-1) are characterized by short-lived mRNAs and proteins and hence the consequences of CDK9 inhibition include anti-proliferative and pro-apoptotic effects through loss of function at many cellular pathways. Tumor types that are dependent on labile pro-survival proteins (e.g., Mcl-1), which includes multiple myeloma, CLL, breast, melanoma and pancreatic cancers as well as the MYC-driven tumors (multiple cancer types) would be susceptible to CDK9 inhibition. CDK9 inhibitors might also be effective in combination with standard of care in tumors in which NF-κB is constitutively active and contributing to chemo resistance. This includes hematologic malignancies as well as solid tumors (breast, colorectal, prostate, melanoma and pancreatic). Thus, CDK9 inhibition targets multiple cancer-relevant pathways by inhibition of a single protein and thereby renders CDK9 as an attractive target for anti-cancer therapy. (Nature Reviews Cancer: 2009, 9, 153-166).

CDK9 inhibitors can also find therapeutic application in cardiology and virology as many viruses depend on the infected host for transcription of their genome. (Cyclin-dependent kinase 9: a key transcriptional regulator and potential drug target in oncology, virology and cardiology. Trends in Pharmacol. Sci. 2009, 29. 302-312; Pharmacological targeting of CDK9 in cardiac hypertrophy. Med Res. Rev. 2010 30:646-66; Novel HIV-1 therapeutics through targeting altered host cell pathways. Expert Opin Biol Ther. 2009 9:1369-82).

CDK9 inhibitors have also been reported as potential therapeutics for the treatment of chronic, inflammatory and neuropathic pain (WO2008/049856; WO2009/047359).

In view of the above, there is a need in the art for small molecule therapeutics that can inhibit the activity of CDK9. The present invention fulfills at least this need.

SUMMARY OF THE INVENTION

In one embodiment, the present invention relates to compounds of Formula (Ia) or a pharmaceutically acceptable salt thereof,

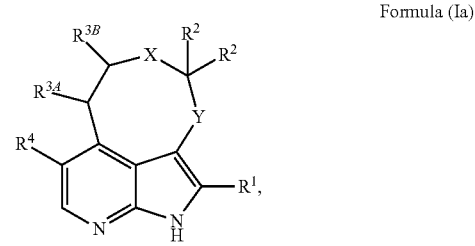

Formula (Ia)

wherein

X is O or $NR^{2A}$;

Y is $C(R^2)_2$ or is absent;

$R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, (O), OH, CN, $NO_2$, F, Cl, Br and I;

$R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, C(O)OH, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting $C_1$-$C_8$ alkyl, $C_2$-$C_6$ alkenyl, and $C_2$-$C_6$ alkynyl;

$R^{2A}$ is hydrogen or $C_1$-$C_4$ alkyl; wherein the $R^{2A}$ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I;

$R^{2B}$ is $C_1$-$C_4$ alkyl;

$R^{3A}$ and $R^{3B}$, taken together, form $R^3$;

$R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I;

$R^4$ is selected from the group consisting of hydrogen, $C_1$-$C_4$ alkyl, $C_1$-$C_4$ alkoxy, CN, F, Cl, Br, and I;

$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHSO_2R^7$, $NR^7SO_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, (O), OH, CN, $NO_2$, F, Cl, Br and I;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycloalkyl, heterocycloalkenyl, $NH_2$, $C(O)H$, $C(O)OH$, OH, CN, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHSO_2R^8$, $NR^8SO_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I;

$R^7$, at each occurrence, is independently selected from the group consisting of $C_1$-$C_6$ alkyl, $C_2$-$C_6$ alkenyl, and $C_2$-$C_6$ alkynyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $OR^9$, $SR^9$, $S(O)R^9$, $SO_2R^9$, $C(O)R^9$, $CO(O)R^9$, $OC(O)R^9$, $OC(O)OR^9$, $NH_2$, $C(O)H$, $C(O)OH$, OH, CN, $NO_2$, F, Cl, Br and I;

$R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I; and $R^9$, at each occurrence, is independently selected from the group consisting of $C_1$-$C_6$ alkyl, $C_2$-$C_6$ alkenyl, and $C_2$-$C_6$ alkynyl.

In one embodiment of Formula (Ia), Y is absent. In another embodiment of Formula (Ia), Y is absent, and X is $NR^{2A}$. In another embodiment of Formula (Ia), Y is absent, X is $NR^{2A}$, and $R^4$ is selected from the group consisting of hydrogen, F, Cl, Br, and I. In another embodiment of Formula (Ia), Y is absent, X is $NR^{2A}$, and $R^3$ is phenyl; wherein the $R^3$ phenyl is optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, OH, CN, $NO_2$, F, Cl, Br and I. In another embodiment of Formula (Ia), Y is absent, X is $NR^{2A}$, and $R^3$ is phenyl; wherein the $R^3$ phenyl is substituted with one F. In another embodiment of Formula (Ia), Y is absent, X is $NR^{2A}$, and $R^1$ is selected from the group consisting of cycloalkyl, cycloalkenyl, aryl, heteroaryl, heterocycloalkyl, and heterocycloalkenyl; wherein the R' cycloalkyl, cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, $C(O)OH$, F, Cl, Br and I.

Still another embodiment pertains to compounds of Formula (Ia), selected from the group consisting of:

10-fluoro-7-methyl-5-(1,2,3,6-tetrahydropyridin-4-yl)-6,7-dihydro-4H-3,4,7-triazadibenzo[cd,f]azulene;

tert-butyl 4-(10-fluoro-7-methyl-6,7-dihydro-4H-3,4,7-triazadibenzo[cd,f]azulen-5-yl)-3,6-dihydropyridine-1(2H)-carboxylate;

ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate;

10-fluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-7-propyl-6,7-dihydro-4H-3,4,7-triazadibenzo[cd,f]azulene;

10-fluoro-5-[1-(methylsulfonyl)-1,2,3,6-tetrahydropyridin-4-yl]-7-(tetrahydro-2H-pyran-4-ylmethyl)-6,7-dihydro-4H-3,4,7-triazadibenzo[cd,f]azulene;

tert-butyl 4-(6-ethyl-10-fluoro-7-methyl-6,7-dihydro-4H-3,4,7-triazadibenzo[cd,f]azulen-5-yl)-3,6-dihydropyridine-1(2H)-carboxylate;

6-ethyl-10-fluoro-7-methyl-5-(1,2,3,6-tetrahydropyridin-4-yl)-6,7-dihydro-4H-3,4,7-triazadibenzo[cd,f]azulene dihydrochloride;

10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene;

6-ethyl-10-fluoro-7-methyl-5-[1-(methylsulfonyl)-1,2,3,6-tetrahydropyridin-4-yl]-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

4-(10-fluoro-7-methyl-6,7-dihydro-4H-3,4,7-triazadibenzo[cd,f]azulen-5-yl)-N-methyl-3,6-dihydropyridine-1(2H)-carboxamide;

10-fluoro-5-(1,2,3,6-tetrahydropyridin-4-yl)-4,6-dihydro-7-oxa-3,4-diazadibenzo[cd,f]azulene;

10-fluoro-5-[1-(methylsulfonyl)-1,2,3,6-tetrahydropyridin-4-yl]-4,6-dihydro-7-oxa-3,4-diazadibenzo[cd,f]azulene;

[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride;

2-[4-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(10-fluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene;

10-fluoro-7-methyl-5-(piperidin-4-yl)-6,7-dihydro-4H-3,4,7-triazadibenzo[cd,f]azulene;

tert-butyl[4-(10-fluoro-7-methyl-6,7-dihydro-4H-3,4,7-triazadibenzo[cd,f]azulen-5-yl)piperidin-1-yl]acetate;

[4-(10-fluoro-7-methyl-6,7-dihydro-4H-3,4,7-triazadibenzo[cd,f]azulen-5-yl)piperidin-1-yl]acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-N-methyl-2-oxo ethanesulfonamide;

2-[4-(10-fluoro-7-methyl-6,7-dihydro-4H-3,4,7-triazadibenzo[cd,f]azulen-5-yl)piperidin-1-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)piperidin-1-yl]-N-(2-hydroxyethyl)-N-methylacetamide;

ethyl 10-fluoro-7-methyl-5-(1,2,3,6-tetrahydropyridin-4-yl)-6,7-dihydro-4H-3,4,7-triazadibenzo[cd,f]azulene-6-carboxylate;

N-[4-(10-fluoro-7-methyl-6,7-dihydro-4H-3,4,7-triazadibenzo[cd,f]azulen-5-yl)cyclohex-3-en-1-yl]-D-valine;

N-[4-(10-fluoro-7-methyl-6,7-dihydro-4H-3,4,7-triazadibenzo[cd,f]azulen-5-yl)cyclohex-3-en-1-yl]-L-alanine;

N-[4-(10-fluoro-7-methyl-6,7-dihydro-4H-3,4,7-triazadibenzo[cd,f]azulen-5-yl)cyclohex-3-en-1-yl]glycine;

(2S)-{[4-(10-fluoro-7-methyl-6,7-dihydro-4H-3,4,7-triazadibenzo[cd,f]azulen-5-yl)cyclohex-3-en-1-yl]amino}(phenyl)acetic acid;

10-fluoro-7-methyl-5-(1,2,3,6-tetrahydropyridin-4-yl)-6,7-dihydro-4H-3,4,7-triazadibenzo[cd,f]azulene-6-carboxylic acid;

N-[4-(10-fluoro-7-methyl-6,7-dihydro-4H-3,4,7-triazadibenzo[cd,f]azulen-5-yl)cyclohex-3-en-1-yl]-L-valine;

N-[4-(10-fluoro-7-methyl-6,7-dihydro-4H-3,4,7-triazadibenzo[cd,f]azulen-5-yl)cyclohex-3-en-1-yl]-L-phenylalanine;

N-[4-(10-fluoro-7-methyl-6,7-dihydro-4H-3,4,7-triazadibenzo[cd,f]azulen-5-yl)cyclohex-3-en-1-yl]-3-methyl-L-valine;

1-[4-(10-fluoro-7-methyl-6,7-dihydro-4H-3,4,7-triazadibenzo[cd,f]azulen-5-yl)cyclohex-3-en-1-yl]-L-proline;

N-[4-(10-fluoro-7-methyl-6,7-dihydro-4H-3,4,7-triazadibenzo[cd,f]azulen-5-yl)cyclohex-3-en-1-yl]-L-serine;

N-[4-(10-fluoro-7-methyl-6,7-dihydro-4H-3,4,7-triazadibenzo[cd,f]azulen-5-yl)cyclohex-3-en-1-yl]-L-norvaline;

N-[4-(10-fluoro-7-methyl-6,7-dihydro-4H-3,4,7-triazadibenzo[cd,f]azulen-5-yl)cyclohex-3-en-1-yl]-L-tyrosine;

4-(10-fluoro-7-methyl-6,7-dihydro-4H-3,4,7-triazadibenzo[cd,f]azulen-5-yl)cyclohex-3-ene-1-carboxylic acid;

2-[4-(10-fluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

10-fluoro-7-methyl-5-[4-(methylsulfonyl)phenyl]-6,7-dihydro-4H-3,4,7-triazadibenzo[cd,f]azulene;

10-fluoro-7-methyl-5-(pyridin-4-yl)-6,7-dihydro-4H-3,4,7-triazadibenzo[cd,f]azulene;

10-fluoro-7-methyl-5-[6-(methylsulfonyl)pyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)pyrimidin-2-amine;

4-(10-fluoro-7-methyl-6,7-dihydro-4H-3,4,7-triazadibenzo[cd,f]azulen-5-yl)benzoic acid;

1,10-difluoro-7-methyl-5-(1,2,3,6-tetrahydropyridin-4-yl)-6,7-dihydro-4H-3,4,7-triazadibenzo[cd,f]azulene;

tert-butyl 4-(1,10-difluoro-7-methyl-6,7-dihydro-4H-3,4,7-triazadibenzo[cd,f]azulen-5-yl)-3,6-dihydropyridine-1(2H)-carboxylate;

4-(10-fluoro-7-methyl-6,7-dihydro-4H-3,4,7-triazadibenzo[cd,f]azulen-5-yl)-N,N-dimethylcyclohex-3-ene-1-carboxamide;

[4-(10-fluoro-7-methyl-6,7-dihydro-4H-3,4,7-triazadibenzo[cd,f]azulen-5-yl)cyclohex-3-en-1-yl](3-hydroxyazetidin-1-yl)methanone;

4-(10-fluoro-7-methyl-6,7-dihydro-4H-3,4,7-triazadibenzo[cd,f]azulen-5-yl)-N-methylcyclohex-3-ene-1-carboxamide;

2-[4-(10-fluoro-7-methyl-6,7-dihydro-4H-3,4,7-triazadibenzo[cd,f]azulen-5-yl)-3,6-dihydropyridin-1(2H)-yl]-N,N-bis(2-hydroxyethyl)acetamide;

1-(3,3-difluoroazetidin-1-yl)-2-[4-(10-fluoro-7-methyl-6,7-dihydro-4H-3,4,7-triazadibenzo[cd,f]azulen-5-yl)-3,6-dihydropyridin-1(2H)-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N,N-dimethylacetamide;

10-fluoro-7-methyl-5-[(1R,5S)-8-(methylsulfonyl)-8-azabicyclo[3.2.1]oct-2-en-3-yl]-6,7-dihydro-4H-3,4,7-triazadibenzo[cd,f]azulene;

(1R,5S)-3-(10-fluoro-7-methyl-6,7-dihydro-4H-3,4,7-triazadibenzo[cd,f]azulen-5-yl)-N-methyl-8-azabicyclo[3.2.1]oct-2-ene-8-carboxamide;

[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid;

10-fluoro-5-(1,2,3,3a,4,6a-hexahydrocyclopenta[c]pyrrol-5-yl)-7-methyl-6,7-dihydro-4H-3,4,7-triazadibenzo[cd,f]azulene;

10-fluoro-7-methyl-5-(pyridin-3-yl)-6,7-dihydro-4H-3,4,7-triazadibenzo[cd,f]azulene;

ethyl 4-(10-fluoro-7-methyl-6,7-dihydro-4H-3,4,7-triazadibenzo[cd,f]azulen-5-yl)cyclohex-3-ene-1-carboxylate;

5-[(1R,5S)-8-azabicyclo[3.2.1]oct-2-en-3-yl]-10-fluoro-7-methyl-6,7-dihydro-4H-3,4,7-triazadibenzo[cd,f]azulene;

N-(2,3-dihydroxypropyl)-2-[4-(10-fluoro-7-methyl-6,7-dihydro-4H-3,4,7-triazadibenzo[cd,f]azulen-5-yl)-3,6-dihydropyridin-1(2H)-yl]-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

tert-butyl[4-(1,10-difluoro-7-methyl-6,7-dihydro-4H-3,4,7-triazadibenzo[cd,f]azulen-5-yl)-3,6-dihydropyridin-1(2H)-yl]acetate;

2-[4-(1,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;

[4-(1,10-difluoro-7-methyl-6,7-dihydro-4H-3,4,7-triazadibenzo[cd,f]azulen-5-yl)-3,6-dihydropyridin-1(2H)-yl]acetic acid;

1,10-difluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-{2-[(2-methoxyethyl)sulfonyl]-1,2,3,3a,4,6a-hexahydrocyclopenta[c]pyrrol-5-yl}-7-methyl-6,7-dihydro-4H-3,4,7-triazadibenzo[cd,f]azulene;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

2-[4-(1,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[3-(hydroxymethyl)azetidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

5-(10-fluoro-7-methyl-6,7-dihydro-4H-3,4,7-triazadibenzo[cd,f]azulen-5-yl)-N-methyl-3,3a,4,6a-tetrahydrocyclopenta[c]pyrrole-2(1H)-carboxamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N,N-dimethylacetamide;

10-fluoro-7-methyl-5-[2-(methylsulfonyl)-1,2,3,3a,4,6a-hexahydrocyclopenta[c]pyrrol-5-yl]-6,7-dihydro-4H-3,4,7-triazadibenzo[cd,f]azulene;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-[(2S)-2-(hydroxymethyl)pyrrolidin-1-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-(3-hydroxyazetidin-1-yl)ethanone;

[4-(10-fluoro-7-methyl-6,7-dihydro-4H-3,4,7-triazadibenzo[cd,f]azulen-5-yl)phenyl]acetic acid;

[3-(10-fluoro-7-methyl-6,7-dihydro-4H-3,4,7-triazadibenzo[cd,f]azulen-5-yl)phenyl]acetic acid;

N-(2,3-dihydroxypropyl)-2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-methylacetamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-1-(3-hydroxyazetidin-1-yl)ethanone;

N-(2,3-dihydroxypropyl)-2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-methylacetamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(2-hydroxyethyl)-N-methylacetamide;

10-fluoro-7-methyl-5-(2,3,6,7-tetrahydro-1H-azepin-4-yl)-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-N,N-dimethylacetamide;

10-fluoro-7-methyl-5-[1-(methylsulfonyl)-2,3,6,7-tetrahydro-1H-azepin-4-yl]-6,7-dihydro-4H-3,4,7-triazadibenzo[cd,f]azulene;

[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-1-(3-hydroxyazetidin-1-yl)ethanone;

5-(3,3-dimethyl-1,2,3,6-tetrahydropyridin-4-yl)-10-fluoro-7-methyl-6,7-dihydro-4H-3,4,7-triazadibenzo[cd,f]azulene;

10-fluoro-7-methyl-5-(1,2,5,6-tetrahydropyridin-3-yl)-6,7-dihydro-4H-3,4,7-triazadibenzo[cd,f]azulene;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(3-hydroxycyclobutyl)-N-methylacetamide;

10-fluoro-7-methyl-5-[1-(methylsulfonyl)-1,2,5,6-tetrahydropyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)-N-methyl-3,6-dihydropyridine-1(2H)-carboxamide;

2-[5-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-(3-hydroxycyclobutyl)-N-methylacetamide;

10-fluoro-7-methyl-5-[9-(methylsulfonyl)-9-azabicyclo[3.3.1]non-2-en-3-yl]-6,7-dihydro-4H-3,4,7-triazadibenzo[cd,f]azulene;

3-(10-fluoro-7-methyl-6,7-dihydro-4H-3,4,7-triazadibenzo[cd,f]azulen-5-yl)-N-methyl-9-azabicyclo[3.3.1]non-2-ene-9-carboxamide;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N,N-dimethylacetamide;

3-[3-(10-fluoro-7-methyl-6,7-dihydro-4H-3,4,7-triazadibenzo[cd,f]azulen-5-yl)-9-azabicyclo[3.3.1]non-2-en-9-yl]-3-oxopropanenitrile;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(2-hydroxyethyl)-N-methylacetamide;

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-[(2S)-2-(hydroxymethyl)pyrrolidin-1-yl]ethanone;

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-(3-hydroxyazetidin-1-yl)ethanone;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(3-hydroxycyclobutyl)-N-methylacetamide;

N-(2,3-dihydroxypropyl)-2-[3-(10-fluoro-7-methyl-6,7-dihydro-4H-3,4,7-triazadibenzo[cd,f]azulen-5-yl)-9-azabicyclo[3.3.1]non-2-en-9-yl]-N-methylacetamide;

[3-(10-fluoro-7-methyl-6,7-dihydro-4H-3,4,7-triazadibenzo[cd,f]azulen-5-yl)-9-azabicyclo[3.3.1]non-2-en-9-yl]acetic acid;

2-[4-(1,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

2-[4-(1,10-difluoro-7-methyl-6,7-dihydro-4H-3,4,7-triazadibenzo[cd,f]azulen-5-yl)-3,6-dihydropyridin-1(2H)-yl]-N-(2,3-dihydroxypropyl)-N-methylacetamide;

[4-(10-fluoro-7-methyl-6,7-dihydro-4H-3,4,7-triazadibenzo[cd,f]azulen-5-yl)-3,3-dimethyl-3,6-dihydropyridin-1(2H)-yl]acetic acid;

[5-(10-fluoro-7-methyl-6,7-dihydro-4H-3,4,7-triazadibenzo[cd,f]azulen-5-yl)-3,6-dihydropyridin-1(2H)-yl]acetic acid;

5-[3,3-dimethyl-1-(methylsulfonyl)-1,2,3,6-tetrahydropyridin-4-yl]-10-fluoro-7-methyl-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N,N-dimethylacetamide;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(2-hydroxyethyl)-N-methylacetamide;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-(3-hydroxyazetidin-1-yl)ethanone;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(3-hydroxycyclobutyl)-N-methylacetamide;

N-(2,3-dihydroxypropyl)-2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-methylacetamide;

2-[5-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[5-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[5-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

N-(2,3-dihydroxypropyl)-2-[5-(10-fluoro-7-methyl-6,7-dihydro-4H-3,4,7-triazadibenzo[cd,f]azulen-5-yl)-3,6-dihydropyridin-1(2H)-yl]-N-methylacetamide;

{cis-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;

(8aR)-7-(9,10-difluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

[(2R)-4-(9,10-difluoro-7-methyl-6,7-dihydro-4H-3,4,7-triazadibenzo[cd,f]azulen-5-yl)-1,2,5,6-tetrahydropyridin-2-yl]methanol;

8-fluoro-5-methyl-2-(1,2,3,6-tetrahydropyridin-4-yl)-1,3,4,5-tetrahydro-1,5,12-triazabenzo[4,5]cycloocta[1,2,3-cd]indene;

8-fluoro-5-methyl-2-[1-(methylsulfonyl)-1,2,3,6-tetrahydropyridin-4-yl]-1,3,4,5-tetrahydro-1,5,12-triazabenzo[4,5]cycloocta[1,2,3-cd]indene;

2-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]-N,N-dimethylacetamide;

{trans-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;

9,10-difluoro-7-methyl-5-[1-(methylsulfonyl)-1,2,3,6-tetrahydropyridin-4-yl]-6,7-dihydro-4H-3,4,7-triazadibenzo[cd,f]azulene;

2-[4-(9,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;

methyl{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;

methyl{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;

7-methyl-5-(1,2,3,6-tetrahydropyridin-4-yl)-6,7-dihydro-4H-3,4,7,8-tetraazadibenzo[cd,f]azulene;

{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-[4-(9,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

7-methyl-5-[1-(methylsulfonyl)-1,2,3,6-tetrahydropyridin-4-yl]-6,7-dihydro-4H-3,4,7,8-tetraazadibenzo[cd,f]azulene;

N-methyl-4-(7-methyl-6,7-dihydro-4H-3,4,7,8-tetraazadibenzo[cd,f]azulen-5-yl)-3,6-dihydropyridine-1(2H)-carboxamide;

{3-[4-(10-fluoro-7-methyl-6,7-dihydro-4H-3,4,7-triazadibenzo[cd,f]azulen-5-yl)-3,6-dihydropyridin-1(2H)-yl]cyclobutyl}acetic acid;

trans-4-[4-(10-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

(6S)-6-ethyl-10-fluoro-7-methyl-5-(1,2,3,6-tetrahydropyridin-4-yl)-6,7-dihydro-4H-3,4,7-triazadibenzo[cd,f]azulene;

(6R)-6-ethyl-10-fluoro-7-methyl-5-(1,2,3,6-tetrahydropyridin-4-yl)-6,7-dihydro-4H-3,4,7-triazadibenzo[cd,f]azulene;

9,10-difluoro-7-methyl-5-(1,2,3,6-tetrahydropyridin-4-yl)-6,7-dihydro-4H-3,4,7-triazadibenzo[cd,f]azulene;

[4-(9,10-difluoro-7-methyl-6,7-dihydro-4H-3,4,7-triazadibenzo[cd,f]azulen-5-yl)-3,6-dihydropyridin-1(2H)-yl]acetic acid;

{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-[4-(9,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(9,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

N,N-dimethyl-2-[4-(7-methyl-6,7-dihydro-4H-3,4,7,8-tetraazadibenzo[cd,f]azulen-5-yl)-3,6-dihydropyridin-1(2H)-yl]acetamide;

trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;

(8aR)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

(8aS)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

(8aR)-7-(10-fluoro-7-methyl-6,7-dihydro-4H-3,4,7-triazadibenzo[cd,f]azulen-5-yl)-1,5,8,8a-tetrahydro[1,3]oxazolo[3,4-a]pyridin-3-one;

[(2R)-4-(10-fluoro-7-methyl-6,7-dihydro-4H-3,4,7-triazadibenzo[cd,f]azulen-5-yl)-1,2,5,6-tetrahydropyridin-2-yl]methanol;

[(2S)-4-(10-fluoro-7-methyl-6,7-dihydro-4H-3,4,7-triaza-dibenzo[cd,f]azulen-5-yl)-1,2,5,6-tetrahydropyridin-2-yl]methanol;

[(2R)-4-(10-fluoro-7-methyl-6,7-dihydro-4H-3,4,7-triaza-dibenzo[cd,f]azulen-5-yl)-1,2,3,6-tetrahydropyridin-2-yl]methanol;

2-[4-(9,10-difluoro-7-methyl-6,7-dihydro-4H-3,4,7-triaza-dibenzo[cd,f]azulen-5-yl)-3,6-dihydropyridin-1(2H)-yl]-N-(2-hydroxyethyl)-N-methylacetamide;

7-methyl-5-(1,2,3,6-tetrahydropyridin-4-yl)-6,7-dihydro-4H-3,4,7-triazadibenzo[cd,f]azulene;

1-fluoro-7-methyl-5-(1,2,3,6-tetrahydropyridin-4-yl)-6,7-dihydro-4H-3,4,7-triazadibenzo[cd,f]azulene;

7-methyl-5-[1-(methylsulfonyl)-1,2,3,6-tetrahydropyridin-4-yl]-6,7-dihydro-4H-3,4,7-triazadibenzo[cd,f]azulene;

1-fluoro-7-methyl-5-[1-(methylsulfonyl)-1,2,3,6-tetrahydropyridin-4-yl]-6,7-dihydro-4H-3,4,7-triazadibenzo[cd,f]azulene;

N,N-dimethyl-2-[4-(7-methyl-6,7-dihydro-4H-3,4,7-triaza-dibenzo[cd,f]azulen-5-yl)-3,6-dihydropyridin-1(2H)-yl]acetamide;

2-[4-(1-fluoro-7-methyl-6,7-dihydro-4H-3,4,7-triaza-dibenzo[cd,f]azulen-5-yl)-3,6-dihydropyridin-1(2H)-yl]-N,N-dimethylacetamide;

3-[4-(10-fluoro-4,6-dihydro-7-oxa-3,4-diazadibenzo[cd,f]azulen-5-yl)-3,6-dihydropyridin-1(2H)-yl]propane-1,2-diol;

{4-[4-(10-fluoro-4,6-dihydro-7-oxa-3,4-diazadibenzo[cd,f]azulen-5-yl)-3,6-dihydropyridin-1(2H)-yl]cyclohexyl}acetic acid;

trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;

{trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}-N,N-dimethylacetamide;

{trans-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

{cis-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

trans-4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

{4-[4-(10-fluoro-7-methyl-6,7-dihydro-4H-3,4,7-triaza-dibenzo[cd,f]azulen-5-yl)-3,6-dihydropyridin-1(2H)-yl]cyclohexylidene}acetonitrile;

methyl 2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoate;

tert-butyl{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetate;

2-{4-[4-(10-fluoro-7-methyl-6,7-dihydro-4H-3,4,7-triaza-dibenzo[cd,f]azulen-5-yl)-3,6-dihydropyridin-1(2H)-yl]cyclohexylidene}propanoic acid;

{4-[4-(10-fluoro-7-methyl-6,7-dihydro-4H-3,4,7-triaza-dibenzo[cd,f]azulen-5-yl)-3,6-dihydropyridin-1(2H)-yl]cyclohexylidene}acetic acid;

2-[4-(10-fluoro-7-methyl-6,7-dihydro-4H-3,4,7-triaza-dibenzo[cd,f]azulen-5-yl)-3,6-dihydropyridin-1(2H)-yl]-N,N-dimethylethanesulfonamide;

2-[4-(10-fluoro-7-methyl-6,7-dihydro-4H-3,4,7-triaza-dibenzo[cd,f]azulen-5-yl)-3,6-dihydropyridin-1(2H)-yl]ethanesulfonamide;

{trans-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;

trans-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

{cis-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;

cis-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

{4-[4-(10-fluoro-7-methyl-6,7-dihydro-4H-3,4,7-triaza-dibenzo[cd,f]azulen-5-yl)-2,3,6,7-tetrahydro-1H-azepin-1-yl]cyclohexylidene}acetic acid;

2-{4-[4-(10-fluoro-7-methyl-6,7-dihydro-4H-3,4,7-triaza-dibenzo[cd,f]azulen-5-yl)-3,6-dihydropyridin-1(2H)-yl]cyclohexyl}-2-methylpropanoic acid;

methyl cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylate;

cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;

cis-3-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]cyclobutanecarboxylic acid;

trans-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;

trans-3-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]cyclobutanecarboxylic acid;

cyano{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;

{3-[4-(1,10-difluoro-7-methyl-6,7-dihydro-4H-3,4,7-triazadibenzo[cd,f]azulen-5-yl)-3,6-dihydropyridin-1(2H)-yl]cyclobutyl}acetic acid;

3-[4-(1,10-difluoro-7-methyl-6,7-dihydro-4H-3,4,7-triazadibenzo[cd,f]azulen-5-yl)-3,6-dihydropyridin-1(2H)-yl]cyclobutanecarboxylic acid; and pharmaceutically acceptable salts thereof.

In another embodiment, the present invention relates to pharmaceutical compositions comprising a pharmaceutically acceptable excipient and a therapeutically effective amount of a compound of Formula (Ia), or a pharmaceutically acceptable salt thereof.

In another embodiment, the present invention relates to methods of treating cancer in a patient, comprising administering to a patient suffering from a cancer a therapeutically effective amount of a compound of Formula (Ia), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. The use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated radical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of alkyls include methyl, ethyl, n-propyl, isopropyl, n-butyl, isobutyl, sec-butyl, tert-butyl, pentyl, isoamyl, hexyl, pentan-3-y), 2,2-dimethylpropan-2-yl), heptan-4-yl, and 2,6-dimethylheptan-4-yl, and the like. The term "$C_1$-$C_8$ alkyl" refers to an alkyl substituent containing from 1 to 8 carbon atoms, "$C_1$-$C_6$ alkyl" refers to an alkyl substituent containing from 1 to 6 carbon atoms, and "$C_1$-$C_4$ alkyl" refers to an alkyl substituent containing from 1 to 4 carbon atoms.

The term "alkenyl" (alone or in combination with another term(s)) means a straight- or branched-chain radical of an alkene containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like. The term "$C_2$-$C_6$ alkenyl" means an alkenyl group containing 2-6 carbon atoms. The term "$C_2$-$C_6$ alkenyl" also includes alkenyl substituents on saturated or partially saturated ring systems in which one of the unsaturated carbon atoms is within the ring. An example of a ring system substituted with a $C_2$-alkenyl substituent in which one of the unsaturated carbon atoms of the $C_2$-alkenyl substituent is within the ring is methylenecyclohexane.

The term "alkynyl" (alone or in combination with another term(s)) means a straight- or branched-chain radical of an an alkyne containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butyryl, and 3-butynyl and the like. The term "$C_2$-$C_6$ alkynyl" means an alkynyl group of 2 to 6 carbon atoms.

The term "cycloalkyl" (alone or in combination with another term(s)) means a saturated cyclic hydrocarbyl substituent containing from 3 or more carbon ring atoms ("ring atoms" are the atoms bound together to form the ring or rings of a cyclic substituent). A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic (contain more than one ring). Examples of polycyclic cycloalkyls include bridged, fused, and spirocyclic cycloalkyls.

The term "$C_3$-$C_7$ cycloalkyl" (alone or in combination with another term(s)) means a saturated cyclic radical of a monocyclic cycloalkane containing from 3 to 7 carbon ring atoms. Examples of monocyclic cycloalkyl groups include, but are not limited to, cyclopropyl (cyclopropanyl), cyclobutyl (cyclobutanyl), cyclopentyl (cyclopentanyl), cyclopentenyl, cyclohexyl (cyclohexanyl), and cycloheptyl.

The term "cycloalkenyl" (alone or in combination with another term(s)) means a partially unsaturated cyclic hydrocarbyl substituent containing from 4 or more carbon ring atoms ("ring atoms" are the atoms bound together to form the ring or rings of a cyclic substituent). A cycloalkenyl may be a single carbon ring, which typically contains from 4 to 8 carbon ring atoms and more typically from 4 to 6 ring atoms. Examples of single-ring cycloalkenyls include cyclobutenyl, cyclopentenyl, and cyclohexenyl. A cycloalkenyl may alternatively be polycyclic (contain more than one ring). Examples of polycyclic cycloalkenyls include bridged, fused, and spirocyclic cycloalkenyls.

The term "$C_5$-$C_7$ cycloalkenyl" (alone or in combination with another term(s)) means a partially unsaturated monocylic cycloalkane radical containing from 5 to 7 carbon ring atoms. Examples of single-ring cycloalkenyls include cyclopentenyl, cyclohexenyl, and cycloheptenyl.

The term "heterocycloalkyl" (alone or in combination with another term(s)) means a non-aromatic saturated monocyclic or polycyclic heterocycloalkane radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkyl may be a single carbon ring, which typically contains from 3 to 8 ring atoms and more typically from 3 to 6 ring atoms. Examples of single-ring heterocycloalkyls include oxetanyl, azetidinyl, thietanyl, tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, 3-pyrrolinyl, tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, trithianyl, azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl, azocanyl, thiocanyl, oxocanyl, tetrahydro-2H-thiopyranyl 1,1-dioxide and 3,4,5,6-tetrahydro-2H-oxocinyl. A heterocycloalkyl may alternatively be polycyclic (contain more than one ring). Examples of polycyclic heterocycloalkyls include bridged, fused, and spirocyclic heterocycloalkyls in which at least one ring is a heterocycloalkyl and the others are heterocycloalkyl, or cycloalkyl rings.

The term "heterocycloalkenyl" (alone or in combination with another term(s)) means a non-aromatic partially unsaturated monocyclic or polycyclic heterocycloalkene radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkenyl may be a single carbon ring, which typically contains from 3 to 8 ring atoms and more typically from 3 to 6 ring atoms. Examples of single-ring heterocycloalkenyls include 1,2,3,6-tetrahydropyridinyl, and 4,5-dihydro-1H-imidazolyl. A heterocycloalkenyl may alternatively be polycyclic (contain more than one ring). Examples of polycyclic heterocycloalkenyls include bridged, fused, and spirocyclic heterocycloalkenyls in which at least one ring is a heterocycloalkenyl and the others are heterocycloalkenyl, heterocycloalkyl, cycloalkenyl or cycloalkyl rings. Alternatively, a polycyclic heterocycloalkenyl may consist of one or more heterocycloalkyl rings and one or more cycloalkenyl rings. Examples of polycyclic heterocycloalkenyls include 8-azabicyclo[3.2.1]oct-2-enyl, and 1,2,3,3a,4,6a-hexahydrocyclopenta[c]pyrrolyl.

The term "5 to 7-membered heterocycloalkyl" (alone or in combination with another term(s)) means a 5 to 7-membered, non-aromatic monocyclic radical having carbon atoms and 1 to 3 heteroatoms independently selected from S, N or O, wherein when two O atoms or one O atom and one S atom are present, the two O atoms or one O atom and one S atom are not bonded to each other, respectively.

The term "4-membered monocyclic heterocycloalkyl" (alone or in combination with another term(s)) means a 4-membered, monocyclic radical having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

The term "5-membered monocyclic heterocycloalkyl" (alone or in combination with another term(s)) means a 5-membered, monocyclic radical having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

The term "6-membered monocyclic heterocycloalkyl" (alone or in combination with another term(s)) means a 6-membered, monocyclic radical having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

The term "7-membered monocyclic heterocycloalkyl" (alone or in combination with another term(s)) means a 7-membered, monocyclic radical having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1O; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

The term "8-membered monocyclic heterocycloalkyl" (alone or in combination with another term(s)) means a 8-membered, monocyclic radical having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl(N-attached) or piperidin-4-yl (C-attached).

The term "aryl" (alone or in combination with another term(s)) means an aromatic hydrocarbon radical. Furthermore, the term "aryl" includes polycyclic aryl groups, such as bicyclic, e.g., naphthyl. Typical aryl groups include phenyl, and naphthyl. The term "aryl" also includes a "9- to 12-membered bicyclic aryl," which is a ring structure formed by the fusion of a benzene ring to: (1) a cycloalkyl or cycloalkenyl (e.g., indanyl; 1,2,3,4-tetrahydro-naphthalenyl; 6,7,8,9-tetrahydro-5H-benzocycloheptenyl, etc.); (2) another benzene ring (e.g., naphthalenyl); wherein the fusion junctions are at adjacent carbons on the benzene ring; or (3) a heterocycloalkyl or heterocycloalkenyl (e.g., benzo[d][1,3]dioxolyl, isoindolinyl).

The term "heteroaryl" (alone or in combination with another term(s)) means a monocyclic 5 or 6 membered heteroaryl or a bicyclic heteroaryl.

The term "5-membered heteroaryl" (alone or in combination with another term(s)) means a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

The term "6-membered heteroaryl" (alone or in combination with another term(s)) means a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

The term "bicyclic heteroaryl" (alone or in combination with another term(s)) means a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a cycloalkyl or cycloalkenyl; (4) a heterocycloalkyl or heterocycloalkenyl; or (5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat," "treating," and "treatment" refer to a method of alleviating or abrogating a disease and/or its attendant symptoms.

The terms "prevent," "preventing," and "prevention" refer to a method of preventing the onset of a disease and/or its attendant symptoms or barring a subject from acquiring a disease. As used herein, "prevent," "preventing," and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK9 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to CDK9 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Embodiments

Suitable groups for X, Y, $R^1$, $R^2$, $R^{3A}$, $R^{3B}$, and $R^4$ in compounds of Formula (I) and (Ia), $R^1$, $R^2$, $R^{2A}$, $R^{3A}$, $R^{3B}$, and $R^4$ in compounds of Formula (II) and (IIa), and $R^1$, $R^2$, $R^{3A}$, $R^{3B}$, and $R^4$, in compounds of Formula (III) and (IIIa), are independently selected. The described embodiments of the present invention may be combined. Such combination is contemplated and within the scope of the present invention. For example, it is contemplated that embodiments for any of X, Y, $R^1$, $R^2$, $R^{3A}$, $R^{3B}$, and $R^4$, in compounds of Formula (Ia) can be combined with embodiments defined for any other of X, Y, $R^1$, $R^2$, $R^{3A}$, $R^{3B}$, and $R^4$ in compounds of Formula (Ia).

Embodiments of Formula (I)

In one embodiment, the present invention relates to compounds of Formula (I) or a pharmaceutically acceptable salt thereof,

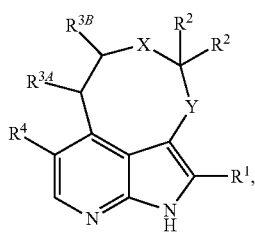

Formula (I)

wherein
X is O or $NR^{2A}$;
Y is $C(R^2)_2$ or is absent;
$R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, $OH$, $CN$, $NO_2$, F, Cl, Br and I;
$R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, C(O)OH, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting of $C_1$-$C_8$ alkyl, $C_2$-$C_6$ alkenyl, and $C_2$-$C_6$ alkynyl;

$R^{2A}$ is hydrogen or $C_1$-$C_4$ alkyl; wherein the $R^{2A}$ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I;
$R^{2B}$ is $C_1$-$C_4$ alkyl;
$R^{3A}$ and $R^{3B}$, taken together, form $R^3$;
$R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I;
$R^4$ is selected from the group consisting of hydrogen, $C_1$-$C_4$ alkyl, $C_1$-$C_4$ alkoxy, CN, F, Cl, Br, and I;
$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $OH$, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $OH$, CN, $NO_2$, F, Cl, Br and I;
$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycloalkyl, heterocycloalkenyl, $NH_2$, C(O)H, C(O)OH, OH, CN, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $OH$, $CN$, $NO_2$, F, Cl, Br and I;

$R^7$, at each occurrence, is independently selected from the group consisting of $C_1$-$C_6$ alkyl, $C_2$-$C_6$ alkenyl, and $C_2$-$C_6$ alkynyl; and $R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, C(O)H, C(O)OH, OH, CN, $NO_2$, F, Cl, Br and I.

In one embodiment of Formula (I), X is O or $NR^{2A}$. In another embodiment of Formula (I), X is O. In another embodiment of Formula (I), X is $NR^{2A}$.

In one embodiment of Formula (I), Y is $C(R^2)_2$ or is absent. In another embodiment of Formula (I), Y is $C(R^2)_2$. In another embodiment of Formula (I), Y is absent.

In one embodiment of Formula (I), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, C(O)NHOH, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, C(O)H, C(O)OH, OH, CN, $NO_2$, F, Cl, Br and I. In another embodiment of Formula (I), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $SO_2R^5$, C(O)$R^5$, CO(O)$R^5$, $NH_2$, $NHR^5$, $C(O)NHR^5$, $C(O)N(R^5)_2$, $SO_2NHC(O)OR^5$, C(O)OH, F, Cl, Br and I. In another embodiment of Formula (I), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and C(O)OH. In another embodiment of Formula (I), $R^1$ is cycloalkenyl; wherein the $R^1$ cycloalkenyl is optionally substituted as described herein. In another embodiment of Formula (I), $R^1$ is aryl; wherein the $R^1$ aryl is optionally substituted as described herein. In another embodiment of Formula (I), $R^1$ is heteroaryl; wherein the $R^1$ heteroaryl is optionally substituted as described herein. In another embodiment of Formula (I), $R^1$ is heterocycloalkyl; wherein the $R^1$ heterocycloalkyl is optionally substituted as described herein. In another embodiment of Formula (I), $R^1$ is heterocycloalkenyl; wherein the $R^1$ heterocycloalkenyl is optionally substituted as described herein. In another embodiment of Formula (I), $R^1$ is pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, or 8-azabicyclo[3.2.1]oct-2-enyl; wherein the $R^1$ pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, and 8-azabicyclo[3.2.1]oct-2-enyl are optionally substituted as described herein for substituents on $R^1$. In another embodiment of Formula (I), $R^1$ is 1,2,3,6-tetrahydropyridinyl; wherein the $R^1$ 1,2,3,6-tetrahydropyridinyl is optionally substituted as described herein for substituents on $R^1$.

In one embodiment of Formula (I), $R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, C(O)OH, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting of $C_1$-$C_8$ alkyl, $C_2$-$C_6$ alkenyl, and $C_2$-$C_6$ alkynyl. In another embodiment of Formula (I), $R^2$, at each occurrence, is independently selected from the group consisting of hydrogen, $C_1$-$C_4$ alkyl, heteroaryl, C(O)OH, and $C(O)OR^{2B}$; wherein each $R^2$ heteroaryl is optionally substituted with one or more $C_1$-$C_8$ alkyl. In another embodiment of Formula (I), $R^2$, at each occurrence, is independently hydrogen or $C_1$-$C_4$ alkyl. In another embodiment of Formula (I), $R^2$, at each occurrence, is independently hydrogen. In another embodiment of Formula (I), $R^2$, at each occurrence, is independently $C_1$-$C_4$ alkyl.

In one embodiment of Formula (I), $R^{2A}$ is hydrogen or $C_1$-$C_4$ alkyl; wherein the $R^{2A}$ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I. In another embodiment of Formula (I), $R^{2A}$ is hydrogen or $C_1$-$C_4$ alkyl; wherein the $R^{2A}$ $C_1$-$C_4$ alkyl is optionally substituted with one or more substituents independently selected from the group consisting of heterocycloalkyl, F, Cl, Br and I. In another embodiment of Formula (I), $R^{2A}$ is hydrogen or $C_1$-$C_4$ alkyl; wherein the $R^{2A}$ $C_1$-$C_4$ alkyl is optionally substituted with one or more heterocycloalkyl. In another embodiment of Formula (I), $R^{2A}$ is hydrogen. In another embodiment of Formula (I), $R^{2A}$ is $C_1$-$C_4$ alkyl; wherein the $R^{2A}$ $C_1$-$C_4$ alkyl is optionally substituted with one or more heterocycloalkyl.

In one embodiment of Formula (I), $R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I. In another embodiment of Formula (I), $R^3$ is phenyl; wherein the $R^3$ phenyl is optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I. In another embodiment of Formula (I), $R^3$ is phenyl; wherein the $R^3$ phenyl is optionally substituted with one or more substituents independently selected from the group consisting of F, Cl, Br and I. In another embodiment of Formula (I), $R^3$ is phenyl; wherein the $R^3$ phenyl is optionally substituted with F. In another embodiment of Formula (I), $R^3$ is phenyl; wherein the $R^3$ phenyl is substituted with F.

In one embodiment of Formula (I), $R^4$ is selected from the group consisting of hydrogen, $C_1$-$C_4$ alkyl, $C_1$-$C_4$ alkoxy, CN, F, Cl, Br, and I. In another embodiment of Formula (I), $R^4$ is selected from the group consisting of hydrogen, F, Cl, Br, and I. In another embodiment of Formula (I), $R^4$ is F. In another embodiment of Formula (I), $R^4$ is hydrogen.

In one embodiment of Formula (I),

X is O or $NR^{2A}$;

Y is absent;

$R^1$ is selected from the group consisting of cycloalkenyl, aryl, heteroaryl, heterocycloalkyl, and heterocycloalkenyl;

wherein the R¹ cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and $C(O)OH$;

$R^2$, at each occurrence, is independently selected from the group consisting of hydrogen, $C_1$-$C_4$ alkyl, heteroaryl, $C(O)OH$, and $C(O)OR^{2B}$; wherein each $R^2$ heteroaryl is optionally substituted with one or more $C_1$-$C_8$ alkyl;

$R^{2A}$ is hydrogen or $C_1$-$C_4$ alkyl; wherein the $R^{2A}$ $C_1$-$C_4$ alkyl is optionally substituted with one heterocycloalkyl;

$R^{2B}$ is $C_1$-$C_4$ alkyl;

$R^{3A}$ and $R^{3B}$, taken together, form $R^3$;

$R^3$ is phenyl; wherein the $R^3$ phenyl is optionally substituted with one or more F;

$R^4$ is selected from the group consisting of hydrogen, F, Cl, Br, and I;

$R^5$, at each occurrence, is independently selected from the group consisting of $C_1$-$C_8$ alkyl, heterocycloalkyl; wherein each $R^5$ $C_1$-$C_8$ alkyl is optionally substituted with one or more substituents independently selected from the group consisting of $R^6$, $OR^6$, $C(O)R^6$, $CO(O)R^6$, $N(R^6)_2$, $C(O)N(R^6)_2$, $SO_2NHR^6$, $C(O)OH$, and OH; wherein each $R^5$ heterocycloalkyl is optionally substituted with one or more substituents independently selected from the group consisting of $C(O)OH$, and OH;

$R^6$, at each occurrence, is independently selected from the group consisting of $C_1$-$C_6$ alkyl, aryl, heterocycloalkyl, and cycloalkyl; wherein each $R^6$ $C_1$-$C_6$ alkyl is optionally substituted with one or more OH; wherein each $R^6$ aryl, cycloalkyl, and heterocycloalkyl is optionally substituted with one or more substituents independently selected from the group consisting of $R^8$, OH, F, Cl, Br and I; and $R^8$, at each occurrence, is independently $C_1$-$C_6$ alkyl; wherein each $R^8$ $C_1$-$C_6$ alkyl is optionally substituted with one or more OH.

Still another embodiment pertains to compounds of Formula (I), selected from the group consisting of:

10-fluoro-7-methyl-5-(1,2,3,6-tetrahydropyridin-4-yl)-6,7-dihydro-4H-3,4,7-triazadibenzo[cd,f]azulene;

tert-butyl 4-(10-fluoro-7-methyl-6,7-dihydro-4H-3,4,7-triazadibenzo[cd,f]azulen-5-yl)-3,6-dihydropyridine-1(2H)-carboxylate;

ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate;

10-fluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-7-propyl-6,7-dihydro-4H-3,4,7-triazadibenzo[cd,f]azulene;

10-fluoro-5-[1-(methylsulfonyl)-1,2,3,6-tetrahydropyridin-4-yl]-7-(tetrahydro-2H-pyran-4-ylmethyl)-6,7-dihydro-4H-3,4,7-triazadibenzo[cd,f]azulene;

tert-butyl 4-(6-ethyl-10-fluoro-7-methyl-6,7-dihydro-4H-3,4,7-triazadibenzo[cd,f]azulen-5-yl)-3,6-dihydropyridine-1(2H)-carboxylate;

6-ethyl-10-fluoro-7-methyl-5-(1,2,3,6-tetrahydropyridin-4-yl)-6,7-dihydro-4H-3,4,7-triazadibenzo[cd,f]azulene dihydrochloride;

10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene;

6-ethyl-10-fluoro-7-methyl-5-[1-(methylsulfonyl)-1,2,3,6-tetrahydropyridin-4-yl]-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

4-(10-fluoro-7-methyl-6,7-dihydro-4H-3,4,7-triazadibenzo[cd,f]azulen-5-yl)-N-methyl-3,6-dihydropyridine-1(2H)-carboxamide;

10-fluoro-5-(1,2,3,6-tetrahydropyridin-4-yl)-4,6-dihydro-7-oxa-3,4-diazadibenzo[cd,f]azulene;

10-fluoro-5-[1-(methylsulfonyl)-1,2,3,6-tetrahydropyridin-4-yl]-4,6-dihydro-7-oxa-3,4-diazadibenzo[cd,f]azulene;

[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride;

2-[4-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(10-fluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene;

10-fluoro-7-methyl-5-(piperidin-4-yl)-6,7-dihydro-4H-3,4,7-triazadibenzo[cd,f]azulene;

tert-butyl[4-(10-fluoro-7-methyl-6,7-dihydro-4H-3,4,7-triazadibenzo[cd,f]azulen-5-yl)piperidin-1-yl]acetate;

[4-(10-fluoro-7-methyl-6,7-dihydro-4H-3,4,7-triazadibenzo[cd,f]azulen-5-yl)piperidin-1-yl]acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-N-methyl-2-oxo ethanesulfonamide;

2-[4-(10-fluoro-7-methyl-6,7-dihydro-4H-3,4,7-triazadibenzo[cd,f]azulen-5-yl)piperidin-1-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)piperidin-1-yl]-N-(2-hydroxyethyl)-N-methylacetamide;

ethyl 10-fluoro-7-methyl-5-(1,2,3,6-tetrahydropyridin-4-yl)-6,7-dihydro-4H-3,4,7-triazadibenzo[cd,f]azulene-6-carboxylate;

N-[4-(10-fluoro-7-methyl-6,7-dihydro-4H-3,4,7-triazadibenzo[cd,f]azulen-5-yl)cyclohex-3-en-1-yl]-D-valine;

N-[4-(10-fluoro-7-methyl-6,7-dihydro-4H-3,4,7-triazadibenzo[cd,f]azulen-5-yl)cyclohex-3-en-1-yl]-L-alanine;

N-[4-(10-fluoro-7-methyl-6,7-dihydro-4H-3,4,7-triazadibenzo[cd,f]azulen-5-yl)cyclohex-3-en-1-yl]glycine;

(2S)-{[4-(10-fluoro-7-methyl-6,7-dihydro-4H-3,4,7-triazadibenzo[cd,f]azulen-5-yl)cyclohex-3-en-1-yl]amino}(phenyl)acetic acid;

10-fluoro-7-methyl-5-(1,2,3,6-tetrahydropyridin-4-yl)-6,7-dihydro-4H-3,4,7-triazadibenzo[cd,f]azulene-6-carboxylic acid;

N-[4-(10-fluoro-7-methyl-6,7-dihydro-4H-3,4,7-triazadibenzo[cd,f]azulen-5-yl)cyclohex-3-en-1-yl]-L-valine;

N-[4-(10-fluoro-7-methyl-6,7-dihydro-4H-3,4,7-triazadibenzo[cd,f]azulen-5-yl)cyclohex-3-en-1-yl]-L-phenylalanine;

N-[4-(10-fluoro-7-methyl-6,7-dihydro-4H-3,4,7-triazadibenzo[cd,f]azulen-5-yl)cyclohex-3-en-1-yl]-3-methyl-L-valine;
1-[4-(10-fluoro-7-methyl-6,7-dihydro-4H-3,4,7-triazadibenzo[cd,f]azulen-5-yl)cyclohex-3-en-1-yl]-L-proline;
N-[4-(10-fluoro-7-methyl-6,7-dihydro-4H-3,4,7-triazadibenzo[cd,f]azulen-5-yl)cyclohex-3-en-1-yl]-L-serine;
N-[4-(10-fluoro-7-methyl-6,7-dihydro-4H-3,4,7-triazadibenzo[cd,f]azulen-5-yl)cyclohex-3-en-1-yl]-L-norvaline;
N-[4-(10-fluoro-7-methyl-6,7-dihydro-4H-3,4,7-triazadibenzo[cd,f]azulen-5-yl)cyclohex-3-en-1-yl]-L-tyrosine;
4-(10-fluoro-7-methyl-6,7-dihydro-4H-3,4,7-triazadibenzo[cd,f]azulen-5-yl)cyclohex-3-ene-1-carboxylic acid;
2-[4-(10-fluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;
10-fluoro-7-methyl-5-[4-(methylsulfonyl)phenyl]-6,7-dihydro-4H-3,4,7-triazadibenzo[cd,f]azulene;
10-fluoro-7-methyl-5-(pyridin-4-yl)-6,7-dihydro-4H-3,4,7-triazadibenzo[cd,f]azulene;
10-fluoro-7-methyl-5-[6-(methylsulfonyl)pyridin-3-yl]-6,7-dihydro-4H-3,4,7-triazadibenzo[cd,f]azulene;
5-(10-fluoro-7-methyl-6,7-dihydro-4H-3,4,7-triazadibenzo[cd,f]azulen-5-yl)pyrimidin-2-amine;
4-(10-fluoro-7-methyl-6,7-dihydro-4H-3,4,7-triazadibenzo[cd,f]azulen-5-yl)benzoic acid;
1,10-difluoro-7-methyl-5-(1,2,3,6-tetrahydropyridin-4-yl)-6,7-dihydro-4H-3,4,7-triazadibenzo[cd,f]azulene;
tert-butyl 4-(1,10-difluoro-7-methyl-6,7-dihydro-4H-3,4,7-triazadibenzo[cd,f]azulen-5-yl)-3,6-dihydropyridine-1(2H)-carboxylate;
4-(10-fluoro-7-methyl-6,7-dihydro-4H-3,4,7-triazadibenzo[cd,f]azulen-5-yl)-N,N-dimethylcyclohex-3-ene-1-carboxamide;
[4-(10-fluoro-7-methyl-6,7-dihydro-4H-3,4,7-triazadibenzo[cd,f]azulen-5-yl)cyclohex-3-en-1-yl](3-hydroxyazetidin-1-yl)methanone;
4-(10-fluoro-7-methyl-6,7-dihydro-4H-3,4,7-triazadibenzo[cd,f]azulen-5-yl)-N-methylcyclohex-3-ene-1-carboxamide;
2-[4-(10-fluoro-7-methyl-6,7-dihydro-4H-3,4,7-triazadibenzo[cd,f]azulen-5-yl)-3,6-dihydropyridin-1(2H)-yl]-N,N-bis(2-hydroxyethyl)acetamide;
1-(3,3-difluoroazetidin-1-yl)-2-[4-(10-fluoro-7-methyl-6,7-dihydro-4H-3,4,7-triazadibenzo[cd,f]azulen-5-yl)-3,6-dihydropyridin-1(2H)-yl]ethanone;
2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N,N-dimethylacetamide;
10-fluoro-7-methyl-5-[(1R,5S)-8-(methylsulfonyl)-8-azabicyclo[3.2.1]oct-2-en-3-yl]-6,7-dihydro-4H-3,4,7-triazadibenzo[cd,f]azulene;
(1R,5S)-3-(10-fluoro-7-methyl-6,7-dihydro-4H-3,4,7-triazadibenzo[cd,f]azulen-5-yl)-N-methyl-8-azabicyclo[3.2.1]oct-2-ene-8-carboxamide;
[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid;
10-fluoro-5-(1,2,3,3a,4,6a-hexahydrocyclopenta[c]pyrrol-5-yl)-7-methyl-6,7-dihydro-4H-3,4,7-triazadibenzo[cd,f]azulene;
10-fluoro-7-methyl-5-(pyridin-3-yl)-6,7-dihydro-4H-3,4,7-triazadibenzo[cd,f]azulene;
ethyl 4-(10-fluoro-7-methyl-6,7-dihydro-4H-3,4,7-triazadibenzo[cd,f]azulen-5-yl)cyclohex-3-ene-1-carboxylate;
5-[(1R,5S)-8-azabicyclo[3.2.1]oct-2-en-3-yl]-10-fluoro-7-methyl-6,7-dihydro-4H-3,4,7-triazadibenzo[cd,f]azulene;
N-(2,3-dihydroxypropyl)-2-[4-(10-fluoro-7-methyl-6,7-dihydro-4H-3,4,7-triazadibenzo[cd,f]azulen-5-yl)-3,6-dihydropyridin-1(2H)-yl]-N-methylacetamide;
2-[4-(10-fluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;
tert-butyl[4-(1,10-difluoro-7-methyl-6,7-dihydro-4H-3,4,7-triazadibenzo[cd,f]azulen-5-yl)-3,6-dihydropyridin-1(2H)-yl]acetate;
2-[4-(1,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;
[4-(1,10-difluoro-7-methyl-6,7-dihydro-4H-3,4,7-triazadibenzo[cd,f]azulen-5-yl)-3,6-dihydropyridin-1(2H)-yl]acetic acid;
1,10-difluoro-7-methyl-5-[1-(methylsulfonyl)-1,2,3,6-tetrahydropyridin-4-yl]-6,7-dihydro-4H-3,4,7-triazadibenzo[cd,f]azulene;
10-fluoro-5-{2-[(2-methoxyethyl)sulfonyl]-1,2,3,3a,4,6a-hexahydrocyclopenta[c]pyrrol-5-yl}-7-methyl-6,7-dihydro-4H-3,4,7-triazadibenzo[cd,f]azulene;
2-[4-(1,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;
2-[4-(1,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-1-[3-(hydroxymethyl)azetidin-1-yl]ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;
5-(10-fluoro-7-methyl-6,7-dihydro-4H-3,4,7-triazadibenzo[cd,f]azulen-5-yl)-N-methyl-3,3a,4,6a-tetrahydrocyclopenta[c]pyrrole-2(1H)-carboxamide;
2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N,N-dimethylacetamide;
10-fluoro-7-methyl-5-[2-(methylsulfonyl)-1,2,3,3a,4,6a-hexahydrocyclopenta[c]pyrrol-5-yl]-6,7-dihydro-4H-3,4,7-triazadibenzo[cd,f]azulene;
2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-[(2S)-2-(hydroxymethyl)pyrrolidin-1-yl]ethanone;
2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-(3-hydroxyazetidin-1-yl)ethanone;
[4-(10-fluoro-7-methyl-6,7-dihydro-4H-3,4,7-triazadibenzo[cd,f]azulen-5-yl)phenyl]acetic acid;
[3-(10-fluoro-7-methyl-6,7-dihydro-4H-3,4,7-triazadibenzo[cd,f]azulen-5-yl)phenyl]acetic acid;
N-(2,3-dihydroxypropyl)-2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-methylacetamide;

2-[5-(10-fluoro-7-methyl-6,7-dihydro-4H-3,4,7-triaza-dibenzo[cd,f]azulen-5-yl)-3,3a,4,6a-tetrahydrocyclopenta[c]pyrrol-2(1H)-yl]-1-(3-hydroxyazetidin-1-yl)ethanone;

N-(2,3-dihydroxypropyl)-2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-methylacetamide;

2-[5-(10-fluoro-7-methyl-6,7-dihydro-4H-3,4,7-triaza-dibenzo[cd,f]azulen-5-yl)-3,3a,4,6a-tetrahydrocyclopenta[c]pyrrol-2(1H)-yl]-N-(2-hydroxyethyl)-N-methylacetamide;

10-fluoro-7-methyl-5-(2,3,6,7-tetrahydro-1H-azepin-4-yl)-6,7-dihydro-4H-3,4,7-triazadibenzo[cd,f]azulene;

2-[4-(10-fluoro-7-methyl-6,7-dihydro-4H-3,4,7-triaza-dibenzo[cd,f]azulen-5-yl)-2,3,6,7-tetrahydro-1H-azepin-1-yl]-N,N-dimethylacetamide;

10-fluoro-7-methyl-5-[1-(methylsulfonyl)-2,3,6,7-tetrahydro-1H-azepin-4-yl]-6,7-dihydro-4H-3,4,7-triazadibenzo[cd,f]azulene;

[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid;

2-[4-(10-fluoro-7-methyl-6,7-dihydro-4H-3,4,7-triaza-dibenzo[cd,f]azulen-5-yl)-2,3,6,7-tetrahydro-1H-azepin-1-yl]-1-(3-hydroxyazetidin-1-yl)ethanone;

5-(3,3-dimethyl-1,2,3,6-tetrahydropyridin-4-yl)-10-fluoro-7-methyl-6,7-dihydro-4H-3,4,7-triazadibenzo[cd,f]azulene;

10-fluoro-7-methyl-5-(1,2,5,6-tetrahydropyridin-3-yl)-6,7-dihydro-4H-3,4,7-triazadibenzo[cd,f]azulene;

2-[5-(10-fluoro-7-methyl-6,7-dihydro-4H-3,4,7-triaza-dibenzo[cd,f]azulen-5-yl)-3,3a,4,6a-tetrahydrocyclopenta[c]pyrrol-2(1H)-yl]-N-(3-hydroxycyclobutyl)-N-methylacetamide;

10-fluoro-7-methyl-5-[1-(methylsulfonyl)-1,2,5,6-tetrahydropyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)-N-methyl-3,6-dihydropyridine-1(2H)-carboxamide;

2-[5-(10-fluoro-7-methyl-6,7-dihydro-4H-3,4,7-triaza-dibenzo[cd,f]azulen-5-yl)-3,6-dihydropyridin-1(2H)-yl]-N,N-dimethylacetamide;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-(3-hydroxycyclobutyl)-N-methylacetamide;

and pharmaceutically acceptable salts thereof.

Embodiments of Formula (II)

In another embodiment, the present invention relates to compounds of Formula (II) or a pharmaceutically acceptable salt thereof,

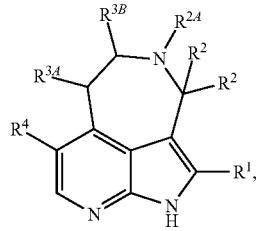

Formula (II)

wherein
$R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, OH, CN, $NO_2$, F, Cl, Br and I;

$R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, $C(O)OH$, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting of $C_1$-$C_8$ alkyl, $C_2$-$C_6$ alkenyl, and $C_2$-$C_6$ alkynyl;

$R^{2A}$ is hydrogen or $C_1$-$C_4$ alkyl; wherein the $R^{2A}$ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I;

$R^{2B}$ is $C_1$-$C_4$ alkyl;

$R^{3A}$ and $R^{3B}$, taken together, form $R^3$;

$R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, OH, CN, $NO_2$, F, Cl, Br and I;

$R^4$ is selected from the group consisting of hydrogen, $C_1$-$C_4$ alkyl, $C_1$-$C_4$ alkoxy, CN, F, Cl, Br, and I;

$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, OH, CN, $NO_2$, F, Cl, Br and I;

R⁶, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each R⁶ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycyloalkyl, heterocycloalkenyl, $NH_2$, C(O)H, C(O)OH, OH, CN, $NO_2$, F, Cl, Br and I; wherein each R⁶ aryl, cycloalkyl, cycloalkenyl, heteroaryl, heterocycloalkyl, and heterocycloalkenyl is optionally substituted with one or more substituents independently selected from the group consisting of R⁸, OR⁸, SR⁸, S(O)R⁸, $SO_2R^8$, C(O)R⁸, CO(O)R⁸, OC(O)R⁸, OC(O)OR⁸, $NH_2$, NHR⁸, N(R⁸)₂, NHC(O)R⁸, NR⁸C(O)R⁸, NHS(O)₂R⁸, NR⁸S(O)₂R⁸, NHC(O)OR⁸, NR⁸C(O)OR⁸, NHC(O)NH₂, NHC(O)NHR⁸, NHC(O)N(R⁸)₂, NR⁸C(O)NHR⁸, NR⁸C(O)N(R⁸)₂, C(O)NH₂, C(O)NHR⁸, C(O)N(R⁸)₂, C(O)NHOH, C(O)NHOR⁸, C(O)NHSO₂R⁸, C(O)NR⁸SO₂R⁸, SO₂NH₂, SO₂NHR⁸, SO₂N(R⁸)₂, C(O)H, C(O)OH, OH, CN, NO₂, F, Cl, Br and I;

R⁷, at each occurrence, is independently selected from the group consisting of $C_1$-$C_6$ alkyl, $C_2$-$C_6$ alkenyl, and $C_2$-$C_6$ alkynyl; and R⁸, at each occurrence, is independently selected from the group consisting of $C_1$-$C_6$ alkyl, $C_2$-$C_6$ alkenyl, and $C_2$-$C_6$ alkynyl; wherein each R⁸ $C_1$-$C_6$ alkyl, $C_2$-$C_6$ alkenyl, and $C_2$-$C_6$ alkynyl is optionally substituted with one or more substituents independently selected from the group consisting of NH₂, C(O)H, C(O)OH, OH, CN, NO₂, F, Cl, Br and I.

In one embodiment of Formula (II), R¹ is selected from the group consisting of cycloalkyl, cycloalkenyl, aryl, heteroaryl, heterocycloalkyl, and heterocycloalkenyl; wherein the R¹ cycloalkyl, cycloalkenyl, aryl, heteroaryl, heterocycloalkyl, and heterocycloalkenyl are optionally substituted with one or more substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC(O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O)NH₂, C(O)NHR⁵, C(O)N(R⁵)₂, C(O)NHOH, C(O)NHOR⁵, NHSO₂R⁵, C(O)NR⁵SO₂R⁵, SO₂NH₂, SO₂NHR⁵, SO₂N(R⁵)₂, SO₂NHC(O)OR⁵, C(O)H, C(O)OH, OH, CN, NO₂, F, Cl, Br and I. In another embodiment of Formula (II), R¹ is selected from the group consisting of cycloalkyl, cycloalkenyl, aryl, heteroaryl, heterocycloalkyl, and heterocycloalkenyl; wherein the R¹ cycloalkyl, cycloalkenyl, aryl, heteroaryl, heterocycloalkyl, and heterocycloalkenyl are optionally substituted with one or more substituents independently selected from the group consisting of R⁵, SO₂R⁵, C(O)R⁵, CO(O)R⁵, NH₂, NHR⁵, C(O)NHR⁵, C(O)N(R⁵)₂, SO₂NHC(O)OR⁵, C(O)OH, F, Cl, Br and I. In another embodiment of Formula (II), R¹ is selected from the group consisting of cycloalkyl, cycloalkenyl, aryl, heteroaryl, heterocycloalkyl, and heterocycloalkenyl; wherein the R¹ cycloalkyl, cycloalkenyl, aryl, heteroaryl, heterocycloalkyl, and heterocycloalkenyl are optionally substituted with one or more substituents independently selected from the group consisting of R⁵, SO₂R⁵, C(O)R⁵, CO(O)R⁵, NH₂, NHR⁵, C(O)NHR⁵, C(O)N(R⁵)₂, SO₂NHC(O)OR⁵, and C(O)OH. In another embodiment of Formula (II), R¹ is cycloalkenyl; wherein the R¹ cycloalkenyl is optionally substituted as described herein. In another embodiment of Formula (II), R¹ is aryl; wherein the R¹ aryl is optionally substituted as described herein. In another embodiment of Formula (II), R¹ is heteroaryl; wherein the R¹ heteroaryl is optionally substituted as described herein. In another embodiment of Formula (II), R¹ is heterocycloalkyl; wherein the R¹ heterocycloalkyl is optionally substituted as described herein. In another embodiment of Formula (II), R¹ is heterocycloalkenyl; wherein the R¹ heterocycloalkenyl is optionally substituted as described herein. In another embodiment of Formula (II), R¹ is pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, or 8-azabicyclo[3.2.1]oct-2-enyl; wherein the R¹ pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, and 8-azabicyclo[3.2.1]oct-2-enyl are optionally substituted as described herein for substituents on R¹. In another embodiment of Formula (II), R¹ is 1,2,3,6-tetrahydropyridinyl; wherein the R¹ 1,2,3,6-tetrahydropyridinyl is optionally substituted as described herein for substituents on R¹.

In one embodiment of Formula (II), R², at each occurrence, is independently selected from the group consisting of hydrogen, $C_1$-$C_4$ alkyl, cycloalkyl, cycloalkenyl, heteroaryl, heterocycloalkyl, heterocycloalkenyl, C(O)OH, and C(O)OR²ᴮ; wherein each R² cycloalkyl, cycloalkenyl, heteroaryl, heterocycloalkyl, and heterocycloalkenyl is optionally substituted with one or more substituents independently selected from the group consisting of $C_1$-$C_8$ alkyl, $C_2$-$C_6$ alkenyl, and $C_2$-$C_6$ alkynyl. In another embodiment of Formula (II), R², at each occurrence, is independently selected from the group consisting of hydrogen, $C_1$-$C_4$ alkyl, heteroaryl, C(O)OH, and C(O)OR²ᴮ; wherein each R² heteroaryl is optionally substituted with one or more $C_1$-$C_8$ alkyl. In another embodiment of Formula (II), R², at each occurrence, is independently hydrogen or $C_1$-$C_4$ alkyl. In another embodiment of Formula (II), R², at each occurrence, is independently hydrogen. In another embodiment of Formula (II), R², at each occurrence, is independently $C_1$-$C_4$ alkyl.

In one embodiment of Formula (II), R²ᴬ is hydrogen or $C_1$-$C_4$ alkyl; wherein the R²ᴬ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I. In another embodiment of Formula (II), R²ᴬ is hydrogen or $C_1$-$C_4$ alkyl; wherein the R²ᴬ $C_1$-$C_4$ alkyl is optionally substituted with one or more substituents independently selected from the group consisting of heterocycloalkyl, F, Cl, Br and I. In another embodiment of Formula (II), R²ᴬ is hydrogen or $C_1$-$C_4$ alkyl; wherein the R²ᴬ $C_1$-$C_4$ alkyl is optionally substituted with one or more heterocycloalkyl. In another embodiment of Formula (II), R²ᴬ is hydrogen. In another embodiment of Formula (II), R²ᴬ is $C_1$-$C_4$ alkyl; wherein the R²ᴬ $C_1$-$C_4$ alkyl is optionally substituted with one or more heterocycloalkyl.

In one embodiment of Formula (II), R³ is selected from the group consisting of phenyl and pyridinyl; wherein the R³ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, NH₂, C(O)H, C(O)OH, OH, CN, NO₂, F, Cl, Br and I. In another embodiment of Formula (II), R³ is phenyl; wherein the R³ phenyl is optionally substituted with one or more substituents independently selected from the group consisting of $C_1$-$C_6$ alkyl, $C_2$-$C_6$ alkenyl, $C_2$-$C_6$ alkynyl, NH₂, C(O)H, C(O)OH, OH, CN, NO₂, F, Cl, Br and I. In another embodiment of Formula (II), R³ is phenyl; wherein the R³ phenyl is optionally substituted with one or more substituents independently selected from the group consisting of F, Cl, Br and I. In another embodiment of Formula (II), $R^3$ is phenyl; wherein the $R^3$ phenyl is optionally substituted with F. In another embodiment of Formula (II), $R^3$ is phenyl; wherein the $R^3$ phenyl is substituted with F.

In one embodiment of Formula (II), $R^4$ is selected from the group consisting of hydrogen, $C_1$-$C_4$ alkyl, $C_1$-$C_4$ alkoxy, CN, F, Cl, Br, and I. In another embodiment of Formula (II), $R^4$ is selected from the group consisting of hydrogen, F, Cl, Br, and I. In another embodiment of Formula (II), $R^4$ is F. In another embodiment of Formula (II), $R^4$ is hydrogen.

In one embodiment of Formula (II), $R^1$ is selected from the group consisting of cycloalkenyl, aryl, heteroaryl, heterocycloalkyl, and heterocycloalkenyl; wherein the $R^1$ cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and $C(O)OH$;

$R^2$, at each occurrence, is independently selected from the group consisting of hydrogen, $C_1$-$C_4$ alkyl, heteroaryl, $C(O)OH$, and $C(O)OR^{2B}$; wherein each $R^2$ heteroaryl is optionally substituted with one or more $C_1$-$C_8$ alkyl;

$R^{2A}$ is hydrogen or $C_1$-$C_4$ alkyl; wherein the $R^{2A}$ $C_1$-$C_4$ alkyl is optionally substituted with one heterocycloalkyl;

$R^{2B}$ is $C_1$-$C_4$ alkyl;

$R^{3A}$ and $R^{3B}$, taken together, form $R^3$;

$R^3$ is phenyl; wherein the $R^3$ phenyl is optionally substituted with one or more F;

$R^4$ is selected from the group consisting of hydrogen, F, Cl, Br, and I;

$R^5$, at each occurrence, is independently selected from the group consisting of $C_1$-$C_8$ alkyl, heterocycloalkyl; wherein each $R^5$ $C_1$-$C_8$ alkyl is optionally substituted with one or more substituents independently selected from the group consisting of $R^6$, $OR^6$, $C(O)R^6$, $CO(O)R^6$, $N(R^6)_2$, $C(O)N(R^6)_2$, $SO_2NHR^6$, $C(O)OH$, and OH; wherein each $R^5$ heterocycloalkyl is optionally substituted with one or more substituents independently selected from the group consisting of $C(O)OH$, and OH;

$R^6$, at each occurrence, is independently selected from the group consisting of $C_1$-$C_6$ alkyl, aryl, heterocycloalkyl, and cycloalkyl; wherein each $R^6$ $C_1$-$C_6$ alkyl is optionally substituted with one or more OH; wherein each $R^6$ aryl, cycloalkyl, and heterocycloalkyl is optionally substituted with one or more substituents independently selected from the group consisting of $R^8$, OH, F, Cl, Br and I; and $R^8$, at each occurrence, is independently $C_1$-$C_6$ alkyl; wherein each $R^8$ $C_1$-$C_6$ alkyl is optionally substituted with one or more OH.

Still another embodiment pertains to compounds of Formula (II), selected from the group consisting of:
10-fluoro-7-methyl-5-(1,2,3,6-tetrahydropyridin-4-yl)-6,7-dihydro-4H-3,4,7-triazadibenzo[cd,f]azulene;
tert-butyl 4-(10-fluoro-7-methyl-6,7-dihydro-4H-3,4,7-triazadibenzo[cd,f]azulen-5-yl)-3,6-dihydropyridine-1(2H)-carboxylate;
ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate;
10-fluoro-7-methyl-5-[1-(methylsulfonyl)-1,2,3,6-tetrahydropyridin-4-yl]-6,7-dihydro-4H-3,4,7-triazadibenzo[cd,f]azulene;
10-fluoro-5-[1-(methylsulfonyl)-1,2,3,6-tetrahydropyridin-4-yl]-6,7-dihydro-4H-3,4,7-triazadibenzo[cd,f]azulene;
10-fluoro-5-[1-(methylsulfonyl)-1,2,3,6-tetrahydropyridin-4-yl]-7-propyl-6,7-dihydro-4H-3,4,7-triazadibenzo[cd,f]azulene;
10-fluoro-5-[1-(methylsulfonyl)-1,2,3,6-tetrahydropyridin-4-yl]-7-(tetrahydro-2H-pyran-4-ylmethyl)-6,7-dihydro-4H-3,4,7-triazadibenzo[cd,f]azulene;
tert-butyl 4-(6-ethyl-10-fluoro-7-methyl-6,7-dihydro-4H-3,4,7-triazadibenzo[cd,f]azulen-5-yl)-3,6-dihydropyridine-1(2H)-carboxylate;
6-ethyl-10-fluoro-7-methyl-5-(1,2,3,6-tetrahydropyridin-4-yl)-6,7-dihydro-4H-3,4,7-triazadibenzo[cd,f]azulene dihydrochloride;
10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene;
6-ethyl-10-fluoro-7-methyl-5-[1-(methylsulfonyl)-1,2,3,6-tetrahydropyridin-4-yl]-6,7-dihydro-4H-3,4,7-triazadibenzo[cd,f]azulene;
2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;
4-(10-fluoro-7-methyl-6,7-dihydro-4H-3,4,7-triazadibenzo[cd,f]azulen-5-yl)-N-methyl-3,6-dihydropyridine-1(2H)-carboxamide;
[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride;
2-[4-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;
2-[4-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;
2-[4-(10-fluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;
10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene;
10-fluoro-7-methyl-5-(piperidin-4-yl)-6,7-dihydro-4H-3,4,7-triazadibenzo[cd,f]azulene;
tert-butyl[4-(10-fluoro-7-methyl-6,7-dihydro-4H-3,4,7-triazadibenzo[cd,f]azulen-5-yl)piperidin-1-yl]acetate;
[4-(10-fluoro-7-methyl-6,7-dihydro-4H-3,4,7-triazadibenzo[cd,f]azulen-5-yl)piperidin-1-yl]acetic acid;
2-[4-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;
2-[4-(10-fluoro-7-methyl-6,7-dihydro-4H-3,4,7-triazadibenzo[cd,f]azulen-5-yl)-3,6-dihydropyridin-1(2H)-yl]-N-methyl-2-oxoethanesulfonamide;
2-[4-(10-fluoro-7-methyl-6,7-dihydro-4H-3,4,7-triazadibenzo[cd,f]azulen-5-yl)piperidin-1-yl]-1-[(2S)-2-(hydroxymethyl)pyrrolidin-1-yl]ethanone;
2-[4-(10-fluoro-7-methyl-6,7-dihydro-4H-3,4,7-triazadibenzo[cd,f]azulen-5-yl)piperidin-1-yl]-N-(2-hydroxyethyl)-N-methylacetamide;
ethyl 10-fluoro-7-methyl-5-(1,2,3,6-tetrahydropyridin-4-yl)-6,7-dihydro-4H-3,4,7-triazadibenzo[cd,f]azulene-6-carboxylate;
N-[4-(10-fluoro-7-methyl-6,7-dihydro-4H-3,4,7-triazadibenzo[cd,f]azulen-5-yl)cyclohex-3-en-1-yl]-D-valine;
N-[4-(10-fluoro-7-methyl-6,7-dihydro-4H-3,4,7-triazadibenzo[cd,f]azulen-5-yl)cyclohex-3-en-1-yl]-L-alanine;
N-[4-(10-fluoro-7-methyl-6,7-dihydro-4H-3,4,7-triazadibenzo[cd,f]azulen-5-yl)cyclohex-3-en-1-yl]glycine;

(2S)-{[4-(10-fluoro-7-methyl-6,7-dihydro-4H-3,4,7-triazadibenzo[cd,f]azulen-5-yl)cyclohex-3-en-1-yl]amino}(phenyl)acetic acid;

10-fluoro-7-methyl-5-(1,2,3,6-tetrahydropyridin-4-yl)-6,7-dihydro-4H-3,4,7-triazadibenzo[cd,f]azulene-6-carboxylic acid;

N-[4-(10-fluoro-7-methyl-6,7-dihydro-4H-3,4,7-triazadibenzo[cd,f]azulen-5-yl)cyclohex-3-en-1-yl]-L-valine;

N-[4-(10-fluoro-7-methyl-6,7-dihydro-4H-3,4,7-triazadibenzo[cd,f]azulen-5-yl)cyclohex-3-en-1-yl]-L-phenylalanine;

N-[4-(10-fluoro-7-methyl-6,7-dihydro-4H-3,4,7-triazadibenzo[cd,f]azulen-5-yl)cyclohex-3-en-1-yl]-3-methyl-L-valine;

1-[4-(10-fluoro-7-methyl-6,7-dihydro-4H-3,4,7-triazadibenzo[cd,f]azulen-5-yl)cyclohex-3-en-1-yl]-L-proline;

N-[4-(10-fluoro-7-methyl-6,7-dihydro-4H-3,4,7-triazadibenzo[cd,f]azulen-5-yl)cyclohex-3-en-1-yl]-L-serine;

N-[4-(10-fluoro-7-methyl-6,7-dihydro-4H-3,4,7-triazadibenzo[cd,f]azulen-5-yl)cyclohex-3-en-1-yl]-L-norvaline;

N-[4-(10-fluoro-7-methyl-6,7-dihydro-4H-3,4,7-triazadibenzo[cd,f]azulen-5-yl)cyclohex-3-en-1-yl]-L-tyrosine;

4-(10-fluoro-7-methyl-6,7-dihydro-4H-3,4,7-triazadibenzo[cd,f]azulen-5-yl)cyclohex-3-ene-1-carboxylic acid;

2-[4-(10-fluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

10-fluoro-7-methyl-5-[4-(methylsulfonyl)phenyl]-6,7-dihydro-4H-3,4,7-triazadibenzo[cd,f]azulene;

10-fluoro-7-methyl-5-(pyridin-4-yl)-6,7-dihydro-4H-3,4,7-triazadibenzo[cd,f]azulene;

10-fluoro-7-methyl-5-[6-(methylsulfonyl)pyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)pyrimidin-2-amine;

4-(10-fluoro-7-methyl-6,7-dihydro-4H-3,4,7-triazadibenzo[cd,f]azulen-5-yl)benzoic acid;

1,10-difluoro-7-methyl-5-(1,2,3,6-tetrahydropyridin-4-yl)-6,7-dihydro-4H-3,4,7-triazadibenzo[cd,f]azulene;

tert-butyl 4-(1,10-difluoro-7-methyl-6,7-dihydro-4H-3,4,7-triazadibenzo[cd,f]azulen-5-yl)-3,6-dihydropyridine-1(2H)-carboxylate;

4-(10-fluoro-7-methyl-6,7-dihydro-4H-3,4,7-triazadibenzo[cd,f]azulen-5-yl)-N,N-dimethylcyclohex-3-ene-1-carboxamide;

[4-(10-fluoro-7-methyl-6,7-dihydro-4H-3,4,7-triazadibenzo[cd,f]azulen-5-yl)cyclohex-3-en-1-yl](3-hydroxyazetidin-1-yl)methanone;

4-(10-fluoro-7-methyl-6,7-dihydro-4H-3,4,7-triazadibenzo[cd,f]azulen-5-yl)-N-methylcyclohex-3-ene-1-carboxamide;

2-[4-(10-fluoro-7-methyl-6,7-dihydro-4H-3,4,7-triazadibenzo[cd,f]azulen-5-yl)-3,6-dihydropyridin-1(2H)-yl]-N,N-bis(2-hydroxyethyl)acetamide;

1-(3,3-difluoro azetidin-1-yl)-2-[4-(10-fluoro-7-methyl-6,7-dihydro-4H-3,4,7-triazadibenzo[cd,f]azulen-5-yl)-3,6-dihydropyridin-1(2H)-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N,N-dimethylacetamide;

10-fluoro-7-methyl-5-[(1R,5S)-8-(methylsulfonyl)-8-azabicyclo[3.2.1]oct-2-en-3-yl]-6,7-dihydro-4H-3,4,7-triazadibenzo[cd,f]azulene;

(1R,5S)-3-(10-fluoro-7-methyl-6,7-dihydro-4H-3,4,7-triazadibenzo[cd,f]azulen-5-yl)-N-methyl-8-azabicyclo[3.2.1]oct-2-ene-8-carboxamide;

[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid;

10-fluoro-7-methyl-5-(1,2,3,3a,4,6a-hexahydrocyclopenta[c]pyrrol-5-yl)-7-methyl-6,7-dihydro-4H-3,4,7-triazadibenzo[cd,f]azulene;

10-fluoro-7-methyl-5-(pyridin-3-yl)-6,7-dihydro-4H-3,4,7-triazadibenzo[cd,f]azulene;

ethyl 4-(10-fluoro-7-methyl-6,7-dihydro-4H-3,4,7-triazadibenzo[cd,f]azulen-5-yl)cyclohex-3-ene-1-carboxylate;

5-[(1R,5S)-8-azabicyclo[3.2.1]oct-2-en-3-yl]-10-fluoro-7-methyl-6,7-dihydro-4H-3,4,7-triazadibenzo[cd,f]azulene;

N-(2,3-dihydroxypropyl)-2-[4-(10-fluoro-7-methyl-6,7-dihydro-4H-3,4,7-triazadibenzo[cd,f]azulen-5-yl)-3,6-dihydropyridin-1(2H)-yl]-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

tert-butyl[4-(1,10-difluoro-7-methyl-6,7-dihydro-4H-3,4,7-triazadibenzo[cd,f]azulen-5-yl)-3,6-dihydropyridin-1(2H)-yl]acetate;

2-[4-(1,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;

[4-(1,10-difluoro-7-methyl-6,7-dihydro-4H-3,4,7-triazadibenzo[cd,f]azulen-5-yl)-3,6-dihydropyridin-1(2H)-yl]acetic acid;

1,10-difluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-{2-[(2-methoxyethyl)sulfonyl]-1,2,3,3a,4,6a-hexahydrocyclopenta[c]pyrrol-5-yl}-7-methyl-6,7-dihydro-4H-3,4,7-triazadibenzo[cd,f]azulene;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

2-[4-(1,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[3-(hydroxymethyl)azetidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

5-(10-fluoro-7-methyl-6,7-dihydro-4H-3,4,7-triazadibenzo[cd,f]azulen-5-yl)-N-methyl-3,3a,4,6a-tetrahydrocyclopenta[c]pyrrole-2(1H)-carboxamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N,N-dimethylacetamide;

10-fluoro-7-methyl-5-[2-(methylsulfonyl)-1,2,3,3a,4,6a-hexahydrocyclopenta[c]pyrrol-5-yl]-6,7-dihydro-4H-3,4,7-triazadibenzo[cd,f]azulene;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-[(2S)-2-(hydroxymethyl)pyrrolidin-1-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-(3-hydroxyazetidin-1-yl)ethanone;

[4-(10-fluoro-7-methyl-6,7-dihydro-4H-3,4,7-triazadibenzo [cd,f]azulen-5-yl)phenyl]acetic acid;

[3-(10-fluoro-7-methyl-6,7-dihydro-4H-3,4,7-triazadibenzo [cd,f]azulen-5-yl)phenyl]acetic acid;

N-(2,3-dihydroxypropyl)-2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-methylacetamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-1-(3-hydroxyazetidin-1-yl)ethanone;

N-(2,3-dihydroxypropyl)-2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-methylacetamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(2-hydroxyethyl)-N-methylacetamide;

10-fluoro-7-methyl-5-(2,3,6,7-tetrahydro-1H-azepin-4-yl)-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-N,N-dimethylacetamide;

10-fluoro-7-methyl-5-[1-(methylsulfonyl)-2,3,6,7-tetrahydro-1H-azepin-4-yl]-6,7-dihydro-4H-3,4,7-triazadibenzo[cd,f]azulene;

[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-1-(3-hydroxyazetidin-1-yl)ethanone;

5-(3,3-dimethyl-1,2,3,6-tetrahydropyridin-4-yl)-10-fluoro-7-methyl-6,7-dihydro-4H-3,4,7-triazadibenzo[cd,f]azulene;

10-fluoro-7-methyl-5-(1,2,5,6-tetrahydropyridin-3-yl)-6,7-dihydro-4H-3,4,7-triazadibenzo[cd,f]azulene;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(3-hydroxycyclobutyl)-N-methylacetamide;

10-fluoro-7-methyl-5-[1-(methylsulfonyl)-1,2,5,6-tetrahydropyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)-N-methyl-3,6-dihydropyridine-1(2H)-carboxamide;

2-[5-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-(3-hydroxycyclobutyl)-N-methylacetamide; and pharmaceutically acceptable salts thereof.

Embodiments of Formula (III)

In another embodiment, the present invention relates to compounds of Formula (III) or a pharmaceutically acceptable salt thereof,

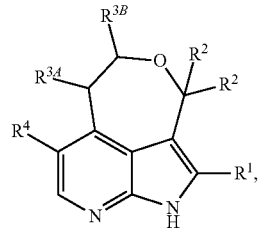

Formula (III)

wherein $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, $OH$, $CN$, $NO_2$, F, Cl, Br and I;

$R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, $C(O)OH$, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting of $C_1$-$C_8$ alkyl, $C_2$-$C_6$ alkenyl, and $C_2$-$C_6$ alkynyl;

$R^{2B}$ is $C_1$-$C_4$ alkyl;

$R^{3A}$ and $R^{3B}$, taken together, form $R^3$;

$R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, $OH$, $CN$, $NO_2$, F, Cl, Br and I;

$R^4$ is selected from the group consisting of hydrogen, $C_1$-$C_4$ alkyl, $C_1$-$C_4$ alkoxy, CN, F, Cl, Br, and I;

$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $OH$, $CN$, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $OH$, $CN$, $NO_2$, $F$, $Cl$, $Br$ and $I$;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycloalkyl, heterocycloalkenyl, $NH_2$, $C(O)H$, $C(O)OH$, $OH$, $CN$, $NO_2$, $F$, $Cl$, $Br$ and $I$; wherein each $R^6$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $OH$, $CN$, $NO_2$, $F$, $Cl$, $Br$ and $I$;

$R^7$, at each occurrence, is independently selected from the group consisting of $C_1$-$C_6$ alkyl, $C_2$-$C_6$ alkenyl, and $C_2$-$C_6$ alkynyl; and $R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, $OH$, $CN$, $NO_2$, $F$, $Cl$, $Br$ and $I$.

In one embodiment of Formula (III), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, $OH$, $CN$, $NO_2$, $F$, $Cl$, $Br$ and $I$. In another embodiment of Formula (III), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, $C(O)OH$, $F$, $Cl$, $Br$ and $I$. In another embodiment of Formula (III), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and $C(O)OH$. In another embodiment of Formula (III), $R^1$ is cycloalkenyl; wherein the $R^1$ cycloalkenyl is optionally substituted as described herein. In another embodiment of Formula (III), $R^1$ is aryl; wherein the $R^1$ aryl is optionally substituted as described herein. In another embodiment of Formula (III), $R^1$ is heteroaryl; wherein the $R^1$ heteroaryl is optionally substituted as described herein. In another embodiment of Formula (III), $R^1$ is heterocycloalkyl; wherein the $R^1$ heterocycloalkyl is optionally substituted as described herein. In another embodiment of Formula (III), $R^1$ is heterocycloalkenyl; wherein the $R^1$ heterocycloalkenyl is optionally substituted as described herein. In another embodiment of Formula (III), $R^1$ is pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, or 8-azabicyclo[3.2.1]oct-2-enyl; wherein the $R^1$ pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, and 8-azabicyclo[3.2.1]oct-2-enyl are optionally substituted as described herein for substituents on R'. In another embodiment of Formula (III), $R^1$ is 1,2,3,6-tetrahydropyridinyl; wherein the $R^1$ 1,2,3,6-tetrahydropyridinyl is optionally substituted as described herein for substituents on R'.

In one embodiment of Formula (III), $R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, $C(O)OH$, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting of $C_1$-$C_8$ alkyl, $C_2$-$C_6$ alkenyl, and $C_2$-$C_6$ alkynyl. In another embodiment of Formula (III), $R^2$, at each occurrence, is independently selected from the group consisting of hydrogen, $C_1$-$C_4$ alkyl, heteroaryl, $C(O)OH$, and $C(O)OR^{2B}$; wherein each $R^2$ heteroaryl is optionally substituted with one or more $C_1$-$C_8$ alkyl. In another embodiment of Formula (III), $R^2$, at each occurrence, is independently hydrogen or $C_1$-$C_4$ alkyl. In another embodiment of Formula (III), $R^2$, at each occurrence, is independently hydrogen. In another embodiment of Formula (III), $R^2$, at each occurrence, is independently $C_1$-$C_4$ alkyl.

In one embodiment of Formula (III), $R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, $OH$, $CN$, $NO_2$, $F$, $Cl$, $Br$ and $I$. In another embodiment of Formula (III), $R^3$ is phenyl; wherein the $R^3$ phenyl is optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, $OH$, $CN$, $NO_2$, $F$, $Cl$, $Br$ and $I$. In another embodiment of Formula (III), $R^3$ is phenyl; wherein the $R^3$ phenyl is optionally substituted with one or more substituents independently selected from the group consisting of $F$, $Cl$, $Br$ and $I$. In another embodiment of Formula (III), $R^3$ is phenyl; wherein the $R^3$ phenyl is optionally substituted with $F$. In another embodiment of Formula (III), $R^3$ is phenyl; wherein the $R^3$ phenyl is substituted with $F$.

In one embodiment of Formula (III), $R^4$ is selected from the group consisting of hydrogen, $C_1$-$C_4$ alkyl, $C_1$-$C_4$ alkoxy, $CN$, $F$, $Cl$, $Br$, and $I$. In another embodiment of Formula (III), $R^4$ is selected from the group consisting of hydrogen, $F$, $Cl$, $Br$, and $I$. In another embodiment of Formula (III), $R^4$ is $F$. In another embodiment of Formula (III), $R^4$ is hydrogen.

In one embodiment of Formula (III),

R$^1$ is selected from the group consisting of cycloalkenyl, aryl, heteroaryl, heterocycloalkyl, and heterocycloalkenyl; wherein the R$^1$ cycloalkenyl, aryl, heteroaryl, heterocycloalkyl, and heterocycloalkenyl are optionally substituted with one or more substituents independently selected from the group consisting of R$^5$, SO$_2$R$^5$, C(O)R$^5$, CO(O)R$^5$, NH$_2$, NHR$^5$, C(O)NHR$^5$, C(O)N(R$^5$)$_2$, SO$_2$NHC(O)OR$^5$, and C(O)OH;

R$^2$, at each occurrence, is independently selected from the group consisting of hydrogen, C$_1$-C$_4$ alkyl, heteroaryl, C(O)OH, and C(O)OR$^{2B}$; wherein each R$^2$ heteroaryl is optionally substituted with one or more C$_1$-C$_8$ alkyl;

R$^{2B}$ is C$_1$-C$_4$ alkyl;

R$^{3A}$ and R$^{3B}$, taken together, form R$^3$;

R$^3$ is phenyl; wherein the R$^3$ phenyl is optionally substituted with one or more F;

R$^4$ is selected from the group consisting of hydrogen, F, Cl, Br, and I;

R$^5$, at each occurrence, is independently selected from the group consisting of C$_1$-C$_8$ alkyl, heterocycloalkyl; wherein each R$^5$ C$_1$-C$_8$ alkyl is optionally substituted with one or more substituents independently selected from the group consisting of R$^6$, OR$^6$, C(O)R$^6$, CO(O)R$^6$, N(R$^6$)$_2$, C(O)N(R$^6$)$_2$, SO$_2$NHR$^6$, C(O)OH, and OH; wherein each R$^5$ heterocycloalkyl is optionally substituted with one or more substituents independently selected from the group consisting of C(O)OH, and OH;

R$^6$, at each occurrence, is independently selected from the group consisting of C$_1$-C$_6$ alkyl, aryl, heterocycloalkyl, and cycloalkyl; wherein each R$^6$ C$_1$-C$_6$ alkyl is optionally substituted with one or more OH; wherein each R$^6$ aryl, cycloalkyl, and heterocycloalkyl is optionally substituted with one or more substituents independently selected from the group consisting of R$^8$, OH, F, Cl, Br and I; and R$^8$, at each occurrence, is independently C$_1$-C$_6$ alkyl; wherein each R$^8$ C$_1$-C$_6$ alkyl is optionally substituted with one or more OH.

Still another embodiment pertains to compounds of Formula (III), selected from the group consisting of:
10-fluoro-5-(1,2,3,6-tetrahydropyridin-4-yl)-4,6-dihydro-7-oxa-3,4-diazadibenzo[cd,f]azulene;
10-fluoro-5-[1-(methylsulfonyl)-1,2,3,6-tetrahydropyridin-4-yl]-4,6-dihydro-7-oxa-3,4-diazadibenzo[cd,f]azulene;
and pharmaceutically acceptable salts thereof.

Embodiments of Formula (Ia)

In one embodiment, the present invention relates to compounds of Formula (Ia) or a pharmaceutically acceptable salt thereof,

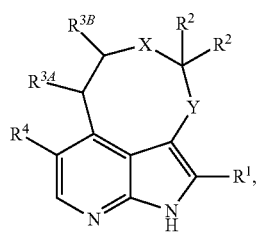

Formula (Ia)

wherein
X is O or NR$^{2A}$;
Y is C(R$^2$)$_2$ or is absent;

R$^1$ is selected from the group consisting of cycloalkyl, cycloalkenyl, aryl, heteroaryl, heterocycloalkyl, and heterocycloalkenyl; wherein the R$^1$ cycloalkyl, cycloalkenyl, aryl, heteroaryl, heterocycloalkyl, and heterocycloalkenyl are optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHSO$_2$R$^5$, NR$^5$SO$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, SO$_2$NHC(O)OR$^5$, C(O)H, C(O)OH, (O), OH, CN, NO$_2$, F, Cl, Br and I;

R$^2$, at each occurrence, is independently selected from the group consisting of hydrogen, C$_1$-C$_4$ alkyl, cycloalkyl, cycloalkenyl, heteroaryl, heterocycloalkyl, heterocycloalkenyl, C(O)OH, and C(O)OR$^{2B}$; wherein each R$^2$ cycloalkyl, cycloalkenyl, heteroaryl, heterocycloalkyl, and heterocycloalkenyl is optionally substituted with one or more substituents independently selected from the group consisting C$_1$-C$_8$ alkyl, C$_2$-C$_6$ alkenyl, and C$_2$-C$_6$ alkynyl;

R$^{2A}$ is hydrogen or C$_1$-C$_4$ alkyl; wherein the R$^{2A}$ C$_1$-C$_4$ alkyl is optionally substituted with one or more substituents independently selected from the group consisting of cycloalkyl, cycloalkenyl, heterocycloalkyl, heterocycloalkenyl, C$_1$-C$_6$ alkoxy, OH, CN, F, Cl, Br and I;

R$^{2B}$ is C$_1$-C$_4$ alkyl;

R$^{3A}$ and R$^{3B}$, taken together, form R$^3$;

R$^3$ is selected from the group consisting of phenyl and pyridinyl; wherein the R$^3$ phenyl and pyridinyl are optionally substituted with one or more substituents independently selected from the group consisting of C$_1$-C$_6$ alkyl, C$_2$-C$_6$ alkenyl, C$_2$-C$_6$ alkynyl, NH$_2$, C(O)H, C(O)OH, OH, CN, NO$_2$, F, Cl, Br and I;

R$^4$ is selected from the group consisting of hydrogen, C$_1$-C$_4$ alkyl, C$_1$-C$_4$ alkoxy, CN, F, Cl, Br, and I;

R$^5$, at each occurrence, is independently selected from the group consisting of C$_1$-C$_8$ alkyl, C$_2$-C$_6$ alkenyl, C$_2$-C$_6$ alkynyl, aryl, heteroaryl, heterocycloalkyl, heterocycloalkenyl, cycloalkyl, and cycloalkenyl; wherein each R$^5$ C$_1$-C$_8$ alkyl, C$_2$-C$_6$ alkenyl, and C$_2$-C$_6$ alkynyl is optionally substituted with one or more substituents independently selected from the group consisting of R$^6$, OR$^6$, SR$^6$, S(O)R$^6$, SO$_2$R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHSO$_2$R$^6$, NR$^6$SO$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, OH, CN, NO$_2$, F, Cl, Br and I; wherein each R$^5$ aryl, cycloalkyl, cycloalkenyl, heteroaryl, heterocycloalkyl, and heterocycloalkenyl is optionally substituted with one or more substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHSO$_2$R$^7$, NR$^7$SO$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, (O), OH, CN, NO$_2$, F, Cl, Br and I;

R$^6$, at each occurrence, is independently selected from the group consisting of C$_1$-C$_6$ alkyl, C$_2$-C$_6$ alkenyl, C$_2$-C$_6$ alkynyl, aryl, heteroaryl, heterocycloalkyl, heterocycloalkenyl, cycloalkyl, and cycloalkenyl; wherein each R$^6$ C$_1$-C$_6$ alkyl, C$_2$-C$_6$ alkenyl, and C$_2$-C$_6$ alkynyl is optionally substituted with one or more substituents independently selected from the group consisting of aryl, heteroaryl, cycloalkyl, cycloalkenyl, heterocycyloalkyl, heterocycloalkenyl, NH$_2$, C(O)H, C(O)OH, OH, CN, NO$_2$, F, Cl, Br and I; wherein each R$^6$ aryl, cycloalkyl, cycloalkenyl, heteroaryl, heterocycloalkyl, and heterocycloalkenyl is optionally substituted with one or more substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHSO$_2$R$^8$, NR$^8$SO$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I;

R$^7$, at each occurrence, is independently selected from the group consisting of C$_1$-C$_6$ alkyl, C$_2$-C$_6$ alkenyl, and C$_2$-C$_6$ alkynyl; wherein each R$^7$ C$_1$-C$_6$ alkyl, C$_2$-C$_6$ alkenyl, and C$_2$-C$_6$ alkynyl is optionally substituted with one or more substituents independently selected from the group consisting of OR$^9$, SR$^9$, S(O)R$^9$, SO$_2$R$^9$, C(O)R$^9$, CO(O)R$^9$, OC(O)R$^9$, OC(O)OR$^9$, NH$_2$, C(O)H, C(O)OH, OH, CN, NO$_2$, F, Cl, Br and I;

R$^8$, at each occurrence, is independently selected from the group consisting of C$_1$-C$_6$ alkyl, C$_2$-C$_6$ alkenyl, and C$_2$-C$_6$ alkynyl; wherein each R$^8$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)H, C(O)OH, OH, CN, NO$_2$, F, Cl, Br and I; and R$^9$, at each occurrence, is independently selected from the group consisting of C$_1$-C$_6$ alkyl, C$_2$-C$_6$ alkenyl, and C$_2$-C$_6$ alkynyl.

In one embodiment of Formula (Ia), X is O or NR$^{2A}$. In another embodiment of Formula (Ia), X is O. In another embodiment of Formula (Ia), X is NR$^{2A}$.

In one embodiment of Formula (Ia), Y is C(R$^2$)$_2$ or is absent. In another embodiment of Formula (Ia), Y is C(R$^2$)$_2$. In another embodiment of Formula (Ia), Y is absent.

In one embodiment of Formula (Ia), R$^1$ is selected from the group consisting of cycloalkyl, cycloalkenyl, aryl, heteroaryl, heterocycloalkyl, and heterocycloalkenyl; wherein the R$^1$ cycloalkyl, cycloalkenyl, aryl, heteroaryl, heterocycloalkyl, and heterocycloalkenyl are optionally substituted with one or more substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, SO$_2$NHC(O)OR$^5$, C(O)H, C(O)OH, OH, CN, NO$_2$, F, Cl, Br and I. In another embodiment of Formula (Ia), R$^1$ is selected from the group consisting of cycloalkyl, cycloalkenyl, aryl, heteroaryl, heterocycloalkyl, and heterocycloalkenyl; wherein the R$^1$ cycloalkyl, cycloalkenyl, aryl, heteroaryl, heterocycloalkyl, and heterocycloalkenyl are optionally substituted with one or more substituents independently selected from the group consisting of R$^5$, SO$_2$R$^5$, C(O)R$^5$, CO(O)R$^5$, NH$_2$, NHR$^5$, C(O)NHR$^5$, C(O)N(R$^5$)$_2$, SO$_2$NHC(O)OR$^5$, C(O)OH, F, Cl, Br and I. In another embodiment of Formula (Ia), R$^1$ is selected from the group consisting of cycloalkyl, cycloalkenyl, aryl, heteroaryl, heterocycloalkyl, and heterocycloalkenyl; wherein the R$^1$ cycloalkyl, cycloalkenyl, aryl, heteroaryl, heterocycloalkyl, and heterocycloalkenyl are optionally substituted with one or more substituents independently selected from the group consisting of R$^5$, SO$_2$R$^5$, C(O)R$^5$, CO(O)R$^5$, NH$_2$, NHR$^5$, C(O)NHR$^5$, C(O)N(R$^5$)$_2$, SO$_2$NHC(O)OR$^5$, and C(O)OH. In another embodiment of Formula (Ia), R$^1$ is cycloalkenyl; wherein the R$^1$ cycloalkenyl is optionally substituted as described herein. In another embodiment of Formula (Ia), R$^1$ is aryl; wherein the R$^1$ aryl is optionally substituted as described herein. In another embodiment of Formula (Ia), R$^1$ is heteroaryl; wherein the R$^1$ heteroaryl is optionally substituted as described herein. In another embodiment of Formula (Ia), R$^1$ is heterocycloalkyl; wherein the R$^1$ heterocycloalkyl is optionally substituted as described herein. In another embodiment of Formula (Ia), R$^1$ is heterocycloalkenyl; wherein the R$^1$ heterocycloalkenyl is optionally substituted as described herein. In another embodiment of Formula (Ia), R$^1$ is pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, 8,8a-dihydro-1H-oxazolo[3,4-a]pyridin-3(5H)-onyl, 5,6-dihydro-1H-oxazolo[3,4-a]pyridin-3(8aH)-onyl, 9-azabicyclo[3.3.1]non-3-enyl, or 8-azabicyclo[3.2.1]oct-2-enyl; wherein the R$^1$ pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, 8,8a-dihydro-1H-oxazolo[3,4-a]pyridin-3(5H)-onyl, 5,6-dihydro-1H-oxazolo[3,4-a]pyridin-3(8aH)-onyl, 9-azabicyclo[3.3.1]non-3-enyl, and 8-azabicyclo[3.2.1]oct-2-enyl are optionally substituted as described herein for substituents on R$^1$. In another embodiment of Formula (Ia), R$^1$ is 1,2,3,6-tetrahydropyridinyl; wherein the R$^1$ 1,2,3,6-tetrahydropyridinyl is optionally substituted as described herein for substituents on R$^1$.

In one embodiment of Formula (Ia), R$^2$, at each occurrence, is independently selected from the group consisting of hydrogen, C$_1$-C$_4$ alkyl, cycloalkyl, cycloalkenyl, heteroaryl, heterocycloalkyl, heterocycloalkenyl, C(O)OH, and C(O)OR$^{2B}$; wherein each R$^2$ cycloalkyl, cycloalkenyl, heteroaryl, heterocycloalkyl, and heterocycloalkenyl is optionally substituted with one or more substituents independently selected from the group consisting of C$_1$-C$_8$ alkyl, C$_2$-C$_6$ alkenyl, and C$_2$-C$_6$ alkynyl. In another embodiment of Formula (Ia), R$^2$, at each occurrence, is independently selected from the group consisting of hydrogen, C$_1$-C$_4$ alkyl, heteroaryl, C(O)OH, and C(O)OR$^{2B}$; wherein each R$^2$ heteroaryl is optionally substituted with one or more C$_1$-C$_8$ alkyl. In another embodiment of Formula (Ia), R$^2$, at each occurrence, is independently hydrogen or C$_1$-C$_4$ alkyl. In another embodiment of Formula (Ia), R$^2$, at each occurrence, is independently hydrogen. In another embodiment of Formula (Ia), R$^2$, at each occurrence, is independently C$_1$-C$_4$ alkyl.

In one embodiment of Formula (Ia), R$^{2A}$ is hydrogen or C$_1$-C$_4$ alkyl; wherein the R$^{2A}$ C$_1$-C$_4$ alkyl is optionally substituted with one or more substituents independently selected from the group consisting of cycloalkyl, cycloalkenyl, heterocycloalkyl, heterocycloalkenyl, C$_1$-C$_6$ alkoxy, OH, CN, F, Cl, Br and I. In another embodiment of Formula (Ia), R$^{2A}$ is hydrogen or C$_1$-C$_4$ alkyl; wherein the R$^{2A}$ C$_1$-C$_4$ alkyl is optionally substituted with one or more substituents independently selected from the group consisting of heterocycloalkyl, F, Cl, Br and I. In another embodiment of Formula (Ia), $R^{2A}$ is hydrogen or $C_1$-$C_4$ alkyl; wherein the $R^{2A}$ $C_1$-$C_4$ alkyl is optionally substituted with one or more heterocycloalkyl. In another embodiment of Formula (Ia), $R^{2A}$ is hydrogen. In another embodiment of Formula (Ia), $R^{2A}$ is $C_1$-$C_4$ alkyl; wherein the $R^{2A}$ $C_1$-$C_4$ alkyl is optionally substituted with one or more heterocycloalkyl.

In one embodiment of Formula (Ia), $R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I. In another embodiment of Formula (Ia), $R^3$ is phenyl; wherein the $R^3$ phenyl is optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I. In another embodiment of Formula (Ia), $R^3$ is phenyl; wherein the $R^3$ phenyl is optionally substituted with one or more substituents independently selected from the group consisting of F, Cl, Br and I. In another embodiment of Formula (Ia), $R^3$ is phenyl; wherein the $R^3$ phenyl is optionally substituted with F. In another embodiment of Formula (Ia), $R^3$ is phenyl; wherein the $R^3$ phenyl is substituted with F. In another embodiment of Formula (Ia), $R^3$ is phenyl; wherein the $R^3$ phenyl is unsubstituted.

In another embodiment of Formula (Ia), $R^3$ is pyridinyl; wherein the $R^3$ pyridinyl is optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I. In another embodiment of Formula (Ia), $R^3$ is pyridinyl; wherein the $R^3$ pyridinyl is optionally substituted with one or more substituents independently selected from the group consisting of F, Cl, Br and I. In another embodiment of Formula (Ia), $R^3$ is pyridinyl; wherein the $R^3$ pyridinyl is optionally substituted with F. In another embodiment of Formula (Ia), $R^3$ is pyridinyl; wherein the $R^3$ pyridinyl is substituted with F. In another embodiment of Formula (Ia), $R^3$ is pyridinyl; wherein the $R^3$ pyridinyl is unsubstituted.

In one embodiment of Formula (Ia), $R^4$ is selected from the group consisting of hydrogen, $C_1$-$C_4$ alkyl, $C_1$-$C_4$ alkoxy, CN, F, Cl, Br, and I. In another embodiment of Formula (Ia), $R^4$ is selected from the group consisting of hydrogen, F, Cl, Br, and I. In another embodiment of Formula (Ia), $R^4$ is F. In another embodiment of Formula (Ia), $R^4$ is hydrogen.

In one embodiment of Formula (Ia),
X is o or $NR^{2A}$;
Y is $C(R^2)_2$ or is absent;
$R^1$ is selected from the group consisting of cycloalkenyl, aryl, heteroaryl, heterocycloalkyl, and heterocycloalkenyl; wherein the $R^1$ cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and C(O)OH;
$R^2$, at each occurrence, is independently selected from the group consisting of hydrogen, $C_1$-$C_4$ alkyl, heteroaryl, C(O)OH, and $C(O)OR^{2B}$; wherein each $R^2$ heteroaryl is optionally substituted with one or more $C_1$-$C_8$ alkyl;
$R^{2A}$ is hydrogen or $C_1$-$C_4$ alkyl; wherein the $R^{2A}$ $C_1$-$C_4$ alkyl is optionally substituted with one heterocycloalkyl;
$R^{2B}$ is $C_1$-$C_4$ alkyl;
$R^{3A}$ and $R^{3B}$, taken together, form $R^3$;
$R^3$ is phenyl; wherein the $R^3$ phenyl is optionally substituted with one or more F;
$R^4$ is selected from the group consisting of hydrogen, F, Cl, Br, and I;
$R^5$, at each occurrence, is independently selected from the group consisting of $C_1$-$C_8$ alkyl, heterocycloalkyl, and cycloalkyl; wherein each $R^5$ $C_1$-$C_8$ alkyl is optionally substituted with one or more substituents independently selected from the group consisting of $R^6$, $OR^6$, $C(O)R^6$, $CO(O)R^6$, $N(R^6)_2$, $C(O)N(R^6)_2$, $SO_2NH_2$, $SO_2NHR^6$, $SO_2N(R^6)_2$, C(O)OH, CN, and OH; wherein each $R^5$ cycloalkyl and heterocycloalkyl is optionally substituted with one or more substituents independently selected from the group consisting of $R^7$, $C(O)OR^7$, C(O)OH, and OH;
$R^6$, at each occurrence, is independently selected from the group consisting of $C_1$-$C_6$ alkyl, aryl, heterocycloalkyl, and cycloalkyl; wherein each $R^6$ $C_1$-$C_6$ alkyl is optionally substituted with one or more OH; wherein each $R^6$ aryl, cycloalkyl, and heterocycloalkyl is optionally substituted with one or more substituents independently selected from the group consisting of $R^8$, OH, F, Cl, Br and I; and
$R^7$, at each occurrence, is independently selected from the group consisting of $C_1$-$C_6$ alkyl, and $C_2$-$C_6$ alkenyl; wherein each $R^7$ $C_1$-$C_6$ alkyl and $C_2$-$C_6$ alkenyl is optionally substituted with one or more substituents independently selected from the group consisting of $CO(O)R^9$, C(O)OH, and CN;
$R^8$, at each occurrence, is independently $C_1$-$C_6$ alkyl; wherein each $R^8$ $C_1$-$C_6$ alkyl is optionally substituted with one or more OH; and
$R^9$, at each occurrence, is independently $C_1$-$C_6$ alkyl.

Still another embodiment pertains to compounds of Formula (Ia), selected from the group consisting of:

10-fluoro-7-methyl-5-(1,2,3,6-tetrahydropyridin-4-yl)-6,7-dihydro-4H-3,4,7-triazadibenzo[cd,f]azulene;

tert-butyl 4-(10-fluoro-7-methyl-6,7-dihydro-4H-3,4,7-triazadibenzo[cd,f]azulen-5-yl)-3,6-dihydropyridine-1(2H)-carboxylate;

ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate;

10-fluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-7-propyl-6,7-dihydro-4H-3,4,7-triazadibenzo[cd,f]azulene;

10-fluoro-5-[1-(methylsulfonyl)-1,2,3,6-tetrahydropyridin-4-yl]-7-(tetrahydro-2H-pyran-4-ylmethyl)-6,7-dihydro-4H-3,4,7-triazadibenzo[cd,f]azulene;

tert-butyl 4-(6-ethyl-10-fluoro-7-methyl-6,7-dihydro-4H-3,4,7-triazadibenzo[cd,f]azulen-5-yl)-3,6-dihydropyridine-1(2H)-carboxylate;

6-ethyl-10-fluoro-7-methyl-5-(1,2,3,6-tetrahydropyridin-4-yl)-6,7-dihydro-4H-3,4,7-triazadibenzo[cd,f]azulene dihydrochloride;

10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene;

6-ethyl-10-fluoro-7-methyl-5-[1-(methylsulfonyl)-1,2,3,6-tetrahydropyridin-4-yl]-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

4-(10-fluoro-7-methyl-6,7-dihydro-4H-3,4,7-triazadibenzo[cd,f]azulen-5-yl)-N-methyl-3,6-dihydropyridine-1(2H)-carboxamide;

10-fluoro-5-(1,2,3,6-tetrahydropyridin-4-yl)-4,6-dihydro-7-oxa-3,4-diazadibenzo[cd,f]azulene;

10-fluoro-5-[1-(methylsulfonyl)-1,2,3,6-tetrahydropyridin-4-yl]-4,6-dihydro-7-oxa-3,4-diazadibenzo[cd,f]azulene;

[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride;

2-[4-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(10-fluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene;

10-fluoro-7-methyl-5-(piperidin-4-yl)-6,7-dihydro-4H-3,4,7-triazadibenzo[cd,f]azulene;

tert-butyl [4-(10-fluoro-7-methyl-6,7-dihydro-4H-3,4,7-triazadibenzo[cd,f]azulen-5-yl)piperidin-1-yl]acetate;

[4-(10-fluoro-7-methyl-6,7-dihydro-4H-3,4,7-triazadibenzo[cd,f]azulen-5-yl)piperidin-1-yl]acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-N-methyl-2-oxoethanesulfonamide;

2-[4-(10-fluoro-7-methyl-6,7-dihydro-4H-3,4,7-triazadibenzo[cd,f]azulen-5-yl)piperidin-1-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)piperidin-1-yl]-N-(2-hydroxyethyl)-N-methylacetamide;

ethyl 10-fluoro-7-methyl-5-(1,2,3,6-tetrahydropyridin-4-yl)-6,7-dihydro-4H-3,4,7-triazadibenzo[cd,f]azulene-6-carboxylate;

N-[4-(10-fluoro-7-methyl-6,7-dihydro-4H-3,4,7-triazadibenzo[cd,f]azulen-5-yl)cyclohex-3-en-1-yl]-D-valine;

N-[4-(10-fluoro-7-methyl-6,7-dihydro-4H-3,4,7-triazadibenzo[cd,f]azulen-5-yl)cyclohex-3-en-1-yl]-L-alanine;

N-[4-(10-fluoro-7-methyl-6,7-dihydro-4H-3,4,7-triazadibenzo[cd,f]azulen-5-yl)cyclohex-3-en-1-yl]glycine;

(2S)-{[4-(10-fluoro-7-methyl-6,7-dihydro-4H-3,4,7-triazadibenzo[cd,f]azulen-5-yl)cyclohex-3-en-1-yl]amino}(phenyl)acetic acid;

10-fluoro-7-methyl-5-(1,2,3,6-tetrahydropyridin-4-yl)-6,7-dihydro-4H-3,4,7-triazadibenzo[cd,f]azulene-6-carboxylic acid;

N-[4-(10-fluoro-7-methyl-6,7-dihydro-4H-3,4,7-triazadibenzo[cd,f]azulen-5-yl)cyclohex-3-en-1-yl]-L-valine;

N-[4-(10-fluoro-7-methyl-6,7-dihydro-4H-3,4,7-triazadibenzo[cd,f]azulen-5-yl)cyclohex-3-en-1-yl]-L-phenylalanine;

N-[4-(10-fluoro-7-methyl-6,7-dihydro-4H-3,4,7-triazadibenzo[cd,f]azulen-5-yl)cyclohex-3-en-1-yl]-3-methyl-L-valine;

1-[4-(10-fluoro-7-methyl-6,7-dihydro-4H-3,4,7-triazadibenzo[cd,f]azulen-5-yl)cyclohex-3-en-1-yl]-L-proline;

N-[4-(10-fluoro-7-methyl-6,7-dihydro-4H-3,4,7-triazadibenzo[cd,f]azulen-5-yl)cyclohex-3-en-1-yl]-L-serine;

N-[4-(10-fluoro-7-methyl-6,7-dihydro-4H-3,4,7-triazadibenzo[cd,f]azulen-5-yl)cyclohex-3-en-1-yl]-L-norvaline;

N-[4-(10-fluoro-7-methyl-6,7-dihydro-4H-3,4,7-triazadibenzo[cd,f]azulen-5-yl)cyclohex-3-en-1-yl]-L-tyrosine;

4-(10-fluoro-7-methyl-6,7-dihydro-4H-3,4,7-triazadibenzo[cd,f]azulen-5-yl)cyclohex-3-ene-1-carboxylic acid;

2-[4-(10-fluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

10-fluoro-7-methyl-5-[4-(methylsulfonyl)phenyl]-6,7-dihydro-4H-3,4,7-triazadibenzo[cd,f]azulene;

10-fluoro-7-methyl-5-(pyridin-4-yl)-6,7-dihydro-4H-3,4,7-triazadibenzo[cd,f]azulene;

10-fluoro-7-methyl-5-[6-(methylsulfonyl)pyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)pyrimidin-2-amine;

4-(10-fluoro-7-methyl-6,7-dihydro-4H-3,4,7-triazadibenzo[cd,f]azulen-5-yl)benzoic acid;

1,10-difluoro-7-methyl-5-(1,2,3,6-tetrahydropyridin-4-yl)-6,7-dihydro-4H-3,4,7-triazadibenzo[cd,f]azulene;

tert-butyl 4-(1,10-difluoro-7-methyl-6,7-dihydro-4H-3,4,7-triazadibenzo[cd,f]azulen-5-yl)-3,6-dihydropyridine-1(2H)-carboxylate;

4-(10-fluoro-7-methyl-6,7-dihydro-4H-3,4,7-triazadibenzo[cd,f]azulen-5-yl)-N,N-dimethylcyclohex-3-ene-1-carboxamide;

[4-(10-fluoro-7-methyl-6,7-dihydro-4H-3,4,7-triazadibenzo[cd,f]azulen-5-yl)cyclohex-3-en-1-yl](3-hydroxyazetidin-1-yl)methanone;

4-(10-fluoro-7-methyl-6,7-dihydro-4H-3,4,7-triazadibenzo[cd,f]azulen-5-yl)-N-methylcyclohex-3-ene-1-carboxamide;

2-[4-(10-fluoro-7-methyl-6,7-dihydro-4H-3,4,7-triazadibenzo[cd,f]azulen-5-yl)-3,6-dihydropyridin-1(2H)-yl]-N,N-bis(2-hydroxyethyl)acetamide;

1-(3,3-difluoroazetidin-1-yl)-2-[4-(10-fluoro-7-methyl-6,7-dihydro-4H-3,4,7-triazadibenzo[cd,f]azulen-5-yl)-3,6-dihydropyridin-1(2H)-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N,N-dimethylacetamide;

10-fluoro-7-methyl-5-[(1R,5S)-8-(methylsulfonyl)-8-azabicyclo[3.2.1]oct-2-en-3-yl]-6,7-dihydro-4H-3,4,7-triazadibenzo[cd,f]azulene;

(1R,5S)-3-(10-fluoro-7-methyl-6,7-dihydro-4H-3,4,7-triazadibenzo[cd,f]azulen-5-yl)-N-methyl-8-azabicyclo[3.2.1]oct-2-ene-8-carboxamide;

[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid;

10-fluoro-5-(1,2,3,3a,4,6a-hexahydrocyclopenta[c]pyrrol-5-yl)-7-methyl-6,7-dihydro-4H-3,4,7-triazadibenzo[cd,f]azulene;

10-fluoro-7-methyl-5-(pyridin-3-yl)-6,7-dihydro-4H-3,4,7-triazadibenzo[cd,f]azulene;

ethyl 4-(10-fluoro-7-methyl-6,7-dihydro-4H-3,4,7-triazadibenzo[cd,f]azulen-5-yl)cyclohex-3-ene-1-carboxylate;

5-[(1R,5S)-8-azabicyclo[3.2.1]oct-2-en-3-yl]-10-fluoro-7-methyl-6,7-dihydro-4H-3,4,7-triazadibenzo[cd,f]azulene;

N-(2,3-dihydroxypropyl)-2-[4-(10-fluoro-7-methyl-6,7-dihydro-4H-3,4,7-triazadibenzo[cd,f]azulen-5-yl)-3,6-dihydropyridin-1(2H)-yl]-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

tert-butyl[4-(1,10-difluoro-7-methyl-6,7-dihydro-4H-3,4,7-triazadibenzo[cd,f]azulen-5-yl)-3,6-dihydropyridin-1(2H)-yl]acetate;

2-[4-(1,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;

[4-(1,10-difluoro-7-methyl-6,7-dihydro-4H-3,4,7-triazadibenzo[cd,f]azulen-5-yl)-3,6-dihydropyridin-1(2H)-yl]acetic acid;

1,10-difluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-{2-[(2-methoxyethyl)sulfonyl]-1,2,3,3a,4,6a-hexahydrocyclopenta[c]pyrrol-5-yl}-7-methyl-6,7-dihydro-4H-3,4,7-triazadibenzo[cd,f]azulene;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

2-[4-(1,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[3-(hydroxymethyl)azetidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

5-(10-fluoro-7-methyl-6,7-dihydro-4H-3,4,7-triazadibenzo[cd,f]azulen-5-yl)-N-methyl-3,3a,4,6a-tetrahydrocyclopenta[c]pyrrole-2(1H)-carboxamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N,N-dimethylacetamide;

10-fluoro-7-methyl-5-[2-(methylsulfonyl)-1,2,3,3a,4,6a-hexahydrocyclopenta[c]pyrrol-5-yl]-6,7-dihydro-4H-3,4,7-triazadibenzo[cd,f]azulene;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-[(2S)-2-(hydroxymethyl)pyrrolidin-1-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-(3-hydroxyazetidin-1-yl)ethanone;

[4-(10-fluoro-7-methyl-6,7-dihydro-4H-3,4,7-triazadibenzo[cd,f]azulen-5-yl)phenyl]acetic acid;

[3-(10-fluoro-7-methyl-6,7-dihydro-4H-3,4,7-triazadibenzo[cd,f]azulen-5-yl)phenyl]acetic acid;

N-(2,3-dihydroxypropyl)-2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-methylacetamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-1-(3-hydroxyazetidin-1-yl)ethanone;

N-(2,3-dihydroxypropyl)-2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-methylacetamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(2-hydroxyethyl)-N-methylacetamide;

10-fluoro-7-methyl-5-(2,3,6,7-tetrahydro-1H-azepin-4-yl)-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-N,N-dimethylacetamide;

10-fluoro-7-methyl-5-[1-(methylsulfonyl)-2,3,6,7-tetrahydro-1H-azepin-4-yl]-6,7-dihydro-4H-3,4,7-triazadibenzo[cd,f]azulene;

[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-1-(3-hydroxyazetidin-1-yl)ethanone;

5-(3,3-dimethyl-1,2,3,6-tetrahydropyridin-4-yl)-10-fluoro-7-methyl-6,7-dihydro-4H-3,4,7-triazadibenzo[cd,f]azulene;

10-fluoro-7-methyl-5-(1,2,5,6-tetrahydropyridin-3-yl)-6,7-dihydro-4H-3,4,7-triazadibenzo[cd,f]azulene;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(3-hydroxycyclobutyl)-N-methylacetamide;

10-fluoro-7-methyl-5-[1-(methylsulfonyl)-1,2,5,6-tetrahydropyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)-N-methyl-3,6-dihydropyridine-1(2H)-carboxamide;

2-[5-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-(3-hydroxycyclobutyl)-N-methylacetamide;

10-fluoro-7-methyl-5-[9-(methylsulfonyl)-9-azabicyclo[3.3.1]non-2-en-3-yl]-6,7-dihydro-4H-3,4,7-triazadibenzo[cd,f]azulene;

3-(10-fluoro-7-methyl-6,7-dihydro-4H-3,4,7-triazadibenzo[cd,f]azulen-5-yl)-N-methyl-9-azabicyclo[3.3.1]non-2-ene-9-carboxamide;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N,N-dimethylacetamide;

3-[3-(10-fluoro-7-methyl-6,7-dihydro-4H-3,4,7-triazadibenzo[cd,f]azulen-5-yl)-9-azabicyclo[3.3.1]non-2-en-9-yl]-3-oxopropanenitrile;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(2-hydroxyethyl)-N-methylacetamide;

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-[(2S)-2-(hydroxymethyl)pyrrolidin-1-yl]ethanone;

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-(3-hydroxyazetidin-1-yl)ethanone;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(3-hydroxycyclobutyl)-N-methylacetamide;

N-(2,3-dihydroxypropyl)-2-[3-(10-fluoro-7-methyl-6,7-dihydro-4H-3,4,7-triazadibenzo[cd,f]azulen-5-yl)-9-azabicyclo[3.3.1]non-2-en-9-yl]-N-methylacetamide;

[3-(10-fluoro-7-methyl-6,7-dihydro-4H-3,4,7-triazadibenzo[cd,f]azulen-5-yl)-9-azabicyclo[3.3.1]non-2-en-9-yl]acetic acid;
2-[4-(1,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;
2-[4-(1,10-difluoro-7-methyl-6,7-dihydro-4H-3,4,7-triazadibenzo[cd,f]azulen-5-yl)-3,6-dihydropyridin-1(2H)-yl]-N-(2,3-dihydroxypropyl)-N-methylacetamide;
[4-(10-fluoro-7-methyl-6,7-dihydro-4H-3,4,7-triazadibenzo[cd,f]azulen-5-yl)-3,3-dimethyl-3,6-dihydropyridin-1(2H)-yl]acetic acid;
[5-(10-fluoro-7-methyl-6,7-dihydro-4H-3,4,7-triazadibenzo[cd,f]azulen-5-yl)-3,6-dihydropyridin-1(2H)-yl]acetic acid;
5-[3,3-dimethyl-1-(methylsulfonyl)-1,2,3,6-tetrahydropyridin-4-yl]-10-fluoro-7-methyl-6,7-dihydro-4H-3,4,7-triazadibenzo[cd,f]azulene;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N,N-dimethylacetamide;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-[(2S)-2-(hydroxymethyl)pyrrolidin-1-yl]ethanone;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(2-hydroxyethyl)-N-methylacetamide;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-(3-hydroxyazetidin-1-yl)ethanone;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(3-hydroxycyclobutyl)-N-methylacetamide;
N-(2,3-dihydroxypropyl)-2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-methylacetamide;
2-[5-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;
2-[5-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;
2-[5-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;
N-(2,3-dihydroxypropyl)-2-[5-(10-fluoro-7-methyl-6,7-dihydro-4H-3,4,7-triazadibenzo[cd,f]azulen-5-yl)-3,6-dihydropyridin-1(2H)-yl]-N-methylacetamide;
{cis-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;
(8aR)-7-(9,10-difluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;
[(2R)-4-(9,10-difluoro-7-methyl-6,7-dihydro-4H-3,4,7-triazadibenzo[cd,f]azulen-5-yl)-1,2,5,6-tetrahydropyridin-2-yl]methanol;
8-fluoro-5-methyl-2-(1,2,3,6-tetrahydropyridin-4-yl)-1,3,4,5-tetrahydro-1,5,12-triazabenzo[4,5]cycloocta[1,2,3-cd]indene;
8-fluoro-5-methyl-2-[1-(methylsulfonyl)-1,2,3,6-tetrahydropyridin-4-yl]-1,3,4,5-tetrahydro-1,5,12-triazabenzo[4,5]cycloocta[1,2,3-cd]indene;
2-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]-N,N-dimethylacetamide;
{trans-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;
9,10-difluoro-7-methyl-5-[1-(methylsulfonyl)-1,2,3,6-tetrahydropyridin-4-yl]-6,7-dihydro-4H-3,4,7-triazadibenzo[cd,f]azulene;
2-[4-(9,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;
methyl{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;
methyl{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;
7-methyl-5-(1,2,3,6-tetrahydropyridin-4-yl)-6,7-dihydro-4H-3,4,7,8-tetraazadibenzo[cd,f]azulene;
{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;
2-[4-(9,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;
7-methyl-5-[1-(methylsulfonyl)-1,2,3,6-tetrahydropyridin-4-yl]-6,7-dihydro-4H-3,4,7,8-tetraazadibenzo[cd,f]azulene;
N-methyl-4-(7-methyl-6,7-dihydro-4H-3,4,7,8-tetraazadibenzo[cd,f]azulen-5-yl)-3,6-dihydropyridine-1(2H)-carboxamide;
{3-[4-(10-fluoro-7-methyl-6,7-dihydro-4H-3,4,7-triazadibenzo[cd,f]azulen-5-yl)-3,6-dihydropyridin-1(2H)-yl]cyclobutyl}acetic acid;
trans-4-[4-(10-fluoro-7-methyl-6,7-dihydro-4H-3,4,7-triazadibenzo[cd,f]azulen-5-yl)-3,6-dihydropyridin-1(2H)-yl]cyclohexanecarboxylic acid;
(6S)-6-ethyl-10-fluoro-7-methyl-5-(1,2,3,6-tetrahydropyridin-4-yl)-6,7-dihydro-4H-3,4,7-triazadibenzo[cd,f]azulene;
(6R)-6-ethyl-10-fluoro-7-methyl-5-(1,2,3,6-tetrahydropyridin-4-yl)-6,7-dihydro-4H-3,4,7-triazadibenzo[cd,f]azulene;
9,10-difluoro-7-methyl-5-(1,2,3,6-tetrahydropyridin-4-yl)-6,7-dihydro-4H-3,4,7-triazadibenzo[cd,f]azulene;
[4-(9,10-difluoro-7-methyl-6,7-dihydro-4H-3,4,7-triazadibenzo[cd,f]azulen-5-yl)-3,6-dihydropyridin-1(2H)-yl]acetic acid;
{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;
2-[4-(9,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;
2-[4-(9,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;
N,N-dimethyl-2-[4-(7-methyl-6,7-dihydro-4H-3,4,7,8-tetraazadibenzo[cd,f]azulen-5-yl)-3,6-dihydropyridin-1(2H)-yl]acetamide;
trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;
(8aR)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

(8aS)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

(8aR)-7-(10-fluoro-7-methyl-6,7-dihydro-4H-3,4,7-triazadibenzo[cd,f]azulen-5-yl)-1,5,8,8a-tetrahydro[1,3]oxazolo[3,4-a]pyridin-3-one;

[(2R)-4-(10-fluoro-7-methyl-6,7-dihydro-4H-3,4,7-triazadibenzo[cd,f]azulen-5-yl)-1,2,5,6-tetrahydropyridin-2-yl]methanol;

[(2S)-4-(10-fluoro-7-methyl-6,7-dihydro-4H-3,4,7-triazadibenzo[cd,f]azulen-5-yl)-1,2,5,6-tetrahydropyridin-2-yl]methanol;

[(2R)-4-(10-fluoro-7-methyl-6,7-dihydro-4H-3,4,7-triazadibenzo[cd,f]azulen-5-yl)-1,2,3,6-tetrahydropyridin-2-yl]methanol;

2-[4-(9,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

7-methyl-5-(1,2,3,6-tetrahydropyridin-4-yl)-6,7-dihydro-4H-3,4,7-triazadibenzo[cd,f]azulene;

1-fluoro-7-methyl-5-(1,2,3,6-tetrahydropyridin-4-yl)-6,7-dihydro-4H-3,4,7-triazadibenzo[cd,f]azulene;

7-methyl-5-[1-(methylsulfonyl)-1,2,3,6-tetrahydropyridin-4-yl]-6,7-dihydro-4H-3,4,7-triazadibenzo[cd,f]azulene;

1-fluoro-7-methyl-5-[1-(methylsulfonyl)-1,2,3,6-tetrahydropyridin-4-yl]-6,7-dihydro-4H-3,4,7-triazadibenzo[cd,f]azulene;

N,N-dimethyl-2-[4-(7-methyl-6,7-dihydro-4H-3,4,7-triazadibenzo[cd,f]azulen-5-yl)-3,6-dihydropyridin-1(2H)-yl]acetamide;

2-[4-(1-fluoro-7-methyl-6,7-dihydro-4H-3,4,7-triazadibenzo[cd,f]azulen-5-yl)-3,6-dihydropyridin-1(2H)-yl]-N,N-dimethylacetamide;

3-[4-(10-fluoro-4,6-dihydro-7-oxa-3,4-diazadibenzo[cd,f]azulen-5-yl)-3,6-dihydropyridin-1(2H)-yl]propane-1,2-diol;

{4-[4-(10-fluoro-4,6-dihydro-7-oxa-3,4-diazadibenzo[cd,f]azulen-5-yl)-3,6-dihydropyridin-1(2H)-yl]cyclohexyl}acetic acid;

trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;

{trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}-N,N-dimethylacetamide;

{trans-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

{cis-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

trans-4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetonitrile;

methyl 2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoate;

tert-butyl{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetate;

2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoic acid;

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylethanesulfonamide;

2-[4-(10-fluoro-7-methyl-6,7-dihydro-4H-3,4,7-triazadibenzo[cd,f]azulen-5-yl)-3,6-dihydropyridin-1(2H)-yl]ethanesulfonamide;

{trans-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;

trans-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

{cis-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;

cis-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

{4-[4-(10-fluoro-7-methyl-6,7-dihydro-4H-3,4,7-triazadibenzo[cd,f]azulen-5-yl)-2,3,6,7-tetrahydro-1H-azepin-1-yl]cyclohexylidene}acetic acid;

2-{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}-2-methylpropanoic acid;

methyl cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylate;

cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;

cis-3-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]cyclobutanecarboxylic acid;

trans-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;

trans-3-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]cyclobutanecarboxylic acid;

cyano{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;

{3-[4-(1,10-difluoro-7-methyl-6,7-dihydro-4H-3,4,7-triazadibenzo[cd,f]azulen-5-yl)-3,6-dihydropyridin-1(2H)-yl]cyclobutyl}acetic acid;

3-[4-(1,10-difluoro-7-methyl-6,7-dihydro-4H-3,4,7-triazadibenzo[cd,f]azulen-5-yl)-3,6-dihydropyridin-1(2H)-yl]cyclobutanecarboxylic acid; and pharmaceutically acceptable salts thereof.

Embodiments of Formula (IIa)

In another embodiment, the present invention relates to compounds of Formula (IIa) or a pharmaceutically acceptable salt thereof, Formula (IIa)

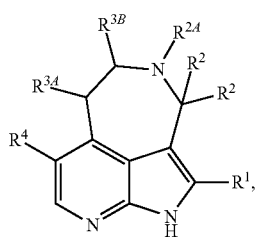

wherein
- $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, (O), OH, CN, $NO_2$, F, Cl, Br and I;
- $R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, $C(O)OH$, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting $C_1$-$C_8$ alkyl, $C_2$-$C_6$ alkenyl, and $C_2$-$C_6$ alkynyl;
- $R^{2A}$ is hydrogen or $C_1$-$C_4$ alkyl; wherein the $R^{2A}$ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I;
- $R^{2B}$ is $C_1$-$C_4$ alkyl;
- $R^{3A}$ and $R^{3B}$, taken together, form $R^3$;
- $R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, OH, CN, $NO_2$, F, Cl, Br and I;
- $R^4$ is selected from the group consisting of hydrogen, $C_1$-$C_4$ alkyl, $C_1$-$C_4$ alkoxy, CN, F, Cl, Br, and I;
- $R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHSO_2R^7$, $NR^7SO_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, (O), OH, CN, $NO_2$, F, Cl, Br and I;
- $R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycloalkyl, heterocycloalkenyl, $NH_2$, $C(O)H$, $C(O)OH$, OH, CN, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHSO_2R^8$, $NR^8SO_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, (O), OH, CN, $NO_2$, F, Cl, Br and I;
- $R^7$, at each occurrence, is independently selected from the group consisting of $C_1$-$C_6$ alkyl, $C_2$-$C_6$ alkenyl, and $C_2$-$C_6$ alkynyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $OR^9$, $SR^9$, $S(O)R^9$, $SO_2R^9$, $C(O)R^9$, $CO(O)R^9$, $OC(O)R^9$, $OC(O)OR^9$, $NH_2$, $C(O)H$, $C(O)OH$, OH, CN, $NO_2$, F, Cl, Br and I;
- $R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)H$, $C(O)OH$, OH, CN, $NO_2$, F, Cl, Br and I; and
- $R^9$, at each occurrence, is independently selected from the group consisting of $C_1$-$C_6$ alkyl, $C_2$-$C_6$ alkenyl, and $C_2$-$C_6$ alkynyl.

In one embodiment of Formula (IIa), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N$ $(R^5)_2$, $SO_2NHC(O)OR^5$, $C(O)H$, $C(O)OH$, OH, CN, $NO_2$, F, Cl, Br and I. In another embodiment of Formula (IIa), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, $C(O)OH$, F, Cl, Br and I. In another embodiment of Formula (IIa), $R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and $C(O)OH$. In another embodiment of Formula (IIa), $R^1$ is cycloalkenyl; wherein the $R^1$ cycloalkenyl is optionally substituted as described herein. In another embodiment of Formula (IIa), $R^1$ is aryl; wherein the $R^1$ aryl is optionally substituted as described herein. In another embodiment of Formula (IIa), $R^1$ is heteroaryl; wherein the $R^1$ heteroaryl is optionally substituted as described herein. In another embodiment of Formula (IIa), $R^1$ is heterocycloalkyl; wherein the $R^1$ heterocycloalkyl is optionally substituted as described herein. In another embodiment of Formula (IIa), $R^1$ is heterocycloalkenyl; wherein the $R^1$ heterocycloalkenyl is optionally substituted as described herein. In another embodiment of Formula (IIa), $R^1$ is pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, 8,8a-dihydro-1H-oxazolo[3,4-a]pyridin-3(5H)-onyl, 5,6-dihydro-1H-oxazolo[3,4-a]pyridin-3(8aH)-onyl, 9-azabicyclo[3.3.1]non-3-enyl, or 8-azabicyclo[3.2.1]oct-2-enyl; wherein the $R^1$ pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, 8,8a-dihydro-1H-oxazolo[3,4-a]pyridin-3(5H)-onyl, 5,6-dihydro-1H-oxazolo[3,4-a]pyridin-3(8aH)-onyl, 9-azabicyclo[3.3.1]non-3-enyl, and 8-azabicyclo[3.2.1]oct-2-enyl are optionally substituted as described herein for substituents on R'. In another embodiment of Formula (IIa), R's 1,2,3,6-tetrahydropyridinyl; wherein the $R^1$ 1,2,3,6-tetrahydropyridinyl is optionally substituted as described herein for substituents on $R^1$.

In one embodiment of Formula (IIa), $R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, $C(O)OH$, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting of $C_1$-$C_8$ alkyl, $C_2$-$C_6$ alkenyl, and $C_2$-$C_6$ alkynyl. In another embodiment of Formula (IIa), $R^2$, at each occurrence, is independently selected from the group consisting of hydrogen, $C_1$-$C_4$ alkyl, heteroaryl, $C(O)OH$, and $C(O)OR^{2B}$; wherein each $R^2$ heteroaryl is optionally substituted with one or more $C_1$-$C_8$ alkyl. In another embodiment of Formula (IIa), $R^2$, at each occurrence, is independently hydrogen or $C_1$-$C_4$ alkyl. In another embodiment of Formula (IIa), $R^2$, at each occurrence, is independently hydrogen. In another embodiment of Formula (IIa), $R^2$, at each occurrence, is independently $C_1$-$C_4$ alkyl.

In one embodiment of Formula (IIa), $R^{2A}$ is hydrogen or $C_1$-$C_4$ alkyl; wherein the $R^{2A}$ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I. In another embodiment of Formula (IIa), $R^{2A}$ is hydrogen or $C_1$-$C_4$ alkyl; wherein the $R^{2A}$ $C_1$-$C_4$ alkyl is optionally substituted with one or more substituents independently selected from the group consisting of heterocycloalkyl, F, Cl, Br and I. In another embodiment of Formula (IIa), $R^{2A}$ is hydrogen or $C_1$-$C_4$ alkyl; wherein the $R^{2A}$ $C_1$-$C_4$ alkyl is optionally substituted with one or more heterocycloalkyl. In another embodiment of Formula (IIa), $R^{2A}$ is hydrogen. In another embodiment of Formula (IIa), $R^{2A}$ is $C_1$-$C_4$ alkyl; wherein the $R^{2A}$ $C_1$-$C_4$ alkyl is optionally substituted with one or more heterocycloalkyl.

In one embodiment of Formula (IIa), $R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, OH, CN, $NO_2$, F, Cl, Br and I. In another embodiment of Formula (IIa), $R^3$ is phenyl; wherein the $R^3$ phenyl is optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, OH, CN, $NO_2$, F, Cl, Br and I. In another embodiment of Formula (IIa), $R^3$ is phenyl; wherein the $R^3$ phenyl is optionally substituted with one or more substituents independently selected from the group consisting of F, Cl, Br and I. In another embodiment of Formula (IIa), $R^3$ is phenyl; wherein the $R^3$ phenyl is optionally substituted with F. In another embodiment of Formula (IIa), $R^3$ is phenyl; wherein the $R^3$ phenyl is substituted with F. In another embodiment of Formula (IIa), $R^3$ is phenyl; wherein the $R^3$ phenyl is unsubstituted.

In another embodiment of Formula (IIa), $R^3$ is pyridinyl; wherein the $R^3$ pyridinyl is optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, OH, CN, $NO_2$, F, Cl, Br and I. In another embodiment of Formula (IIa), $R^3$ is pyridinyl; wherein the $R^3$ pyridinyl is optionally substituted with one or more substituents independently selected from the group consisting of F, Cl, Br and I. In another embodiment of Formula (IIa), $R^3$ is pyridinyl; wherein the $R^3$ pyridinyl is optionally substituted with F. In another embodiment of Formula (IIa), $R^3$ is pyridinyl; wherein the $R^3$ pyridinyl is substituted with F. In another embodiment of Formula (IIa), $R^3$ is pyridinyl; wherein the $R^3$ pyridinyl is unsubstituted.

In one embodiment of Formula (IIa), $R^4$ is selected from the group consisting of hydrogen, $C_1$-$C_4$ alkyl, $C_1$-$C_4$ alkoxy, CN, F, Cl, Br, and I. In another embodiment of Formula (IIa), $R^4$ is selected from the group consisting of hydrogen, F, Cl, Br, and I. In another embodiment of Formula (IIa), $R^4$ is F. In another embodiment of Formula (IIa), $R^4$ is hydrogen.

In one embodiment of Formula (IIa),
$R^1$ is selected from the group consisting of cycloalkenyl, aryl, heteroaryl, heterocycloalkyl, and heterocycloalkenyl; wherein the $R^1$ cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and $C(O)OH$;
$R^2$, at each occurrence, is independently selected from the group consisting of hydrogen, $C_1$-$C_4$ alkyl, heteroaryl, $C(O)OH$, and $C(O)OR^{2B}$; wherein each $R^2$ heteroaryl is optionally substituted with one or more $C_1$-$C_8$ alkyl;

R²ᴬ is hydrogen or C₁-C₄ alkyl; wherein the R²ᴬ C₁-C₄ alkyl is optionally substituted with one heterocycloalkyl;

R²ᴮ is C₁-C₄ alkyl;

R³ᴬ and R³ᴮ, taken together, form R³;

R³ is phenyl; wherein the R³ phenyl is optionally substituted with one or more F;

R⁴ is selected from the group consisting of hydrogen, F, Cl, Br, and I;

R⁵, at each occurrence, is independently selected from the group consisting of C₁-C₈ alkyl, heterocycloalkyl, and cycloalkyl; wherein each R⁵ C₁-C₈ alkyl is optionally substituted with one or more substituents independently selected from the group consisting of R⁶, OR⁶, C(O)R⁶, CO(O)R⁶, N(R⁶)₂, C(O)N(R⁶)₂, SO₂NH₂, SO₂NHR⁶, SO₂N(R⁶)₂, C(O)OH, CN, and OH; wherein each R⁵ cycloalkyl and heterocycloalkyl is optionally substituted with one or more substituents independently selected from the group consisting of R⁷, C(O)OR⁷, C(O)OH, and OH;

R⁶, at each occurrence, is independently selected from the group consisting of C₁-C₆ alkyl, aryl, heterocycloalkyl, and cycloalkyl; wherein each R⁶ C₁-C₆ alkyl is optionally substituted with one or more OH; wherein each R⁶ aryl, cycloalkyl, and heterocycloalkyl is optionally substituted with one or more substituents independently selected from the group consisting of R⁸, OH, F, Cl, Br and I; and R⁷, at each occurrence, is independently selected from the group consisting of C₁-C₆ alkyl, and C₂-C₆ alkenyl; wherein each R⁷ C₁-C₆ alkyl and C₂-C₆ alkenyl is optionally substituted with one or more substituents independently selected from the group consisting of CO(O)R⁹, C(O)OH, and CN;

R⁸, at each occurrence, is independently C₁-C₆ alkyl; wherein each R⁸ C₁-C₆ alkyl is optionally substituted with one or more OH; and R⁹, at each occurrence, is independently C₁-C₆ alkyl.

Still another embodiment pertains to compounds of Formula (IIa), selected from the group consisting of:

10-fluoro-7-methyl-5-(1,2,3,6-tetrahydropyridin-4-yl)-6,7-dihydro-4H-3,4,7-triazadibenzo[cd,f]azulene;

tert-butyl 4-(10-fluoro-7-methyl-6,7-dihydro-4H-3,4,7-triazadibenzo[cd,f]azulen-5-yl)-3,6-dihydropyridine-1(2H)-carboxylate;

ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate;

10-fluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-7-propyl-6,7-dihydro-4H-3,4,7-triazadibenzo[cd,f]azulene;

10-fluoro-5-[1-(methylsulfonyl)-1,2,3,6-tetrahydropyridin-4-yl]-7-(tetrahydro-2H-pyran-4-ylmethyl)-6,7-dihydro-4H-3,4,7-triazadibenzo[cd,f]azulene;

tert-butyl 4-(6-ethyl-10-fluoro-7-methyl-6,7-dihydro-4H-3,4,7-triazadibenzo[cd,f]azulen-5-yl)-3,6-dihydropyridine-1(2H)-carboxylate;

6-ethyl-10-fluoro-7-methyl-5-(1,2,3,6-tetrahydropyridin-4-yl)-6,7-dihydro-4H-3,4,7-triazadibenzo[cd,f]azulene dihydrochloride;

10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene;

6-ethyl-10-fluoro-7-methyl-5-[1-(methylsulfonyl)-1,2,3,6-tetrahydropyridin-4-yl]-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

4-(10-fluoro-7-methyl-6,7-dihydro-4H-3,4,7-triazadibenzo[cd,f]azulen-5-yl)-N-methyl-3,6-dihydropyridine-1(2H)-carboxamide;

[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride;

2-[4-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(10-fluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene;

10-fluoro-7-methyl-5-(piperidin-4-yl)-6,7-dihydro-4H-3,4,7-triazadibenzo[cd,f]azulene;

tert-butyl[4-(10-fluoro-7-methyl-6,7-dihydro-4H-3,4,7-triazadibenzo[cd,f]azulen-5-yl)piperidin-1-yl]acetate;

[4-(10-fluoro-7-methyl-6,7-dihydro-4H-3,4,7-triazadibenzo[cd,f]azulen-5-yl)piperidin-1-yl]acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-N-methyl-2-oxoethanesulfonamide;

2-[4-(10-fluoro-7-methyl-6,7-dihydro-4H-3,4,7-triazadibenzo[cd,f]azulen-5-yl)piperidin-1-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)piperidin-1-yl]-N-(2-hydroxyethyl)-N-methylacetamide;

ethyl 10-fluoro-7-methyl-5-(1,2,3,6-tetrahydropyridin-4-yl)-6,7-dihydro-4H-3,4,7-triazadibenzo[cd,f]azulene-6-carboxylate;

N-[4-(10-fluoro-7-methyl-6,7-dihydro-4H-3,4,7-triazadibenzo[cd,f]azulen-5-yl)cyclohex-3-en-1-yl]-D-valine;

N-[4-(10-fluoro-7-methyl-6,7-dihydro-4H-3,4,7-triazadibenzo[cd,f]azulen-5-yl)cyclohex-3-en-1-yl]-L-alanine;

N-[4-(10-fluoro-7-methyl-6,7-dihydro-4H-3,4,7-triazadibenzo[cd,f]azulen-5-yl)cyclohex-3-en-1-yl]glycine;

(2S)-{[4-(10-fluoro-7-methyl-6,7-dihydro-4H-3,4,7-triazadibenzo[cd,f]azulen-5-yl)cyclohex-3-en-1-yl]amino}(phenyl)acetic acid;

10-fluoro-7-methyl-5-(1,2,3,6-tetrahydropyridin-4-yl)-6,7-dihydro-4H-3,4,7-triazadibenzo[cd,f]azulene-6-carboxylic acid;

N-[4-(10-fluoro-7-methyl-6,7-dihydro-4H-3,4,7-triazadibenzo[cd,f]azulen-5-yl)cyclohex-3-en-1-yl]-L-valine;

N-[4-(10-fluoro-7-methyl-6,7-dihydro-4H-3,4,7-triazadibenzo[cd,f]azulen-5-yl)cyclohex-3-en-1-yl]-L-phenylalanine;

N-[4-(10-fluoro-7-methyl-6,7-dihydro-4H-3,4,7-triazadibenzo[cd,f]azulen-5-yl)cyclohex-3-en-1-yl]-3-methyl-L-valine;

1-[4-(10-fluoro-7-methyl-6,7-dihydro-4H-3,4,7-triazadibenzo[cd,f]azulen-5-yl)cyclohex-3-en-1-yl]-L-proline;

N-[4-(10-fluoro-7-methyl-6,7-dihydro-4H-3,4,7-triazadibenzo[cd,f]azulen-5-yl)cyclohex-3-en-1-yl]-L-serine;

N-[4-(10-fluoro-7-methyl-6,7-dihydro-4H-3,4,7-triazadibenzo[cd,f]azulen-5-yl)cyclohex-3-en-1-yl]-L-norvaline;
N-[4-(10-fluoro-7-methyl-6,7-dihydro-4H-3,4,7-triazadibenzo[cd,f]azulen-5-yl)cyclohex-3-en-1-yl]-L-tyrosine;
4-(10-fluoro-7-methyl-6,7-dihydro-4H-3,4,7-triazadibenzo[cd,f]azulen-5-yl)cyclohex-3-ene-1-carboxylic acid;
2-[4-(10-fluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;
10-fluoro-7-methyl-5-[4-(methylsulfonyl)phenyl]-6,7-dihydro-4H-3,4,7-triazadibenzo[cd,f]azulene;
10-fluoro-7-methyl-5-(pyridin-4-yl)-6,7-dihydro-4H-3,4,7-triazadibenzo[cd,f]azulene;
10-fluoro-7-methyl-5-[6-(methylsulfonyl)pyridin-3-yl]-6,7-dihydro-4H-3,4,7-triazadibenzo[cd,f]azulene;
5-(10-fluoro-7-methyl-6,7-dihydro-4H-3,4,7-triazadibenzo[cd,f]azulen-5-yl)pyrimidin-2-amine;
4-(10-fluoro-7-methyl-6,7-dihydro-4H-3,4,7-triazadibenzo[cd,f]azulen-5-yl)benzoic acid;
1,10-difluoro-7-methyl-5-(1,2,3,6-tetrahydropyridin-4-yl)-6,7-dihydro-4H-3,4,7-triazadibenzo[cd,f]azulene;
tert-butyl 4-(1,10-difluoro-7-methyl-6,7-dihydro-4H-3,4,7-triazadibenzo[cd,f]azulen-5-yl)-3,6-dihydropyridine-1(2H)-carboxylate;
4-(10-fluoro-7-methyl-6,7-dihydro-4H-3,4,7-triazadibenzo[cd,f]azulen-5-yl)-N,N-dimethylcyclohex-3-ene-1-carboxamide;
[4-(10-fluoro-7-methyl-6,7-dihydro-4H-3,4,7-triazadibenzo[cd,f]azulen-5-yl)cyclohex-3-en-1-yl](3-hydroxyazetidin-1-yl)methanone;
4-(10-fluoro-7-methyl-6,7-dihydro-4H-3,4,7-triazadibenzo[cd,f]azulen-5-yl)-N-methylcyclohex-3-ene-1-carboxamide;
2-[4-(10-fluoro-7-methyl-6,7-dihydro-4H-3,4,7-triazadibenzo[cd,f]azulen-5-yl)-3,6-dihydropyridin-1(2H)-yl]-N,N-bis(2-hydroxyethyl)acetamide;
1-(3,3-difluoroazetidin-1-yl)-2-[4-(10-fluoro-7-methyl-6,7-dihydro-4H-3,4,7-triazadibenzo[cd,f]azulen-5-yl)-3,6-dihydropyridin-1(2H)-yl]ethanone;
2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N,N-dimethylacetamide;
10-fluoro-7-methyl-5-[(1R,5S)-8-(methylsulfonyl)-8-azabicyclo[3.2.1]oct-2-en-3-yl]-6,7-dihydro-4H-3,4,7-triazadibenzo[cd,f]azulene;
(1R,5S)-3-(10-fluoro-7-methyl-6,7-dihydro-4H-3,4,7-triazadibenzo[cd,f]azulen-5-yl)-N-methyl-8-azabicyclo[3.2.1]oct-2-ene-8-carboxamide;
[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid;
10-fluoro-5-(1,2,3,3a,4,6a-hexahydrocyclopenta[c]pyrrol-5-yl)-7-methyl-6,7-dihydro-4H-3,4,7-triazadibenzo[cd,f]azulene;
10-fluoro-7-methyl-5-(pyridin-3-yl)-6,7-dihydro-4H-3,4,7-triazadibenzo[cd,f]azulene;
ethyl 4-(10-fluoro-7-methyl-6,7-dihydro-4H-3,4,7-triazadibenzo[cd,f]azulen-5-yl)cyclohex-3-ene-1-carboxylate;
5-[(1R,5S)-8-azabicyclo[3.2.1]oct-2-en-3-yl]-10-fluoro-7-methyl-6,7-dihydro-4H-3,4,7-triazadibenzo[cd,f]azulene;
N-(2,3-dihydroxypropyl)-2-[4-(10-fluoro-7-methyl-6,7-dihydro-4H-3,4,7-triazadibenzo[cd,f]azulen-5-yl)-3,6-dihydropyridin-1(2H)-yl]-N-methylacetamide;
2-[4-(10-fluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;
tert-butyl[4-(1,10-difluoro-7-methyl-6,7-dihydro-4H-3,4,7-triazadibenzo[cd,f]azulen-5-yl)-3,6-dihydropyridin-1(2H)-yl]acetate;
2-[4-(1,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;
[4-(1,10-difluoro-7-methyl-6,7-dihydro-4H-3,4,7-triazadibenzo[cd,f]azulen-5-yl)-3,6-dihydropyridin-1(2H)-yl]acetic acid;
1,10-difluoro-7-methyl-5-[1-(methylsulfonyl)-1,2,3,6-tetrahydropyridin-4-yl]-6,7-dihydro-4H-3,4,7-triazadibenzo[cd,f]azulene;
10-fluoro-5-{2-[(2-methoxyethyl)sulfonyl]-1,2,3,3a,4,6a-hexahydrocyclopenta[c]pyrrol-5-yl}-7-methyl-6,7-dihydro-4H-3,4,7-triazadibenzo[cd,f]azulene;
2-[4-(1,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;
2-[4-(1,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-1-[3-(hydroxymethyl)azetidin-1-yl]ethanone;
2-[4-(1,10-difluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;
5-(10-fluoro-7-methyl-6,7-dihydro-4H-3,4,7-triazadibenzo[cd,f]azulen-5-yl)-N-methyl-3,3a,4,6a-tetrahydrocyclopenta[c]pyrrole-2(1H)-carboxamide;
2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N,N-dimethylacetamide;
10-fluoro-7-methyl-5-[2-(methylsulfonyl)-1,2,3,3a,4,6a-hexahydrocyclopenta[c]pyrrol-5-yl]-6,7-dihydro-4H-3,4,7-triazadibenzo[cd,f]azulene;
2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-[(2S)-2-(hydroxymethyl)pyrrolidin-1-yl]ethanone;
2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-(3-hydroxyazetidin-1-yl)ethanone;
[4-(10-fluoro-7-methyl-6,7-dihydro-4H-3,4,7-triazadibenzo[cd,f]azulen-5-yl)phenyl]acetic acid;
[3-(10-fluoro-7-methyl-6,7-dihydro-4H-3,4,7-triazadibenzo[cd,f]azulen-5-yl)phenyl]acetic acid;
N-(2,3-dihydroxypropyl)-2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-methylacetamide;
2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-1-(3-hydroxyazetidin-1-yl)ethanone;
N-(2,3-dihydroxypropyl)-2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-methylacetamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2 (1H)-yl]-N-(2-hydroxyethyl)-N-methylacetamide;

10-fluoro-7-methyl-5-(2,3,6,7-tetrahydro-1H-azepin-4-yl)-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-N,N-dimethylacetamide;

10-fluoro-7-methyl-5-[1-(methylsulfonyl)-2,3,6,7-tetrahydro-1H-azepin-4-yl]-6,7-dihydro-4H-3,4,7-triazadibenzo[cd,f]azulene;

[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid;

2-[4-(10-fluoro-7-methyl-6,7-dihydro-4H-3,4,7-triazadibenzo[cd,f]azulen-5-yl)-2,3,6,7-tetrahydro-1H-azepin-1-yl]-1-(3-hydroxyazetidin-1-yl)ethanone;

5-(3,3-dimethyl-1,2,3,6-tetrahydropyridin-4-yl)-10-fluoro-7-methyl-6,7-dihydro-4H-3,4,7-triazadibenzo[cd,f]azulene;

10-fluoro-7-methyl-5-(1,2,5,6-tetrahydropyridin-3-yl)-6,7-dihydro-4H-3,4,7-triazadibenzo[cd,f]azulene;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(3-hydroxycyclobutyl)-N-methylacetamide;

10-fluoro-7-methyl-5-[1-(methylsulfonyl)-1,2,5,6-tetrahydropyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)-N-methyl-3,6-dihydropyridine-1(2H)-carboxamide;

2-[5-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-(3-hydroxycyclobutyl)-N-methylacetamide;

10-fluoro-7-methyl-5-[9-(methylsulfonyl)-9-azabicyclo[3.3.1]non-2-en-3-yl]-6,7-dihydro-4H-3,4,7-triazadibenzo[cd,f]azulene;

3-(10-fluoro-7-methyl-6,7-dihydro-4H-3,4,7-triazadibenzo[cd,f]azulen-5-yl)-N-methyl-9-azabicyclo[3.3.1]non-2-ene-9-carboxamide;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N,N-dimethylacetamide;

3-[3-(10-fluoro-7-methyl-6,7-dihydro-4H-3,4,7-triazadibenzo[cd,f]azulen-5-yl)-9-azabicyclo[3.3.1]non-2-en-9-yl]-3-oxopropanenitrile;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(2-hydroxyethyl)-N-methylacetamide;

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-[(2S)-2-(hydroxymethyl)pyrrolidin-1-yl]ethanone;

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-(3-hydroxyazetidin-1-yl)ethanone;

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(3-hydroxycyclobutyl)-N-methylacetamide;

N-(2,3-dihydroxypropyl)-2-[3-(10-fluoro-7-methyl-6,7-dihydro-4H-3,4,7-triazadibenzo[cd,f]azulen-5-yl)-9-azabicyclo[3.3.1]non-2-en-9-yl]-N-methylacetamide;

[3-(10-fluoro-7-methyl-6,7-dihydro-4H-3,4,7-triazadibenzo[cd,f]azulen-5-yl)-9-azabicyclo[3.3.1]non-2-en-9-yl]acetic acid;

2-[4-(1,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

2-[4-(1,10-difluoro-7-methyl-6,7-dihydro-4H-3,4,7-triazadibenzo[cd,f]azulen-5-yl)-3,6-dihydropyridin-1(2H)-yl]-N-(2,3-dihydroxypropyl)-N-methylacetamide;

[4-(10-fluoro-7-methyl-6,7-dihydro-4H-3,4,7-triazadibenzo[cd,f]azulen-5-yl)-3,3-dimethyl-3,6-dihydropyridin-1(2H)-yl]acetic acid;

[5-(10-fluoro-7-methyl-6,7-dihydro-4H-3,4,7-triazadibenzo[cd,f]azulen-5-yl)-3,6-dihydropyridin-1(2H)-yl]acetic acid;

5-[3,3-dimethyl-1-(methylsulfonyl)-1,2,3,6-tetrahydropyridin-4-yl]-10-fluoro-7-methyl-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N,N-dimethylacetamide;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(2-hydroxyethyl)-N-methylacetamide;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-(3-hydroxyazetidin-1-yl)ethanone;

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(3-hydroxycyclobutyl)-N-methylacetamide;

N-(2,3-dihydroxypropyl)-2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-methylacetamide;

2-[5-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[5-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[5-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

N-(2,3-dihydroxypropyl)-2-[5-(10-fluoro-7-methyl-6,7-dihydro-4H-3,4,7-triazadibenzo[cd,f]azulen-5-yl)-3,6-dihydropyridin-1(2H)-yl]-N-methylacetamide;

{cis-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;

(8aR)-7-(9,10-difluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

[(2R)-4-(9,10-difluoro-7-methyl-6,7-dihydro-4H-3,4,7-triazadibenzo[cd,f]azulen-5-yl)-1,2,5,6-tetrahydropyridin-2-yl]methanol;

{trans-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;

9,10-difluoro-7-methyl-5-[1-(methylsulfonyl)-1,2,3,6-tetrahydropyridin-4-yl]-6,7-dihydro-4H-3,4,7-triazadibenzo[cd,f]azulene;

2-[4-(9,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;

methyl{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;

methyl{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;

7-methyl-5-(1,2,3,6-tetrahydropyridin-4-yl)-6,7-dihydro-4H-3,4,7,8-tetraazadibenzo[cd,f]azulene;

{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-[4-(9,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

7-methyl-5-[1-(methylsulfonyl)-1,2,3,6-tetrahydropyridin-4-yl]-6,7-dihydro-4H-3,4,7,8-tetraazadibenzo[cd,f]azulene;

N-methyl-4-(7-methyl-6,7-dihydro-4H-3,4,7,8-tetraazadibenzo[cd,f]azulen-5-yl)-3,6-dihydropyridine-1(2H)-carboxamide;

{3-[4-(10-fluoro-7-methyl-6,7-dihydro-4H-3,4,7-triazadibenzo[cd,f]azulen-5-yl)-3,6-dihydropyridin-1(2H)-yl]cyclobutyl}acetic acid;

trans-4-[4-(10-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

(6S)-6-ethyl-10-fluoro-7-methyl-5-(1,2,3,6-tetrahydropyridin-4-yl)-6,7-dihydro-4H-3,4,7-triazadibenzo[cd,f]azulene;

(6R)-6-ethyl-10-fluoro-7-methyl-5-(1,2,3,6-tetrahydropyridin-4-yl)-6,7-dihydro-4H-3,4,7-triazadibenzo[cd,f]azulene;

9,10-difluoro-7-methyl-5-(1,2,3,6-tetrahydropyridin-4-yl)-6,7-dihydro-4H-3,4,7-triazadibenzo[cd,f]azulene;

[4-(9,10-difluoro-7-methyl-6,7-dihydro-4H-3,4,7-triazadibenzo[cd,f]azulen-5-yl)-3,6-dihydropyridin-1(2H)-yl]acetic acid;

{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-[4-(9,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(9,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

N,N-dimethyl-2-[4-(7-methyl-6,7-dihydro-4H-3,4,7,8-tetraazadibenzo[cd,f]azulen-5-yl)-3,6-dihydropyridin-1(2H)-yl]acetamide;

trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;

(8aR)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

(8aS)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;

(8aR)-7-(10-fluoro-7-methyl-6,7-dihydro-4H-3,4,7-triazadibenzo[cd,f]azulen-5-yl)-1,5,8,8a-tetrahydro[1,3]oxazolo[3,4-a]pyridin-3-one;

[(2R)-4-(10-fluoro-7-methyl-6,7-dihydro-4H-3,4,7-triazadibenzo[cd,f]azulen-5-yl)-1,2,5,6-tetrahydropyridin-2-yl]methanol;

[(2S)-4-(10-fluoro-7-methyl-6,7-dihydro-4H-3,4,7-triazadibenzo[cd,f]azulen-5-yl)-1,2,5,6-tetrahydropyridin-2-yl]methanol;

[(2R)-4-(10-fluoro-7-methyl-6,7-dihydro-4H-3,4,7-triazadibenzo[cd,f]azulen-5-yl)-1,2,3,6-tetrahydropyridin-2-yl]methanol;

2-[4-(9,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

7-methyl-5-(1,2,3,6-tetrahydropyridin-4-yl)-6,7-dihydro-4H-3,4,7-triazadibenzo[cd,f]azulene;

1-fluoro-7-methyl-5-(1,2,3,6-tetrahydropyridin-4-yl)-6,7-dihydro-4H-3,4,7-triazadibenzo[cd,f]azulene;

7-methyl-5-[1-(methylsulfonyl)-1,2,3,6-tetrahydropyridin-4-yl]-6,7-dihydro-4H-3,4,7-triazadibenzo[cd,f]azulene;

1-fluoro-7-methyl-5-[1-(methylsulfonyl)-1,2,3,6-tetrahydropyridin-4-yl]-6,7-dihydro-4H-3,4,7-triazadibenzo[cd,f]azulene;

N,N-dimethyl-2-[4-(7-methyl-6,7-dihydro-4H-3,4,7-triazadibenzo[cd,f]azulen-5-yl)-3,6-dihydropyridin-1(2H)-yl]acetamide;

2-[4-(1-fluoro-7-methyl-6,7-dihydro-4H-3,4,7-triazadibenzo[cd,f]azulen-5-yl)-3,6-dihydropyridin-1(2H)-yl]-N,N-dimethylacetamide;

trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;

{trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}-N,N-dimethylacetamide;

{trans-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

{cis-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

trans-4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetonitrile;

methyl 2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoate;

tert-butyl{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetate;

2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoic acid;

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylethanesulfonamide;

2-[4-(10-fluoro-7-methyl-6,7-dihydro-4H-3,4,7-triazadibenzo[cd,f]azulen-5-yl)-3,6-dihydropyridin-1(2H)-yl]ethanesulfonamide;

{trans-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;
trans-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;
{cis-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;
cis-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;
{4-[4-(10-fluoro-7-methyl-6,7-dihydro-4H-3,4,7-triazadibenzo[cd,f]azulen-5-yl)-2,3,6,7-tetrahydro-1H-azepin-1-yl]cyclohexylidene}acetic acid;
2-{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}-2-methylpropanoic acid;
methyl cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylate;
cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;
trans-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;
cyano{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;
{3-[4-(1,10-difluoro-7-methyl-6,7-dihydro-4H-3,4,7-triazadibenzo[cd,f]azulen-5-yl)-3,6-dihydropyridin-1(2H)-yl]cyclobutyl}acetic acid;
3-[4-(1,10-difluoro-7-methyl-6,7-dihydro-4H-3,4,7-triazadibenzo[cd,f]azulen-5-yl)-3,6-dihydropyridin-1(2H)-yl]cyclobutanecarboxylic acid; and pharmaceutically acceptable salts thereof.

Embodiments of Formula (IIIa)

In another embodiment, the present invention relates to compounds of Formula (IIIa) or a pharmaceutically acceptable salt thereof,

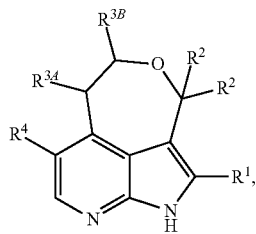

Formula (IIIa)

wherein
$R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, $(O)$, $OH$, $CN$, $NO_2$, F, Cl, Br and I;

$R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, $C(O)OH$, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting $C_1$-$C_8$ alkyl, $C_2$-$C_6$ alkenyl, and $C_2$-$C_6$ alkynyl;

$R^{2B}$ is $C_1$-$C_4$ alkyl;
$R^{3A}$ and $R^{3B}$, taken together, form $R^3$;
$R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, $C(O)H$, $C(O)OH$, $OH$, $CN$, $NO_2$, F, Cl, Br and I;
$R^4$ is selected from the group consisting of hydrogen, $C_1$-$C_4$ alkyl, $C_1$-$C_4$ alkoxy, CN, F, Cl, Br, and I;
$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5$ $C_1$-$C_8$ alkyl, $C_2$-$C_6$ alkenyl, and $C_2$-$C_6$ alkynyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $OH$, $CN$, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHSO_2R^7$, $NR^7SO_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $(O)$, $OH$, $CN$, $NO_2$, F, Cl, Br and I;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycloalkyl, heterocycloalkenyl, $NH_2$, $C(O)H$, $C(O)OH$, $OH$, $CN$, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHSO$_2$R$^8$, NR$^8$SO$_2$R$^8$, NHC(O)OR$^8$, NR$^8$C(O)OR$^8$, NHC(O) NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O) NR$^8$SO$_2$R$^8$, SO$_2$NH$_2$, SO$_2$NHR$^8$, SO$_2$N(R$^8$)$_2$, C(O)H, C(O)OH, (O), OH, CN, NO$_2$, F, Cl, Br and I;

R$^7$, at each occurrence, is independently selected from the group consisting of C$_1$-C$_6$ alkyl, C$_2$-C$_6$ alkenyl, and C$_2$-C$_6$ alkynyl; wherein each R$^7$ C$_1$-C$_6$ alkyl, C$_2$-C$_6$ alkenyl, and C$_2$-C$_6$ alkynyl is optionally substituted with one or more substituents independently selected from the group consisting of OR$^9$, SR$^9$, S(O)R$^9$, SO$_2$R$^9$, C(O) R$^9$, CO(O)R$^9$, OC(O)R$^9$, OC(O)OR$^9$, NH$_2$, C(O)H, C(O)OH, OH, CN, NO$_2$, F, Cl, Br and I;

R$^8$, at each occurrence, is independently selected from the group consisting of C$_1$-C$_6$ alkyl, C$_2$-C$_6$ alkenyl, and C$_2$-C$_6$ alkynyl; wherein each R$^8$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)H, C(O)OH, OH, CN, NO$_2$, F, Cl, Br and I; and R$^9$, at each occurrence, is independently selected from the group consisting of C$_1$-C$_6$ alkyl, C$_2$-C$_6$ alkenyl, and C$_2$-C$_6$ alkynyl.

In one embodiment of Formula (IIIa), R$^1$ is selected from the group consisting of cycloalkyl, cycloalkenyl, aryl, heteroaryl, heterocycloalkyl, and heterocycloalkenyl; wherein the R$^1$ cycloalkyl, cycloalkenyl, aryl, heteroaryl, heterocycloalkyl, and heterocycloalkenyl are optionally substituted with one or more substituents independently selected from the group consisting of R$^5$, OR$^5$, SR$^5$, S(O)R$^5$, SO$_2$R$^5$, C(O) R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC (O)OR$^5$, NR$^5$C(O)OR$^5$, NHC(O)NH$_2$, NHC(O)NHR$^5$, NHC (O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O) NHSO$_2$R$^5$, C(O)NR$^5$SO$_2$R$^5$, SO$_2$NH$_2$, SO$_2$NHR$^5$, SO$_2$N (R$^5$)$_2$, SO$_2$NHC(O)OR$^5$, C(O)H, C(O)OH, OH, CN, NO$_2$, F, Cl, Br and I. In another embodiment of Formula (IIIa), R$^1$ is selected from the group consisting of cycloalkyl, cycloalkenyl, aryl, heteroaryl, heterocycloalkyl, and heterocycloalkenyl; wherein the R$^1$ cycloalkyl, cycloalkenyl, aryl, heteroaryl, heterocycloalkyl, and heterocycloalkenyl are optionally substituted with one or more substituents independently selected from the group consisting of R$^5$, SO$_2$R$^5$, C(O) R$^5$, CO(O)R$^5$, NH$_2$, NHR$^5$, C(O)NHR$^5$, C(O)N(R$^5$)$_2$, SO$_2$NHC(O)OR$^5$, C(O)OH, F, Cl, Br and I. In another embodiment of Formula (IIIa), R$^1$ is selected from the group consisting of cycloalkyl, cycloalkenyl, aryl, heteroaryl, heterocycloalkyl, and heterocycloalkenyl; wherein the R' cycloalkyl, cycloalkenyl, aryl, heteroaryl, heterocycloalkyl, and heterocycloalkenyl are optionally substituted with one or more substituents independently selected from the group consisting of R$^5$, SO$_2$R$^5$, C(O)R$^5$, CO(O)R$^5$, NH$_2$, NHR$^5$, C(O) NHR$^5$, C(O)N(R$^5$)$_2$, SO$_2$NHC(O)OR$^5$, and C(O)OH. In another embodiment of Formula (IIIa), R$^1$ is cycloalkenyl; wherein the R$^1$ cycloalkenyl is optionally substituted as described herein. In another embodiment of Formula (IIIa), R$^1$ is aryl; wherein the R$^1$ aryl is optionally substituted as described herein. In another embodiment of Formula (IIIa), R$^1$ is heteroaryl; wherein the R$^1$ heteroaryl is optionally substituted as described herein. In another embodiment of Formula (IIIa), R' is heterocycloalkyl; wherein the R$^1$ heterocycloalkyl is optionally substituted as described herein. In another embodiment of Formula (IIIa), R$^1$ is heterocycloalkenyl; wherein the R$^1$ heterocycloalkenyl is optionally substituted as described herein. In another embodiment of Formula (IIIa), R$^1$ is pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, 8,8a-dihydro-1H-oxazolo[3,4-a]pyridin-3(5H)-onyl, 5,6-dihydro-1H-oxazolo[3,4-a]pyridin-3(8aH)-onyl, 9-azabicyclo [3.3.1]non-3-enyl, or 8-azabicyclo[3.2.1]oct-2-enyl; wherein the R$^1$ pyrimidine, pyridinyl, phenyl, 1,2,3,6-tetrahydropyridinyl, piperidinyl, cyclohexenyl, 1,2,3,3a,4,6a-hexahydrocyclopenta[c]pyrrolyl, 2,3,6,7-tetrahydro-1H-azepinyl, 8,8a-dihydro-1H-oxazolo[3,4-a]pyridin-3(5H)-onyl, 5,6-dihydro-1H-oxazolo[3,4-a]pyridin-3(8aH)-onyl, 9-azabicyclo[3.3.1] non-3-enyl, and 8-azabicyclo[3.2.1]oct-2-enyl are optionally substituted as described herein for substituents on R$^1$. In another embodiment of Formula (IIIa), R$^1$ is 1,2,3,6-tetrahydropyridinyl; wherein the R$^1$ 1,2,3,6-tetrahydropyridinyl is optionally substituted as described herein for substituents on R$^1$. In one embodiment of Formula (IIIa), R$^2$, at each occurrence, is independently selected from the group consisting of hydrogen, C$_1$-C$_4$ alkyl, cycloalkyl, cycloalkenyl, heteroaryl, heterocycloalkyl, heterocycloalkenyl, C(O)OH, and C(O) OR$^{2B}$; wherein each R$^2$ cycloalkyl, cycloalkenyl, heteroaryl, heterocycloalkyl, and heterocycloalkenyl is optionally substituted with one or more substituents independently selected from the group consisting of C$_1$-C$_8$ alkyl, C$_2$-C$_6$ alkenyl, and C$_2$-C$_6$ alkynyl.

In another embodiment of Formula (IIIa), R$^2$, at each occurrence, is independently selected from the group consisting of hydrogen, C$_1$-C$_4$ alkyl, heteroaryl, C(O)OH, and C(O) OR$^{2B}$; wherein each R$^2$ heteroaryl is optionally substituted with one or more C$_1$-C$_8$ alkyl. In another embodiment of Formula (IIIa), R$^2$, at each occurrence, is independently hydrogen or C$_1$-C$_4$ alkyl. In another embodiment of Formula (IIIa), R$^2$, at each occurrence, is independently hydrogen. In another embodiment of Formula (IIIa), R$^2$, at each occurrence, is independently C$_1$-C$_4$ alkyl.

In one embodiment of Formula (IIIa), R$^3$ is selected from the group consisting of phenyl and pyridinyl; wherein the R$^3$ phenyl and pyridinyl are optionally substituted with one or more substituents independently selected from the group consisting of C$_1$-C$_6$ alkyl, C$_2$-C$_6$ alkenyl, C$_2$-C$_6$ alkynyl, NH$_2$, C(O)H, C(O)OH, OH, CN, NO$_2$, F, Cl, Br and I. In another embodiment of Formula (IIIa), R$^3$ is phenyl; wherein the R$^3$ phenyl is optionally substituted with one or more substituents independently selected from the group consisting of C$_1$-C$_6$ alkyl, C$_2$-C$_6$ alkenyl, C$_2$-C$_6$ alkynyl, NH$_2$, C(O)H, C(O)OH, OH, CN, NO$_2$, F, Cl, Br and I. In another embodiment of Formula (IIIa), R$^3$ is phenyl; wherein the R$^3$ phenyl is optionally substituted with one or more substituents independently selected from the group consisting of F, Cl, Br and I. In another embodiment of Formula (IIIa), R$^3$ is phenyl; wherein the R$^3$ phenyl is optionally substituted with F. In another embodiment of Formula (IIIa), R$^3$ is phenyl; wherein the R$^3$ phenyl is substituted with F. In another embodiment of Formula (IIIa), R$^3$ is phenyl; wherein the R$^3$ phenyl is unsubstituted.

In another embodiment of Formula (IIIa), R$^3$ is pyridinyl; wherein the R$^3$ pyridinyl is optionally substituted with one or more substituents independently selected from the group consisting of C$_1$-C$_6$ alkyl, C$_2$-C$_6$ alkenyl, C$_2$-C$_6$ alkynyl, NH$_2$, C(O)H, C(O)OH, OH, CN, NO$_2$, F, Cl, Br and I. In another embodiment of Formula (IIIa), R$^3$ is pyridinyl; wherein the R$^3$ pyridinyl is optionally substituted with one or more substituents independently selected from the group consisting of F, Cl, Br and I. In another embodiment of Formula (IIIa), R$^3$ is pyridinyl; wherein the R$^3$ pyridinyl is optionally substituted with F. In another embodiment of Formula (IIIa), $R^3$ is pyridinyl; wherein the $R^3$ pyridinyl is substituted with F. In another embodiment of Formula (IIIa), $R^3$ is pyridinyl; wherein the $R^3$ pyridinyl is unsubstituted.

In one embodiment of Formula (IIIa), $R^4$ is selected from the group consisting of hydrogen, $C_1$-$C_4$ alkyl, $C_1$-$C_4$ alkoxy, CN, F, Cl, Br, and I. In another embodiment of Formula (IIIa), $R^4$ is selected from the group consisting of hydrogen, F, Cl, Br, and I. In another embodiment of Formula (IIIa), $R^4$ is F. In another embodiment of Formula (IIIa), $R^4$ is hydrogen.

In one embodiment of Formula (IIIa), $R^1$ is selected from the group consisting of cycloalkenyl, aryl, heteroaryl, heterocycloalkyl, and heterocycloalkenyl; wherein the $R^1$ cycloalkenyl, aryl, heteroaryl, heterocycloalkyl, and heterocycloalkenyl are optionally substituted with one or more substituents independently selected from the group consisting of $R^5$, $SO_2R^5$, $C(O)R^5$, $CO(O)R^5$, $NH_2$, $NHR^5$, $C(O)NHR^5$, $C(O)N(R^5)_2$, $SO_2NHC(O)OR^5$, and $C(O)OH$;

$R^2$, at each occurrence, is independently selected from the group consisting of hydrogen, $C_1$-$C_4$ alkyl, heteroaryl, $C(O)OH$, and $C(O)OR^{2B}$; wherein each $R^2$ heteroaryl is optionally substituted with one or more $C_1$-$C_8$ alkyl;

$R^{2B}$ is $C_1$-$C_4$ alkyl;

$R^{3A}$ and $R^{3B}$, taken together, form $R^3$;

$R^3$ is phenyl; wherein the $R^3$ phenyl is optionally substituted with one or more F;

$R^4$ is selected from the group consisting of hydrogen, F, Cl, Br, and I;

$R^5$, at each occurrence, is independently selected from the group consisting of $C_1$-$C_8$ alkyl, heterocycloalkyl, and cycloalkyl; wherein each $R^5$ $C_1$-$C_8$ alkyl is optionally substituted with one or more substituents independently selected from the group consisting of $R^6$, $OR^6$, $C(O)R^6$, $CO(O)R^6$, $N(R^6)_2$, $C(O)N(R^6)_2$, $SO_2NH_2$, $SO_2NHR^6$, $SO_2N(R^6)_2$, $C(O)OH$, CN, and OH; wherein each $R^5$ cycloalkyl and heterocycloalkyl is optionally substituted with one or more substituents independently selected from the group consisting of $R^7$, $C(O)OR^7$, $C(O)OH$, and OH;

$R^6$, at each occurrence, is independently selected from the group consisting of $C_1$-$C_6$ alkyl, aryl, heterocycloalkyl, and cycloalkyl; wherein each $R^6$ $C_1$-$C_6$ alkyl is optionally substituted with one or more OH; wherein each $R^6$ aryl, cycloalkyl, and heterocycloalkyl is optionally substituted with one or more substituents independently selected from the group consisting of $R^8$, OH, F, Cl, Br and I; and $R^7$, at each occurrence, is independently selected from the group consisting of $C_1$-$C_6$ alkyl, and $C_2$-$C_6$ alkenyl; wherein each $R^7$ $C_1$-$C_6$ alkyl and $C_2$-$C_6$ alkenyl is optionally substituted with one or more substituents independently selected from the group consisting of $CO(O)R^9$, $C(O)OH$, and CN;

$R^8$, at each occurrence, is independently $C_1$-$C_6$ alkyl; wherein each $R^8$ $C_1$-$C_6$ alkyl is optionally substituted with one or more OH; and $R^9$, at each occurrence, is independently $C_1$-$C_6$ alkyl.

Still another embodiment pertains to compounds of Formula (IIIa), selected from the group consisting of:
10-fluoro-5-(1,2,3,6-tetrahydropyridin-4-yl)-4,6-dihydro-7-oxa-3,4-diazadibenzo[cd,f]azulene;
10-fluoro-5-[1-(methylsulfonyl)-1,2,3,6-tetrahydropyridin-4-yl]-4,6-dihydro-7-oxa-3,4-diazadibenzo[cd,f]azulene;
3-[4-(10-fluoro-4,6-dihydro-7-oxa-3,4-diazadibenzo[cd,f] azulen-5-yl)-3,6-dihydropyridin-1(2H)-yl]propane-1,2-diol;
{4-[4-(10-fluoro-4,6-dihydro-7-oxa-3,4-diazadibenzo[cd,f] azulen-5-yl)-3,6-dihydropyridin-1(2H)-yl] cyclohexyl}acetic acid;
and pharmaceutically acceptable salts thereof.

In another embodiment, the present invention relates to pharmaceutical compositions comprising a pharmaceutically acceptable excipient and a therapeutically effective amount of a compound of the invention or a pharmaceutically acceptable salt thereof.

In another embodiment, the present invention relates to methods of treating cancer in a patient, comprising administering to a patient suffering from a cancer a therapeutically effective amount of a compound of the invention, or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

Pharmaceutically acceptable salts have been described in S. M. Berge et al. J. Pharmaceutical Sciences, 1977, 66: 1-19.

Compounds of the invention may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula (Ia), or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of Formula (Ia), alone or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of Formula (Ia). In certain embodiments, the compound of Formula (Ia) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject.

For administration, compounds of the Formula (Ia) can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of Formula (Ia) may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of Formula (Ia), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of Formula (Ia), or pharmaceutically acceptable salts thereof, and pharmaceutical compositions comprising a compound of Formula (Ia), or a pharmaceutically acceptable salt thereof, can be administered to a subject suffering from a CDK9-mediated disorder or condition. A "CDK9-mediated disorder or condition" is characterized by the participation of one or more CDK9 kinases in the inception, manifestation of one or more symptoms or disease markers, severity, or progression of a disorder or condition. An example of a CDK9-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

The term "administering" or "administered" refers to the method of contacting a compound with a subject. Thus, the compounds of Formula (Ia) can be administered by injection, that is, intravenously, intramuscularly, intracutaneously, subcutaneously, intraduodenally, parentally, or intraperitoneally. In certain embodiments, a compound of Formula (Ia) may be administered orally. Also, the compounds described herein can be administered by inhalation, for example, intranasally. Additionally, the compounds of Formula (Ia) can be administered transdermally, topically, via implantation, transdermally, topically, and via implantation. In certain embodiments, the compounds of the Formula (Ia) may be delivered orally. The compounds can also be delivered rectally, bucally, intravaginally, ocularly, andially, or by insufflation. CDK9-mediated disorders and conditions can be treated prophylactically, acutely, and chronically using compounds of Formula (Ia), depending on the nature of the disorder or condition. Typically, the host or subject in each of these methods is human, although other mammals can also benefit from the administration of a compound of Formula (Ia).

The compounds of Formula (Ia) can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Pik) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN®(melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((-)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like.

Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (IIa) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIA-MYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S) protopanaxadiol (aPPD) and 20(S) protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRA-CLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; and $PPh_3$ means triphenylphosphine.

Schemes

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Scheme 1

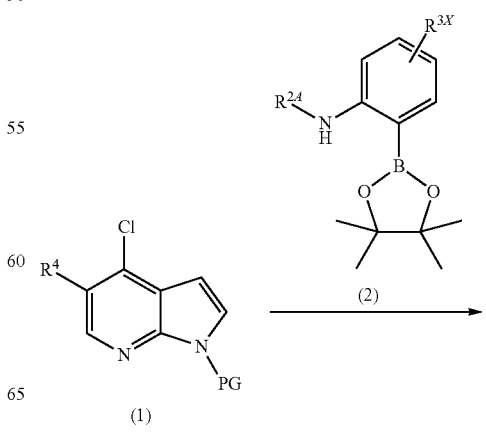

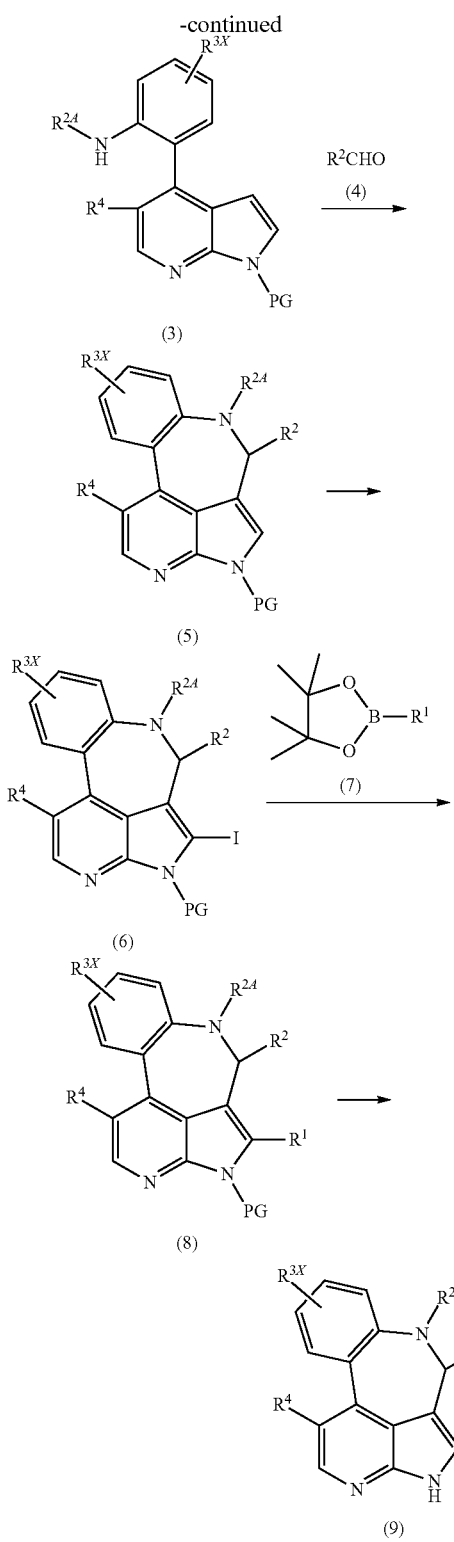

ducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(O), tris(dibenzylideneacetone)dipalladium(O), bis(triphenylphosphine)palladium(II)dichloride, 1,1'-bis(diphenylphosphino)ferrocene-palladium(II)dichloride dichloromethane complex phenylallylchloro[1,3-bis(diisopropylphenyl)-2-imidazol-2-ylidene]palladium(II), and palladium(II)acetate. Examples of suitable bases that may be employed include, but not limited to, carbonates or phosphates of sodium, potassium, and cesium, acetates of sodium or potassium, and cesium fluoride. Examples of suitable ligands include, but are not limited to, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl)ferrocene. Non-limiting examples of suitable solvent include methanol, ethanol, dimethoxyethane, N,N-dimethylformamide, dimethylsulfoxide, dioxane, tetrahydropyran, and water, or a mixture thereof. Compounds of formula (5) can be prepared by reacting compounds of formula (3) with compounds of formula (4), wherein $R^2$ is as described herein for Formula (Ia), in the presence of a Lewis acid such as, but not limited to titanium tetrachloride. The reaction is typically performed at reduced temperature in a solvent such as but not limited to tetrahydrofuran. Compounds of formula (5) can be treated with a base such as, but not limited to, lithium diisopropylamide, followed by iodine, to prepare compounds of formula (6). The reaction is typically performed at a reduced temperature in a solvent such as, but not limited to, tetrahydrofuran. Compounds of formula (6), can be reacted with a boronic ester (or the equivalent boronic acid) of formula (7), wherein $R^1$ is as described herein for Formula (Ia), under Suzuki coupling reaction conditions as described above to provide compounds of formula (8). Compounds of formula (9), which are representative of compounds of Formula (Ia), can be prepared by removal of the protecting group, which typically involves the use of acid or base, depending on the protecting group that is used.

Scheme 2

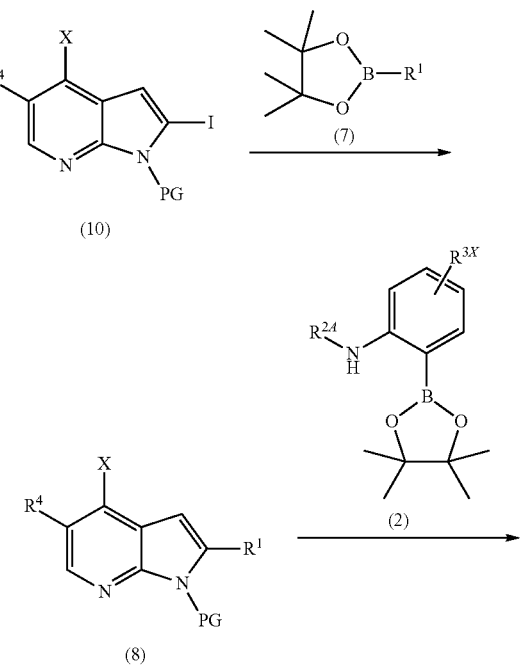

Compounds of formula (1), wherein $R^4$ is as described herein for Formula (Ia) and PG is a protecting group, can be reacted with a boronic ester (or the equivalent boronic acid) of formula (2), wherein $R^{2A}$ is as described herein for Formula (Ia) and $R^{3X}$ is as described for substituents on $R^3$ in Formula (Ia), under Suzuki coupling reaction conditions (N. Miyama and A. Suzuki, Chem. Rev. 1995, 95:2457-2483, J. Organomet. Chem. 1999, 576:147-148) to provide compounds of formula (3). For example, the coupling reaction may be con-

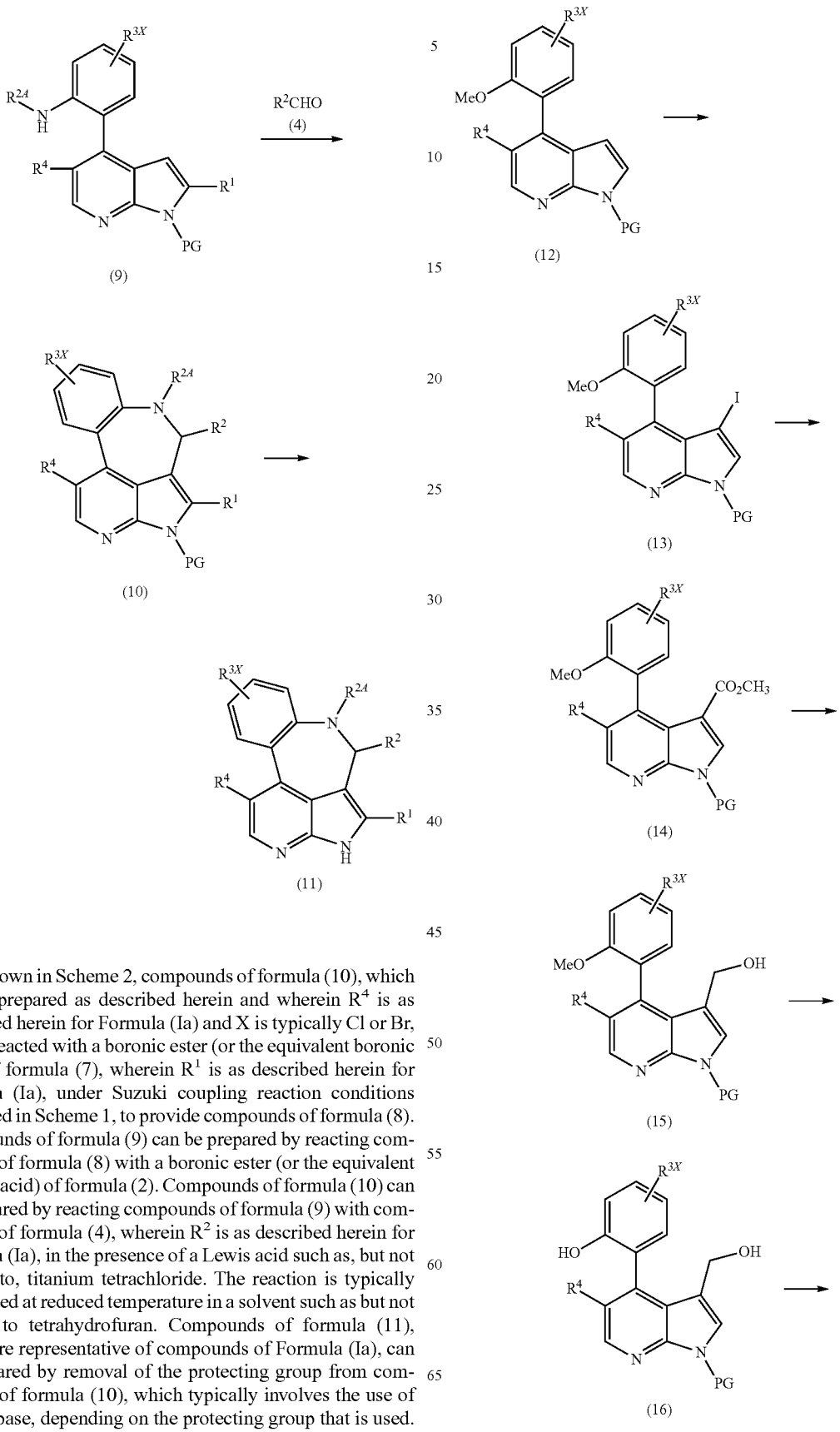

Scheme 3

As shown in Scheme 2, compounds of formula (10), which can be prepared as described herein and wherein $R^4$ is as described herein for Formula (Ia) and X is typically Cl or Br, can be reacted with a boronic ester (or the equivalent boronic acid) of formula (7), wherein $R^1$ is as described herein for Formula (Ia), under Suzuki coupling reaction conditions described in Scheme 1, to provide compounds of formula (8). Compounds of formula (9) can be prepared by reacting compounds of formula (8) with a boronic ester (or the equivalent boronic acid) of formula (2). Compounds of formula (10) can be prepared by reacting compounds of formula (9) with compounds of formula (4), wherein $R^2$ is as described herein for Formula (Ia), in the presence of a Lewis acid such as, but not limited to, titanium tetrachloride. The reaction is typically performed at reduced temperature in a solvent such as but not limited to tetrahydrofuran. Compounds of formula (11), which are representative of compounds of Formula (Ia), can be prepared by removal of the protecting group from compounds of formula (10), which typically involves the use of acid or base, depending on the protecting group that is used.

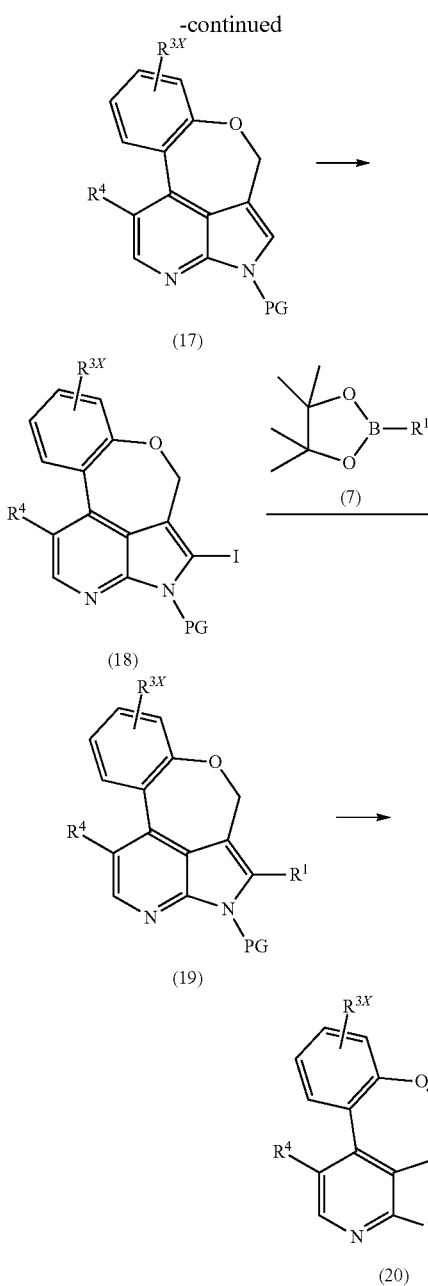

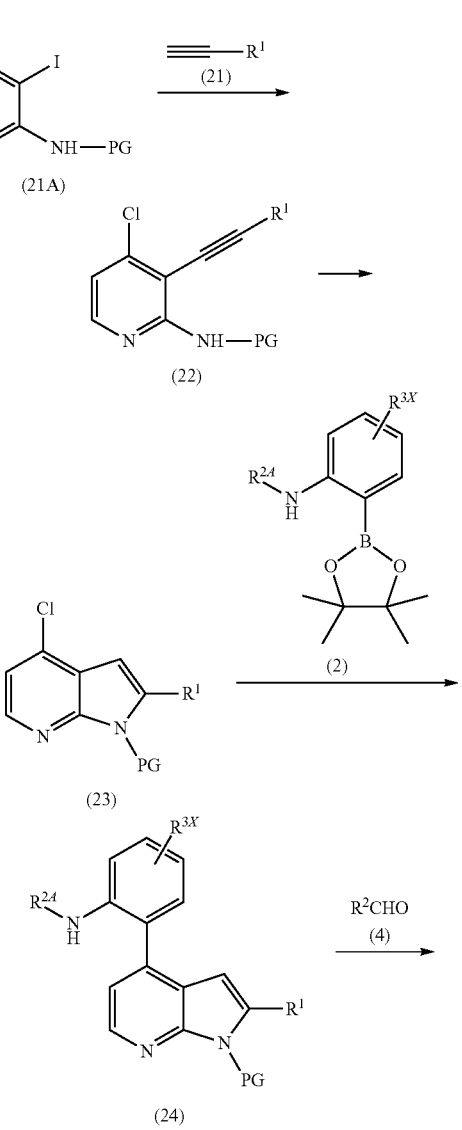

ing compounds of formula (15) with sodium ethanethiolate. The reaction is typically performed at an elevated temperature in a solvent such as, but not limited to, N-methylpyrrolidine. Compounds of formula (16) can be treated with cyanomethylenetributylphosphorane at an elevated temperature to provide compounds of formula (17). The reaction is typically performed at an elevated temperature. Compounds of formula (17) can be treated with a base such as, but not limited to, lithium diisopropylamide, followed by iodine, to provide compounds of formula (18). The reaction is typically performed at a reduced temperature in a solvent such as, but not limited to, tetrahydrofuran. Compounds of formula (18) can be reacted with a boronic ester (or the equivalent boronic acid) of formula (7), wherein $R^1$ is as described herein for Formula (Ia), under Suzuki coupling reaction conditions described in Scheme 1, to provide compounds of formula (19). Compounds of formula (20), which are representative of compounds of Formula (Ia), can be prepared by removal of the protecting group from compounds of formula (19), which typically involves the use of acid or base, depending on the protecting group that is used.

Compounds of formula (12), wherein $R^4$ is as described herein for Formula (Ia) and $R^{3X}$ is as described for substituents on $R^3$ in Formula (Ia), PG is a protecting group, and which can be prepared as described herein, can be reacted with N-iodosuccinimide to provide compounds of formula (13). The reaction is typically performed at ambient temperature in a solvent such as, but not limited to, acetonitrile. Compounds of formula (13) can be treated with carbon monoxide, in the presence of methanol, a base such as but not limited to triethylamine, and a palladium catalyst such as, but not limited to, [1,1'-bis(diphenylphosphino)ferrocene]palladium(II)dichloride, at an elevated temperature to provide compounds of formula (14). Compounds of formula (14) can be treated with lithium aluminum hydride to provide compounds of formula (15). The addition is typically performed at reduced temperature before warming up to ambient temperature in a solvent such as, but not limited to, tetrahydrofuran. Compounds of formula (16) can be prepared by treat- -continued

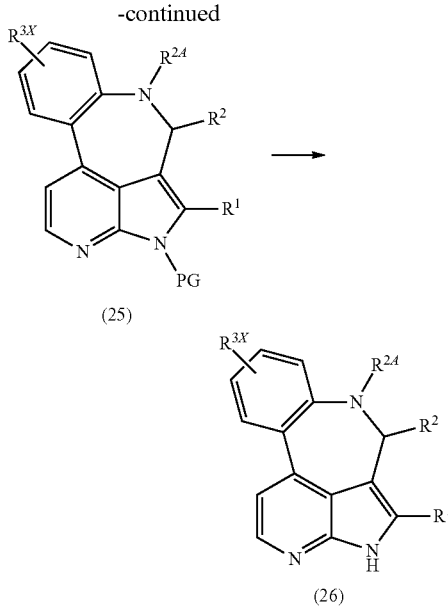

As shown in Scheme 4, compounds of formula (21A), wherein PG is an appropriate protecting group, can be reacted with compounds of formula (21), wherein $R^1$ is as described herein for Formula (Ia), copper(II) iodide, a palladium catalyst such as, but not limited to, bis(triphenylphosphine)palladium chloride, and a base such as, but not limited to, triethylamine, to provide compounds of formula (22). The reaction is typically performed at ambient temperature in a solvent such as, but not limited to, tetrahydrofuran. Compounds of formula (22) can be treated with a base such as, but not limited to, potassium t-butoxide, in the presence of 18-crown-6 to provide compounds of formula (23). The reaction is typically performed at an elevated temperature in a solvent such as, but not limited to, toluene. Compounds of formula (23) can be reacted with a boronic ester (or the equivalent boronic acid) of formula (2), wherein $R^{2A}$ is as described herein for Formula (Ia) and $R^{3X}$ is as described for substituents on $R^3$ in Formula (Ia), under Suzuki coupling reaction conditions as described in Scheme 1, to provide compounds of formula (24). Compounds of formula (25) can be prepared by reacting compounds of formula (24) with compounds of formula (4), wherein $R^2$ is as described herein for Formula (Ia), in the presence of a Lewis acid such as, but not limited to titanium tetrachloride. The reaction is typically performed at reduced temperature in a solvent such as, but not limited to, tetrahydrofuran. Compounds of formula (26), which are representative of compounds of Formula (Ia), can be prepared by removal of the protecting group from compounds of formula (25), which typically involves the use of acid or base, depending on the protecting group that is used.

EXPERIMENTALS

The following examples are presented to provide what is believed to be the most useful and readily understood description of procedures and conceptual aspects of this invention. Each exemplified compound and intermediate was named using ACD/ChemSketch 2012 Release ((Build 59026, 3 Sep. 2012), Advanced Chemistry Development Inc., Toronto, Ontario), or ChemDraw® Ver. 9.0.7 (CambridgeSoft, Cambridge, Mass.).

Example 1

10-fluoro-7-methyl-5-(1,2,3,6-tetrahydropyridin-4-yl)-6,7-dihydro-4H-3,4,7-triazadibenzo[cd,f]azulene Example 1A 4-fluoro-N-methyl-2-(4,4,5,5-tetramethyl-1,3,2-dioxaborolan-2-yl)aniline A mixture of 2-bromo-4-fluoro-N-methylaniline (2 g, 9.8 mmol), 4,4,4',4',5,5,5',5'-octamethyl-2,2'-bi-1,3,2-dioxaborolane (2.99 g, 11.76 mmol), 1,1'-bis(diphenylphosphino)ferrocenedichloro palladium(II) dichloromethane complex (359 mg, 0.490 mmol) and potassium acetate (2.89 g, 29.4 mmol) in 1,2-dimethoxyethane (60 mL) was purged with nitrogen and heated at 80° C. overnight. After cooling, heptane (100 mL) was added and the mixture was filtered through diatomaceous earth and washed with 3:1 heptane/ethyl acetate. The filtrate was concentrated and the residue was purified by flash chromatography on silica gel (Teledyne CombiFlash Rf, 5-30% ethyl acetate in heptane) to provide the title compound, which was contaminated by corresponding boronic acid. MS (DCI/$NH_3$) m/z 252 (M+H)$^+$.

Example 1B 4-chloro-1-tosyl-1H-pyrrolo[2,3-b]pyridine

To a suspension of 4-chloro-7-azaindole (2.32 g, 15.2 mmol) and p-toluenesulfonyl chloride (3.04 g, 15.96 mmol) in toluene (60 mL) and tetrabutylammonium sulfate (0.175 mL, 0.152 mmol, 50% solution in water) was added a solution of sodium hydroxide (0.913 g, 22.8 mmol) in water (36 mL). The biphasic mixture was stirred vigorously overnight, and was partitioned between ethyl acetate and brine. The aqueous layer was separated and extracted with ethyl acetate. The combined organics were dried over sodium sulfate, filtered and concentrated under reduced pressure. The residue was purified by flash chromatography on silica gel (Teledyne CombiFlash Rf, 0-20% ethyl acetate in hexane) to provide the title compound. MS (DCI/$NH_3$) m/z 307 (M+H)$^+$.

Example 1C 4-chloro-2-iodo-1-tosyl-1H-pyrrolo[2,3-b]pyridine

To a cold (−78° C.) solution of Example 1B (4.9 g, 15.97 mmol) in tetrahydrofuran (150 mL) was added freshly prepared lithium diisopropylamide (7.67 mmol) in 25 mL tetrahydrofuran. The mixture was stirred at −78° C. for 1 hour, and a solution of iodine (5.68 g, 22.36 mmol) in tetrahydrofuran (25 mL) was added. After 15 minutes, the reaction was quenched with saturated aqueous sodium thiosulfate and diluted with ethyl acetate. The layers were separated, and the aqueous phase was extracted with ethyl acetate. The combined organics were dried over sodium sulfate, filtered and concentrated under reduced pressure. The residue was purified by flash chromatography on silica gel (Teledyne CombiFlash Rf, 25% ethyl acetate in hexane) to provide the title compound. MS (DCI/$NH_3$) m/z 432 (M+H)$^+$.

Example 1D tert-butyl 4-(4-chloro-1-tosyl-1H-pyrrolo[2,3-b]pyridin-2-yl)-5,6-dihydropyridine-1(2H)-carboxylate A suspension of Example 1C (1.56 g, 3.61 mmol), tert-butyl 4-(4,4,5,5-tetramethyl-1,3,2-dioxaborolan-2-yl)-5,6- dihydropyridine-1(2H)-carboxylate (1.33 g, 4.33 mmol), 1,1'-bis(diphenylphosphino)ferrocene-palladium(II)dichloride dichloromethane complex (0.088 g, 0.108 mmol) and sodium carbonate (0.803 g, 7.57 mmol) in a 6:2:1 mixture of tetrahydrofuran/water/methanol (23 mL) was purged with nitrogen and heated at 85° C. overnight. The mixture was partitioned between ethyl acetate and brine and the aqueous layer was extracted with ethyl acetate. The combined organic layers were washed with brine, dried over magnesium sulfate, filtered and concentrated. The residue was purified by flash chromatography on silica gel (Teledyne CombiFlash Rf, 20% ethyl acetate/heptane) to provide the title compound. MS (DCI/NH$_3$) m/z 488 (M+H)$^+$.

Example 1E tert-butyl 4-(4-chloro-1H-pyrrolo[2,3-b]pyridin-2-yl)-5,6-dihydropyridine-1(2H)-carboxylate A mixture of Example 1D (9 g, 18.44 mmol), sodium hydroxide (1M in water, 92 mL, 92 mmol) in 1,4-dioxane (160 mL) was stirred at 90° C. overnight. After cooling, the mixture was acidified to pH 6 and diluted with water. The solid was collected by filtration, washed with 1:3 dioxane/water and water and dried in vacuo to provide the title compound. MS (DCI/NH$_3$) m/z 488 (M+H)$^+$.

Example 1F tert-butyl 4-(4-(5-fluoro-2-(methylamino)phenyl)-1H-pyrrolo[2,3-b]pyridin-2-yl)-5,6-dihydropyridine-1(2H)-carboxylate A mixture of Example 1E (1.5 g, 4.47 mmol), Example 1A (1.12 g, 4.47 mmol), phenylallylchloro[1,3-bis(diisopropylphenyl)-2-imidazol-2-ylidene]palladium(II) (87 mg, 0.134 mmol) and potassium phosphate (2.84 g, 13.40 mmol) was suspended in tetrahydrofuran (30 mL) and water (10 mL), and purged with nitrogen and heated at 60° C. for 2 hours. After cooling, the mixture was partitioned between ethyl acetate and brine. The organic phase was washed with brine, and concentrated. The residue was purified by flash chromatography on silica gel (Teledyne CombiFlash Rf, 50-90% ethyl acetate in heptane) to provide the title compound. MS (DCI/NH$_3$) m/z 425 (M+H)$^+$.

Example 1G tert-butyl 4-(7-fluoro-4-methyl-3,4-dihydro-1H-1,4,11-triazadibenzo[cd,f]azulen-2-yl)-5,6-dihydropyridine-1(2H)-carboxylate To a suspension of Example 1F (2.35 g, 5.56 mmol) and paraformaldehyde (835 mg, 27.8 mmol) in tetrahydrofuran (150 mL) was slowly added titanium tetrachloride (1M in tetrahydrofuran, 11.12 mL, 11.12 mmol) at 10'C over 10 minutes. After the addition, the cooling bath was removed and the mixture was stirred at room temperature overnight. A solution of sodium hydroxide (2 g) in water (10 mL) was added and the mixture was partitioned between ethyl acetate and brine. The organic phase was washed with water, concentrated and the residue was purified by flash chromatography on silica gel (Teledyne CombiFlash Rf, 60-90% ethyl acetate in hexane) to provide the title compound. MS (DCI/NH$_3$) m/z 435 (M+H)$^+$.

Example 1H 10-fluoro-7-methyl-5-(1,2,3,6-tetrahydropyridin-4-yl)-6,7-dihydro-4H-3,4,7-triazadibenzo[cd,f]azulene To a solution of Example 1G (1.755 g, 4.04 mmol) in dichloromethane (50 mL) was added trifluoroacetic acid (10 mL). The solution was stirred at room temperature for 1 hour and concentrated. The residue was partitioned between ethyl acetate and dilute sodium hydroxide, and the organic phase was washed with water and concentrated to provide the title compound as the free base. $^1$H NMR (400 MHz, DMSO-d$_6$): δ 2.79-2.84 (m, 2H), 2.90 (s, 3H), 3.36-3.41 (m, 2H), 3.84-3.88 (m, 2H), 4.20 (m, 2H), 5.88 (s, 1H), 7.26-7.37 (m, 2H), 7.43 (d, J=5.49 Hz, 1H), 7.76 (dd, J=10.53, 2.90 Hz, 1H), 8.32 (d, J=5.49 Hz, 1H), 9.00 (s, 1H), 11.91 (s, 1H). MS (DCI/NH$_3$) m/z 335 (M+H)$^+$.

Example 2 tert-butyl 4-(10-fluoro-7-methyl-6,7-dihydro-4H-3,4,7-triazadibenzo[cd,f]azulen-5-yl)-3,6-dihydropyridine-1(2H)-carboxylate The title compound was prepared as described in Example 1G. $^1$H NMR (400 MHz, DMSO-d$_6$): δ 1.45 (s, 9H), 2.57-2.61 (m, 2H), 2.88 (s, 3H), 3.56 (t, J=5.34 Hz, 2H), 4.05-4.09 (m, 2H), 4.15 (s, 2H), 5.89 (s, 1H), 7.19-7.33 (m, 3H), 7.69 (dd, J=10.53, 2.90 Hz, 1H), 8.23 (d, J=5.19 Hz, 1H), 11.53 (s, 1H). MS (DCI/NH$_3$) m/z 335 (M+H)$^+$.

Example 3 ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate Example 3A (tert-butoxycarbonyl)((4-(dimethylamino)pyridin-1-ium-1-yl)sulfonyl)amide To a solution of t-butanol (2.6 mL, 27.2 mmol) in dichloromethane (20 mL) was added dropwise with ice cooling chlorosulfonyl isocyanate (2.4 mL, 27.6 mL) over 15 minutes. After stirring for 15 minutes, 4-(dimethylamino)pyridine (6.9 g, 56.5 mmol) was added, the cooling bath was removed, and more dichloromethane (100 mL) was added. The mixture was stirred at room temperature for 1 hour, and diluted with 130 mL dichloromethane. The mixture was washed with water and brine, and the organic layer was dried over sodium sulfate, filtered, and concentrated in vacuo to provide the title compound as a crystalline solid. MS (DCI/NH$_3$) m/z 301 (M+H)$^+$.

Example 3B ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate To a suspension of Example 1 (62 mg, 0.185 mmol) in dichloromethane (5 mL) was added triethylamine (0.129 mL, 0.927 mmol) and Example 3A (61 mg, 0.222 mmol) at room temperature. The mixture was stirred overnight and was purified by flash chromatography (Teledyne CombiFlash Rf, 0-15% methanol in 2:1 ethyl acetate/hexane) to provide the title compound. $^1$H NMR (400 MHz, DMSO-d$_6$): δ 1.18 (t, J=7.02 Hz, 3H), 2.68-2.70 (m, 2H), 2.89 (s, 3H), 3.51 (t, J=5.65 Hz, 2H), 4.05 (d, J=2.44 Hz, 2H), 4.10 (q, J=7.22 Hz, 2H), 4.15 (s, 2H), 5.90 (s, 1H), 7.21-7.33 (m, 3H), 7.70 (dd, J=10.38, 3.05 Hz, 1H), 8.24 (d, J=5.19 Hz, 1H), 11.41 (s, 1H), 11.57 (s, 1H). MS (ESI$^+$) m/z 486 (M+H)$^+$.

Example 4

10-fluoro-7-methyl-5-[1-(methylsulfonyl)-1,2,3,6-tetrahydropyridin-4-yl]-6,7-dihydro-4H-3,4,7-triazadibenzo[cd,f]azulene To a suspension of Example 1 (60 mg, 0.179 mmol) in dichloromethane (5 mL) was added triethylamine (0.1 mL, 0.718 mmol) and methanesulfonyl chloride (31 mg, 0.269 mmol). The solution was stirred at room temperature overnight and was purified by flash chromatography on silica gel (Teledyne CombiFlash Rf, 0-15% methanol in 2:1 ethyl acetate/hexane) to provide the title compound. $^1$H NMR (400 MHz, DMSO-d$_6$): δ 2.72-2.75 (m, 2H), 2.89 (s, 3H), 2.97 (s, 3H), 3.41 (t, J=5.65 Hz, 2H), 3.93-3.96 (m, J=2.75 Hz, 1H), 4.15 (s, 2H), 5.91 (s, 1H), 7.22-7.34 (m, 3H), 7.70 (dd, J=10.38, 3.05 Hz, 1H), 8.25 (d, J=5.19 Hz, 1H), 11.59 (s, 1H). MS (ESI$^+$) m/z 413 (M+H)$^+$.

Example 5

10-fluoro-5-[1-(methylsulfonyl)-1,2,3,6-tetrahydropyridin-4-yl]-6,7-dihydro-4H-3,4,7-triazadibenzo[cd,f]azulene

Example 5A

4-bromo-1-tosyl-1H-pyrrolo[2,3-b]pyridine

To a suspension of 4-bromo-1H-pyrrolo[2,3-b]pyridine (15 g, 76 mmol) and p-toluenesulfonyl chloride (21.77 g, 114 mmol) in toluene (200 mL) was added a solution of tetrabutylammonium hydrogen sulfate (2.58 g, 7.61 mmol) in water (10 mL) and the mixture was cooled to 0° C. A solution of sodium hydroxide (9.13 g, 228 mmol) in water (30 mL) was added and the mixture was stirred at room temperature overnight. The mixture was diluted with ethyl acetate, and the organic layer was washed with brine, dried over sodium sulfate, filtered and concentrated to provide the title compound. MS (CI) m/z 352 (M+H)$^+$.

Example 5B

4-bromo-2-iodo-1-tosyl-1H-pyrrolo[2,3-b]pyridine

To a solution of Example 5A (25 g, 71.2 mmol) in tetrahydrofuran (600 ml) at −78° C. was slowly added lithium diisopropylamide (2M in tetrahydrofuran, 39.1 mL, 78 mmol) and the mixture was stirred at −78° C. for 1 hour. A solution of iodine (19.87 g, 78 mmol) in tetrahydrofuran (100 mL) was added slowly and the mixture was stirred for 3 hours. Saturated aqueous sodium thiosulfate, water and ethyl acetate were added and the aqueous layer was extracted with ethyl acetate. The combined organics were dried over sodium sulfate, filtered and concentrated to provide the title compound. MS (CI) m/z 477 (M+H)$^+$.

Example 5C tert-butyl 4-(4-bromo-1-tosyl-1H-pyrrolo[2,3-b]pyridin-2-yl)-5,6-dihydropyridine-1(2H)-carboxylate To a suspension of Example 5B (20 g, 41.9 mmol), tert-butyl 4-(4,4,5,5-tetramethyl-1,3,2-dioxaborolan-2-yl)-5,6-dihydropyridine-1(2H)-carboxylate (16.85 g, 54.5 mmol), and tetrakis(triphenylphosphine)palladium(0) (4.84 g, 4.19 mmol) in N,N-dimethylformamide (500 mL) was added a solution of sodium bicarbonate (7.04 g, 84 mmol) in water (40 mL) and the mixture was stirred at 80° C. for 12 hours. Saturated aqueous sodium thiosulfate, water and ethyl acetate were added and the aqueous layer was extracted with ethyl acetate. The combined organics were dried over sodium sulfate, filtered and concentrated to provide the title compound. MS (CI) m/z 532 (M+H)$^+$.

Example 5D

4-bromo-2-(1,2,3,6-tetrahydropyridin-4-yl)-1-tosyl-1H-pyrrolo[2,3-b]pyridine A mixture of Example 5C (8 g, 15.02 mmol) and trifluoroacetic acid (11.58 mL, 150 mmol) in dichloromethane (100 mL) was stirred at 20° C. for 12 hours and the mixture was concentrated to provide the title compound as a trifluoroacetic acid salt. MS (CI) m/z 432 (M+H)$^+$.

Example 5E

4-bromo-2-(1-(methylsulfonyl)-1,2,3,6-tetrahydropyridin-4-yl)-1-tosyl-1H-pyrrolo[2,3-b]pyridine To a mixture of Example 5D (6 g, 13.88 mmol) and triethylamine (9.67 mL, 69.4 mmol) in N,N-dimethylformamide (150 mL) at 0° C. was added methanesulfonyl chloride (2.16 mL, 27.8 mmol) and the mixture was stirred at 0° C. for 2 hours. The mixture was diluted with water, filtered and the solid was washed with water to provide the title compound. MS (CI) m/z 511 (M+H)$^+$.

Example 5F

4-bromo-2-(1-(methylsulfonyl)-1,2,3,6-tetrahydropyridin-4-yl)-1H-pyrrolo[2,3-b]pyridine To a solution of Example 5E (6.5 g, 12.73 mmol) in 1,4-dioxane (50 mL) was added a solution of sodium hydroxide (1.528 g, 38.2 mmol) in water (5 mL) and the mixture was stirred at 60° C. for 12 hours. The mixture was concentrated and the residue was suspended in water and N,N-dimethylformamide. The suspension was filtered and the solid was washed with ethyl acetate to provide the title compound. MS (CI) m/z 356 (M+H)$^+$.

Example 5G

4-fluoro-2-(2-(1-(methylsulfonyl)-1,2,3,6-tetrahydropyridin-4-yl)-1H-pyrrolo[2,3-b]pyridin-4-yl)aniline To a mixture of Example 5F (500 mg, 1.404 mmol), 4-fluoro-2-(4,4,5,5-tetramethyl-1,3,2-dioxaborolan-2-yl) aniline (399 mg, 1.684 mmol) and dichlorobis(triphenylphosphine)palladium (II) (99 mg, 0.14 mmol) in 7:3:2 1,2-dimethoxyethane/water/ethanol (14 mL) was added 2.45 mL 2M aqueous sodium carbonate. The suspension was stirred at room temperature for a few seconds and then stirred in a microwave reactor (Biotage Initiator) at 150° C. for 30 minutes. The mixture was partitioned between ethyl acetate and brine and the organic phase was concentrated. The residue was stirred in 2% methanol in methylene chloride and the solid was collected by filtration to provide the title compound. The mother liquor was purified by flash chromatography on silica gel (Teledyne CombiFlash Rf, 0-15% methanol in dichloromethane) to provide additional title compound. MS (ESI$^+$) m/z 387 (M+H)$^+$.

Example 5H 10-fluoro-5-[1-(methylsulfonyl)-1,2,3,6-tetrahydro-pyridin-4-yl]-6,7-dihydro-4H-3,4,7-triazadibenzo[cd,f]azulene To a suspension of Example 5G (490 mg, 1.268 mmol) and paraformaldehyde (190 mg, 6.34 mmol) in tetrahydrofuran (40 mL) was slowly added titanium tetrachloride (1 M in tetrahydrofuran, 2.54 mL, 2.54 mmol) over 5 minutes. This mixture was stirred at room temperature overnight, and partitioned between ethyl acetate and brine. The aqueous phase was extracted with ethyl acetate and the combined organic layers were washed with brine, and concentrated. The residue was purified by flash chromatography on silica gel (Teledyne CombiFlash Rf, 0-15% methanol in 2:1 ethyl acetate/hexane) to provide the title compound. $^1$H NMR (400 MHz, DMSO-d$_6$): δ 2.71-2.73 (m, 2H), 2.97 (s, 3H), 3.41 (t, J=5.65 Hz, 2H), 3.94 (d, J=2.75 Hz, 2H), 4.21 (d, J=2.75 Hz, 2H), 5.93 (d, J=19.84 Hz, 2H), 7.09-7.13 (m, 2H), 7.37 (d, J=5.49 Hz, 1H), 7.73 (d, J=10.68 Hz, 1H), 8.23 (d, J=5.49 Hz, 1H), 11.56 (s, 1H). MS (ESI$^+$) m/z 399 (M+H)$^+$.

Example 6

10-fluoro-5-[1-(methylsulfonyl)-1,2,3,6-tetrahydro-pyridin-4-yl]-7-propyl-6,7-dihydro-4H-3,4,7-triaza-dibenzo[cd,f]azulene To a suspension of Example 5 (50 mg, 0.125 mmol) and propionaldehyde (22 mg, 0.376 mmol) in methanol (7 mL) was added zinc chloride (34 mg, 0.251 mmol). This mixture was stirred at room temperature for 30 minutes, sodium cyanoborohydride (16 mg, 0.251 mmol) was added, and the mixture was heated at 60° C. overnight. The mixture was concentrated and the residue was dissolved in water/trifluoroacetic acid/methanol. The mixture was filtered and purified by a Gilson HPLC system (Zorbax, C-18 column, eluting with 0.1% trifluoroacetic acid in water/0.1% trifluoroacetic acid in acetonitrile; 0-100% gradient) to provide the title compound as trifluoroacetate salt. The trifluoroacetate salt was converted to the hydrochloride salt by dissolving in methylene chloride and methanol and treating with hydrogen chloride in ether. Concentration provided the title compound as the hydrochloride salt. $^1$H NMR (400 MHz, CD$_3$OD): δ 0.73 (t, J=7.32 Hz, 3H), 1.45-1.53 (m, 2H), 2.76-2.82 (m, 2H), 2.97 (s, 3H), 3.11-3.16 (m, 2H), 3.59 (t, J=5.49 Hz, 2H), 4.10 (d, J=2.75 Hz, 2H), 4.72 (s, 2H), 6.13 (s, 1H), 7.43-7.48 (m, 1H), 7.76 (dd, J=8.85, 4.88 Hz, 1H), 7.86 (d, J=6.41 Hz, 1H), 8.02 (dd, J=9.92, 2.90 Hz, 1H), 8.44 (d, J=6.10 Hz, 1H). MS (ESI$^+$) m/z 441 (M+H)$^+$.

Example 7

10-fluoro-5-[1-(methylsulfonyl)-1,2,3,6-tetrahydro-pyridin-4-yl]-7-(tetrahydro-2H-pyran-4-ylmethyl)-6,7-dihydro-4H-3,4,7-triazadibenzo[cd,f]azulene The title compound was prepared as the hydrochloride salt, as described in Example 6, substituting tetrahydro-2H-pyran-4-carbaldehyde for propionaldehyde. $^1$H NMR (400 MHz, DMSO-d$_6$): δ 0.91-1.01 (m, 2H), 1.38 (d, J=12.82 Hz, 2H), 1.48-1.55 (m, 1H), 2.67-2.72 (m, 1H), 2.80 (d, J=7.02 Hz, 2H), 2.98 (s, 3H), 3.09 (t, J=10.99 Hz, 2H), 3.43 (t, J=5.65 Hz, 2H), 3.69 (dd, J=11.14, 2.59 Hz, 2H), 3.94-3.98 (m, 2H), 4.17-4.22 (m, 2H), 5.92 (s, 1H), 7.17-7.25 (m, 1H), 7.29-7.38 (m, 2H), 7.72 (dd, J=10.53, 2.90 Hz, 1H), 8.25 (d, J=5.19 Hz, 1H), 11.56 (s, 1H). MS (ESI$^+$) m/z 497 (M+H)$^+$.

Example 8 tert-butyl 4-(6-ethyl-10-fluoro-7-methyl-6,7-dihydro-4H-3,4,7-triazadibenzo[cd,f]azulen-5-yl)-3,6-dihydropyridine-1(2H)-carboxylate To a suspension of Example 1F (100 mg, 0.237 mmol) and propionaldehyde (55 mg, 0.947 mmol) in tetrahydrofuran (6 mL) was slowly added titanium tetrachloride (1M in tetrahydrofuran, 0.473 mL, 0.473 mmol) and the mixture was stirred at room temperature for 60 hours. The mixture was partitioned between ethyl acetate and aqueous sodium hydroxide, and the organic phase was washed with brine and concentrated. The residue was purified by flash chromatography on silica gel (Teledyne CombiFlash Rf, 50-80% ethyl acetate in hexane) to provide the title compound. $^1$H NMR (400 MHz, CDCl$_3$): δ 0.91 (t, J=7.32 Hz, 3H), 1.31-1.39 (m, 2H), 1.53 (s, 9H), 2.68 (s, 2H), 2.95 (s, 3H), 3.64-3.70 (m, 1H), 3.74-3.81 (m, 1H), 4.13-4.24 (m, 2H), 4.32 (dd, J=8.85, 5.80 Hz, 1H), 6.09 (s, 1H), 7.08-7.14 (m, 1H), 7.25-7.30 (m, 2H), 7.62 (dd, J=10.38, 3.05 Hz, 1H), 8.25 (d, J=5.19 Hz, 1H), 10.95 (s, 1H). MS (ESI$^+$) m/z 463 (M+H)$^+$.

Example 9

6-ethyl-10-fluoro-7-methyl-5-(1,2,3,6-tetrahydropy-ridin-4-yl)-6,7-dihydro-4H-3,4,7-triazadibenzo[cd,f]azulene dihydrochloride The title compound was prepared as described in Example 1H, substituting Example 8 for Example 1G. $^1$H NMR (400 MHz, CD$_3$OD): δ 0.96 (t, J=7.32 Hz, 3H), 1.41-1.48 (m, 1H), 1.70-1.75 (m, 1H), 2.94-2.98 (m, 2H), 3.04 (s, 3H), 3.53-3.62 (m, 2H), 4.00-4.06 (m, 2H), 6.31 (s, 1H), 7.46-7.52 (m, 1H), 7.83 (dd, J=8.85, 4.88 Hz, 1H), 7.94 (d, J=6.41 Hz, 1H), 8.11 (dd, J=9.92, 2.90 Hz, 1H), 8.48 (d, J=6.41 Hz, 1H). MS (ESI$^+$) m/z 363 (M+H)$^+$.

Example 10

10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene Example 10A tert-butyl 4-(7-fluoro-4-methyl-3-(1-methyl-1H-pyrazol-4-yl)-3,4-dihydro-1H-1,4,11-triazadibenzo[cd,f]azulen-2-yl)-5,6-dihydropyridine-1(2H)-carboxylate The title compound was prepared as described in Example 8, substituting 1-methyl-1H-pyrazole-4-carbaldehyde for propionaldehyde.

Example 10B

10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene The title compound was prepared as described in Example 1H, substituting Example 10A for Example 1G. $^1$H NMR (400 MHz, CD$_3$OD): δ 2.69-2.75 (m, 1H), 3.02 (s, 3H), 3.07-3.13 (m, 1H), 3.47-3.55 (m, 2H), 3.64 (s, 3H), 3.81-3.96 (m, 2H), 5.72 (s, 1H), 5.89 (t, J=3.36 Hz, 1H), 7.08 (s, 1H), 7.11-7.15 (m, 3H), 7.71 (d, J=6.10 Hz, 1H), 7.75-7.79 (m, 1H), 8.42 (d, J=6.10 Hz, 1H). MS (ESI$^+$) m/z 416 (M+H)$^+$.

Example 11

6-ethyl-10-fluoro-7-methyl-5-[1-(methylsulfonyl)-1,2,3,6-tetrahydropyridin-4-yl]-6,7-dihydro-4H-3,4,7-triazadibenzo[cd,f]azulene To a suspension of Example 9 (35 mg, 0.08 mmol) in dichloromethane (5 mL) was added triethylamine (0.07 mL, 0.482 mmol) and methanesulfonyl chloride (14 mg, 0.121 mmol). The mixture was stirred at room temperature for 2 hours, and purified by flash chromatography on silica gel (Teledyne CombiFlash Rf, 0-15% methanol in 2:1 ethyl acetate/hexane) to provide the title compound. $^1$H NMR (400 MHz, CD$_3$OD): δ 0.81-0.86 (m, 3H), 1.22-1.30 (m, 1H), 1.37-1.45 (m, 1H), 2.62-2.69 (m, 1H), 2.73-2.81 (m, 1H), 2.88 (s, 3H), 2.98 (s, 3H), 3.36-3.41 (m, 1H), 3.42-3.48 (m, 1H), 3.96 (dd, J=5.80, 3.05 Hz, 2H), 4.28 (dd, J=9.00, 5.65 Hz, 1H), 6.11 (s, 1H), 7.21-7.29 (m, 2H), 7.35 (d, J=5.49 Hz, 1H), 7.77 (dd, J=10.68, 2.75 Hz, 1H), 8.22 (d, J=5.19 Hz, 1H), 11.51 (s, 1H). MS (ESI$^+$) m/z 441 (M+H)$^+$.

Example 12

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide To a suspension of Example 1 (200 mg, 0.598 mmol) in N,N-dimethylformamide (6 mL) was added triethylamine (0.5 mL, 3.59 mmol) and 2-chloro-N,N-dimethylacetamide (87 mg, 0.718 mmol) and the mixture was heated at 70° C. for 2 hours. After cooling, the mixture was partitioned between ethyl acetate and brine and the organic phase was washed with brine and concentrated. The residue was purified by flash chromatography on silica gel (Teledyne CombiFlash Rf, 10-20% methanol in 2:1 ethyl acetate/hexane) to provide the title compound. $^1$H NMR (400 MHz, DMSO-d$_6$): δ 2.58-2.61 (m, 2H), 2.74 (t, J=5.49 Hz, 2H), 2.84 (s, 3H), 2.89 (s, 3H), 3.03 (s, 3H), 3.24-3.26 (m, 2H), 3.30 (s, 2H), 4.15 (s, 2H), 5.87 (s, 1H), 7.21-7.25 (m, 1H), 7.28 (d, J=5.49 Hz, 1H), 7.31 (d, J=5.49 Hz, 1H), 7.69 (dd, J=10.38, 3.05 Hz, 1H), 8.22 (d, J=5.19 Hz, 1H), 11.47 (s, 1H). MS (ESI$^+$) m/z 420 (M+H)$^+$.

Example 13

4-(10-fluoro-7-methyl-6,7-dihydro-4H-3,4,7-triazadibenzo[cd,f]azulen-5-yl)-N-methyl-3,6-dihydropyridine-1(2H)-carboxamide To a suspension of Example 1 (80 mg, 0.239 mmol) in dichloromethane (7 mL) was added triethylamine (0.1 mL, 0.718 mmol) and N-succinimidyl-N-methylcarbamate (62 mg, 0.359 mmol) and the mixture was stirred at room temperature overnight. Methanol was added to dissolve the solid, and the mixture was purified by flash chromatography on silica gel (Teledyne CombiFlash Rf, 5-20% methanol in 2:1 ethyl acetate/hexane) to provide the title compound. $^1$H NMR (400 MHz, DMSO-d$_6$): δ 2.55-2.58 (m, 2H), 2.61 (d, J=4.58 Hz, 3H), 2.89 (s, 3H), 3.54 (t, J=5.49 Hz, 2H), 4.02-4.04 (m, 2H), 4.15 (s, 2H), 5.90 (s, 1H), 6.47-6.50 (m, 1H), 7.21-7.26 (m, 1H), 7.27-7.30 (m, 1H), 7.31-7.33 (m, 1H), 7.69 (dd, J=10.68, 3.05 Hz, 1H), 8.23 (d, J=5.19 Hz, 1H), 11.52 (s, 1H). MS (ESI$^+$) m/z 420 (M+H)$^+$.

Example 14

10-fluoro-5-(1,2,3,6-tetrahydropyridin-4-yl)-4,6-dihydro-7-oxa-3,4-diazadibenzo[cd,f]azulene

Example 14A

4-(5-fluoro-2-methoxyphenyl)-1H-pyrrolo[2,3-b]pyridine

A solution of 4-chloro-1H-pyrrolo[2,3-b]pyridine (15 g, 98 mmol), (5-fluoro-2-methoxyphenyl)boronic acid (18.38 g, 108 mmol), potassium phosphate (62.6 g, 295 mmol), and {1,3-bis(2,6-diisopropylphenyl)imidazol-2-ylidene}chloro{3-phenylallyl}palladium(II) (0.637 g, 0.983 mmol) in tetrahydrofuran (400 mL) and water (133 mL) was purged with nitrogen and heated at 65° C. overnight. The mixture was cooled and poured into water. Ethyl acetate was added, the mixture was stirred for 15 minutes and the organic layer was washed with brine. The combined aqueous extracts were extracted with ethyl acetate and the combined organic layers were dried over sodium sulfate, filtered, and concentrated. The residue was dissolved in dichloromethane and placed on a bed of silica gel equilibrated in 30% ethyl acetate/heptanes that was packed in a coarse Buchner funnel. The material was eluted with 30-40% ethyl acetate/heptanes to provide the title compound. MS (ESI$^+$) m/z 243.2 (M+H)$^+$.

Example 14B

4-(5-fluoro-2-methoxyphenyl)-3-iodo-1H-pyrrolo[2,3-b]pyridine

To a solution of Example 14A (22.4 g, 92 mmol) in acetonitrile (1 L) under nitrogen was added N-iodosuccinimide (21.84 g, 97 mmol) at ambient temperature. After stirring approximately 1 hour the reaction was complete. Solids started to crash out of the mixture and they were filtered off and washed with acetonitrile to provide the title compound as a solid. The filtrate was concentrated, mixed with 50 mL of dichloromethane, and sonicated for 30 minutes. Some solid did not dissolve and was filtered, washed with dichloromethane, and dried to give additional title compound. The filtrate was purified on an Analogix MPLC using a silica gel column eluting with 30-40% ethyl acetate/heptanes to give additional title compound. MS (ESI$^+$) m/z 369.0 (M+H)$^+$.

Example 14C

4-(5-fluoro-2-methoxyphenyl)-3-iodo-1-((2-(trimethylsilyl)ethoxy)methyl)-1H-pyrrolo[2,3-b]pyridine A solution of Example 14B (15.1 g, 41.0 mmol) in tetrahydrofuran under nitrogen was cooled to −8° C. and 60% sodium hydride in mineral oil (2.461 g, 61.5 mmol) was added in portions at a rate such that the temperature was maintained at or below −5° C. The solution was stirred 30 minutes at −5° C. and 2-(trimethylsilyl)ethoxymethyl chloride (8.73 mL, 49.2 mmol) was added dropwise over 15 minutes. The mixture was stirred for 30 minutes at −5° C. and allowed to warm to ambient temperature and stirred overnight. The reaction was quenched carefully with aqueous saturated ammonium chloride and diluted with ethyl acetate. The organic layer was washed with brine, dried over sodium sulfate, filtered, and concentrated. The residue was purified on an Analogix MPLC using a silica gel column eluting with 100% heptane followed by 7% ethyl acetate/heptanes to provide the title compound. MS (ESI$^+$) m/z 498.8 (M+H)$^+$.

Example 14D methyl 4-(5-fluoro-2-methoxyphenyl)-14(2-(trimethylsilyl)ethoxy)methyl)-1H-pyrrolo[2,3-b]pyridine-3-carboxylate To Example 14C (2.55 g, 5.12 mmol) and [1,1'-bis(diphenylphosphino)ferrocene]palladium(II)dichloride (0.075 g, 0.102 mmol) in a 50 mL pressure bottle was add methanol (20 ml) and triethylamine (1.426 mL, 10.23 mmol). The mixture was degassed with argon several times and charged with carbon monoxide and the mixture was heated at 70° C. for 16 hours. The mixture was concentrated and the concentrate was treated with ethyl acetate. After filtration, the filtrate was concentrated and purified on silica using the ISCO Companion flash system eluting with heptanes/ethyl acetate (7:3) to provide the title compound. MS (ESI$^+$) m/z 431.0 (M+H)$^+$.

Example 14E (4-(5-fluoro-2-methoxyphenyl)-1-((2-(trimethylsilyl)ethoxy)methyl)-1H-pyrrolo[2,3-b]pyridin-3-yl)methanol To a solution of Example 14D (2.12 g, 4.92 mmol) in tetrahydrofuran (60 mL) at 0° C. was added 2M lithium aluminum hydride in tetrahydrofuran (2.71 mL, 5.42 mmol) and the mixture was stirred at room temperature for 3 hours. The mixture was quenched with ice and saturated sodium bicarbonate and extracted with ethyl acetate (twice). The combined organic layers were dried over magnesium sulfate, filtered, concentrated, and purified on silica using the ISCO Companion flash system eluting with heptanes/ethyl acetate (6:4 to 4:6) to provide the title compound. MS (ESI$^+$) m/z 403.2 (M+H)$^+$.

Example 14F 4-fluoro-2-(3-(hydroxymethyl)-1-((2-(trimethylsilyl)ethoxy)methyl)-1H-pyrrolo[2,3-b]pyridin-4-yl)phenol A mixture of Example 14E (920.0 mg, 2.286 mmol) and sodium ethanethiolate (641 mg, 6.86 mmol) in N-methylpyrrolidine (40 mL) was stirred at 120° C. for 3 hours. The mixture was treated with brine, acidified to pH 4-5 with 5% citric acid, and extracted with ethyl acetate (twice). The combined organic layers were washed with brine, dried over magnesium sulfate, filtered, concentrated, and purified on silica using the ISCO Companion flash system eluting with heptanes/ethyl acetate (5:5 to 4:6) to provide the title compound. MS (ESI$^+$) m/z 389.0 (M+H)$^+$.

Example 14G 7-fluoro-1-((2-(trimethylsilyl)ethoxy)methyl)-1,3-dihydro-4-oxa-1,11-diazadibenzo[cd,f]azulene A mixture of cyanomethylenetributylphosphorane (0.617 mL, 2.353 mmol) and Example 14F (795.0 mg, 2.046 mmol) in toluene (35 mL) was stirred at 70° C. for 5 hours. The mixture was concentrated and purified on silica using the ISCO Companion flash system eluting with heptanes/ethyl acetate (8:2) to provide the title compound. MS (ESI$^+$) m/z 370.9 (M+H)$^+$.

Example 14H 7-fluoro-2-iodo-1-((2-(trimethylsilyl)ethoxy)methyl)-1,3-dihydro-4-oxa-1,11-diazadibenzo[cd,f]azulene To a solution of Example 14G (310.0 mg, 0.837 mmol) in tetrahydrofuran (8 mL) at −78° C. was added 2M lithium diisopropylamide (1.255 mL, 2.51 mmol) in tetrahydrofuran/heptane/ethylbenzene dropwise. After 60 minutes, a solution of iodine (531 mg, 2.092 mmol) in tetrahydrofuran (3 mL) was cannulated into the reaction mixture and the mixture was stirred at −78° C. for 2 hours. The mixture was quenched with aqueous sodium thiosulfate and extracted with ethyl acetate (twice). The combined organic layers were dried over magnesium sulfate, filtered, concentrated, and purified on silica using the ISCO Companion flash system eluting with heptanes/ethyl acetate (9:1 to 8:2) to provide the title compound. MS (ESI$^+$) m/z 496.8 (M+H)$^+$.

Example 14I tert-butyl 4-(7-fluoro-1-((2-(trimethylsilyl)ethoxy)methyl)-1,3-dihydro-4-oxa-1,11-diazadibenzo[cd,f]azulen-2-yl)-5,6-dihydropyridine-1(2H)-carboxylate A mixture of Example 14H (200 mg, 0.403 mmol), tert-butyl 4-(4,4,5,5-tetramethyl-1,3,2-dioxaborolan-2-yl)-5,6-dihydropyridine-1(2H)-carboxylate (137 mg, 0.443 mmol), tetrakis(triphenylphosphine)palladium(0) (23.28 mg, 0.020 mmol), and sodium bicarbonate solution (1.5 mL, 0.403 mmol) in N,N-dimethylformamide (6 mL) was degassed and heated at 80° C. for 5 hours. After cooling, the mixture was filtered, treated with water and brine and extracted with ethyl acetate (twice). The combined organic layers were washed with brine, dried over magnesium sulfate, filtered, concentrated, and purified on silica using the ISCO Companion flash system eluting with ethyl acetate/heptanes (15:85 to 20:80) to provide the title compound. MS (ESI$^+$) m/z 552.0 (M+H)$^+$.

Example 14J 10-fluoro-5-(1,2,3,6-tetrahydropyridin-4-yl)-4,6-dihydro-7-oxa-3,4-diazadibenzo[cd,f]azulene A mixture of Example 14I (150 mg, 0.272 mmol) and concentrated hydrochloric acid (0.5 mL, 16.46 mmol) in tetrahydrofuran (3 mL) was heated at 65° C. for 5 hours. After cooling, the precipitate was filtered, rinsed with tetrahydrofuran, and oven-dried to provide the title compound as a hydrochloride salt. $^1$H NMR (400 MHz, methanol-d$_4$) δ 2.92-2.99 (m, 2H), 3.56 (t, J=6.1 Hz, 2H), 3.97-4.03 (m, 2H), 5.31

(bs, 2H), 6.00-6.06 (m, 1H), 7.35 (dd, J=6.3, 1.7 Hz, 2H), 7.84-7.95 (m, 2H), 8.44 (d, J=6.4 Hz, 1H). MS (ESI$^+$) m/z 322.1 (M+H)$^+$.

Example 15

10-fluoro-5-[1-(methylsulfonyl)-1,2,3,6-tetrahydropyridin-4-yl]-4,6-dihydro-7-oxa-3,4-diazadibenzo [cd,f]azulene To a solution of Example 14J (79.5 mg, 0.202 mmol) in N-methylpyrrolidine (2 mL) was added triethylamine (0.169 mL, 1.210 mmol) and methanesulfonyl chloride (0.031 mL, 0.403 mmol) and the mixture was stirred for 3 hours. The mixture was treated with water (~5 mL) and stirred for 10 minutes. The precipitate was filtered, washed with water, and oven-dried. The free base was suspended in 1 mL methanol and treated with 1 mL of 2M hydrogen chloride in diethyl ether. The suspension was diluted with 1 mL of diethyl ether, stirred for 20 minutes, filtered, washed with ether, and vacuum oven-dried to provide the title compound as a hydrochloride salt. $^1$H NMR (500 MHz, DMSO-d$_6$) δ 2.74 (bs, 2H), 2.98 (s, 3H), 3.42 (t, J=5.7 Hz, 2H), 3.94-3.99 (m, 2H), 5.23 (bs, 2H), 5.93 (bs, 1H), 7.21-7.36 (m, 2H), 7.59 (d, J=5.5 Hz, 1H), 7.91 (dd, J=10.1, 2.9 Hz, 1H), 8.35 (d, J=5.4 Hz, 1H), 12.10 (bs, 1H). MS (ESI$^+$) m/z 400.2 (M+H)$^+$.

Example 16

[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride Example 16A tert-butyl 2-(4-(7-fluoro-4-methyl-3,4-dihydro-1H-1, 4,11-triazadibenzo[cd,f]azulen-2-yl)-5,6-dihydropyridin-1(2H)-yl)acetate To a suspension of Example 1 (500 mg, 1.495 mmol) in N,N-dimethylformamide (15 mL) was added triethylamine (1.25 mL, 8.97 mmol) and tert-butyl bromoacetate (350 mg, 1.794 mmol) and the mixture was stirred at room temperature overnight. The mixture was partitioned between ethyl acetate and brine and the organic phase was washed with brine and concentrated. The residue was purified by flash chromatography on silica gel (Teledyne CombiFlash Rf, 10-20% methanol in 2:1 ethyl acetate/hexane) to provide the title compound. MS (ESI$^+$) m/z 449 (M+H)$^+$.

Example 16B

[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride To a solution of Example 16A (550 mg, 1.226 mmol) in dichloromethane (5 mL) was added trifluoroacetic acid (10 mL) and the mixture was stirred at room temperature overnight. After concentration, the residue was by purified by a Gilson HPLC system (Zorbax, C-18 column, eluting with 0.1% trifluoroacetic acid in water/0.1% trifluoroacetic acid in acetonitrile; 0-100% gradient) to provide the title compound as the trifluoroacetate salt. The trifluoroacetate salt was converted to hydrochloride salt by dissolving in dichloromethane and methanol and treating with 2N hydrogen chloride in ether. Concentration provided the title compound as the hydrochloride salt. $^1$H NMR (400 MHz, DMSO-d$_6$): δ 2.79-2.86 (m, 4H), 2.94-3.03 (m, 2H), 3.80-3.95 (m, 2H), 4.05-4.10 (m, 2H), 4.28 (s, 2H), 4.42-4.53 (m, 2H), 5.93 (s, 1H), 7.47 (s, 1H), 7.68 (d, J=4.58 Hz, 1H), 7.99 (s, 1H), 8.41 (d, J=5.19 Hz, 1H), 10.79 (s, 1H), 12.57 (s, 1H). MS (ESI$^+$) m/z 420 (M+H)$^+$.

Example 17

2-[4-(10-fluoro-7-methyl-6,7-dihydro-4H-3,4,7-triazadibenzo[cd,f]azulen-5-yl)-3,6-dihydropyridin-1 (2H)-yl]-1-[(2S)-2-(hydroxymethyl)pyrrolidin-1-yl] ethanone To a solution of Example 16 (140 mg, 0.300 mmol) and L-prolinol (61 mg, 0.6 mmol) in N,N-dimethylformamide (4 mL) was added triethylamine (0.251 mL, 1.797 mmol) and 1-[bis(dimethylamino)methylene]-1H-1,2,3-triazolo[4,5-b] pyridinium 3-oxidhexafluorophosphate (137 mg, 0.359 mmol). The mixture was stirred at room temperature for 60 hours, diluted with 6 mL water and acidified with trifluoroacetic acid. The solution was filtered and purified by a Gilson HPLC system (Zorbax, C-18 column, eluting with 0.1% trifluoroacetic acid in water/0.1% trifluoroacetic acid in acetonitrile; 0-100% gradient) to provide the title compound as the trifluoroacetate salt. The material was dissolved in dichloromethane and methanol and treated with hydrogen chloride in ether. Concentration provided the title compound as the hydrochloride salt. $^1$H NMR (400 MHz, CD$_3$OD): δ 1.95-2.05 (m, 2H), 2.07-2.14 (m, 2H), 3.07 (s, 3H), 3.09-3.14 (m, 2H), 3.51-3.55 (m, 2H), 3.57-3.62 (m, 1H), 3.65-3.69 (m, 1H), 3.72-3.78 (m, 1H), 3.88-3.93 (m, 1H), 4.16-4.19 (m, 2H), 4.31-4.43 (m, 2H), 4.76 (s, 2H), 6.10 (s, 1H), 7.50 (dd, J=6.87, 2.29 Hz, 1H), 7.85 (dd, J=8.85, 4.88 Hz, 1H), 7.94 (d, J=6.10 Hz, 1H), 8.04 (dd, J=9.61, 2.59 Hz, 1H), 8.51 (d, J=6.10 Hz, 1H). MS (ESI$^+$) m/z 476 (M+H)$^+$.

Example 18

2-[4-(10-fluoro-7-methyl-6,7-dihydro-4H-3,4,7-triazadibenzo[cd,f]azulen-5-yl)-3,6-dihydropyridin-1 (2H)-yl]-1-(3-hydroxyazetidin-1-yl)ethanone The title compound was prepared as described in Example 17, substituting 3-hydroxyazetidine hydrochloride for L-prolinol. $^1$H NMR (400 MHz, DMSO-d$_6$): δ 2.60-2.63 (m, 2H), 2.74-2.77 (m, 2H), 2.89 (s, 3H), 3.14-3.16 (m, 2H), 3.24-3.27 (m, 2H), 3.61 (dd, J=10.22, 4.43 Hz, 1H), 3.91-3.94 (m, 1H), 4.07 (dd, J=9.77, 7.02 Hz, 1H), 4.14 (s, 2H), 4.33-4.39 (m, 1H), 4.44-4.49 (m, 1H), 5.71 (d, J=6.10 Hz, 1H), 5.86 (s, 1H), 7.21-7.33 (m, 3H), 7.69 (dd, J=10.68, 3.05 Hz, 1H), 8.23 (d, J=5.19 Hz, 1H), 11.49 (s, 1H). MS (ESI$^+$) m/z 448 (M+H)$^+$.

Example 19

2-[4-(10-fluoro-7-methyl-6,7-dihydro-4H-3,4,7-triazadibenzo[cd,f]azulen-5-yl)-3,6-dihydropyridin-1 (2H)-yl]-N-(2-hydroxyethyl)-N-methylacetamide The title compound was prepared as described in Example 17, substituting 2-(methylamino)ethanol for L-prolinol. $^1$H NMR (400 MHz, DMSO-d$_6$): δ 2.60 (m, 1H), 2.74 (m, 2H), 2.84 (s, 3H), 3.07 (s, 3H), 3.24 (dd, J=10.68, 2.14 Hz, 2H), 3.29 (m, 2H), 3.34-3.36 (m, 2H), 3.47-3.50 (m, 1H), 3.56 (q, J=4.98 Hz, 1H), 4.14 (s, 2H), 4.66 (t, J=5.34 Hz, 1H), 4.91 (t, J=5.19 Hz, 1H), 5.86 (s, 1H), 7.20-7.34 (m, 3H), 7.69 (dd, J=10.38, 3.05 Hz, 1H), 8.22 (d, J=5.19 Hz, 1H), 11.48 (s, 1H). MS (ESI+) m/z 450 (M+H)+.

Example 20

10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene

Example 20A tert-butyl 4-(7-fluoro-3,4-dimethyl-3,4-dihydro-1H-1,4,11-triazadibenzo[cd,f]azulen-2-yl)-5,6-dihydropyridine-1(2H)-carboxylate The title compound was prepared as described in Example 8, substituting acetaldehyde for propionaldehyde.

Example 20B 7-fluoro-3,4-dimethyl-2-(1,2,3,6-tetrahydropyridin-4-yl)-3,4-dihydro-1H-1,4,11-triazadibenzo[cd,f]azulene The title compound was prepared as described in Example 1H, substituting Example 20A for Example 1G.

Example 20C 10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene The title compound was prepared as described in Example 11, substituting Example 20B for Example 9. $^1$H NMR (400 MHz, DMSO-$d_6$): δ 1.03 (d, J=6.71 Hz, 3H), 2.80 (s, 3H), 2.89-2.95 (m, 2H), 2.97 (s, 3H), 3.42 (q, J=5.49 Hz, 2H), 3.91-3.98 (m, 2H), 4.43 (q, J=7.02 Hz, 1H), 6.07 (s, 1H), 7.20-7.25 (m, 2H), 7.36 (d, J=5.49 Hz, 1H), 7.73-7.75 (m, 1H), 8.25 (d, J=5.19 Hz, 1H), 11.52 (s, 1H). MS (ESI+) m/z 427 (M+H)+.

Example 21

10-fluoro-7-methyl-5-(piperidin-4-yl)-6,7-dihydro-4H-3,4,7-triazadibenzo[cd,f]azulene

Example 21A dimethyl 1-diazo-2-oxopropylphosphonate

To a suspension of sodium hydride (0.32 g, 13.2 mmol) in 100 mL 6/1 benzene/tetrahydrofuran was added dimethyl 2-oxopropylphosphonate (2.0 g, 12 mmol) dropwise at 0° C. After the addition, the mixture was stirred at 0° C. for 1 hour and p-toluenesulfonyl azide (13% in toluene, 19.2 g, 12.6 mmol) was added dropwise. The mixture was allowed to warm to room temperature and stirred overnight. Water was added and extracted with ethyl acetate (twice). The combined organic layers were washed with brine and concentrated to provide the crude title compound which was used in the next step without purification. MS (DCI/NH$_3$) m/z 193 (M+H)+.

Example 21B tert-butyl 4-ethynylpiperidine-1-carboxylate

To a solution of tert-butyl 4-formylpiperidine-1-carboxylate (2.2 g, 10.4 mmol) and potassium carbonate (2.9 g, 20.8 mmol) in methanol (100 mL) was added Example 21A (2.0 g, 10.4 mmol) in methanol (20 mL) and the mixture was stirred at room temperature overnight. Water was added and the mixture was extracted with ethyl acetate (twice). The combined organic layers were washed with brine and concentrated. Purification by flash chromatography on silica gel (Teledyne CombiFlash Rf, 1:5 ethyl acetate/hexane) gave the title compound. MS (DCI/NH$_3$) m/z 210 (M+H)+.

Example 21C tert-butyl 4-((2-(tert-butoxycarbonylamino)-4-chloropyridin-3-yl)ethynyl)piperidine-1-carboxylate To a solution of Example 21B (1.6 g, 7.7 mmol) in tetrahydrofuran (20 mL) was added tert-butyl 4-chloro-3-iodopyridin-2-ylcarbamate (2.98 g, 8.4 mmol), copper(II) iodide (58 mg, 0.3 mmol), bis(triphenylphosphine)palladium chloride (268 mg, 0.38 mmol) and triethylamine (2.3 g, 23 mmol). The mixture was purged with nitrogen and was stirred at room temperature for 3 days. The mixture was filtrated and the filtrate was concentrated and purified by flash chromatography on silica gel (Teledyne CombiFlash Rf, 1/3 ethyl acetate/hexane) to provide the title compound. MS (DCI/NH$_3$) m/z 436 (M+H)+.

Example 21D tert-butyl 4-(4-chloro-1H-pyrrolo[2,3-b]pyridin-2-yl)piperidine-1-carboxylate To a solution of Example 21C (3.2 g, 7.3 mmol) in toluene (50 mL) was added potassium t-butoxide (2.0 g, 18.24 mmol) and 18-crown-6 (193 mg, 0.73 mmol) and the mixture was heated at 80° C. overnight. Water was added and the mixture was extracted with ethyl acetate (three times). The combined organic phases were concentrated and the residue was washed with ethyl acetate to provide the title compound. MS (DCI/NH$_3$) m/z 336 (M+H)+.

Example 21E 10-fluoro-7-methyl-5-(piperidin-4-yl)-6,7-dihydro-4H-3,4,7-triazadibenzo[cd,f]azulene The title compound was prepared as described in Examples 1F-H, substituting Example 21D for Example 1E. $^1$H NMR (400 MHz, CD$_3$OD): δ 2.14-2.21 (m, 3H), 2.25-2.35 (m, 2H), 3.09 (s, 3H), 3.21-3.29 (m, 3H), 3.51-3.63 (m, 3H), 7.50-7.56 (m, 1H), 7.92-7.96 (m, 1H), 8.01 (d, J=6.41 Hz, 1H), 8.12 (dd, J=9.77, 2.75 Hz, 1H), 8.50 (d, J=6.41 Hz, 1H). MS (ESI+) m/z 337 (M+H)+.

Example 22 tert-butyl[4-(10-fluoro-7-methyl-6,7-dihydro-4H-3,4,7-triazadibenzo[cd,f]azulen-5-yl)piperidin-1-yl]acetate The title compound was prepared as described in Example 16A, substituting Example 21E for Example 1. $^1$H NMR (400 MHz, DMSO-$d_6$): δ 1.43 (s, 9H), 1.66-1.70 (m, 2H), 1.89-1.97 (m, 2H), 2.29-2.34 (m, 2H), 2.74-2.80 (m, 1H), 2.88 (s, 3H), 2.94 (d, J=11.29 Hz, 2H), 3.15 (s, 2H), 4.09 (s, 2H), 7.18-7.22 (m, 1H), 7.24-7.28 (m, 2H), 7.69 (dd, J=10.68, 3.05 Hz, 1H), 8.16 (d, J=5.19 Hz, 1H), 11.35 (s, 1H). MS (ESI+) m/z 451 (M+H)+.

Example 23

[4-(10-fluoro-7-methyl-6,7-dihydro-4H-3,4,7-triazadibenzo[cd,f]azulen-5-yl)piperidin-1-yl]acetic acid The title compound was prepared essentially as described in Examples 16B, substituting Example 22 for Example 16A. $^1$H NMR (400 MHz, DMSO-$d_6$): δ 1.97-2.09 (m, 2H), 2.23-2.38 (m, 2H), 2.84 (s, 3H), 3.30 (m, 2H), 3.58-3.68 (m, 4H), 4.14-4.20 (m, 2H), 4.47-4.60 (m, 2H), 7.48 (s, 1H), 7.71 (d, J=5.80 Hz, 1H), 8.03 (s, 1H), 8.37 (d, J=5.49 Hz, 1H), 10.26 (s, 1H), 12.55 (s, 1H). MS (ESI$^+$) m/z 395 (M+H)$^+$.

Example 24

2-[4-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide The title compound was prepared as described in Example 17, substituting 3-(methylamino)cyclobutanol hydrochloride for L-prolinol. $^1$H NMR (400 MHz, DMSO-$d_6$): δ 1.18-1.27 (m, 1H), 1.88-1.95 (m, 1H), 2.00-2.06 (m, 1H), 2.31-2.38 (m, 1H), 2.42-2.46 (m, 1H), 2.57-2.61 (m, 2H), 2.69-2.75 (m, 2H), 2.82 (s, 1.5H), 2.88 (s, 3H), 2.96 (s, 1.5H), 3.22 (d, J=19.84 Hz, 1H), 3.29-3.34 (m, 2H), 3.76-3.82 (m, 1H), 4.14 (s, 2H), 5.08 (t, J=6.10 Hz, 1H), 5.87 (s, 1H), 7.20-7.33 (m, 3H), 7.69 (dd, J=10.53, 2.90 Hz, 1H), 8.22 (d, J=5.19 Hz, 1H), 11.47 (d, J=5.19 Hz, 1H). MS (ESI$^+$) m/z 476 (M+H)$^+$.

Example 25

2-[4-(10-fluoro-7-methyl-6,7-dihydro-4H-3,4,7-triazadibenzo[cd,f]azulen-5-yl)-3,6-dihydropyridin-1(2H)-yl]-N-methyl-2-oxoethanesulfonamide To a suspension of Example 1 (80 mg, 0.239 mmol) and 2-(N-methylsulfamoyl)acetic acid (44 mg, 0.287 mmol) in N,N-dimethylformamide (5 mL) was added triethylamine (0.2 mL, 1.435 mmol) and 1-[bis(dimethylamino)methylene]-1H-1,2,3-triazolo[4,5-b]pyridinium 3-oxidhexafluorophosphate (109 mg, 0.287 mmol). The mixture was stirred at room temperature overnight and partitioned between ethyl acetate and brine. The organic phase was washed with brine, concentrated and purified by flash chromatography on silica gel (Teledyne CombiFlash Rf, 15-25% methanol in 2:1 ethyl acetate/hexane) to provide the title compound. $^1$H NMR (400 MHz, DMSO-$d_6$): δ 2.61-2.66 (m, 3H), 2.71-2.73 (m, 1H), 2.88 (s, 3H), 3.73-3.79 (m, 2H), 4.16 (d, J=7.32 Hz, 2H), 4.23 (d, J=1.83 Hz, 1H), 4.34-4.39 (m, 3H), 5.90 (d, J=12.51 Hz, 1H), 7.14 (d, J=4.58 Hz, 1H), 7.21-7.26 (m, 1H), 7.28-7.33 (m, 2H), 7.68-7.71 (m, 1H), 8.24 (d, J=5.19 Hz, 1H), 11.58 (s, 1H). MS (ESI$^+$) m/z 470 (M+H)$^+$.

Example 26

2-[4-(10-fluoro-7-methyl-6,7-dihydro-4H-3,4,7-triazadibenzo[cd,f]azulen-5-yl)piperidin-1-yl]-1-[(2S)-2-(hydroxymethyl)pyrrolidin-1-yl]ethanone The title compound was prepared as described in Example 17, substituting Example 23 for Example 16. $^1$H NMR (400 MHz, DMSO-$d_6$): δ 1.68 (d, J=12.21 Hz, 2H), 1.78-1.98 (m, 6H), 2.17-2.25 (m, 2H), 2.78 (t, J=12.05 Hz, 1H), 2.88 (s, 3H), 2.98 (d, J=10.07 Hz, 1H), 3.11-3.16 (m, 2H), 3.25-3.30 (m, 2H), 3.49-3.56 (m, 2H), 3.93-3.99 (m, 1H), 4.09 (s, 2H), 4.76 (t, J=5.49 Hz, 1H), 7.16-7.23 (m, 1H), 7.23-7.28 (m, 2H), 7.69 (dd, J=10.53, 2.90 Hz, 1H), 8.16 (d, J=5.19 Hz, 1H), 11.34 (s, 1H). MS (ESI$^+$) m/z 478 (M+H)$^+$.

Example 27

2-[4-(10-fluoro-7-methyl-6,7-dihydro-4H-3,4,7-triazadibenzo[cd,f]azulen-5-yl)piperidin-1-yl]-N-(2-hydroxyethyl)-N-methylacetamide The title compound was prepared as described in Example 17, substituting Example 23 for Example 16 and 2-(methylamino)ethanol for L-prolinol. $^1$H NMR (400 MHz, DMSO-$d_6$): δ 2.05-2.10 (m, 1H), 2.21-2.26 (m, 1H), 2.38 (t, J=12.66 Hz, 1H), 2.56-2.64 (m, 1H), 3.04 (s, 2H), 3.07 (s, 3H), 3.10 (s, 1H), 3.33-3.41 (m, 2H), 3.45-3.65 (m, 4H), 3.72-3.76 (m, 2H), 3.78-3.84 (m, 2H), 4.34 (s, 1H), 4.42 (s, 1H), 4.68-4.72 (m, 2H), 7.42-7.48 (m, 1H), 7.75 (dd, J=8.70, 4.73 Hz, 1H), 7.86-7.92 (m, 1H), 8.00 (dd, J=10.07, 2.44 Hz, 1H), 8.41-8.47 (m, 1H). MS (ESI$^+$) m/z 452 (M+H)$^+$.

Example 28 ethyl 10-fluoro-7-methyl-5-(1,2,3,6-tetrahydropyridin-4-yl)-6,7-dihydro-4H-3,4,7-triazadibenzo[cd,f]azulene-6-carboxylate To a solution of Example 1F (150 mg, 0.355 mmol) and ethyl 2-oxoacetate (145 mg, 1.42 mmol) in tetrahydrofuran (5 mL) was added titanium tetrachloride (0.7 mL, 1M in dichloromethane) and the mixture was stirred at room temperature overnight. The mixture was partitioned between ethyl acetate and brine and the organic phase was concentrated and purified by reverse-phase HPLC on a Zorbax RX-C18 column using a gradient of 15-100% methanol/0.1% aqueous trifluoroacetic acid to afford the title compound as the trifluoroacetic acid salt. $^1$H NMR (400 MHz, methanol-$d_4$) δ 1.00 (t, J=7.1 Hz, 3H), 2.52-2.91 (m, 1H), 3.09 (dtd, J=17.9, 5.5, 2.9 Hz, 1H), 3.22 (s, 3H), 3.38-3.73 (m, 2H), 3.80-4.18 (m, 4H), 5.11 (s, 1H), 5.96 (tt, J=3.3, 1.6 Hz, 1H), 7.26 (ddd, J=9.0, 7.5, 3.0 Hz, 1H), 7.41 (dd, J=9.1, 5.2 Hz, 1H), 7.57 (d, J=6.0 Hz, 1H), 7.72 (dd, J=10.1, 3.0 Hz, 1H), 8.34 (d, J=5.9 Hz, 1H). MS (ESI$^+$) m/z 407 (M+H)$^+$.

Example 29

N-[4-(10-fluoro-7-methyl-6,7-dihydro-4H-3,4,7-triazadibenzo[cd,f]azulen-5-yl)cyclohex-3-en-1-yl]-D-valine

Example 29A 4-chloro-2-(1,4-dioxaspiro[4.5]dec-7-en-8-yl)-1-tosyl-1H-pyrrolo[2,3-b]pyridine The title compound was prepared using the procedure described in Example 1D, using 4,4,5,5-tetramethyl-2-(1,4-dioxaspiro[4.5]dec-7-en-8-yl)-1,3,2-dioxaborolane in place of tert-butyl 4-(4,4,5,5-tetramethyl-1,3,2-dioxaborolan-2-yl)-5,6-dihydropyridine-1(2H)-carboxylate. LCMS: 445 (M+H)$^+$.

Example 29B 2-(2-(1,4-dioxaspiro[4.5]dec-7-en-8-yl)-1-tosyl-1H-pyrrolo[2,3-b]pyridin-4-yl)-4-fluoro-N-methylaniline The title compound was prepared using the procedure described in Example 1F, using Example 29A in place of Example 1E. LCMS: 534 (M+H)$^+$.

Example 29C 7-fluoro-4-methyl-2-(1,4-dioxaspiro[4.5]dec-7-en-8-yl)-1-tosyl-3,4-dihydro-1H-1,4,11-triazadibenzo[cd,f]azulene The title compound was prepared using the procedure described in Example 1 G, using Example 29B in place of Example 1F. LCMS: 546 (M+H)$^+$.

Example 29D 7-fluoro-4-methyl-2-(1,4-dioxaspiro[4.5]dec-7-en-8-yl)-3,4-dihydro-1H-1,4,11-triazadibenzo[cd,f]azulene The title compound was prepared using the procedure described in Example 1E, using Example 29C in place of Example 1D. LCMS: 392 (M+H)$^+$.

Example 29E 4-(7-fluoro-4-methyl-3,4-dihydro-1H-1,4,11-triazadibenzo[cd,f]azulen-2-yl)cyclohex-3-enone The title compound was prepared using the procedure described in Example 1H, using Example 29D in place of Example 1G. LCMS: 348 (M+H)$^+$.

Example 29F

N-[4-(10-fluoro-7-methyl-6,7-dihydro-4H-3,4,7-triazadibenzo[cd,f]azulen-5-yl)cyclohex-3-en-1-yl]-D-valine To a mixture of Example 29E (70 mg, 0.2 mmol), triethylamine (51.3 mg, 0.51 mmol) and acetic acid (69 mg, 1.2 mmol) in dichloromethane (2 mL) was added (R)-tert-butyl 2-amino-3-methylbutanoate (80 mg, 0.46 mmol) and MP-cyanoborohydride (378 mg, 0.92 mmol) and the mixture was stirred at room temperature overnight. The mixture was diluted with ethyl acetate, filtered, concentrated and purified by flash chromatography using a Teledyne CombiFlash Rf (30% ethyl acetate in heptane) to provide the BOC-protected intermediate. The intermediate was dissolved in dichloromethane (10 mL) and treated with trifluoroacetic acid (1 mL). The mixture was concentrated and purified by reverse-phase HPLC on a Zorbax RX-C18 column using a gradient of 15-100% methanol/0.1% aqueous trifluoroacetic acid to afford the title compound as the trifluoroacetic acid salt. $^1$H NMR (500 MHz, methanol-d$_4$) δ 1.15 (dd, J=6.8, 2.6 Hz, 3H), 1.23 (dd, J=7.1, 2.3 Hz, 3H), 1.96-2.19 (m, 1H), 2.39-2.56 (m, 2H), 2.65 (t, J=9.9 Hz, 1H), 2.75-3.02 (m, 3H), 3.04 (s, 3H), 3.50-3.80 (m, 1H), 4.19 (dd, J=22.1, 3.5 Hz, 1H), 4.85 (s, 2H), 5.97-6.12 (m, 1H), 7.54 (ddd, J=9.3, 7.1, 2.7 Hz, 1H), 8.03 (dt, J=17.7, 5.7 Hz, 2H), 8.10 (dd, J=9.7, 2.8 Hz, 1H), 8.52 (d, J=6.0 Hz, 1H). MS (ESI$^+$) m/z 449 (M+1).

Example 30

N-[4-(10-fluoro-7-methyl-6,7-dihydro-4H-3,4,7-triazadibenzo[cd,f]azulen-5-yl)cyclohex-3-en-1-yl]-L-alanine The title compound was prepared using the procedure described in Example 29F, using L-alanine tert-butyl ester in place of (R)-tert-butyl 2-amino-3-methylbutanoate. $^1$H NMR (400 MHz, methanol-d$_4$) δ 1.70 (d, J=7.0 Hz, 3H), 1.93-2.16 (m, 1H), 2.32-2.50 (m, 1H), 2.63 (dd, J=19.2, 9.3 Hz, 1H), 2.74-3.01 (m, 2H), 3.06 (s, 3H), 3.35 (s, 3H), 3.61-3.85 (m, 1H), 4.33 (dt, J=7.2, 3.5 Hz, 1H), 6.01-6.15 (m, 1H), 7.59 (ddd, J=9.5, 7.1, 2.8 Hz, 1H), 8.09 (d, J=6.3 Hz, 1H), 8.16 (ddd, J=9.4, 6.2, 3.7 Hz, 2H), 8.57 (d, J=6.3 Hz, 1H). MS (ESI$^+$) m/z 421 (M+1).

Example 31

N-[4-(10-fluoro-7-methyl-6,7-dihydro-4H-3,4,7-triazadibenzo[cd,f]azulen-5-yl)cyclohex-3-en-1-yl] glycine The title compound was prepared using the procedure described in Example 29F, using tert-butyl 2-aminoacetate in place of (R)-tert-butyl 2-amino-3-methylbutanoate. $^1$H NMR (400 MHz, methanol-d$_4$) δ 2.03 (dq, J=12.3, 9.8, 7.8 Hz, 1H), 2.36-2.50 (m, 1H), 2.58 (ddt, J=18.1, 9.3, 2.8 Hz, 1H), 2.82 (d, J=12.2 Hz, 2H), 2.87-3.00 (m, 1H), 3.05 (s, 3H), 3.57-3.76 (m, 1H), 3.89 (s, 2H), 4.10 (s, 1H), 4.17 (s, 1H), 5.40-6.49 (m, 1H), 7.54 (ddd, J=9.4, 7.1, 2.8 Hz, 1H), 8.01 (dd, J=7.7, 4.8 Hz, 2H), 8.10 (dd, J=9.7, 2.9 Hz, 1H), 8.52 (d, J=6.3 Hz, 1H). MS (ESI$^+$) m/z 407 (M+1).

Example 32

(2S)-{[4-(10-fluoro-7-methyl-6,7-dihydro-4H-3,4,7-triazadibenzo[cd,f]azulen-5-yl)cyclohex-3-en-1-yl]amino}(phenyl)acetic acid The title compound was prepared using the procedure described in Example 29F, using (S)-tert-butyl 2-amino-2-phenylacetate in place of (R)-tert-butyl 2-amino-3-methylbutanoate. $^1$H NMR (400 MHz, methanol-d$_4$) δ 1.88-2.12 (m, 1H), 2.34-2.77 (m, 3H), 2.77-2.97 (m, 2H), 3.05 (s, 3H), 3.40-3.66 (m, 1H), 4.81 (d, J=2.8 Hz, 2H), 5.39 (d, J=5.3 Hz, 1H), 6.02 (td, J=6.2, 3.2 Hz, 1H), 7.45-7.59 (m, 4H), 7.60-7.70 (m, 2H), 7.93-8.04 (m, 2H), 8.08 (dd, J=9.7, 2.9 Hz, 1H), 8.50 (dd, J=6.2, 1.2 Hz, 1H). MS (ESI$^+$) m/z 483 (M+1).

Example 33

10-fluoro-7-methyl-5-(1,2,3,6-tetrahydropyridin-4-yl)-6,7-dihydro-4H-3,4,7-triazadibenzo[cd,f]azulene-6-carboxylic acid To Example 28 (60 mg, 0.15 mmol) in tetrahydrofuran (2 mL) and methanol (1 mL) was added sodium hydroxide (6 mg in 0.5 mL water) and the mixture was stirred 60° C. overnight. The mixture was concentrated and purified by reverse-phase HPLC on a Zorbax RX-C18 column using a gradient of 15-100% methanol/0.1% aqueous trifluoroacetic acid to afford the title compound as the trifluoroacetic acid salt. $^1$H NMR (400 MHz, methanol-d$_4$) δ 2.75 (dddt, J=18.0, 7.8, 5.5, 2.4 Hz, 1H), 3.03-3.17 (m, 1H), 3.23 (s, 3H), 3.54 (tdd, J=12.6, 9.9, 5.6 Hz, 2H), 3.97 (dq, J=5.9, 2.6 Hz, 2H), 5.12 (s, 1H), 6.04 (tt, J=3.4, 1.6 Hz, 1H), 7.28 (ddd, J=9.1, 7.5, 3.0 Hz, 1H), 7.44 (dd, J=9.1, 5.1 Hz, 1H), 7.62 (d, J=6.1 Hz, 1H), 7.73 (dd, J=10.1, 3.0 Hz, 1H), 8.34 (d, J=6.0 Hz, 1H). MS (ESI⁺) m/z 379 (M+1).

Example 34

N-[4-(10-fluoro-7-methyl-6,7-dihydro-4H-3,4,7-triazadibenzo[cd,f]azulen-5-yl)cyclohex-3-en-1-yl]-L-valine The title compound was prepared using the procedure described in Example 29F, using (S)-tert-butyl 2-amino-3-methylbutanoate in place of (R)-tert-butyl 2-amino-3-methylbutanoate. ¹H NMR (500 MHz, methanol-d₄) δ 1.15 (dd, J=6.8, 2.6 Hz, 3H), 1.23 (dd, J=7.1, 2.3 Hz, 3H), 1.96-2.15 (m, 1H), 2.47 (dddd, J=17.1, 13.6, 8.7, 4.9 Hz, 2H), 2.64 (ddt, J=28.5, 18.9, 11.2 Hz, 1H), 2.71-3.01 (m, 3H), 3.04 (s, 3H), 3.53-3.72 (m, 1H), 4.18 (dd, J=21.8, 3.5 Hz, 1H), 4.78 (s, 2H), 5.80-6.26 (m, 1H), 7.51 (ddd, J=9.5, 7.2, 2.8 Hz, 1H), 7.95 (dd, J=9.1, 5.2 Hz, 2H), 8.06 (dd, J=9.8, 2.9 Hz, 1H), 8.48 (d, J=6.2 Hz, 1H). MS (ESI⁺) m/z 449 (M+1).

Example 35

N-[4-(10-fluoro-7-methyl-6,7-dihydro-4H-3,4,7-triazadibenzo[cd,f]azulen-5-yl)cyclohex-3-en-1-yl]-L-phenylalanine The title compound was prepared using the procedure described in Example 29F, using (S)-tert-butyl 2-amino-3-phenylpropanoate in place of (R)-tert-butyl 2-amino-3-methylbutanoate. ¹H NMR (500 MHz, methanol-d₄) δ 2.06 (qd, J=10.6, 9.7, 4.6 Hz, 1H), 2.42 (dd, J=33.5, 11.6 Hz, 1H), 2.54-2.80 (m, 2H), 2.78-2.99 (m, 2H), 3.04 (s, 3H), 3.35 (m, 1H), 3.49 (dt, J=14.1, 5.4 Hz, 1H), 3.61-3.71 (m, 1H), 4.51 (ddd, J=11.0, 7.9, 5.6 Hz, 1H), 4.83 (s, 2H), 5.88-6.21 (m, 1H), 7.31 (t, J=6.7 Hz, 1H), 7.35-7.45 (m, 4H), 7.53 (ddd, J=9.3, 7.0, 2.8 Hz, 1H), 8.01 (dt, J=15.3, 5.1 Hz, 2H), 8.09 (dd, J=9.5, 2.8 Hz, 1H), 8.51 (d, J=6.1 Hz, 1H). MS (ESI⁺) m/z 497 (M+1).

Example 36

N-[4-(10-fluoro-7-methyl-6,7-dihydro-4H-3,4,7-triazadibenzo[cd,f]azulen-5-yl)cyclohex-3-en-1-yl]-3-methyl-L-valine The title compound was prepared using the procedure described in Example 29F, using (S)-tert-butyl 2-amino-3,3-dimethylbutanoate in place of (R)-tert-butyl 2-amino-3-methylbutanoate. ¹H NMR (501 MHz, methanol-d₄) δ 1.24 (s, 9H), 1.94-2.28 (m, 1H), 2.38-2.68 (m, 2H), 2.71-2.95 (m, 3H), 3.03 (s, 3H), 3.48-3.68 (m, 1H), 4.04 (d, J=29.1 Hz, 1H), 4.79 (s, 2H), 6.03 (d, J=5.2 Hz, 1H), 7.46-7.56 (m, 1H), 7.98 (dd, J=13.7, 6.1 Hz, 2H), 8.07 (dt, J=10.1, 2.5 Hz, 1H), 8.49 (d, J=6.0 Hz, 1H). MS (ESI⁺) m/z 463 (M+1).

Example 37

1-[4-(10-fluoro-7-methyl-6,7-dihydro-4H-3,4,7-triazadibenzo[cd,f]azulen-5-yl)cyclohex-3-en-1-yl]-L-proline The title compound was prepared using the procedure described in Example 29F, using (S)-tert-butyl pyrrolidine-2-carboxylate in place of (R)-tert-butyl 2-amino-3-methylbutanoate. ¹H NMR (500 MHz, methanol-d₄) δ 2.05 (dddd, J=21.3, 14.5, 7.3, 4.2 Hz, 2H), 2.18-2.40 (m, 3H), 2.55-2.74 (m, 2H), 2.76-2.98 (m, 3H), 3.04 (s, 3H), 3.49 (td, J=10.6, 6.7 Hz, 1H), 3.84 (tdd, J=10.9, 8.0, 2.9 Hz, 2H), 4.70 (ddd, J=9.9, 5.9, 2.9 Hz, 1H), 4.75 (s, 2H), 5.71-6.23 (m, 1H), 7.50 (ddd, J=9.6, 7.2, 2.8 Hz, 1H), 7.86-7.97 (m, 2H), 8.05 (dd, J=9.8, 2.9 Hz, 1H), 8.47 (dd, J=6.5, 1.7 Hz, 1H). MS (ESI⁺) m/z 447 (M+1).

Example 38

N-[4-(10-fluoro-7-methyl-6,7-dihydro-4H-3,4,7-triazadibenzo[cd,f]azulen-5-yl)cyclohex-3-en-1-yl]-L-serine The title compound was prepared using the procedure described in Example 29F, using (S)-tert-butyl 2-amino-3-(tert-butoxy)propanoate in place of (R)-tert-butyl 2-amino-3-methylbutanoate. ¹H NMR (500 MHz, methanol-d₄) δ 1.95-2.11 (m, 1H), 2.46 (d, J=11.4 Hz, 1H), 2.60 (d, J=15.2 Hz, 1H), 2.83 (t, J=22.1 Hz, 2H), 2.94 (dt, J=16.1, 5.0 Hz, 1H), 3.04 (s, 3H), 3.67-3.83 (m, 1H), 4.15 (q, J=4.9, 4.1 Hz, 2H), 4.37 (q, J=3.5 Hz, 1H), 4.76 (s, 2H), 6.03 (d, J=5.1 Hz, 1H), 7.50 (ddd, J=9.5, 7.3, 3.0 Hz, 1H), 7.93 (dd, J=14.8, 7.8 Hz, 2H), 8.05 (dd, J=9.8, 3.0 Hz, 1H), 8.47 (d, J=6.3 Hz, 1H). MS (ESI⁺) m/z 437 (M+1).

Example 39

N-[4-(10-fluoro-7-methyl-6,7-dihydro-4H-3,4,7-triazadibenzo[cd,f]azulen-5-yl)cyclohex-3-en-1-yl]-L-norvaline The title compound was prepared using the procedure described in Example 29F, using (S)-tert-butyl 2-aminopentanoate in place of (R)-tert-butyl 2-amino-3-methylbutanoate. ¹H NMR (400 MHz, methanol-d₄) δ 0.97-1.02 (m, 2H), 1.05 (t, J=7.4 Hz, 3H), 1.40-1.68 (m, 2H), 2.04 (ddt, J=17.5, 12.4, 6.5 Hz, 2H), 2.44 (t, J=16.4 Hz, 1H), 2.62 (d, J=11.9 Hz, 1H), 2.70-2.99 (m, 2H), 3.04 (s, 3H), 3.55-3.76 (m, 1H), 4.17-4.34 (m, 1H), 4.82 (s, 2H), 6.04 (d, J=4.6 Hz, 1H), 7.53 (ddd, J=9.4, 7.1, 2.8 Hz, 1H), 7.94-8.02 (m, 2H), 8.08 (dd, J=9.6, 2.8 Hz, 1H), 8.50 (d, J=6.2 Hz, 1H). MS (ESI⁺) m/z 449 (M+1).

Example 40

N-[4-(10-fluoro-7-methyl-6,7-dihydro-4H-3,4,7-triazadibenzo[cd,f]azulen-5-yl)cyclohex-3-en-1-yl]-L-tyrosine The title compound was prepared using the procedure described in Example 29F, using (S)-tert-butyl 2-amino-3-(4-(tert-butoxy)phenyl)propanoate in place of (R)-tert-butyl 2-amino-3-methylbutanoate. ¹H NMR (400 MHz, methanol-d₄) δ 1.89-2.11 (m, 1H), 2.38 (d, J=16.6 Hz, 1H), 2.48-2.74 (m, 2H), 2.76-2.96 (m, 2H), 3.03 (s, 3H), 3.59 (m, 1H), 4.17 (dd, J=7.8, 5.2 Hz, 2H), 4.43 (q, J=6.9 Hz, 1H), 4.69 (s, 2H), 5.99 (t, J=5.6 Hz, 1H), 6.79 (dd, J=8.9, 2.7 Hz, 2H), 7.20 (dd, J=8.4, 1.5 Hz, 2H), 7.48 (ddd, J=9.6, 7.2, 2.9 Hz, 1H), 7.89 (dd, J=14.9, 4.9 Hz, 2H), 8.02 (dd, J=9.8, 3.0 Hz, 1H), 8.45 (d, J=6.2 Hz, 1H). MS (ESI⁺) m/z 513 (M+1).

Example 41

4-(10-fluoro-7-methyl-6,7-dihydro-4H-3,4,7-triaza-dibenzo[cd,f]azulen-5-yl)cyclohex-3-ene-1-carboxylic acid

Example 41A 4-fluoro-N-methyl-2-(1H-pyrrolo[2,3-b]pyridin-4-yl)aniline

A solution of Example 1A (45.9 g, 183 mmol), 4-bromo-1H-pyrrolo[2,3-b]pyridine (30.0 g, 152 mmol) and potassium phosphate tribasic (97 g, 457 mmol) in tetrahydrofuran (381 mL) and water (127 mL) was degassed with nitrogen for 10 minutes with stirring. {1,3-Bis(2,6-diisopropylphenyl)imidazole-2-ylidene}chloro{3-phenylallyl}palladium(II) (3.95 g, 6.09 mmol), degassing was continued for 10 minutes and the mixture was heated at 64° C. overnight. The mixture was poured into ethyl acetate and water and the aqueous layer was extracted with ethyl acetate (twice). The combined organics were dried over magnesium sulfate, filtered, treated with 10 g mercapto silica gel, stirred for 20 minutes and filtered through a small plug of silica gel. The filtrate was concentrated and the residue was purified by flash chromatography (Analogix, 0-75% ethyl acetate/heptane) to provide the title compound. $^1$H NMR (400 MHz, DMSO-$d_6$) δ 8.39 (d, J=5.3 Hz, 1H), 7.97 (d, J=8.4 Hz, 2H), 7.71 (d, J=10.3 Hz, 1H), 7.57 (d, J=5.4 Hz, 1H), 7.42 (d, J=8.3 Hz, 2H), 7.33-7.22 (m, 2H), 4.01 (s, 2H), 2.89 (s, 3H), 2.32 (s, 3H). MS (ESI$^+$) m/z 242.1 (M+H)$^+$.

Example 41B 7-fluoro-4-methyl-3,4-dihydro-1H-1,4,11-triazadibenzo[cd,f]azulene A mixture of paraformaldehyde (12.76 g, 425 mmol), Example 41A (20.5 g, 85 mmol) and acetic acid (243 mL) was stirred at room temperature overnight. The mixture was poured into water and the solid was collected by filtration to provide a mixture of the title compound and (7-fluoro-4-methyl-3,4-dihydro-1H-1,4,11-triazadibenzo[cd,f]azulen-1-yl)methanol. To a solution of this mixture in acetonitrile (506 mL) at room temperature was added 5N aqueous sodium hydroxide (122 mL, 608 mmol) and the mixture was heated at 60° C. for 1 hour. The mixture was cooled to room temperature and poured into water. The solid was collected by filtration to provide the title compound. $^1$H NMR (400 MHz, DMSO-$d_6$) δ 11.42 (s, 1H), 8.26 (d, J=5.2 Hz, 1H), 7.75 (dd, J=10.6, 3.0 Hz, 1H), 7.35 (d, J=5.3 Hz, 1H), 7.32-7.13 (m, 3H), 4.12 (s, 2H), 2.87 (s, 3H). MS (ESI$^+$) m/z 254.3 (M+H)$^+$.

Example 41C 7-fluoro-4-methyl-1-tosyl-3,4-dihydro-1H-1,4,11-triazadibenzo[cd,f]azulene To a solution of Example 41B (18.49 g, 73.0 mmol) in N,N-dimethylformamide (146 mL) at room temperature under nitrogen was added sodium hydride (4.38 g, 110 mmol) in portions. The mixture was stirred for 30 minutes and p-toluenesulfonyl chloride (15.31 g, 80 mmol) was added in portions over 10 minutes. The mixture was stirred overnight at room temperature, poured into water and filtered. The solid was washed with heptanes and placed in a vacuum oven overnight at 50° C. The residue was taken up in dichloromethane/methanol and concentrated to give a solid containing ~10% unreacted starting material. $^1$H NMR (400 MHz, DMSO-$d_6$) δ 8.41 (d, J=5.3 Hz, 1H), 8.01 (d, J=8.4 Hz, 2H), 7.76 (d, J=10.4 Hz, 1H), 7.71 (s, 1H), 7.61 (d, J=5.5 Hz, 1H), 7.41 (d, J=8.1 Hz, 2H), 7.31-7.25 (m, 2H), 4.10 (s, 2H), 2.89 (s, 3H), 2.33 (s, 3H). MS (ESI$^+$) m/z 408.5 (M+H)$^+$.

Example 41D 7-fluoro-2-iodo-4-methyl-1-tosyl-3,4-dihydro-1H-1,4,11-triazadibenzo[cd,f]azulene To a solution of Example 41C (26.6 g, 65.3 mmol) in tetrahydrofuran (326 mL) at −75° C. under nitrogen was added lithium diisopropylamide (49.0 mL, 98 mmol) dropwise. A solution of iodine (33.1 g, 131 mmol) in 250 mL tetrahydrofuran was added dropwise and the mixture was stirred at −75° C. for 2 hours. The reaction was quenched with saturated aqueous sodium thiosulfate and extracted with ethyl acetate (twice). The combined organics were dried over magnesium sulfate, filtered and concentrated. The residue was slurried in hot 40% ethyl acetate in heptanes, cooled to room temperature and filtered and dried in vacuo to provide the title compound. $^1$H NMR (400 MHz, DMSO-$d_6$) δ 8.39 (d, J=5.3 Hz, 1H), 7.97 (d, J=8.4 Hz, 2H), 7.71 (d, J=10.3 Hz, 1H), 7.57 (d, J=5.4 Hz, 1H), 7.42 (d, J=8.3 Hz, 2H), 7.33-7.22 (m, 2H), 4.01 (s, 2H), 2.89 (s, 3H), 2.32 (s, 3H). MS (ESI$^+$) m/z 534.0 (M+H)$^+$.

Example 41E 4-(10-fluoro-7-methyl-6,7-dihydro-4H-3,4,7-triaza-dibenzo[cd,f]azulen-5-yl)cyclohex-3-ene-1-carboxylic acid A mixture of Example 41D (0.5 g, 0.94 mmol), ethyl 4-(4,4,5,5-tetramethyl-1,3,2-dioxaborolan-2-yl)cyclohex-3-enecarboxylate (0.3 g, 1.12 mmol) and bis(triphenylphosphine)palladium(II) chloride (66 mg, 0.094 mmol) was purged with nitrogen and 7/3/2 1,2-dimethoxyethane/ethanol/water (50 mL) and aqueous sodium bicarbonate (0.5 mL, 1.9 mmol) were added. After stirring at 85° C. for 4 hours, the mixture was filtrated, concentrated and purified by flash chromatography using a Teledyne CombiFlash Rf (30% ethyl acetate in heptane) to provide the intermediate ester, which was dissolved in dioxane (50 mL) and treated with sodium hydroxide (150 mg in 1 mL water). The mixture was stirred at 60° C. overnight, concentrated and purified by reverse-phase HPLC on a Zorbax RX-C18 column using a gradient of 15-100% methanol/0.1% aqueous trifluoroacetic acid to afford the title compound as the trifluoroacetate salt. The compound was dissolved in methylene chloride and methanol and treated with hydrogen chloride in ether. Concentration provided the title compound as the hydrochloride salt. $^1$H NMR (500 MHz, DMSO-$d_6$) δ 1.68-1.80 (m, 1H), 2.09 (dq, J=12.5, 4.1 Hz, 1H), 2.40 (ddq, J=18.3, 9.1, 3.0 Hz, 1H), 2.44-2.68 (m, 4H), 2.88 (s, 3H), 4.12 (s, 2H), 5.78-5.95 (m, 1H), 7.18-7.33 (m, 3H), 7.69 (dd, J=10.5, 3.0 Hz, 1H), 8.21 (d, J=5.2 Hz, 1H). MS (ESI$^+$) m/z 378 (M+1).

Example 42

2-[4-(10-fluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone The title compound was prepared as described in Example 17, substituting (S)-3-hydroxypyrrolidine for L-prolinol. $^1$H NMR (400 MHz, DMSO-$d_6$): δ 1.80-2.00 (m, 3H), 2.72-2.85 (m, 2H), 2.81 (s, 3H), 2.96-3.07 (m, 2H), 3.41-3.58 (m, 4H), 3.71-3.76 (m, 1H), 4.04-4.24 (m, 2H), 4.16-4.58 (m, 4H), 5.95 (s, 1H), 7.51 (t, J=6.71 Hz, 1H), 7.75 (d, J=5.80 Hz, 1H), 8.04 (d, J=9.16 Hz, 1H), 8.43 (d, J=5.49 Hz, 1H), 10.46 (s, 1H), 12.81 (s, 1H). MS (ESI$^+$) m/z 462 (M+H)$^+$.

Example 43

10-fluoro-7-methyl-5-[4-(methylsulfonyl)phenyl]-6,7-dihydro-4H-3,4,7-triazadibenzo[cd,f]azulene

Example 43A 7-fluoro-2-iodo-4-methyl-3,4-dihydro-1H-1,4,11-triazadibenzo[cd,f]azulene To a solution of Example 41D (2.0 g, 3.75 mmol) in dioxane (30 mL) was added 1M aqueous sodium hydroxide (15 mL, 15 mmol) and the mixture was stirred at 50° C. overnight. Water was added and the precipitate was filtered, washed with water and hexanes and dried in vacuo to afford the title compound. LC-MS: 380 (M+H)$^+$.

Example 43B 10-fluoro-7-methyl-5-[4-(methylsulfonyl)phenyl]-6,7-dihydro-4H-3,4,7-triazadibenzo[cd,f]azulene A mixture of Example 43A (40 mg, 0.105 mmol), (4-(methylsulfonyl)phenyl)boronic acid (25.3 mg, 0.127 mmol), palladium tetrakis(triphenylphosphine) (6.10 mg, 5.27 μmol) and 2M aqueous sodium carbonate (264 μl, 0.527 mmol) in N,N-dimethylformamide (1.5 mL) in a pressure vial was evacuated and backfilled with nitrogen. The mixture was stirred at 95° C. for 1 hour and the solid was filtered and washed with water and methanol to provide the title compound. $^1$H NMR (500 MHz, DMSO-$d_6$) δ 2.86 (s, 3H) 3.30 (s, 3H) 4.31 (s, 2H) 7.24-7.31 (m, 1H) 7.32-7.37 (m, 1H) 7.42 (d, J=5.19 Hz, 1H) 7.75 (dd, J=10.38, 3.05 Hz, 1H) 7.85 (d, J=8.24 Hz, 2H) 8.06 (d, J=8.24 Hz, 2H) 8.36 (d, J=5.19 Hz, 1H) 12.18 (s, 1H). MS (ESI$^+$) m/z 408 (M+H)$^+$.

Example 44

10-fluoro-7-methyl-5-(pyridin-4-yl)-6,7-dihydro-4H-3,4,7-triazadibenzo[cd,f]azulene The title compound was prepared using the conditions described in Example 43B, substituting (4-(methylsulfonyl)phenyl)boronic acid with pyridin-4-ylboronic acid. $^1$H NMR (500 MHz, DMSO-$d_6$) δ 2.87 (s, 3H) 4.34 (s, 2H) 7.24-7.31 (m, 1H) 7.32-7.36 (m, 1H) 7.42 (d, J=5.19 Hz, 1H) 7.60 (d, J=6.10 Hz, 2H) 7.75 (dd, J=10.38, 2.75 Hz, 1H) 8.37 (d, J=4.88 Hz, 1H) 8.70 (d, J=6.10 Hz, 2H) 12.19 (s, 1H). MS (ESI$^+$) m/z 331 (M+H)$^+$.

Example 45

10-fluoro-7-methyl-5-[6-(methylsulfonyl)pyridin-3-yl]-6,7-dihydro-4H-3,4,7-triazadibenzo[cd,f]azulene The title compound was prepared using the conditions described in Example 43B, substituting (4-(methylsulfonyl)phenyl)boronic acid with (6-(methylsulfonyl)pyridin-3-yl)boronic acid. $^1$H NMR (500 MHz, DMSO-$d_6$) δ 2.87 (s, 3H) 3.36 (s, 3H) 4.34 (s, 2H) 7.26-7.32 (m, 1H) 7.32-7.38 (m, 1H) 7.44 (d, J=5.19 Hz, 1H) 7.77 (dd, J=10.38, 3.05 Hz, 1H) 8.19 (d, J=8.24 Hz, 1H) 8.31 (dd, J=8.24, 2.14 Hz, 1H) 8.39 (d, J=5.19 Hz, 1H) 9.01 (d, J=1.83 Hz, 1H) 12.32 (s, 1H). MS (ESI$^+$) m/z 409 (M+H)$^+$.

Example 46

5-(10-fluoro-7-methyl-6,7-dihydro-4H-3,4,7-triazadibenzo[cd,f]azulen-5-yl)pyrimidin-2-amine The title compound was prepared using the conditions described in Example 43B, substituting (4-(methylsulfonyl)phenyl)boronic acid with (2-aminopyrimidin-5-yl)boronic acid. $^1$H NMR (500 MHz, DMSO-$d_6$) δ 2.86 (s, 3H) 4.20 (s, 2H) 6.97 (s, 2H) 7.21-7.27 (m, 1H) 7.29-7.34 (m, 1H) 7.36 (d, J=5.49 Hz, 1H) 7.72 (dd, J=10.38, 3.05 Hz, 1H) 8.25 (d, J=5.19 Hz, 1H) 8.47 (s, 2H) 11.84 (s, 1H). MS (ESI$^+$) m/z 347 (M+H)$^+$.

Example 47

4-(10-fluoro-7-methyl-6,7-dihydro-4H-3,4,7-triazadibenzo[cd,f]azulen-5-yl)benzoic acid The title compound was prepared using the conditions described in Example 43B, substituting (4-(methylsulfonyl)phenyl)boronic acid with 4-boronobenzoic acid. The mixture was filtered and the filtrate was purified by reverse-phase HPLC on a Phenomenex Luna C8 AXIA column using a Waters PrepLC 4000 System (10-95% acetonitrile/10 mM ammonium acetate in water) to afford the title compound. $^1$H NMR (400 MHz, DMSO-$d_6$) δ 2.85 (s, 3H) 4.31 (s, 2H) 7.24-7.30 (m, 1H) 7.31-7.36 (m, 1H) 7.40 (d, J=5.49 Hz, 1H) 7.69-7.78 (m, 3H) 8.08 (d, J=8.54 Hz, 2H) 8.33 (d, J=5.19 Hz, 1H) 12.09 (s, 1H) 13.03 (s, 1H). MS (ESI$^+$) m/z 374 (M+H)$^+$.

Example 48

1,10-difluoro-7-methyl-5-(1,2,3,6-tetrahydropyridin-4-yl)-6,7-dihydro-4H-3,4,7-triazadibenzo[cd,f]azulene The title compound was prepared as described in Example 1A-H, substituting 4-chloro-5-fluoro-7-azaindole for 4-chloro-7-azaindole in Example 1B. $^1$H NMR (400 MHz, DMSO-$d_6$): δ 2.41-2.47 (m, 2H), 2.88 (s, 3H), 2.92 (t, J=5.49 Hz, 2H), 3.43 (d, J=2.75 Hz, 2H), 4.06 (s, 2H), 5.89 (s, 1H), 7.27-7.32 (m, 1H), 7.37 (dd, J=9.16, 5.49 Hz, 1H), 7.62-7.65 (m, 1H), 8.23 (d, J=4.88 Hz, 1H), 11.60 (s, 1H). MS (ESI$^+$) m/z 353 (M+H)$^+$.

Example 49 tert-butyl 4-(1,10-difluoro-7-methyl-6,7-dihydro-4H-3,4,7-triazadibenzo[cd,f]azulen-5-yl)-3,6-dihydropyridine-1(2H)-carboxylate The title compound was prepared as described in Example 1A-G, substituting 4-chloro-5-fluoro-7-azaindole for 4-chloro-7-azaindole in Example 1B. $^1$H NMR (400 MHz, CDCl$_3$): δ 1.53 (s, 9H), 2.61-2.67 (m, 2H), 2.99 (s, 3H), 3.73 (t, J=5.49 Hz, 2H), 4.15 (s, 2H), 4.21 (s, 2H), 5.84 (s, 1H), 7.09-7.15 (m, 1H), 7.29 (dd, J=9.00, 5.34 Hz, 1H), 7.72-7.78 (m, 1H), 8.17 (d, J=5.19 Hz, 1H), 10.66 (s, 1H). MS (ESI$^+$) m/z 453 (M+H)$^+$.

Example 50

4-(10-fluoro-7-methyl-6,7-dihydro-4H-3,4,7-triazadibenzo[cd,f]azulen-5-yl)-N,N-dimethylcyclohex-3-ene-1-carboxamide To a mixture of Example 41E (50 mg, 0.13 mmol), dimethylamine (12 mg, 0.3 mmol), 1-(3-dimethylaminopropyl)-3-ethylcarbodiimide hydrochloride (50 mg, 0.3 mmol) and 1H-benzotriazol-1-ol (41 mg, 0.3 mmol) in N,N-dimethylformamide (2 mL) was added triethylamine (27 mg, 0.3 mmol) and the mixture was stirred at room temperature overnight. The mixture was purified by HPLC (Zorbax, C-18, 0.1% trifluoroacetic acid in water/0.1% trifluoroacetic acid in acetonitrile; 0-100% gradient) to provide the title compound as the trifluoroacetate salt. The trifluoroacetate salt was dissolved in methylene chloride and methanol and treated with hydrogen chloride in ether. Concentration provided the title compound as the hydrochloride salt. $^1$H NMR (500 MHz, methanol-$d_4$) δ 1.90 (ddd, J=12.8, 9.5, 5.8 Hz, 1H), 2.08 (ddd, J=13.1, 6.0, 3.1 Hz, 1H), 2.54 (q, J=6.3, 5.4 Hz, 2H), 2.69 (d, J=9.0 Hz, 2H), 2.99 (s, 3H), 3.05 (s, 3H), 3.21 (s, 3H), 3.23 (d, J=7.3 Hz, 1H), 3.35 (s, 2H), 5.90-6.30 (m, 1H), 7.56 (ddd, J=9.4, 7.1, 2.7 Hz, 1H), 8.00-8.09 (m, 2H), 8.13 (dd, J=9.5, 2.8 Hz, 1H), 8.51 (d, J=6.3 Hz, 1H). MS (ESI$^+$) m/z 405 (M+H)$^+$.

Example 51

[4-(10-fluoro-7-methyl-6,7-dihydro-4H-3,4,7-triazadibenzo[cd,f]azulen-5-yl)cyclohex-3-en-1-yl](3-hydroxyazetidin-1-yl)methanone The title compound was prepared using the procedure described in Example 50, using azetidin-3-ol in place of dimethylamine $^1$H NMR (400 MHz, methanol-$d_4$) δ 1.89-2.01 (m, 2H), 2.53 (d, J=24.0 Hz, 2H), 2.70 (d, J=34.1 Hz, 3H), 3.04 (s, 3H), 3.79 (d, J=9.6 Hz, 1H), 4.10 (q, J=7.1 Hz, 1H), 4.22 (d, J=8.9 Hz, 1H), 4.53 (m, 1H), 4.62 (dq, J=6.9, 4.2, 3.5 Hz, 1H), 4.69 (s, 2H), 6.11 (m, 1H), 7.49 (ddd, J=9.4, 7.2, 2.9 Hz, 1H), 7.83 (dd, J=9.1, 4.8 Hz, 1H), 7.92 (d, J=6.3 Hz, 1H), 8.02 (dd, J=9.8, 3.0 Hz, 1H), 8.42 (d, J=6.3 Hz, 1H). MS (ESI$^+$) m/z 433 (M+1).

Example 52

4-(10-fluoro-7-methyl-6,7-dihydro-4H-3,4,7-triazadibenzo[cd,f]azulen-5-yl)-N-methylcyclohex-3-ene-1-carboxamide The title compound was prepared using the procedure described in Example 50, using methanamine in place of dimethylamine $^1$H NMR (400 MHz, methanol-$d_4$) δ 1.86-2.01 (m, 1H), 2.12 (dq, J=12.3, 3.7 Hz, 1H), 2.56 (q, J=5.5, 4.3 Hz, 2H), 2.66 (ddt, J=13.8, 10.1, 4.4 Hz, 3H), 2.78 (s, 3H), 3.05 (s, 3H), 4.93 (s, 2H), 6.16 (t, J=3.6 Hz, 1H), 7.59 (ddd, J=9.2, 7.0, 2.9 Hz, 1H), 8.04-8.13 (m, 2H), 8.16 (dd, J=9.6, 2.9 Hz, 1H), 8.53 (d, J=6.3 Hz, 1H). MS (ESI$^+$) m/z 391 (M+1).

Example 53

2-[4-(10-fluoro-7-methyl-6,7-dihydro-4H-3,4,7-triazadibenzo[cd,f]azulen-5-yl)-3,6-dihydropyridin-1(2H)-yl]-N,N-bis(2-hydroxyethyl)acetamide The title compound was prepared as described in Example 17, substituting 2,2'-azanediyldiethanol for L-prolinol. $^1$H NMR (400 MHz, CD$_3$OD): δ 3.07 (s, 3H), 3.05-3.12 (m, 3H), 3.29-3.35 (m, 2H), 3.52-3.65 (m, 4H), 3.75-3.80 (m, 3H), 3.82-3.88 (m, 1H), 4.07-4.15 (m, 1H), 4.26-4.34 (m, 1H), 4.58 (d, J=8.85 Hz, 2H), 4.74 (s, 2H), 6.07 (s, 1H), 7.47-7.52 (m, 1H), 7.84-7.87 (m, 1H), 7.93 (d, J=6.41 Hz, 1H), 8.03 (dd, J=9.77, 2.75 Hz, 1H), 8.50 (d, J=6.41 Hz, 1H). MS (ESI$^+$) m/z 480 (M+H)$^+$.

Example 54

1-(3,3-difluoroazetidin-1-yl)-2-[4-(10-fluoro-7-methyl-6,7-dihydro-4H-3,4,7-triazadibenzo[cd,f]azulen-5-yl)-3,6-dihydropyridin-1(2H)-yl]ethanone The title compound was prepared as described in Example 17, substituting 3,3-difluoroazetidine for L-prolinol. $^1$H NMR (400 MHz, DMSO-$d_6$): δ 2.83 (s, 3H), 2.93-3.03 (m, 2H), 3.42-3.50 (m, 2H), 3.65-3.74 (m, 2H), 3.93-4.13 (m, 2H), 4.27 (s, 2H), 4.46 (t, J=12.36 Hz, 2H), 4.75 (t, J=12.21 Hz, 2H), 5.93 (s, 1H), 7.48 (s, 1H), 7.69 (d, J=5.49 Hz, 1H), 7.99 (s, 1H), 8.42 (d, J=5.49 Hz, 1H), 10.85 (s, 1H), 12.65 (s, 1H). MS (ESI$^+$) m/z 468 (M+H)$^+$.

Example 55

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N,N-dimethylacetamide The title compound was prepared using the procedure described in Example 12, using Example 62 in place of Example 1. $^1$H NMR (500 MHz, methanol-$d_4$) δ 2.26 (dd, J=7.8, 4.8 Hz, 1H), 2.41-2.68 (m, 2H), 3.03 (s, 3H), 3.07 (s, 3H), 3.09 (s, 3H), 3.11 (d, J=3.1 Hz, 2H), 3.42-3.55 (m, 1H), 4.30 (d, J=7.7 Hz, 1H), 4.39-4.43 (m, 1H), 4.54 (q, J=4.0, 2.5 Hz, 1H), 4.82-4.88 (m, 2H), 5.00 (d, J=15.2 Hz, 1H), 6.42 (d, J=5.6 Hz, 1H), 7.55 (ddt, J=9.6, 7.3, 2.6 Hz, 1H), 8.02 (dd, J=12.0, 5.1 Hz, 2H), 8.08-8.15 (m, 1H), 8.57 (d, J=6.2 Hz, 1H). MS (ESI$^+$) m/z 446 (M+1).

Example 56

10-fluoro-7-methyl-5-[(1R,5S)-8-(methylsulfonyl)-8-azabicyclo[3.2.1]oct-2-en-3-yl]-6,7-dihydro-4H-3,4,7-triazadibenzo[cd,f]azulene The title compound was prepared using the procedure described in Example 11, using Example 62 in place of Example 9. $^1$H NMR (400 MHz, methanol-$d_4$) δ 1.95 (dt, J=14.8, 7.6 Hz, 1H), 2.20 (h, J=6.0 Hz, 2H), 2.37 (dd, J=14.0, 7.5 Hz, 1H), 2.65 (d, J=17.3 Hz, 1H), 3.02 (s, 3H), 3.07 (s, 3H), 3.10-3.22 (m, 1H), 4.51 (dd, J=7.6, 4.7 Hz, 1H), 4.59 (d, J=5.5 Hz, 1H), 4.67 (d, J=15.2 Hz, 1H), 4.75 (d, J=15.3 Hz, 1H), 6.40 (d, J=5.9 Hz, 1H), 7.49 (ddd, J=9.8, 7.3, 3.0 Hz, 1H), 7.82 (dd, J=9.1, 4.9 Hz, 1H), 7.93 (d, J=6.3 Hz, 1H), 8.04 (dd, J=9.8, 3.0 Hz, 1H), 8.46 (d, J=6.4 Hz, 1H). MS (ESI$^+$) m/z 439 (M+1).

Example 57

(1R,5S)-3-(10-fluoro-7-methyl-6,7-dihydro-4H-3,4,7-triazadibenzo[cd,f]azulen-5-yl)-N-methyl-8-azabicyclo[3.2.1]oct-2-ene-8-carboxamide The title compound was prepared using the procedure described in Example 13, using Example 62 in place of Example 1. $^1$H NMR (400 MHz, methanol-$d_4$) $^1$H NMR (400

MHz, methanol-d$_4$) δ 1.89-2.02 (m, 1H), 2.09-2.19 (m, 2H), 2.25-2.42 (m, 1H), 2.50 (d, J=17.2 Hz, 1H), 2.78 (s, 3H), 3.03 (s, 3H), 3.15 (dd, J=15.8, 4.5 Hz, 1H), 4.56 (dd, J=7.7, 4.5 Hz, 1H), 4.60-4.67 (m, 1H), 4.78 (s, 2H), 6.44 (d, J=5.1 Hz, 1H), 7.55 (ddd, J=9.5, 7.2, 2.9 Hz, 1H), 7.99 (dd, J=14.4, 5.7 Hz, 2H), 8.10 (dd, J=9.7, 2.9 Hz, 1H), 8.50 (d, J=6.4 Hz, 1H). MS (ESI$^+$) m/z 418 (M+1).

Example 58

[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid Example 58A tert-butyl 2-((1R,5S)-3-(7-fluoro-4-methyl-3,4-dihydro-1H-1,4,11-triazadibenzo[cd,f]azulen-2-yl)-8-azabicyclo[3.2.1]oct-2-en-8-yl)acetate The title compound was prepared using the procedure described in Example 16A, using Example 62 in place of Example 1. LCMS: 475 (M+H)$^+$.

Example 58B

[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid The title compound was prepared using the procedure described in Example 16B, using Example 58A in place of Example 16A. $^1$H NMR (400 MHz, methanol-d$_4$) δ 2.27 (dt, J=14.3, 7.8 Hz, 1H), 2.40-2.68 (m, 3H), 2.97 (d, J=18.7 Hz, 1H), 3.08 (s, 3H), 3.39-3.53 (m, 1H), 4.18 (s, 2H), 4.48 (q, J=8.6, 7.4 Hz, 1H), 4.60 (m, 1H), 4.82 (d, J=16.2 Hz, 1H), 4.98 (d, J=15.2 Hz, 1H), 6.40 (d, J=5.7 Hz, 1H), 7.53 (dtd, J=9.7, 7.0, 2.8 Hz, 1H), 7.98 (ddd, J=14.2, 9.3, 5.6 Hz, 2H), 8.08 (ddd, J=13.9, 9.6, 2.9 Hz, 1H), 8.55 (t, J=6.1 Hz, 1H). MS (ESI$^+$) m/z 419 (M+1).

Example 59

10-fluoro-5-(1,2,3,3a,4,6a-hexahydrocyclopenta[c]pyrrol-5-yl)-7-methyl-6,7-dihydro-4H-3,4,7-triazadibenzo[cd,f]azulene Example 59A tert-butyl 5-(((trifluoromethyl)sulfonyl)oxy)-3,3a,6,6a-tetrahydrocyclopenta[c]pyrrole-2(1H)-carboxylate To a solution of sodium bis(trimethylsilyl)amide (1M in tetrahydrofuran, 14.65 mL, 14.65 mmol) in tetrahydrofuran (12 mL) at –78° C. was slowly added tert-butyl 5-oxohexahydrocyclopenta[c]pyrrole-2(1H)-carboxylate (3.00 g, 13.32 mmol) in tetrahydrofuran (7.5 mL). The mixture was stirred for 30 minutes and treated over 15 minutes with a solution of 1,1,1-trifluoro-N-phenyl-N-((trifluoromethyl)sulfonyl)methanesulfonamide (5.23 g, 14.65 mmol) in tetrahydrofuran (12 mL). The mixture was stirred at –78° C. for 90 minutes and allowed to warm to room temperature for 1 hour. The mixture was quenched with water and extracted with ethyl acetate. The organic layer was washed with brine, dried over sodium sulfate, filtered, and concentrated in vacuo. The residue was purified by flash chromatography on silica gel (Teledyne CombiFlash Rf, 10-80% ethyl acetate/hexanes) to afford the title compound (~75% purity), which was used in the next step without further purification. MS (ESI$^+$) m/z 380 (M+Na)$^+$.

Example 59B tert-butyl 5-(4,4,5,5-tetramethyl-1,3,2-dioxaborolan-2-yl)-3,3a,6,6a-tetrahydrocyclopenta[c]pyrrole-2 (1H)-carboxylate A pressure vial was charged with Example 59A (2 g, ~4.20 mmol), 4,4,4',4',5,5,5',5'-octamethyl-2,2'-bi(1,3,2-dioxaborolane) (1.17 g, 4.62 mmol), potassium acetate (1.24 g, 12.59 mmol), [1,1'-bis(diphenylphosphino)ferrocene]dichloropalladium(II)-dichloromethane adduct (171 mg, 0.210 mmol) and dioxane (16 mL). The vial was capped with a septum, flushed with nitrogen, stirred at 90° C. for 4 hours and used directly in the next step.

Example 59C 10-fluoro-5-(1,2,3,3a,4,6a-hexahydrocyclopenta[c]pyrrol-5-yl)-7-methyl-6,7-dihydro-4H-3,4,7-triazadibenzo[cd,f]azulene The title compound was prepared as described in Example 1A-H, substituting Example 59B for tert-butyl 4-(4,4,5,5-tetramethyl-1,3,2-dioxaborolan-2-yl)-5,6-dihydropyridine-1 (2H)-carboxylate in Example 1D. $^1$H NMR (400 MHz, DMSO-d$_6$): δ 2.60-2.70 (m, 3H), 2.80-2.90 (m, 3H), 2.92 (s, 3H), 3.08 (m, 1H), 3.15 (d, J=4.50 Hz, 1H), 3.35 (m, 1H), 4.20 (s, 2H), 6.00 (s, 1H), 7.25 (m, 3H), 7.73 (m, 1H), 8.22 (d, J=6.80 Hz, 1H), 11.4 (s, 1H). MS (ESI$^+$) m/z 361 (M+H)$^+$.

Example 60

10-fluoro-7-methyl-5-(pyridin-3-yl)-6,7-dihydro-4H-3,4,7-triazadibenzo[cd,f]azulene The title compound was prepared using the conditions described in Example 43B, substituting (4-(methylsulfonyl)phenyl)boronic acid with pyridin-3-ylboronic acid. The mixture was purified by reverse-phase HPLC on a Phenomenex Luna C8 AXIA column using a Waters PrepLC 4000 System (10-95% acetonitrile/10 mM ammonium acetate in water) to afford the title compound. $^1$H NMR (400 MHz, DMSO-d$_6$) δ 2.86 (s, 3H) 4.28 (s, 2H) 7.23-7.30 (m, 1H) 7.31-7.36 (m, 1H) 7.41 (d, J=5.49 Hz, 1H) 7.57 (dd, J=7.93, 4.88 Hz, 1H) 7.75 (dd, J=10.38, 3.05 Hz, 1H) 7.98-8.06 (m, 1H) 8.33 (d, J=5.19 Hz, 1H) 8.61 (dd, J=4.58, 1.53 Hz, 1H) 8.82 (d, J=1.83 Hz, 1H) 12.11 (s, 1H). MS (ESI$^+$) m/z 331 (M+H)$^+$.

Example 61 ethyl 4-(10-fluoro-7-methyl-6,7-dihydro-4H-3,4,7-triazadibenzo[cd,f]azulen-5-yl)cyclohex-3-ene-1-carboxylate The title compound was prepared using the procedure described in Example 1D, using ethyl 4-(4,4,5,5-tetramethyl-1,3,2-dioxaborolan-2-yl)cyclohex-3-enecarboxylate in place of tert-butyl 4-(4,4,5,5-tetramethyl-1,3,2-dioxaborolan-2-yl)-5,6-dihydropyridine-1(2H)-carboxylate and Example 43A in place of Example 1C. $^1$H NMR (400 MHz, DMSO-d$_6$) δ 1.22 (t, J=7.1 Hz, 3H), 1.76 (ddd, J=9.3, 5.6, 3.1 Hz, 1H), 2.04-2.15 (m, 1H), 2.50 (dq, J=5.7, 3.9, 2.9 Hz, 3H), 2.88 (s, 3H), 3.32 (s, 2H), 4.07-4.18 (m, 4H), 5.84 (t, J=3.9 Hz, 1H), 6.96-7.43 (m, 3H), 7.69 (dd, J=10.4, 3.0 Hz, 1H), 8.21 (d, J=5.2 Hz, 1H). MS (ESI⁺) m/z 406 (M+1).

Example 62

5-[(1R,5S)-8-azabicyclo[3.2.1]oct-2-en-3-yl]-10-fluoro-7-methyl-6,7-dihydro-4H-3,4,7-triazadibenzo[cd,f]azulene Example 62A (1R,5S)-tert-butyl 3-(7-fluoro-4-methyl-3,4-dihydro-1H-1,4,11-triazadibenzo[cd,f]azulen-2-yl)-8-azabicyclo[3.2.1]oct-2-ene-8-carboxylate The title compound was prepared using the procedure described in Example 1D, using (1R,5S)-tert-butyl 3-(4,4,5,5-tetramethyl-1,3,2-dioxaborolan-2-yl)-8-azabicyclo[3.2.1]oct-2-ene-8-carboxylate in place of tert-butyl 4-(4,4,5,5-tetramethyl-1,3,2-dioxaborolan-2-yl)-5,6-dihydropyridine-1(2H)-carboxylate and Example 43A in place of Example 1C. LCMS: 461 (M+H)⁺.

Example 62B

5-[(1R,5S)-8-azabicyclo[3.2.1]oct-2-en-3-yl]-10-fluoro-7-methyl-6,7-dihydro-4H-3,4,7-triazadibenzo[cd,f]azulene The title compound was prepared using the procedure described in Example 1H, using Example 62A in place of Example 1G. ¹H NMR (400 MHz, DMSO-d₆) δ 1.94 (dt, J=14.9, 7.8 Hz, 1H), 2.18 (dt, J=8.4, 3.7 Hz, 2H), 2.27 (td, J=13.1, 6.9 Hz, 1H), 2.85 (s, 3H), 3.03 (q, J=10.3, 9.3 Hz, 2H), 4.23-4.31 (m, 1H), 4.41 (d, J=5.4 Hz, 1H), 4.61 (d, J=65.1 Hz, 2H), 6.11 (d, J=5.6 Hz, 1H), 7.44-7.58 (m, 1H), 7.75 (d, J=5.7 Hz, 1H), 8.04 (d, J=10.1 Hz, 2H), 8.43 (d, J=5.6 Hz, 1H). MS (ESI⁺) m/z 361 (M+1).

Example 63

N-(2,3-dihydroxypropyl)-2-[4-(10-fluoro-7-methyl-6,7-dihydro-4H-3,4,7-triazadibenzo[cd,f]azulen-5-yl)-3,6-dihydropyridin-1(2H)-yl]-N-methylacetamide The title compound was prepared as described in Example 17, substituting 3-(methylamino)propane-1,2-diol for L-prolinol. ¹H NMR (400 MHz, CD₃OD): δ 1.94 (s, 3H), 2.71-2.75 (m, 2H), 2.88 (s, 3H), 2.95 (q, J=5.80 Hz, 2H), 3.01 (s, 2H), 3.18 (s, 1H), 3.39-3.45 (m, 2H), 3.50-3.57 (m, 2H), 3.66-3.73 (m, 2H), 3.84-3.90 (m, 1H), 4.13-4.19 (m, 2H), 5.82 (d, J=14.34 Hz, 1H), 7.11-7.15 (m, 1H), 7.29-7.33 (m, 2H), 7.58-7.64 (m, 1H), 8.20 (dd, J=5.49, 1.53 Hz, 1H). MS (ESI⁺) m/z 480 (M+H)⁺.

Example 64

2-[4-(10-fluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone The title compound was prepared as described in Example 17, substituting D-prolinol for L-prolinol. ¹H NMR (400 MHz, CD₃OD): δ 1.89-2.07 (m, 6H), 2.69-2.73 (m, 2H), 2.89 (s, 3H), 2.90-2.96 (m, 2H), 3.41 (s, 3H), 3.54-3.66 (m, 3H), 4.13-4.21 (m, 1H), 4.19 (s, 2H), 5.84 (s, 1H), 7.10-7.17 (m, 1H), 7.30-7.33 (m, 2H), 7.63 (dd, J=10.38, 3.05 Hz, 1H), 8.21 (d, J=5.49 Hz, 1H). MS (ESI⁺) m/z 476 (M+H)⁺.

Example 65 tert-butyl[4-(1,10-difluoro-7-methyl-6,7-dihydro-4H-3,4,7-triazadibenzo[cd,f]azulen-5-yl)-3,6-dihydropyridin-1(2H)-yl]acetate The title compound was prepared as described in Example 16A, substituting Example 48 for Example 1. ¹H NMR (400 MHz, DMSO-d₆): δ 1.44 (s, 9H), 2.55-2.60 (m, 2H), 2.78 (t, J=5.49 Hz, 2H), 2.88 (s, 3H), 3.26 (s, 2H), 3.30 (d, J=2.14 Hz, 2H), 4.06 (s, 2H), 5.83 (s, 1H), 7.28-7.32 (m, 1H), 7.38 (d, J=3.66 Hz, 1H), 7.63-7.66 (m, 1H), 8.24 (d, J=4.88 Hz, 1H), 11.62 (s, 1H). MS (ESI⁺) m/z 467 (M+H)⁺.

Example 66

2-[4-(1,10-difluoro-7-methyl-6,7-dihydro-4H-3,4,7-triazadibenzo[cd,f]azulen-5-yl)-3,6-dihydropyridin-1(2H)-yl]-N,N-dimethylacetamide To a suspension of Example 48 (100 mg, 0.284 mmol) in N,N-dimethylformamide (4 mL) was added triethylamine (0.237 mL, 1.703 mmol) and 2-chloro-N,N-dimethylacetamide (41.4 mg, 0.341 mmol) and the mixture was heated at 70° C. for 3 hours. After cooling, the mixture was partitioned between ethyl acetate and brine and the organic phase was washed with brine and concentrated. The residue was purified by flash chromatography on silica gel (Teledyne CombiFlash Rf, 10-20% methanol in 2:1 ethyl acetate/hexane) to provide the title compound. ¹H NMR (400 MHz, DMSO-d₆): δ 2.57-2.62 (m, 2H), 2.79 (t, J=5.04 Hz, 2H), 2.84 (s, 3H), 2.89 (s, 3H), 3.03 (s, 3H), 3.30-3.37 (m, 4H), 4.07 (s, 2H), 5.85 (s, 1H), 7.26-7.32 (m, 1H), 7.36-7.39 (m, 1H), 7.62-7.66 (m, 1H), 8.24 (d, J=5.19 Hz, 1H), 11.62 (s, 1H). MS (ESI⁺) m/z 438 (M+H)⁺.

Example 67

[4-(1,10-difluoro-7-methyl-6,7-dihydro-4H-3,4,7-triazadibenzo[cd,f]azulen-5-yl)-3,6-dihydropyridin-1(2H)-yl]acetic acid The title compound was prepared as described in Examples 16B, substituting Example 65 for Example 16A. ¹H NMR (400 MHz, DMSO-d₆): δ 2.83 (s, 3H), 2.96 (s, 2H), 3.63-4.15 (m, 4H), 4.29 (s, 2H), 4.50 (s, 2H), 5.90 (s, 1H), 7.52 (t, J=6.71 Hz, 1H), 7.87 (d, J=9.46 Hz, 1H), 8.08 (s, 1H), 8.43 (d, J=4.58 Hz, 1H), 10.81 (s, 1H), 12.34 (s, 1H). MS (ESI⁺) m/z 411 (M+H)⁺.

Example 68

1,10-difluoro-7-methyl-5-[1-(methylsulfonyl)-1,2,3,6-tetrahydropyridin-4-yl]-6,7-dihydro-4H-3,4,7-triazadibenzo[cd,f]azulene To a suspension of Example 48 (60 mg, 0.17 mmol) in dichloromethane (5 mL) was added triethylamine (0.1 mL, 0.68 mmol) and methanesulfonyl chloride (30 mg, 0.25 mmol) and the mixture was stirred at room temperature overnight. Purification by flash chromatography on silica gel (Teledyne CombiFlash Rf, 0-15% methanol in 2:1 ethyl acetate/hexane) provided the title compound. $^1$H NMR (400 MHz, DMSO-d$_6$): δ 2.71 (s, 1H), 2.89 (s, 3H), 2.97 (s, 3H), 3.36-3.41 (m, 2H), 3.94-3.95 (m, 2H), 4.08 (s, 2H), 5.90 (s, 1H), 7.28-7.32 (m, 1H), 7.39 (dd, J=9.16, 5.49 Hz, 1H), 7.63-7.67 (m, 1H), 8.27 (d, J=4.88 Hz, 1H), 11.72 (s, 1H). MS (ESI$^+$) m/z 411 (M+H)$^+$.

Example 69

10-fluoro-5-{2-[(2-methoxyethyl)sulfonyl]-1,2,3,3a,4,6a-hexahydrocyclopenta[c]pyrrol-5-yl}-7-methyl-6,7-dihydro-4H-3,4,7-triazadibenzo[cd,f]azulene The title compound was prepared as described in Example 4, substituting 2-methoxyethanesulfonyl chloride for methanesulfonyl chloride and Example 59C for Example 1. $^1$H NMR (500 MHz, DMSO-d$_6$): δ 2.75 (m, 1H) 2.92 (s, 3H) 3.09 (m, 3H) 3.22 (s, 3H) 3.33 (m, 3H) 3.48 (m, 2H) 3.62 (m, 3H) 4.24 (s, 2H) 6.06 (s, 1H) 7.30 (m, 2H) 7.39 (d, J=5.49 Hz, 1H) 7.75 (m, 1H) 8.27 (d, J=5.19 Hz, 1H) 11.77 (s, 1H); MS (ESI) m/z 483 (M+H)$^+$.

Example 70

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone The title compound was prepared as described in Example 17, substituting Example 67 for Example 16. $^1$H NMR (400 MHz, DMSO-d$_6$): δ 1.77-1.87 (m, 6H), 2.55-2.62 (m, 2H), 2.76 (t, J=5.34 Hz, 2H), 2.89 (s, 3H), 3.22-3.31 (m, 4H), 3.39-3.55 (m, 3H), 3.95-3.99 (m, 1H), 4.07 (s, 2H), 5.85 (d, J=3.05 Hz, 1H), 7.26-7.32 (m, 1H), 7.35-7.39 (m, 1H), 7.63-7.66 (m, 1H), 8.23 (d, J=4.88 Hz, 1H). MS (ESI$^+$) m/z 494 (M+H)$^+$.

Example 71

2-[4-(1,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide The title compound was prepared as described in Example 17, substituting Example 67 for Example 16 and 2-(methylamino)ethanol for L-prolinol. $^1$H NMR (400 MHz, DMSO-d$_6$): δ 1.89 (s, 3H), 2.57-2.60 (m, 2H), 2.72-2.76 (m, 2H), 2.85 (s, 2H), 2.89 (s, 3H), 3.09 (s, 1H), 3.18-3.45 (m, 7H), 3.64-3.70 (m, 1H), 4.07 (d, J=3.66 Hz, 2H), 5.83-5.88 (m, 1H), 7.27-7.32 (m, 1H), 7.36-7.39 (m, 1H), 7.62-7.66 (m, 1H), 8.24 (d, J=4.88 Hz, 1H). MS (ESI$^+$) m/z 467 (M+H)$^+$.

Example 72

2-[4-(1,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone The title compound was prepared as described in Example 17, substituting Example 67 for Example 16 and 3-hydroxyazetidine hydrochloride for L-prolinol. $^1$H NMR (400 MHz, DMSO-d$_6$): δ 2.57-2.61 (m, 2H), 2.73-2.77 (m, 2H), 2.89 (s, 3H), 3.14 (dd, J=3.66 Hz, 2H), 3.25-3.27 (m, 2H), 3.61 (dd, J=10.07, 4.27 Hz, 1H), 3.92 (dd, J=9.46, 4.27 Hz, 1H), 4.04-4.09 (m, 3H), 4.33-4.38 (m, 1H), 4.43-4.48 (m, 1H), 5.70 (d, J=6.10 Hz, 1H), 5.84 (s, 1H), 7.27-7.31 (m, 1H), 7.35-7.40 (m, 1H), 7.62-7.66 (m, 1H), 8.24 (d, J=4.88 Hz, 1H), 11.61 (s, 1H). MS (ESI$^+$) m/z 466 (M+H)$^+$.

Example 73

2-[4-(1,10-difluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone The title compound was prepared as described in Example 17, substituting Example 67 for Example 16 and (S)-3-hydroxypyrrolidine for L-prolinol. $^1$H NMR (400 MHz, DMSO-d$_6$): δ 1.70-1.94 (m, 4H), 2.56-2.60 (m, 2H), 2.74-2.78 (m, 2H), 2.89 (s, 3H), 3.22-3.45 (m, 6H), 3.53-3.59 (m, 2H), 4.07 (s, 2H), 4.22-4.33 (m, 1H), 5.85 (s, 1H), 7.28-7.31 (m, 1H), 7.36-7.39 (m, 1H), 7.62-7.65 (m, 1H), 8.24 (d, J=4.88 Hz, 1H). MS (ESI$^+$) m/z 480 (M+H)$^+$.

Example 74

2-[4-(1,10-difluoro-7-methyl-6,7-dihydro-4H-3,4,7-triazadibenzo[cd,f]azulen-5-yl)-3,6-dihydropyridin-1(2H)-yl]-1-[3-(hydroxymethyl)azetidin-1-yl]ethanone The title compound was prepared as described in Example 17, substituting Example 67 for Example 16 and azetidin-3-ylmethanol for L-prolinol. $^1$H NMR (400 MHz, DMSO-d$_6$): δ 2.56-2.61 (m, 2H), 2.63-2.67 (m, 2H), 2.72 (t, J=5.49 Hz, 2H), 2.89 (s, 3H), 3.10 (s, 2H), 3.23 (d, J=2.14 Hz, 2H), 3.52 (d, J=6.41 Hz, 2H), 3.59 (dd, J=9.61, 5.34 Hz, 1H), 3.86 (t, J=9.00 Hz, 1H), 3.90 (dd, J=8.85, 5.49 Hz, 1H), 4.07 (s, 2H), 4.18 (t, J=8.55 Hz, 1H), 5.84 (s, 1H), 7.28-7.32 (m, 1H), 7.37 (dd, J=9.16, 5.49 Hz, 1H), 7.62-7.66 (m, 1H), 8.24 (d, J=4.88 Hz, 1H), 11.61 (s, 1H). MS (ESI$^+$) m/z 480 (M+H)$^+$.

Example 75

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone The title compound was prepared as described in Example 17, substituting Example 67 for Example 16 and D-prolinol for L-prolinol. $^1$H NMR (400 MHz, DMSO-d$_6$): δ 1.76-1.93 (m, 6H), 2.55-2.61 (m, 2H), 2.73-2.78 (m, 2H), 2.89 (s, 3H), 3.23-3.31 (m, 4H), 3.40-3.54 (m, 3H), 3.94-3.98 (m, 1H), 4.07 (s, 2H), 5.85 (d, J=3.36 Hz, 1H), 7.26-7.31 (m, 1H), 7.37 (dd, J=9.16, 5.49 Hz, 1H), 7.62-7.65 (m, 1H), 8.24 (d, J=4.88 Hz, 1H). MS (ESI$^+$) m/z 494 (M+H)$^+$.

Example 76

5-(10-fluoro-7-methyl-6,7-dihydro-4H-3,4,7-triazadibenzo[cd,f]azulen-5-yl)-N-methyl-3,3a,4,6a-tetrahydrocyclopenta[c]pyrrole-2(1H)-carboxamide The title compound was prepared using the procedure described in Example 13, using Example 59C in place Example 1. $^1$H NMR (500 MHz, DMSO-d$_6$) δ 2.54 (s, 3H), 2.76 (d, J=22.3 Hz, 1H), 2.86 (s, 3H), 2.99-3.12 (m, 3H), 3.36-3.48 (m, 3H), 3.58 (tdd, J=9.2, 6.8, 3.1 Hz, 2H), 4.55 (s, 2H), 6.26 (s, 1H), 7.43-7.53 (m, 1H), 7.72 (d, J=5.8 Hz, 1H), 8.01 (d, J=10.6 Hz, 2H), 8.38 (d, J=5.7 Hz, 1H). MS (ESI$^+$) m/z 418 (M+1).

Example 77

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N,N-dimethylacetamide The title compound was prepared using the procedure described in Example 12, using Example 59C in place Example 1. $^1$H NMR (400 MHz, DMSO-$d_6$) δ 2.83-2.88 (m, 1H), 2.89 (s, 6H), 2.95 (s, 3H), 2.96-3.28 (m, 3H), 3.30-3.60 (m, 2H), 3.63-3.78 (m, 2H), 3.80-4.09 (m, 2H), 4.32-4.38 (m, 1H), 4.43 (d, J=4.8 Hz, 1H), 6.09-6.30 (m, 1H), 7.43-7.54 (m, 1H), 7.70 (dd, J=6.1, 2.3 Hz, 1H), 7.92-8.06 (m, 1H), 8.39 (d, J=5.6 Hz, 1H). MS (ESI$^+$) m/z 446 (M+1).

Example 78

10-fluoro-7-methyl-5-[2-(methylsulfonyl)-1,2,3,3a,4,6a-hexahydrocyclopenta[c]pyrrol-5-yl]-6,7-dihydro-4H-3,4,7-triazadibenzo[cd,f]azulene The title compound was prepared using the procedure described in Example 11, using Example 59C in place Example 9. $^1$H NMR (400 MHz, DMSO-$d_6$) δ 2.82 (m, 1H), 2.86 (s, 3H), 2.90 (s, 3H), 3.05-3.22 (m, 3H), 3.28 (dd, J=10.1, 2.7 Hz, 1H), 3.47 (ddd, J=29.9, 9.9, 7.8 Hz, 2H), 3.67 (ddq, J=7.7, 5.1, 2.6 Hz, 1H), 4.55 (s, 2H), 6.25 (d, J=2.7 Hz, 1H), 7.49 (ddd, J=10.2, 7.6, 3.0 Hz, 1H), 7.73 (d, J=5.8 Hz, 1H), 7.94 (s, 1H), 7.97-8.05 (m, 1H), 8.39 (d, J=5.7 Hz, 1H). MS (ESI$^+$) m/z 439 (M+1).

Example 79

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-[(2S)-2-(hydroxymethyl)pyrrolidin-1-yl]ethanone The title compound was prepared using the procedure described in Example 50, using (S)-pyrrolidin-2-ylmethanol in place of dimethylamine and Example 58B in place of Example 41E. $^1$H NMR (500 MHz, DMSO-$d_6$) δ 1.76-2.05 (m, 5H), 2.17-2.46 (m, 2H), 2.75 (ddd, J=19.5, 8.1, 4.6 Hz, 1H), 2.93 (s, 3H), 3.28-3.60 (m, 2H), 4.03-4.20 (m, 4H), 4.22-4.58 (m, 7H), 5.72-6.28 (m, 1H), 7.24-7.30 (m, 1H), 7.31-7.37 (m, 1H), 7.40 (dd, J=5.3, 2.3 Hz, 1H), 7.74 (dd, J=10.4, 3.1 Hz, 1H), 8.30 (d, J=5.1 Hz, 1H). MS (ESI$^+$) m/z 502.

Example 80

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-(3-hydroxyazetidin-1-yl)ethanone The title compound was prepared using the procedure described in Example 50, using azetidin-3-ol in place of dimethylamine and Example 58B in place of Example 41E. $^1$H NMR (400 MHz, DMSO-$d_6$) δ 2.06 (m, 1H), 2.23 (t, J=10.7 Hz, 1H), 2.37 (d, J=8.0 Hz, 4H), 2.85 (s, 3H), 3.44-3.82 (m, 2H), 3.90-4.20 (m, 4H), 4.25-4.75 (m, 5H), 6.05-6.28 (m, 1H), 7.52 (q, J=8.6, 8.1 Hz, 1H), 7.77 (d, J=5.7 Hz, 1H), 8.05 (s, 2H), 8.44 (t, J=4.2 Hz, 1H). MS (ESI$^+$) m/z 474.

Example 81

[4-(10-fluoro-7-methyl-6,7-dihydro-4H-3,4,7-triazadibenzo[cd,f]azulen-5-yl)phenyl]acetic acid The title compound was prepared using the conditions described in Example 43B, substituting (4-(methylsulfonyl)phenyl)boronic acid with 2-(4-boronophenyl)acetic acid. The mixture was filtered and the filtrate was purified by reverse-phase HPLC on a Phenomenex Luna C8 AXIA column using a Waters PrepLC 4000 System (10-95% acetonitrile/10 mM ammonium acetate in water) to afford the title compound. $^1$H NMR (400 MHz, DMSO-$d_6$) δ 2.84 (s, 3H) 3.59 (s, 2H) 4.26 (s, 2H) 7.21-7.28 (m, 1H) 7.28-7.34 (m, 1H) 7.36 (d, J=5.49 Hz, 1H) 7.41 (d, J=8.24 Hz, 2H) 7.53 (d, J=8.24 Hz, 2H) 7.73 (dd, J=10.38, 3.05 Hz, 1H) 8.28 (d, J=5.19 Hz, 1H) 11.93 (s, 1H). MS (ESI$^+$) m/z 388 (M+H)$^+$.

Example 82

[3-(10-fluoro-7-methyl-6,7-dihydro-4H-3,4,7-triazadibenzo[cd,f]azulen-5-yl)phenyl]acetic acid The title compound was prepared using the conditions described in Example 43B, substituting (4-(methylsulfonyl)phenyl)boronic acid with 2-(3-boronophenyl)acetic acid. The mixture was filtered and the filtrate was purified by reverse-phase HPLC on a Phenomenex Luna C8 AXIA column using a Waters PrepLC 4000 System (10-95% acetonitrile/10 mM ammonium acetate in water) to afford the title compound. $^1$H NMR (400 MHz, DMSO-$d_6$) δ 2.83 (s, 3H) 3.54 (s, 2H) 4.26 (s, 2H) 7.21-7.34 (m, 3H) 7.36 (d, J=5.49 Hz, 1H) 7.43 (d, J=4.88 Hz, 2H) 7.49 (s, 1H) 7.73 (dd, J=10.53, 2.90 Hz, 1H) 8.28 (d, J=5.19 Hz, 1H) 11.90 (s, 1H). MS (ESI$^+$) m/z 388 (M+H)$^+$.

Example 83

N-(2,3-dihydroxypropyl)-2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-methylacetamide The title compound was prepared using the procedure described in Example 50, using 3-(methylamino)propane-1,2-diol in place of dimethylamine and Example 58B in place of Example 41E. $^1$H NMR (500 MHz, DMSO-$d_6$) δ 2.04 (q, J=10.8, 8.0 Hz, 1H), 2.14-2.31 (m, 2H), 2.38 (dd, J=17.2, 10.6 Hz, 1H), 2.51-2.63 (m, 2H), 2.68-2.78 (m, 1H), 2.81-2.92 (m, 2H), 2.95 (s, 3H), 3.04 (s, 3H), 3.18-3.47 (m, 4H), 3.55-3.96 (m, 2H), 4.16-4.54 (m, 2H), 6.04-6.25 (m, 1H), 7.39-7.60 (m, 1H), 7.72 (dd, J=12.3, 7.1 Hz, 1H), 8.00 (dd, J=32.2, 12.7 Hz, 1H), 8.43 (q, J=4.8 Hz, 1H). MS (ESI$^+$) m/z 506.

Example 84

2-[5-(10-fluoro-7-methyl-6,7-dihydro-4H-3,4,7-tri-azadibenzo[cd,f]azulen-5-yl)-3,3a,4,6a-tetrahydrocyclopenta[c]pyrrol-2(1H)-yl]-1-(3-hydroxyazetidin-1-yl)ethanone

Example 84A tert-butyl 2-(5-(7-fluoro-4-methyl-3,4-dihydro-1H-1,4,11-triazadibenzo[cd,f]azulen-2-yl)-3,3a,6,6a-tetrahydrocyclopenta[c]pyrrol-2(1H)-yl)acetate The title compound was prepared using the procedure described in Example 16A, using Example 59C in place of Example 1. LCMS: 475 (M+H)$^+$.

Example 84B 2-(5-(7-fluoro-4-methyl-3,4-dihydro-1H-1,4,11-triazadibenzo[cd,f]azulen-2-yl)-3,3a,6,6a-tetrahydrocyclopenta[c]pyrrol-2(1H)-yl)acetic acid The title compound was prepared using the procedure described in Example 16B, using Example 84A in place of Example 16A. MS (ESI$^+$) m/z 419 (M+1).

Example 84C

2-[5-(10-fluoro-7-methyl-6,7-dihydro-4H-3,4,7-tri-azadibenzo[cd,f]azulen-5-yl)-3,3a,4,6a-tetrahydrocyclopenta[c]pyrrol-2 (1H)-yl]-1-(3-hydroxyazetidin-1-yl)ethanone The title compound was prepared using the procedure described in Example 50, using azetidin-3-ol in place of dimethylamine and Example 84B in place of Example 41E. $^1$H NMR (500 MHz, DMSO-d$_6$) δ 2.88 (m, 3H), 2.92 (s, 3H), 3.00-3.06 (m, 2H), 3.12-3.42 (m, 3H), 3.46 (m, 1H), 3.51-4.08 (m, 5H), 4.13 (dd, J=13.0, 5.7 Hz, 1H), 4.33 (dd, J=17.0, 9.1 Hz, 1H), 4.51 (q, J=6.5 Hz, 1H), 6.14 (d, J=10.2 Hz, 1H), 7.49 (t, J=8.1 Hz, 1H), 7.71 (d, J=5.7 Hz, 1H), 7.89 (s, 1H), 8.01 (s, 1H), 8.40 (d, J=5.6 Hz, 1H), 10.67 (s, 1H). MS (ESI$^+$) m/z 474.

Example 85

N-(2,3-dihydroxypropyl)-2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-methylacetamide The title compound was prepared using the procedure described in Example 50, using 3-(methylamino)propane-1,2-diol in place of dimethylamine and Example 84B in place of Example 41E. $^1$H NMR (400 MHz, DMSO-d$_6$) δ 2.72 (dq, J=5.7, 3.2, 2.7 Hz, 1H), 2.90 (s, 3H), 2.92 (s, 3H), 2.99 (m, 2H), 3.05 (m, 2H), 3.17-3.39 (m, 4H), 3.40-3.78 (m, 4H), 3.80-4.07 (m, 2H), 4.29-4.51 (m, 2H), 6.11-6.28 (m, 1H), 7.35-7.49 (m, 1H), 7.65 (d, J=5.7 Hz, 1H), 7.86-8.04 (m, 2H), 8.38 (d, J=5.6 Hz, 1H). MS (ESI$^+$) m/z 506.

Example 86

2-[5-(10-fluoro-7-methyl-6,7-dihydro-4H-3,4,7-tri-azadibenzo[cd,f]azulen-5-yl)-3,3a,4,6a-tetrahydrocyclopenta[c]pyrrol-2(1H)-yl]-N-(2-hydroxyethyl)-N-methylacetamide The title compound was prepared using the procedure described in Example 50, using 2-(methylamino)ethanol place of dimethylamine and Example 84B in place of Example 41E. $^1$H NMR (400 MHz, DMSO-d$_6$) δ 2.52-2.60 (m, 1H), 2.72 (m, 1H), 2.88 (s, 3H), 2.90 (s, 3H), 2.97-3.10 (m, 2H), 3.32 (ddt, J=33.5, 22.9, 7.4 Hz, 2H), 3.52 (dq, J=10.8, 5.3 Hz, 2H), 3.63-3.78 (m, 2H), 3.81-4.05 (m, 2H), 4.31-4.51 (m, 4H), 6.07-6.31 (m, 1H), 7.48 (d, J=8.6 Hz, 1H), 7.69 (t, J=5.5 Hz, 1H), 7.79-8.05 (m, 2H), 8.39 (d, J=5.6 Hz, 1H). MS (ESI$^+$) m/z 476.

Example 87

10-fluoro-7-methyl-5-(2,3,6,7-tetrahydro-1H-azepin-4-yl)-6,7-dihydro-4H-3,4,7-triazadibenzo[cd,f]azulene

Example 87A tert-butyl but-3-en-1-yl(but-3-yn-1-yl)carbamate

To a solution of but-3-en-1-amine, hydrochloric acid (10 g, 93 mmol) and but-3-yn-1-yl 4-methylbenzenesulfonate (18 g, 80 mmol) in acetonitrile (803 mL) was added potassium carbonate (55.5 g, 401 mmol) and the mixture was stirred at 85° C. for 3 days and cooled to room temperature. Di-tert-butyl dicarbonate (21.02 g, 96 mmol) was added portionwise, with gas evolution observed for 20-30 minutes. The mixture was stirred overnight at room temperature, filtered through diatomaceous earth, concentrated and purified by flash chromatography on silica using an Analogix system (0-5% ethyl acetate/heptane) to provide the title compound. MS (ESI$^+$) m/z 224 (M+H)$^+$.

Example 87B tert-butyl but-3-en-1-yl(3-(4,4,5,5-tetramethyl-1,3,2-dioxaborolan-2-yl)but-3-en-1-yl)carbamate A mixture of copper(II) chloride (1.33 g, 13.43 mmol) and lithium chloride (0.570 g, 13.45 mmol) was degassed with nitrogen. N,N-Dimethylformamide (24 mL) was added and the mixture was stirred for 1 hour during which time the color changed from pale rust to yellow. Potassium acetate (1.318 g, 13.43 mmol) and 4,4,4',4',5,5,5',5'-octamethyl-2,2'-bi(1,3,2-dioxaborolane) (3.41 g, 13.43 mmol) were added and the mixture was stirred for 2 minutes, during which time the color changed to black. A solution of Example 87A (2.5 g, 11.20 mmol) in N,N-dimethylformamide (6 mL) was added. The mixture was stirred overnight, diluted with saturated ammonium chloride and 1:1 heptane/methyl t-butyl ether, stirred for 30 minutes at room temperature and filtered through diatomaceous earth. The aqueous layer was extracted with ethyl acetate (three times) and the combined extracts were dried over sodium sulfate, filtered, concentrated and purified by flash chromatography on silica using an Analogix system (0-5% ethyl acetate/heptane) to afford the title compound. MS (ESI$^+$) m/z 352 (M+H)$^+$.

Example 87C tert-butyl 4-(4,4,5,5-tetramethyl-1,3,2-dioxaborolan-2-yl)-2,3,6,7-tetrahydro-1H-azepine-1-carboxylate A solution of Example 87B (7.28 g, 20.72 mmol) in methyl cyclohexane (1.5 L) was degassed with nitrogen and (1,3-bis(2,4,6-trimethylphenyl)-2-imidazolidinylidene)dichloro(phenylmethylene)(tricyclohexylphosphine)ruthenium (250 mg, 0.294 mmol) was added. The mixture was stirred at room temperature overnight and diethyleneglycol vinyl ether (0.16 mL) was added to inactivate any remaining active catalyst. The mixture was stirred for 30 minutes, concentrated and purified by flash chromatography on silica using an Analogix system (0-10% ethyl acetate/heptane) to provide the title compound. MS (ESI$^+$) m/z 346 (M+Na)$^+$.

Example 87D tert-butyl 4-(7-fluoro-4-methyl-1-tosyl-3,4-dihydro-1H-1,4,11-triazadibenzo[cd,f]azulen-2-yl)-2,3,6,7-tetrahydro-1H-azepine-1-carboxylate The title compound was prepared according to the procedure described in Example 1D, substituting Example 41D for Example 1C and Example 87C for tert-butyl 4-(4,4,5,5-tetramethyl-1,3,2-dioxaborolan-2-yl)-5,6-dihydropyridine-1(2H)-carboxylate. MS(ESI$^+$) m/z 603 (M+H)$^+$.

Example 87E tert-butyl 4-(7-fluoro-4-methyl-3,4-dihydro-1H-1,4,11-triazadibenzo[cd,f]azulen-2-yl)-2,3,6,7-tetrahydro-1H-azepine-1-carboxylate The title compound was prepared according to the procedure described in Example 1E, substituting Example 87D for Example 1D.

Example 87F 10-fluoro-7-methyl-5-(2,3,6,7-tetrahydro-1H-azepin-4-yl)-6,7-dihydro-4H-3,4,7-triazadibenzo[cd,f]azulene To a solution of Example 87E (560 mg, 1.249 mmol) in 5 mL dichloromethane was added 2,2,2-trifluoroacetic acid (1443 µL, 18.73 mmol) and the mixture was stirred at room temperature overnight. The mixture was concentrated, re-dissolved in 3 mL dichloromethane, treated with 2N hydrogen chloride in ethyl ether, filtered and dried to afford the title compound as the hydrochloride salt. $^1$H NMR (400 MHz, DMSO-d$_6$) δ 2.71 (q, J=5.7 Hz, 2H), 2.83 (s, 3H), 2.97 (dd, J=6.6, 3.5 Hz, 2H), 3.22 (dt, J=34.5, 6.0 Hz, 4H), 4.36 (s, 2H), 5.96 (t, J=6.2 Hz, 1H), 7.42 (t, J=8.6 Hz, 1H), 7.62 (d, J=5.7 Hz, 1H), 7.92 (d, J=10.2 Hz, 1H), 8.35 (d, J=5.6 Hz, 1H), 9.50 (s, 2H), 12.45 (s, 1H). MS (ESI$^+$) m/z 349 (M+H)$^+$.

Example 88

2-[4-(10-fluoro-7-methyl-6,7-dihydro-4H-3,4,7-triazadibenzo[cd,f]azulen-5-yl)-2,3,6,7-tetrahydro-1H-azepin-1-yl]-N,N-dimethylacetamide The title compound was prepared according to the procedure described in Example 12, substituting Example 87F for Example 1. $^1$H NMR (400 MHz, DMSO-d$_6$) δ 1.21-1.66 (m, 2H), 2.40-2.50 (m, 2H), 2.61-2.67 (m, 2H), 2.68-2.72 (m, 4H), 2.83 (s, 3H), 2.87 (s, 3H), 3.07 (s, 3H), 4.08 (bs, 2H), 5.93 (t, J=6.3 Hz, 1H), 7.18-7.34 (m, 3H), 7.69 (dd, J=10.4, 3.0 Hz, 1H), 8.21 (d, J=5.2 Hz, 1H), 11.49 (s, 1H). MS (ESI$^+$) m/z 434 (M+H)$^+$.

Example 89

10-fluoro-7-methyl-5-[1-(methylsulfonyl)-2,3,6,7-tetrahydro-1H-azepin-4-yl]-6,7-dihydro-4H-3,4,7-triazadibenzo[cd,f]azulene The title compound was prepared according to the procedure described in Example 4, substituting Example 87F for Example 1. $^1$H NMR (400 MHz, DMSO-d$_6$) δ 2.55-2.65 (m, 2H), 2.80-2.90 (m, 2H), 2.90-3.00 (s, 3H), 3.28-3.58 (m, 7H), 4.10 (s, 2H), 5.92 (s, 1H), 7.00-7.49 (m, 3H), 7.71 (dd, J=10.4, 3.0 Hz, 1H), 8.24 (d, J=5.2 Hz, 1H), 11.62 (s, 1H). MS (ESI$^+$) m/z 427 (M+H)$^+$.

Example 90

[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid

Example 90A tert-butyl 2-(4-(7-fluoro-4-methyl-3,4-dihydro-1H-1,4,11-triazadibenzo[cd,f]azulen-2-yl)-2,3,6,7-tetrahydro-1H-azepin-1-yl)acetate The title compound was prepared according to the procedure described in Example 16A, substituting Example 87F for Example 1. MS (ESI$^+$) m/z 463 (M+H)$^+$.

Example 90B

[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid The title compound was prepared according to the procedure described in Example 87F, substituting Example 90A for Example 87E. $^1$H NMR (400 MHz, DMSO-d$_6$) δ 2.73 (d, J=−0.2 Hz, 2H), 2.89 (s, 2H), 2.96-3.24 (m, 2H), 3.23-4.11 (m, 5H), 4.40-5.53 (m, 4H), 5.98 (t, J=5.9 Hz, 1H), 7.44-7.52 (m, 1H), 7.70 (d, J=5.7 Hz, 1H), 7.94-7.97 (m, 1H), 8.00 (dd, J=9.0, 4.3 Hz, 1H), 8.39 (d, J=5.6 Hz, 1H), 10.74-10.79 (m, 1H), 12.62-12.72 (m, 1H). MS (ESI$^+$) m/z 407 (M+H)$^+$.

Example 91

2-[4-(10-fluoro-7-methyl-6,7-dihydro-4H-3,4,7-triazadibenzo[cd,f]azulen-5-yl)-2,3,6,7-tetrahydro-1H-azepin-1-yl]-1-(3-hydroxyazetidin-1-yl)ethanone A mixture of Example 90B (60 mg, 0.125 mmol), azetidin-3-ol, hydrochloric acid (20.57 mg, 0.188 mmol), 2-(3H-[1,2,3]triazolo[4,5-b]pyridin-3-yl)-1,1,3,3-tetramethylisouronium hexafluorophosphate (V) (57.1 mg, 0.150 mmol) and triethylamine (87 µL, 0.626 mmol) in 2 mL N,N-dimethylformamide was stirred at room temperature overnight. The mixture was extracted with dichloromethane and purified by flash chromatography on silica using an Analogix system (0-10% methanol/dichloromethane) to provide the title compound. $^1$H NMR (400 MHz, DMSO-d$_6$) δ 2.46-2.90 (m, 10H), 3.17 (d, J=5.1 Hz, 2H), 3.62 (dd, J=10.3, 4.4 Hz, 1H), 3.89-4.14 (m, 5H), 4.33-4.61 (m, 2H), 5.72 (d, J=5.9 Hz, 1H), 5.92 (t, J=6.3 Hz, 1H), 7.18-7.35 (m, 3H), 7.69 (dd, J=10.4, 3.0 Hz, 1H), 8.22 (d, J=5.2 Hz, 1H), 11.51 (s, 1H). MS (ESI+) m/z 462 (M+H)+.

Example 92

5-(3,3-dimethyl-1,2,3,6-tetrahydropyridin-4-yl)-10-fluoro-7-methyl-6,7-dihydro-4H-3,4,7-triazadibenzo[cd,f]azulene Example 92A tert-butyl 4-(7-fluoro-4-methyl-3,4-dihydro-1H-1,4,11-triazadibenzo[cd,f]azulen-2-yl)-5,5-dimethyl-5,6-dihydropyridine-1(2H)-carboxylate The title compound was prepared using the procedure described in Example 1D, using tert-butyl 5,5-dimethyl-4-(4,4,5,5-tetramethyl-1,3,2-dioxaborolan-2-yl)-5,6-dihydropyridine-1(2H)-carboxylate in place of tert-butyl 4-(4,4,5,5-tetramethyl-1,3,2-dioxaborolan-2-yl)-5,6-dihydropyridine-1(2H)-carboxylate and Example 43A in place of Example 1C. LCMS: 463 (M+H)+.

Example 92B 5-(3,3-dimethyl-1,2,3,6-tetrahydropyridin-4-yl)-10-fluoro-7-methyl-6,7-dihydro-4H-3,4,7-triazadibenzo[cd,f]azulene The title compound was prepared using the procedure described in Example 1H, using Example 92A in place of Example 1G. $^1$H NMR (400 MHz, DMSO-$d_6$) δ 1.94 (dt, J=14.9, 7.8 Hz, 1H), 2.18 (dt, J=8.4, 3.7 Hz, 2H), 2.27 (td, J=13.1, 6.9 Hz, 1H), 2.85 (s, 3H), 3.03 (q, J=10.3, 9.3 Hz, 2H), 4.23-4.31 (m, 1H), 4.41 (d, J=5.4 Hz, 1H), 4.61 (d, J=65.1 Hz, 2H), 6.11 (d, J=5.6 Hz, 1H), 7.44-7.58 (m, 1H), 7.75 (d, J=5.7 Hz, 1H), 8.04 (d, J=10.1 Hz, 1H), 8.43 (d, J=5.6 Hz, 1H). MS (ESI+) m/z 363 (M+1).

Example 93

10-fluoro-7-methyl-5-(1,2,5,6-tetrahydropyridin-3-yl)-6,7-dihydro-4H-3,4,7-triazadibenzo[cd,f]azulene Example 93A tert-butyl 3-(7-fluoro-4-methyl-3,4-dihydro-1H-1,4,11-triazadibenzo[cd,f]azulen-2-yl)-5,6-dihydropyridine-1(2H)-carboxylate The title compound was prepared using the procedure described in Example 1D, using tert-butyl 3-(4,4,5,5-tetramethyl-1,3,2-dioxaborolan-2-yl)-5,6-dihydropyridine-1(2H)-carboxylate in place of tert-butyl 4-(4,4,5,5-tetramethyl-1,3,2-dioxaborolan-2-yl)-5,6-dihydropyridine-1(2H)-carboxylate and Example 43A in place of Example 1C. LCMS: 435 (M+H)+.

Example 93B 10-fluoro-7-methyl-5-(1,2,5,6-tetrahydropyridin-3-yl)-6,7-dihydro-4H-3,4,7-triazadibenzo[cd,f]azulene The title compound was prepared using the procedure described in Example 1H, using Example 93A in place of Example 1G. $^1$H NMR (400 MHz, DMSO-$d_6$) δ 1.94 (dt, J=14.9, 7.8 Hz, 1H), 2.18 (dt, J=8.4, 3.7 Hz, 2H), 2.27 (td, J=13.1, 6.9 Hz, 1H), 2.85 (s, 3H), 3.03 (q, J=10.3, 9.3 Hz, 2H), 4.23-4.31 (m, 1H), 4.41 (d, J=5.4 Hz, 1H), 4.61 (d, J=65.1 Hz, 2H), 6.11 (d, J=5.6 Hz, 1H), 7.44-7.58 (m, 1H), 7.75 (d, J=5.7 Hz, 1H), 8.04 (d, J=10.1 Hz, 1H), 8.43 (d, J=5.6 Hz, 1H). MS (ESI+) m/z 335 (M+1).

Example 94

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2 (1H)-yl]-N-(3-hydroxycyclobutyl)-N-methylacetamide The title compound was prepared using the procedure described in Example 50, using 3-(methylamino)cyclobutanol in place of dimethylamine and Example 84B in place of Example 41E. $^1$H NMR (400 MHz, DMSO-$d_6$) δ 2.04 (dh, J=26.7, 8.9, 8.0 Hz, 4H), 2.41 (dq, J=11.7, 6.2 Hz, 2H), 2.84 (s, 3H), 2.95 (s, 3H), 2.98-3.36 (m, 4H), 4.13-4.73 (m, 8H), 6.20 (d, J=5.6 Hz, 1H), 7.49 (tt, J=8.6, 3.8 Hz, 1H), 7.69-7.75 (m, 1H), 7.91-8.07 (m, 2H), 8.42 (t, J=5.5 Hz, 1H). MS (ESI+) m/z 502.

Example 95

10-fluoro-7-methyl-5-[1-(methylsulfonyl)-1,2,5,6-tetrahydropyridin-3-yl]-6,7-dihydro-4H-3,4,7-triazadibenzo[cd,f]azulene The title compound was prepared using the procedure described in Example 11, using Example 93B in place Example 9. $^1$H NMR (400 MHz, DMSO-$d_6$) δ 2.48 (dd, J=6.0, 3.0 Hz, 2H), 2.90 (s, 3H), 3.00 (s, 3H), 3.37 (t, J=5.7 Hz, 2H), 4.18 (s, 4H), 6.01 (p, J=2.4 Hz, 1H), 7.25-7.41 (m, 2H), 7.45 (d, J=5.5 Hz, 1H), 7.77 (dd, J=10.3, 3.0 Hz, 1H), 8.31 (d, J=5.4 Hz, 1H). MS (ESI+) m/z 413.

Example 96

5-(10-fluoro-7-methyl-6,7-dihydro-4H-3,4,7-triazadibenzo[cd,f]azulen-5-yl)-N-methyl-3,6-dihydropyridine-1(2H)-carboxamide The title compound was prepared using the procedure described in Example 13, using Example 93B in place Example 1. $^1$H NMR (500 MHz, DMSO-$d_6$) δ 2.33 (dp, J=5.9, 2.8 Hz, 2H), 2.63 (s, 3H), 2.91 (s, 3H), 3.50 (t, J=5.7 Hz, 2H), 4.21 (s, 2H), 4.26 (d, J=3.0 Hz, 2H), 6.00-6.06 (m, 1H), 6.48 (s, 1H), 7.27-7.41 (m, 2H), 7.47 (d, J=5.5 Hz, 1H), 7.78 (dd, J=10.4, 3.0 Hz, 1H), 8.30 (d, J=5.3 Hz, 1H). MS (ESI+) m/z 392 (M+1).

Example 97

2-[5-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide The title compound was prepared using the procedure described in Example 12, using Example 93B in place Example 1. $^1$H NMR (400 MHz, DMSO-$d_6$) δ 2.73 (d, J=5.1 Hz, 2H), 2.81 (s, 3H), 2.95 (s, 3H), 3.00 (s, 3H), 3.37-3.65 (m, 2H), 4.34 (d, J=9.0 Hz, 2H), 4.47 (s, 2H), 4.55 (s, 2H), 6.13-6.23 (m, 1H), 7.45-7.61 (m, 2H), 7.75 (d, J=5.6 Hz, 1H), 7.97-8.13 (m, 1H), 8.44 (d, J=5.6 Hz, 1H). MS (ESI$^+$) m/z 420 (M+1).

Example 98

2-[(1R,5S)-3-(10-fluoro-7-methyl-6,7-dihydro-4H-3, 4,7-triazadibenzo[cd,f]azulen-5-yl)-8-azabicyclo [3.2.1]oct-2-en-8-yl]-N-(3-hydroxycyclobutyl)-N-methylacetamide The title compound was prepared using the procedure described in Example 50, using 3-(methylamino)cyclobutanol place of dimethylamine and Example 58B in place of Example 41E. $^1$H NMR (400 MHz, DMSO-d$_6$) δ 1.88-2.29 (m, 4H), 2.41 (tq, J=10.1, 6.0, 4.1 Hz, 4H), 2.84 (s, 3H), 2.88-2.94 (m, 2H), 2.95 (s, 3H), 2.97-3.11 (m, 2H), 4.18-4.71 (m, 5H), 6.20 (d, J=5.6 Hz, 1H), 7.48 (ddt, J=14.9, 11.1, 4.8 Hz, 1H), 7.61-7.85 (m, 2H), 7.92-8.13 (m, 1H), 8.42 (t, J=5.5 Hz, 1H). MS (ESI$^+$) m/z 502 (M+1).

Example 99

10-fluoro-7-methyl-5-[9-(methylsulfonyl)-9-azabicyclo[3.3.1]non-2-en-3-yl]-6,7-dihydro-4H-3,4,7-triazadibenzo[cd,f]azulene

Example 99A tert-butyl 3-(((trifluoromethyl)sulfonyl)oxy)-9-azabicyclo[3.3.1]non-3-ene-9-carboxylate To a stirred solution of sodium bis(trimethylsilyl)amide (2.0M in tetrahydrofuran) (11.49 ml, 22.98 mmol) in tetrahydrofuran (30 mL) at −78° C. was added slowly tert-butyl 3-oxo-9-azabicyclo[3.3.1]nonane-9-carboxylate (5.0 g, 20.89 mmol) in tetrahydrofuran (12 mL). The reaction mixture was stirred for 30 minutes and was treated over 15 minutes with a solution of 1,1,1-trifluoro-N-phenyl-N-((trifluoromethyl)sulfonyl)methanesulfonamide (8.21 g, 22.98 mmol) in tetrahydrofuran (20 mL). The mixture was stirred at −78° C. for 1.5 hours, and was allowed to warm to room temperature for 1 hour. The reaction mixture was quenched by the addition of water (7.5 mL) and extracted with ethyl acetate (three times with 100 mL). The combined organic layers were washed with brine, dried over Na$_2$SO$_4$, filtered and concentrated in vacuo. The residue was purified by flash chromatography on Analogix IntelliFlash$^{280}$ eluting with 0 to 40% ethyl acetate/hexanes to provide the title compound. $^1$H NMR (500 MHz, DMSO-d$_6$) δ 1.40 (s, 9H), 1.47-1.78 (m, 6H), 2.24 (d, J=18.0 Hz, 1H), 2.75 (dd, J=17.9, 7.6 Hz, 1H), 4.43 (dd, J=19.9, 7.7 Hz, 1H), 4.72 (d, J=25.1 Hz, 1H), 6.03-6.06 (m, 1H).

Example 99B tert-butyl 3-(4,4,5,5-tetramethyl-1,3,2-dioxaborolan-2-yl)-9-azabicyclo[3.3.1]non-3-ene-9-carboxylate A 50 mL pressure vial was charged with Example 99A (1.0 g, 2.69 mmol), 4,4,4',4',5,5,5',5'-octamethyl-2,2'-bi(1,3,2-dioxaborolane) (0.752 g, 2.96 mmol), potassium acetate (0.793 g, 8.08 mmol), PdCl$_2$(dppf) CH$_2$Cl$_2$ (0.110 g, 0.135 mmol) and dioxane (12 mL). The vial was capped with a septa, evacuated, and backfilled with N$_2$. The reaction mixture was stirred at 80° C. for 4 hours and was directly used in the next step.

Example 99C tert-butyl 3-(7-fluoro-4-methyl-3,4-dihydro-1H-1,4, 11-triazadibenzo[cd,f]azulen-2-yl)-9-azabicyclo [3.3.1]non-3-ene-9-carboxylate To the reaction mixture described in Example 99B (~2.69 mmol) was added Example 43A (0.85 g, 2.242 mmol), sodium carbonate (2.0 M in H$_2$O, 4.48 ml, 8.97 mmol) and PdCl$_2$(dppf) CH$_2$Cl$_2$ (0.092 g, 0.112 mmol). The vial was capped with a septa, evacuated and backfilled with N$_2$. The reaction mixture was stirred at 85° C. for 3 hours. After cooling, the reaction mixture was partitioned between ethyl acetate and brine. The organic layer was washed with brine, dried over Na$_2$SO$_4$, filtered, and concentrated in vacuo. The residue was purified by flash chromatography on silica gel using an AnaLogix system (IntelliFlash$^{280}$) (10-80% ethyl acetate/hexanes) to provide the title compound. LC-MS 475.0 (M+H)$^+$.

Example 99D 2-(9-azabicyclo[3.3.1]non-3-en-3-yl)-7-fluoro-4-methyl-3,4-dihydro-1H-1,4,11-triazadibenzo[cd,f] azulene A solution of Example 99C (1.135 g, 2.392 mmol) in dichloromethane (6 mL) was treated with trifluoroacetic acid (3 mL) at room temperature for 30 minutes, and concentrated in vacuo. The crude product (LC-MS 375.2 (M+H)$^+$) was directly used for next step.

Example 99E 10-fluoro-7-methyl-5-[9-(methylsulfonyl)-9-azabicyclo[3.3.1]non-2-en-3-yl]-6,7-dihydro-4H-3,4,7-triazadibenzo[cd,f]azulene To a suspension of Example 99D (~0.100 mmol) and triethylamine (0.056 mL, 0.398 mmol) in N,N-dimethylformamide (0.8 mL) at 0° C. was added slowly methanesulfonyl chloride (8.51 µl, 0.110 mmol) in N,N-dimethylformamide (0.3 mL). The mixture was stirred at room temperature for 1 hour. The reaction mixture was concentrated in vacuo and the residue was purified by reverse-phase HPLC performed on a Phenomenex Luna C8 AXIA column (30×75 mm, 100 Å) using a gradient of 10% to 95% acetonitrile:10 mM ammonium acetate in water to provide the title compound. $^1$H NMR (400 MHz, DMSO-d$_6$) δ 1.49-1.89 (m, 6H), 2.51-2.53 (m, 1H), 2.85 (s, 3H), 2.95 (s, 3H), 3.01 (dd, J=18.6, 7.6 Hz, 1H), 4.00-4.20 (m, 2H), 4.23 (d, J=7.3 Hz, 1H), 4.39-4.58 (m, 1H), 5.89 (dd, J=4.5, 2.5 Hz, 1H), 7.12-7.44 (m, 3H), 7.72 (dd, J=10.4, 3.0 Hz, 1H), 8.25 (d, J=5.2 Hz, 1H), 11.56 (s, 1H). MS (ESI) m/e 453.2 (M+H)$^+$.

Example 100

3-(10-fluoro-7-methyl-6,7-dihydro-4H-3,4,7-triazadibenzo[cd,f]azulen-5-yl)-N-methyl-9-azabicyclo [3.3.1]non-2-ene-9-carboxamide To a suspension of Example 99D (0.100 mmol) in N,N-dimethylformamide (0.8 mL) were added 2,5-dioxopyrrolidin-1-yl methylcarbamate (20.57 mg, 0.120 mmol) and triethylamine (0.069 mL, 0.498 mmol). The mixture was stirred at room temperature for 1 hour. The reaction mixture was concentrated in vacuo and the residue was purified by reverse-phase HPLC performed on a Phenomenex Luna C8 AXIA column (30×75 mm, 100 Å) using a gradient of 10% to 95% acetonitrile:10 mM ammonium acetate in water to provide the title compound. $^1$H NMR (400 MHz, DMSO-$d_6$) δ 1.46-1.59 (m, 2H), 1.57-1.90 (m, 4H), 2.45 (d, J=17.8 Hz, 1H), 2.61 (d, J=4.1 Hz, 3H), 2.92-2.87 (m, 1H), 2.87 (s, 3H), 4.12 (d, J=3.5 Hz, 2H), 4.30-4.55 (m, 1H), 4.75 (d, J=5.2 Hz, 1H), 5.85 (d, J=5.4 Hz, 1H), 6.48 (q, J=4.3 Hz, 1H), 7.13-7.43 (m, 3H), 7.71 (dd, J=10.5, 3.0 Hz, 1H), 8.24 (d, J=5.2 Hz, 1H), 11.52 (s, 1H). MS (ESI) m/e 432.2 (M+H)$^+$.

Example 101

2-[3-(10-fluoro-7-methyl-6,7-dihydro-4H-3,4,7-triazadibenzo[cd,f]azulen-5-yl)-9-azabicyclo[3.3.1]non-2-en-9-yl]-N,N-dimethylacetamide To a suspension of Example 99D (0.100 mmol) and 2-chloro-N,N-dimethylacetamide (13.32 mg, 0.110 mmol) in N,N-dimethylformamide (0.8 mL) was added N-ethyl-N-isopropylpropan-2-amine (0.087 mL, 0.498 mmol). The mixture was stirred at room temperature for 24 hours. The reaction mixture was concentrated in vacuo and the residue was purified by reverse-phase HPLC performed on a Phenomenex Luna C8 AXIA column (30×75 mm, 100 Å) using a gradient of 10% to 95% acetonitrile:10 mM ammonium acetate in water to provide the title compound. $^1$H NMR (400 MHz, DMSO-$d_6$) δ 1.38-1.89 (m, 6H), 2.25 (d, J=18.2 Hz, 1H), 2.75-3.50 (m, 5H), 2.83 (s, 3H), 2.87 (s, 3H), 3.09 (s, 3H), 3.92-4.31 (m, 2H), 5.57-5.84 (m, 1H), 7.05-7.46 (m, 3H), 7.72 (dd, J=10.5, 3.0 Hz, 1H), 8.23 (d, J=5.2 Hz, 1H), 11.51 (s, 1H). MS (ESI) m/e 460.2 (M+H)$^+$.

Example 102

3-[3-(10-fluoro-7-methyl-6,7-dihydro-4H-3,4,7-triazadibenzo[cd,f]azulen-5-yl)-9-azabicyclo[3.3.1]non-2-en-9-yl]-3-oxopropanenitrile A mixture of Example 99D (0.100 mmol), 2-cyanoacetic acid (10.21 mg, 0.120 mmol), 2-(3H-[1,2,3]triazolo[4,5-b]pyridin-3-yl)-1,1,3,3-tetramethylisouronium hexafluorophosphate(V) (45.6 mg, 0.120 mmol) and triethylamine (69.7 µl, 0.500 mmol) in N,N-dimethylformamide (1 mL) was stirred at room temperature for 1 hour. The reaction mixture was concentrated in vacuo and the residue was purified by reverse-phase HPLC performed on a Phenomenex Luna C8 AXIA column (30×75 mm, 100 Å) using a gradient of 10% to 95% acetonitrile: 10 mM ammonium acetate in water to provide the title compound. $^1$H NMR (400 MHz, DMSO-$d_6$) δ 1.49-1.87 (m, 6H), 2.61 (dd, J=24.7, 17.9 Hz, 1H), 2.87 (d, J=2.9 Hz, 3H), 3.01 (dd, J=17.8, 7.0 Hz, 1H), 3.91-4.90 (m, 6H), 5.84 (dd, J=20.8, 5.4 Hz, 1H), 7.07-7.45 (m, 3H), 7.71 (dt, J=10.5, 2.8 Hz, 1H), 8.25 (d, J=5.2 Hz, 1H), 11.57 (s, 1H). MS (ESI) m/e 442.2 (M+H)$^+$.

Example 103

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(2-hydroxyethyl)-N-methylacetamide Example 103A

[3-(10-fluoro-7-methyl-6,7-dihydro-4H-3,4,7-triazadibenzo[cd,f]azulen-5-yl)-9-azabicyclo[3.3.1]non-2-en-9-yl]acetic acid To a suspension of Example 99D (0.100 mmol) and tert-butyl 2-bromoacetate (194 mg, 0.996 mmol) in N,N-dimethylformamide (6 mL) was added N-ethyl-N-isopropylpropan-2-amine (0.870 mL, 4.98 mmol). The mixture was stirred at room temperature for 24 hours. To the reaction mixture was added water and the mixture was extracted with ethyl acetate. The organics were washed with brine, dried over sodium sulfate, filtered, and concentrated. To the residue was added dichloromethane (2 mL) and trifluoroacetic acid (2 mL). The mixture was stirred at room temperature for 4 hours and concentrated in vacuo. The crude titled product was directly used for next step. (MS (ESI) m/e 433.2 (M+H)$^+$).

Example 103B

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(2-hydroxyethyl)-N-methylacetamide A mixture of Example 103A (~0.10 mmol), 2-(methylamino)ethanol (15.02 mg, 0.200 mmol), 1-[bis(dimethylamino)methylene]-1H-1,2,3-triazolo[4,5-b]pyridinium 3-oxidhexafluorophosphate (HATU) (45.6 mg, 0.120 mmol) and triethylamine (69.7 µl, 0.500 mmol) in N,N-dimethylformamide (1.5 mL) was stirred at room temperature for 1 hour. The reaction mixture was concentrated in vacuo and the residue was purified by reverse-phase HPLC performed on a Phenomenex Luna C8 AXIA column (30×75 mm, 100 Å) using a gradient of 10% to 95% acetonitrile: 10 mM ammonium acetate in water to provide the title compound. $^1$H NMR (400 MHz, DMSO-$d_6$) δ 1.40-1.83 (m, 6H), 2.26 (dd, J=18.3, 10.2 Hz, 1H), 2.76 (dd, J=16.7, 9.9 Hz, 1H), 2.83 (s, 2H), 2.87 (s, 3H), 3.12 (s, 1H), 3.14-3.63 (m, 8H), 4.00-4.23 (m, 2H), 5.73 (d, J=5.0 Hz, 1H), 7.03-7.45 (m, 3H), 7.72 (dd, J=10.5, 2.9 Hz, 1H), 8.24 (d, J=5.2 Hz, 1H). MS (ESI) m/e 490.2 (M+H)$^+$.

Example 104

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-[(2S)-2-(hydroxymethyl)pyrrolidin-1-yl]ethanone The title compound was prepared using the conditions described in Example 103B, substituting (S)-pyrrolidin-2-ylmethanol for 2-(methylamino)ethanol. $^1$H NMR (400 MHz, DMSO-$d_6$) δ 1.37-1.68 (m, 4H), 1.71-1.98 (m, 6H), 2.16-2.36 (m, 1H), 2.69-2.85 (m, 1H), 2.87 (s, 3H), 3.12-3.68 (m, 8H), 3.95 (m, 1H), 4.04-4.30 (m, 2H), 4.75 (s, 1H), 5.74 (q, J=6.2, 5.4 Hz, 1H), 7.02-7.40 (m, 3H), 7.72 (dd, J=10.6, 3.0 Hz, 1H), 8.24 (d, J=5.2 Hz, 1H), 11.52 (d, J=5.7 Hz, 1H). MS (ESI$^+$) m/z 516.3 (M+H)$^+$.

Example 105

2-[3-(10-fluoro-7-methyl-6,7-dihydro-4H-3,4,7-triazadibenzo[cd,f]azulen-5-yl)-9-azabicyclo[3.3.1]non-2-en-9-yl]-1-(3-hydroxyazetidin-1-yl)ethanone The title compound was prepared as described in Example 103B, substituting azetidin-3-ol hydrochloride for 2-(methylamino)ethanol. $^1$H NMR (400 MHz, DMSO-$d_6$) δ 1.38-1.66 (m, 4H), 1.72-1.87 (m, 2H), 2.23 (d, J=18.3 Hz, 1H), 2.68-2.82 (m, 1H), 2.87 (s, 3H), 3.07-3.19 (m, 4H), 3.39-3.46 (m, 1H), 3.56-3.66 (m, 1H), 3.92-4.10 (m, 2H), 4.12 (d, J=4.3 Hz, 2H), 4.35-4.51 (m, 2H), 5.60-5.85 (m, 1H), 7.04-7.47 (m, 3H), 7.71 (dd, J=10.5, 3.0 Hz, 1H), 8.23 (d, J=5.2 Hz, 1H), 11.51 (s, 1H). MS (ESI⁺) m/z 488.2 (M+H)⁺.

Example 106

2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(3-hydroxycyclobutyl)-N-methylacetamide The title compound was prepared using the conditions described in Example 103B, substituting 3-(methylamino)cyclobutanol hydrochloride for 2-(methylamino)ethanol. ¹H NMR (400 MHz, DMSO-d₆) δ 1.38-1.68 (m, 4H), 1.68-1.88 (m, 2H), 1.95-2.48 (m, 4H), 2.80 (s, 3H), 2.87 (s, 3H), 3.02 (s, 1H), 3.12 (s, 1H), 3.23-3.49 (m, 4H), 3.79 (p, J=6.9 Hz, 1H), 4.00-4.39 (m, 3H), 5.07 (s, 1H), 5.73 (d, J=5.0 Hz, 1H), 7.07-7.42 (m, 3H), 7.72 (dd, J=10.4, 3.0 Hz, 1H), 8.24 (d, J=5.3 Hz, 1H), 11.52 (s, 1H). MS (ESI⁺) 516.2 m/z (M+H)⁺.

Example 107

N-(2,3-dihydroxypropyl)-2-[3-(10-fluoro-7-methyl-6,7-dihydro-4H-3,4,7-triazadibenzo[cd,f]azulen-5-yl)-9-azabicyclo[3.3.1]non-2-en-9-yl]-N-methylacetamide The title compound was prepared using the conditions described in Example 103B, substituting 3-(methylamino)propane-1,2-diol for 2-(methylamino)ethanol. ¹H NMR (400 MHz, DMSO-d₆) δ 1.33-1.66 (m, 4H), 1.73-1.89 (m, 2H), 2.20-2.37 (m 1H), 2.67-2.83 (m, 1H), 2.85 (s, 2H), 2.87 (s, 3H), 3.11-3.73 (m, 11H), 3.92-4.29 (m, 3H), 5.74 (t, J=6.6 Hz, 1H), 7.13-7.44 (m, 3H), 7.72 (dd, J=10.6, 3.0 Hz, 1H), 8.24 (d, J=5.2 Hz, 1H), 11.57 (s, 1H). MS (ESI⁺) m/z 520.2 (M+H)⁺.

Example 108

[3-(10-fluoro-7-methyl-6,7-dihydro-4H-3,4,7-triazadibenzo[cd,f]azulen-5-yl)-9-azabicyclo[3.3.1]non-2-en-9-yl]acetic acid The title compound was prepared as described in Example 103A. The crude product was purified by reverse-phase HPLC performed on a Phenomenex Luna C8 AXIA column (30×75 mm, 100 Å) using a gradient of 10% to 95% acetonitrile: 10 mM ammonium acetate in water to provide the title compound. ¹H NMR (400 MHz, DMSO-d₆) δ 1.33-1.71 (m, 4H), 1.88-2.00 (m, 2H), 2.40 (d, J=18.5 Hz, 1H), 2.87 (s, 3H), 2.88-2.96 (m, 1H), 3.27 (s, 2H), 3.44 (s, 1H), 3.82 (s, 1H), 4.04-4.25 (m, 2H), 5.74 (d, J=5.1 Hz, 1H), 6.97-7.57 (m, 3H), 7.72 (dd, J=10.5, 3.0 Hz, 1H), 8.25 (d, J=5.2 Hz, 1H), 11.54 (s, 1H). MS (ESI) m/e 433.2 (M+H)⁺.

Example 109

2-[4-(1,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide The title compound was prepared as described in Example 17, substituting Example 67 for Example 16 and 3-(methylamino)cyclobutanol for L-prolinol. ¹H NMR (400 MHz, CD₃OD) δ 1.95 (s, 3H); 2.00-2.07 (m, 1H), 2.12-2.21 (m, 1H), 2.52-2.69 (m, 4H), 2.88 (s, 3H), 2.92 (s, 1H), 2.96 (s, 1H), 3.40-3.41 (m, 1H), 3.48 (s, 2H), 3.93-4.00 (m, 1H), 4.07-4.18 (m, 3H), 4.34-4.41 (m, 1H), 5.81 (s, 1H), 7.13-7.19 (m, 1H), 7.37 (dd, J=9.00, 5.34 Hz, 1H), 7.64-7.70 (m, 1H), 8.13 (d, J=5.19 Hz, 1H). MS (ESI⁺) m/z 494 (M+H)⁺.

Example 110

2-[4-(1,10-difluoro-7-methyl-6,7-dihydro-4H-3,4,7-triazadibenzo[cd,f]azulen-5-yl)-3,6-dihydropyridin-1(2H)-yl]-N-(2,3-dihydroxypropyl)-N-methylacetamide The title compound was prepared as described in Example 17, substituting Example 67 for Example 16 and 3-(methylamino)propane-1,2-diol for L-prolinol. ¹H NMR (400 MHz, CD₃OD) δ 1.94 (s, 3H), 2.67-2.72 (m, 2H), 2.87-2.94 (m, 4H), 3.37-3.45 (m, 4H), 3.49-3.52 (m, 2H), 3.55 (t, J=4.73 Hz, 2H), 3.65-3.72 (m, 1H), 3.84-3.88 (m, 1H), 4.09 (d, J=5.80 Hz, 2H), 5.78-5.81 (m, 1H), 7.13-7.18 (m, 1H), 7.36 (dd, J=9.00, 5.34 Hz, 1H), 7.63-7.69 (m, 1H), 8.13 (d, J=5.19 Hz, 1H). MS (ESI⁺) m/z 498 (M+H)⁺.

Example 111

[4-(10-fluoro-7-methyl-6,7-dihydro-4H-3,4,7-triazadibenzo[cd,f]azulen-5-yl)-3,3-dimethyl-3,6-dihydropyridin-1(2H)-yl]acetic acid The title compound was prepared as the trifluoroacetic acid salt essentially as described in Example 16A and 16B, substituting Example 92 for Example 1. ¹H NMR (400 MHz, DMSO-d₆) δ 1.21 (s, 6H), 2.87 (s, 3H), 3.39 (m, 2H), 3.94 (d, J=3.4 Hz, 2H), 4.05 (m, 2H), 4.26 (s, 2H), 5.68-5.81 (m, 1H), 7.17-7.38 (m, 2H), 7.44 (d, J=5.4 Hz, 1H), 7.80 (dd, J=10.5, 2.9 Hz, 1H), 8.31 (d, J=5.3 Hz, 1H). MS (ESI⁺) m/z 421 (M+1).

Example 112

[5-(10-fluoro-7-methyl-6,7-dihydro-4H-3,4,7-triazadibenzo[cd,f]azulen-5-yl)-3,6-dihydropyridin-1(2H)-yl]acetic acid The title compound was prepared as the trifluoroacetic acid salt essentially as described in Example 16A and 16B, substituting Example 93 for Example 1. ¹H NMR (400 MHz, DMSO-d₆) δ 2.66 (m, 2H), 2.89 (s, 3H), 3.48 (m, 2H), 4.14 (s, 2H), 4.25 (m, 4H), 6.10 (d, J=4.7 Hz, 1H), 7.20-7.35 (m, 2H), 7.38 (d, J=5.3 Hz, 1H), 7.72 (dd, J=10.5, 3.0 Hz, 1H), 8.28 (d, J=5.3 Hz, 1H). MS (ESI⁺) m/z 393 (M+1).

Example 113

5-[3,3-dimethyl-1-(methylsulfonyl)-1,2,3,6-tetrahydropyridin-4-yl]-10-fluoro-7-methyl-6,7-dihydro-4H-3,4,7-triazadibenzo[cd,f]azulene The title compound was prepared as the HCl salt essentially as described in Example 11, substituting Example 92 for Example 9. ¹H NMR (501 MHz, DMSO-d₆) δ 1.12 (s, 6H), 2.80 (s, 3H), 3.00 (s, 3H), 3.14 (2H), 3.89 (d, J=3.3 Hz, 2H), 4.33 (s, 2H), 5.87 (t, J=3.3 Hz, 1H), 7.13-7.45 (m, 1H), 7.50 (t, J=8.0 Hz, 1H), 7.76 (d, J=5.8 Hz, 1H), 8.06 (d, J=10.1 Hz, 1H), 8.44 (d, J=5.6 Hz, 1H). MS (ESI⁺) m/z 441 (M+1)

Example 114

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N,N-dimethylacetamide The title compound was prepared as the HCl salt essentially as described in Example 12, substituting Example 92 for Example 1. ¹H NMR (501 MHz, DMSO-d₆) δ 1.14 (s, 3H), 1.37 (s, 3H), 2.79 (s, 3H), 2.95 (s, 3H), 3.00 (s, 3H), 3.26 (m, 1H), 3.51 (d, J=11.9 Hz, 1H), 3.90-4.10 (m, 2H), 4.47-4.59 (m, 4H), 5.81-5.99 (m, 1H), 7.36 (t, J=8.0 Hz, 1H), 7.54 (ddd, J=10.1, 7.5, 3.0 Hz, 1H), 7.82 (d, J=5.7 Hz, 1H), 8.12 (dd, J=10.0, 3.1 Hz, 1H), 8.48 (d, J=5.6 Hz, 1H). MS (ESI⁺) m/z 448 (M+1).

Example 115

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-[(2S)-2-(hydroxymethyl)pyrrolidin-1-yl]ethanone The title compound was prepared as the HCl salt essentially as described in Example 50, substituting azetidin-3-ol hydrochloride for dimethylamine and Example 111 for Example 41E. ¹H NMR (501 MHz, DMSO-d₆) δ 1.14 (s, 3H), 1.36 (s, 3H), 1.78-2.06 (m, 4H), 2.79 (s, 3H), 3.28 (dd, J=19.7, 8.3 Hz, 1H), 3.33-3.60 (m, 5H), 3.90-4.14 (m, 3H), 4.31-4.70 (m, 4H), 5.89 (d, J=4.3 Hz, 1H), 7.45-7.57 (m, 2H), 7.81 (d, J=5.7 Hz, 1H), 8.12 (d, J=10.1 Hz, 1H), 8.48 (d, J=5.5 Hz, 1H). MS (ESI⁺) m/z 504 (M+1).

Example 116

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(2-hydroxyethyl)-N-methylacetamide The title compound was prepared as the HCl salt essentially as described in Example 50, substituting 2-(methylamino)ethanol for dimethylamine and Example 111 for Example 41E. ¹H NMR (501 MHz, DMSO-d₆) δ 1.14 (s, 3H), 1.28-1.41 (s, 3H), 2.79 (s, 3H), 3.17 (s, 3H), 3.20-3.40 (m, 2H), 3.39-3.54 (m, 2H), 3.53-3.64 (m, 2H), 3.91-4.14 (m, 2H), 4.38-4.74 (m, 4H), 5.90 (q, J=3.2, 2.5 Hz, 1H), 7.54 (ddd, J=9.7, 7.5, 3.1 Hz, 2H), 7.82 (d, J=5.7 Hz, 1H), 8.06-8.18 (m, 1H), 8.48 (d, J=5.6 Hz, 1H). MS (ESI⁺) m/z 478 (M+1).

Example 117

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-(3-hydroxyazetidin-1-yl)ethanone The title compound was prepared as the HCl salt essentially as described in Example 50, substituting azetidin-3-ol for dimethylamine and Example 111 for Example 41E. ¹H NMR (400 MHz, DMSO-d₆) δ 1.14 (s, 3H), 1.33 (s, 3H), 2.80 (s, 3H), 3.37 (d, J=89.3 Hz, 2H), 3.86 (ddd, J=94.0, 9.3, 4.2 Hz, 4H), 4.07-4.50 (m, 7H), 5.85 (d, J=4.2 Hz, 1H), 7.49 (t, J=8.1 Hz, 2H), 7.75 (d, J=5.7 Hz, 1H), 8.06 (s, 1H), 8.45 (d, J=5.5 Hz, 1H). MS (ESI⁺) m/z 476 (M+1).

Example 118

2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(3-hydroxycyclobutyl)-N-methylacetamide The title compound was prepared as the HCl salt essentially as described in Example 50, substituting 3-(methylamino)cyclobutanol for dimethylamine and Example 111 for Example 41E. ¹H NMR (400 MHz, DMSO-d₆) δ 1.13 (s, 3H), 1.35 (s, 3H), 1.96-2.21 (m, 2H), 2.34-2.52 (m, 4H), 2.79 (s, 3H), 2.94 (s, 3H), 3.23 (m, 1H), 3.50 (d, J=11.9 Hz, 1H), 3.70-3.89 (m, 1H), 3.92-4.11 (m, 2H), 4.49 (m, 3H), 5.89 (s, 1H), 7.29-7.61 (m, 2H), 7.80 (d, J=5.7 Hz, 1H), 8.11 (d, J=10.1 Hz, 1H), 8.47 (d, J=5.6 Hz, 1H). MS (ESI⁺) m/z 504 (M+1).

Example 119

N-(2,3-dihydroxypropyl)-2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-methylacetamide The title compound was prepared as the HCl salt essentially as described in Example 50, substituting 3-(methylamino)propane-1,2-diol for dimethylamine and Example 111 for Example 41E. ¹H NMR (400 MHz, DMSO-d₆) δ 1.14 (s, 3H), 1.36 (s, 3H), 2.79 (s, 3H), 2.97 (s, 3H), 3.22-3.42 (m, 4H), 3.47 (dd, J=11.1, 4.5 Hz, 2H), 3.75 (s, 1H), 3.90-4.13 (m, 2H), 4.49 (d, J=16.2 Hz, 4H), 5.89 (d, J=4.7 Hz, 1H), 7.17-7.62 (m, 2H), 7.81 (d, J=5.7 Hz, 1H), 8.11 (d, J=10.3 Hz, 1H), 8.47 (d, J=5.7 Hz, 1H). MS (ESI⁺) m/z 508 (M+1).

Example 120

2-[5-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone The title compound was prepared as the HCl salt essentially as described in Example 50, substituting (S)-pyrrolidin-2-ylmethanol for dimethylamine and Example 112 for Example 41E. ¹H NMR (400 MHz, DMSO-d₆) δ 1.67-2.05 (m, 4H), 2.58-2.75 (m, 3H), 2.80 (s, 3H), 3.26-3.69 (m, 5H), 4.05 (d, J=23.3 Hz, 2H), 4.12-4.72 (m, 5H), 6.16 (d, J=5.2 Hz, 1H), 7.07-7.55 (m, 2H), 7.72 (d, J=5.7 Hz, 1H), 8.01 (s, 1H), 8.42 (d, J=5.6 Hz, 1H). MS (ESI⁺) m/z 476 (M+1).

Example 121

2-[5-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone The title compound was prepared as the HCl salt essentially as described in Example 50, substituting azetidin-3-ol for dimethylamine and Example 112 for Example 41E. ¹H NMR (400 MHz, DMSO-d₆) δ 2.60-2.76 (m, 3H), 2.80 (s, 3H), 3.32-3.67 (m, 2H), 3.74 (dd, J=10.3, 4.4 Hz, 1H), 3.99 (dd, J=9.2, 4.4 Hz, 1H), 4.19 (q, J=6.7 Hz, 3H), 4.24-4.50 (m, 3H), 4.54 (tt, J=6.9, 4.7 Hz, 2H), 6.16 (d, J=4.1 Hz, 1H), 7.20-7.58 (m, 2H), 7.77 (d, J=5.7 Hz, 1H), 8.06 (d, J=10.1 Hz, 1H), 8.45 (d, J=5.6 Hz, 1H). MS (ESI+) m/z 448 (M+1).

Example 122

2-[5-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide The title compound was prepared as the HCl salt essentially as described in Example 50, substituting 3-(methylamino)cyclobutanol for dimethylamine and Example 112 for Example 41E. $^1$H NMR (400 MHz, DMSO-d$_6$) δ 1.93-2.17 (m, 2H), 2.40 (q, J=7.2, 5.6 Hz, 2H), 2.73 (s, 3H), 2.80 (s, 3H), 3.34-3.62 (m, 2H), 3.70-3.91 (m, 2H), 4.16-4.65 (m, 8H), 6.17 (d, J=4.1 Hz, 1H), 7.20-7.60 (m, 2H), 7.76 (d, J=5.7 Hz, 1H), 8.05 (d, J=10.0 Hz, 1H), 8.44 (d, J=5.6 Hz, 1H). MS (ESI+) m/z 476 (M+1).

Example 123

N-(2,3-dihydroxypropyl)-2-[5-(10-fluoro-7-methyl-6,7-dihydro-4H-3,4,7-triazadibenzo[cd,f]azulen-5-yl)-3,6-dihydropyridin-1(2H)-yl]-N-methylacetamide The title compound was prepared as the HCl salt essentially as described in Example 50, substituting 3-(methylamino)propane-1,2-diol for dimethylamine and Example 112 for Example 41E. $^1$H NMR (400 MHz, DMSO-d$_6$) δ 2.73 (s, 3H), 2.81 (s, 3H), 2.96 (d, J=3.3 Hz, 2H), 3.21-3.37 (m, 3H), 3.44 (dd, J=11.1, 4.8 Hz, 1H), 3.56 (m, 1H), 3.67-3.79 (m, 1H), 4.25 (d, J=75.0 Hz, 3H), 4.41-4.61 (m, 4H), 6.18 (q, J=4.7, 4.0 Hz, 1H), 7.53 (d, J=10.2 Hz, 2H), 7.76 (d, J=5.7 Hz, 1H), 8.05 (d, J=10.0 Hz, 1H), 8.44 (d, J=5.6 Hz, 1H). MS (ESI+) m/z 480 (M+1).

Example 124

{cis-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid Example 124A methyl{cis-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetate To a suspension of Example 1 (500 mg, 1.495 mmol) and methyl 2-(4-oxocyclohexyl)acetate (382 mg, 2.243 mmol) in a mixture of methanol (10 mL) and methylene chloride (10 mL) was added acetic acid (0.514 mL, 8.97 mmol). The mixture was stirred at room temperature for 10 minutes. MP-cyanoborohydride (Biotage, 2.19 mmol/g, 2.73 g) was then added. The suspension was stirred at 35° C. overnight. The solid material was filtered off. The filtrate was concentrated and separated by flash chromatography on silica gel (Teledyne CombiFlash Rf, 0-15% gradient 3% NH$_4$OH/CH$_3$OH in 2/1 ethyl acetate/hexane) to provide the title compound as a faster-eluting fraction (less polar). MS (DCI/NH$_3$) m/z 489 (M+H)+.

Example 124B methyl{trans-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetate To a suspension of Example 1 (500 mg, 1.495 mmol) and methyl 2-(4-oxocyclohexyl)acetate (382 mg, 2.243 mmol) in a mixture of methanol (10 mL) and methylene chloride (10 mL) was added acetic acid (0.514 mL, 8.97 mmol). The mixture was stirred at room temperature for 10 minutes. MP-cyanoborohydride (Biotage, 2.19 mmol/g, 2.73 g) was then added. The suspension was stirred at 35° C. overnight. The solid material was filtered off. The filtrate was concentrated and separated by flash chromatography on silica gel (Teledyne CombiFlash Rf, 0-15% gradient 3% NH$_4$OH/CH$_3$OH in 2/1 ethyl acetate/hexane) to provide the title compound as a slower-eluting fraction (more polar). MS (DCI/NH$_3$) m/z 489 (M+H)+.

Example 124C

{cis-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid To a solution of Example 124A (553 mg, 1.132 mmol) in a mixture of tetrahydrofuran (10 mL) and methanol (5 mL) was added lithium hydroxide monohydrate (95 mg, 2.264 mmol) in water (10 mL). The solution was stirred at room temperature overnight, and was acidified to pH 5. The formed solid material was collected by filtration and dried to provide the title compound. $^1$H NMR (400 MHz, CD$_3$OD) δ 1.44-1.54 (m, 5H), 1.67-1.74 (m, 2H), 1.90-1.97 (m, 1H), 2.20 (d, J=7.02 Hz, 2H), 2.26-2.31 (m, 1H), 2.51 (m, 3H) 2.70 (m, 3H), 2.89 (s, 3H), 4.15 (s, 2H), 5.91 (s, 1H), 7.21-7.33 (m, 3H), 7.68 (d, J=8.85 Hz, 1H), 8.22 (d, J=4.88 Hz, 1H), 11.45 (s, 1H). MS (ESI+) m/z 475 (M+H)+.

Example 125

(8aR)-7-(9,10-difluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one Example 125A (R)-4-vinyloxazolidin-2-one (R)—N-Boc-vinylglycinol (28.7 g, 153.5 mmol) was dissolved in tetrahydrofuran (512 mL). The solution was chilled in an ice bath and thionyl chloride (44.8 mL, 614 mmol) was added dropwise over 20 minutes. The reaction was stirred overnight at ambient temperature, then the mixture was concentrated to dryness and the residue was purified by flash chromatography (330 g g silica gel column, 65 mL/minutes, 0 to 50% ethyl acetate-heptane over 10 minutes then 50 to 100% ethyl acetate over 35 minutes) to give the title compound. MS (ESI+) m/z 130.8 (M+NH$_4$)+.

Example 125B (R)-3-(but-3-yn-1-yl)-4-vinyloxazolidin-2-one

Example 125A (17.86 g, 145 mmol) was dissolved in toluene (1 L) in a 3 L 3-neck flask equipped with a mechanical stirrer and an internal temperature probe. But-3-yn-1-yl4- methylbenzenesulfonate (163 g, 726 mmol), potassium carbonate (120 g, 872 mmol) and tetrabutylammonium bromide (4.68 g, 14.53 mmol) were added. The flask was equipped with a water-cooled condenser capped with a nitrogen inlet and the reaction was heated to 110° C. (internal temperature) for 24 hours, at which time additional portions of but-3-yn-1-yl 4-methylbenzenesulfonate (163 g, 726 mmol) and potassium carbonate (120 g, 872 mmol) were added and the stirring was continued for another 24 hours at 110° C. The mixture was filtered to remove insoluble material and the filter cake was washed with toluene (~1 L). The filtrate was concentrated in vacuo and purified by flash chromatography (Apogee 220HD column, 55 mL/minute, 0 to 20% ethyl acetate-heptane over 10 minutes then 10 to 50% ethyl acetate over 50 minutes) to provide the title compound. MS (ESI$^+$) m/z 166.0 (M+H)$^+$.

Example 125C (R)-3-(3-(4,4,5,5-tetramethyl-1,3,2-dioxaborolan-2-yl)but-3-en-1-yl)-4-vinyloxazolidin-2-one A 1-L, 3-neck round bottom flask was charged with lithium chloride (3.36 g, 79 mmol) and the flask was dried overnight in an 80° C. vacuum oven. After removing from the oven, the flask was flushed with nitrogen. N,N-Dimethylformamide (200 mL) was added, followed by copper(I) chloride (7.84 g, 79 mmol), and the mixture was stirred for 1 hour at room temperature. To this mixture was then added 4,4,4',4',5,5,5',5'-octamethyl-2,2'-bi(1,3,2-dioxaborolane) (20.11 g, 79 mmol), followed by oven-dried potassium acetate (7.77 g, 79 mmol). The mixture was stirred for 5 minutes and a solution of Example 125B (10.90 g, 66.0 mmol) in N,N-dimethylformamide (100 ml) was added via cannula. The resulting mixture was stirred at room temperature for 3 days. Saturated aqueous NH$_4$Cl (300 mL) and 1:1 methyl tert-butyl ether:heptanes (500 mL) were added and the mixture was stirred vigorously for 1 hour. The mixture was filtered through diatomaceous earth, rinsing with 1:1 methyl tert-butyl ether:heptanes (1 L) and water (200 mL). The filtrate was placed into a separatory funnel and the layers were separated. The aqueous layer was extracted with 3×200-mL portions of 1:1 methyl tert-butyl ether:heptanes. The combined extracts were dried (Na$_2$SO$_4$), filtered, and concentrated, and purified by flash chromatography on silica gel (0 to 15% ethyl acetate-heptanes, 220 g Apogee HE column, 60 mL/minute, ramp from 0 to 15% over 1 hour then hold at 15% for 30 minutes) to give the title compound. MS (ESI$^+$) m/z 294.0 (M+H)$^+$.

Example 125D (R)-7-(4,4,5,5-tetramethyl-1,3,2-dioxaborolan-2-yl)-5,6-dihydro-1H-oxazolo[3,4-a]pyridin-3 (8aH)-one A 2-L round bottom flask was charged with (1,3-bis(2,4,6-trimethylphenyl)-2-imidazolidinylidene)dichloro(phenylmethylene)(tricyclohexylphosphine)ruthenium (Grubbs II catalyst, 0.732 g, 0.863 mmol) and the flask was purged with nitrogen. Separately, Example 125C (8.43 g, 28.8 mmol) was dissolved in toluene (1500 mL) and the solution was degassed by bubbling N$_2$ through it for 45 minutes. The toluene solution was transferred by cannula into the flask containing the catalyst and the resulting reaction mixture was stirred overnight at room temperature. Di(ethyleneglycol)vinyl ether (0.22 mL) was added and the solution was stirred for 30 minutes. The mixture was concentrated onto silica gel and purified by flash chromatography on silica gel (Apogee 220 g column, 60 mL/minute, 0 to 25% ethyl acetate-heptane over 15 minutes then 25 to 60% ethyl acetate-heptane from minutes 15 to 60.) After concentration of the product fractions, the product was triturated with ether-heptane to give the title compound. MS (ESI$^+$) m/z 266.1 (M+H)$^+$.

Example 125E (8aR)-7-(9,10-difluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one Example 144I (1.50 g, 3.77 mmol), Example 125D (1 g, 3.77 mmol), PdCl$_2$(PPh$_3$)$_2$ (0.132 g, 0.189 mmol) and NaHCO$_3$ (1.267 g, 15.09 mmol) were combined in N,N-dimethylformamide (15.09 mL) and water (3.77 mL). Nitrogen was bubbled through the mixture for 30 minutes and it was heated to 80° C. for 3.5 hours. The reaction mixture was partitioned between water (25 mL) and ethyl acetate (3×30 mL). The extracts were dried (Na$_2$SO$_4$), filtered, and concentrated and the residue was triturated with ether to give the title compound. $^1$H NMR (500 MHz, DMSO-d$_6$) δ 11.60 (s, 1H), 8.24 (d, J=5.2 Hz, 1H), 7.95 (dd, J=12.5, 9.3 Hz, 1H), 7.36-7.23 (m, 2H), 5.91 (s, 1H), 4.65 (dd, J=6.9, 4.2 Hz, 1H), 4.55 (t, J=8.7 Hz, 1H), 4.21-4.09 (m, 3H), 3.86 (dd, J=13.5, 6.5 Hz, 1H), 3.24 (ddd, J=13.4, 11.7, 4.7 Hz, 1H), 2.92 (s, 3H), 2.72-2.62 (m, 1H), 2.55-2.48 (m, 1H). MS (ESI$^+$) m/z 409.2 (M+H)$^+$.

Example 126

[(2R)-4-(9,10-difluoro-7-methyl-6,7-dihydro-4H-3,4,7-triazadibenzo[cd,f]azulen-5-yl)-1,2,5,6-tetrahydropyridin-2-yl]methanol Example 125E (250 mg, 0.612 mmol) was combined with dioxane (5 mL), water (3.33 mL) and Ba(OH)$_2$ (629 mg, 3.67 mmol) and the mixture was heated to reflux for 5 hours. The mixture was cooled to room temperature, diluted with CH$_2$Cl$_2$ (10 mL), and filtered through a pad of diatomaceous earth, rinsing with additional CH$_2$Cl$_2$. The filtrate was dried over Na$_2$SO$_4$ and filtered. The filtrate was concentrated and then the residue was treated with 4N HCl/dioxane (0.34 mL, 1.35 mmol). The resulting mixture was stirred overnight and the resulting solid was collected by filtration to give the hydrochloride salt of the title compound. $^1$H NMR (400 MHz, DMSO-d$_6$) δ 13.14 (s, 1H), 9.97 (s, 1H), 9.37-9.27 (m, 1H), 8.38 (d, J=6.0 Hz, 1H), 8.17 (dd, J=11.9, 9.5 Hz, 1H), 7.70 (d, J=6.2 Hz, 1H), 7.55-7.43 (m, 1H), 5.90 (s, 1H), 4.33-4.23 (m, 2H), 4.11 (br s, 1H), 3.88-3.75 (m, 2H), 3.47 (d, J=6.6 Hz, 1H), 3.31-3.20 (m, 1H), 2.96 (s, 3H), 2.89 (s, 2H). MS (ESI$^+$) m/z 383.1 (M+H)$^+$.

Example 127

8-fluoro-5-methyl-2-(1,2,3,6-tetrahydropyridin-4-yl)-1,3,4,5-tetrahydro-1,5,12-triazabenzo[4,5]cyclooctа[1,2,3-cd]indene Example 127A 4-chloro-1H-pyrrolo[2,3-b]pyridine-3-carbaldehyde A mixture of 4-chloro-1H-pyrrolo[2,3-b]pyridine (15 g, 98 mmol) and hexamethylenetetramine (25.00 g, 178 mmol) in aqueous acetic acid (33%, 15 mL) was heated at 100° C. overnight. After cooling, the mixture was poured into ice-water and stirred for several minutes. The solid material was collected by filtration, washed with water, and dried in vacuo to provide the title compound. MS (ESI$^+$) m/z 181 (M+H)$^+$.

Example 127B 4-chloro-1-tosyl-1H-pyrrolo[2,3-b]pyridine-3-carb aldehyde

To a suspension of Example 127A (1 g, 5.54 mmol) in toluene (10 mL) was added p-toluenesulfonyl chloride (1.584 g, 8.31 mmol) and tetrabutylammonium hydrogensulfate (0.188 g, 0.554 mmol). The mixture was cooled to 0° C., and a solution of sodium hydroxide (0.554 g, 13.84 mmol) in water (2 mL) was added. The mixture was stirred at room temperature overnight, and partitioned between ethyl acetate and water. The organic phase was washed with water and concentrated. The residue was triturated with 10% ethyl acetate in heptane and filtered to provide the title compound. MS (ESI$^+$) m/z 335 (M+H)$^+$.

Example 127C (Z)-4-chloro-3-(2-methoxyvinyl)-1-tosyl-1H-pyrrolo [2,3-b]pyridine

To a suspension of chloro(methoxymethyl)triphenylphosphorane (9.22 g, 26.9 mmol) in anhydrous tetrahydrofuran (30 mL) was added potassium t-butoxide (3.02 g, 26.9 mmol). The mixture was stirred at room temperature for 2 hours, and then Example 127B (4.5 g, 13.44 mmol) was added as solid. The mixture was stirred at room temperature for 2 hours and partitioned between ethyl acetate and brine. The organic phase was washed with brine, dried over magnesium sulfate, filtered, and concentrated. The residue was separated by silica gel column chromatography (20% ethyl acetate in heptane) to provide the title compound. MS (ESI$^+$) m/z 363 (M+H)$^+$.

Example 127D (Z)-4-fluoro-2-(3-(2-methoxyvinyl)-1-tosyl-1H-pyrrolo[2,3-b]pyridin-4-yl)-N-methylaniline A 250 mL round bottom flask was charged with Example 127C (2.4 g, 6.61 mmol), Example 1A (2.491 g, 9.92 mmol), potassium phosphate (4.21 g, 19.84 mmol), PdCl$_2$(dppf) (0.242 g, 0.331 mmol), tetrahydrofuran (80 mL) and water (20 mL). The mixture was purged with nitrogen and heated at 70° C. overnight. After cooling, the mixture was partitioned between ethyl acetate and brine. The organic phase was washed with brine, and concentrated. The residue was purified by silica gel column chromatography (10% ethyl acetate in heptane) to provide the title compound. MS (ESI$^+$) m/z 452 (M+H)$^+$.

Example 127E 8-fluoro-5-methyl-1-tosyl-1,3,4,5-tetrahydro-1,5,12-triazabenzo[4,5]cycloocta[1,2,3-cd]indene A mixture of Example 127D (11.33 g, 25.09 mmol) and formic acid (34.6 g, 753 mmol) was heated at 60° C. for 3 hours. After cooling, the mixture was partitioned between ethyl acetate and saturated aqueous sodium bicarbonate solution. The organic phase was washed with brine, dried (MgSO$_4$), filtered, and concentrated to provide the title compound. MS (ESI$^+$) m/z 422 (M+H)$^+$.

Example 127F 8-fluoro-2-iodo-5-methyl-1-tosyl-1,3,4,5-tetrahydro-1,5,12-triazabenzo[4,5]cycloocta[1,2,3-cd]indene To a solution of Example 127E (14 g, 33.2 mmol) in tetrahydrofuran (4 mL) was added lithium diisopropylamide (21.59 mL, 43.2 mmol) dropwise at −78° C. After the addition, the mixture was stirred at −78° C. for 1 hour and a solution of iodine (13.49 g, 53.1 mmol) in tetrahydrofuran (10 mL) was added dropwise at the same temperature. The reaction mixture was stirred at −78° C. for 2 hours and warmed to room temperature. After quenching with saturated aqueous sodium thiosulfate, the mixture was partitioned between ethyl acetate and brine. The organic phase was washed with brine and concentrated to provide the title compound. MS (ESI$^+$) m/z 548 (M+H)$^+$.

Example 127G tert-butyl 4-(8-fluoro-5-methyl-1-tosyl-1,3,4,5-tetrahydro-1,5,12-triazabenzo[4,5]cycloocta[1,2,3-cd] inden-2-yl)-5,6-dihydropyridine-1(2H)-carboxylate A 1 L round bottom flask was charged with Example 127F (10.7 g, 19.55 mmol), tert-butyl 4-(4,4,5,5-tetramethyl-1,3,2-dioxaborolan-2-yl)-5,6-dihydropyridine-1(2H)-carboxylate (7.30 g, 23.46 mmol), PdCl$_2$(dppf) (0.715 g, 0.977 mmol), sodium carbonate (6.22 g, 58.6 mmol), 400 mL of dioxane and 100 mL of water. The reaction mixture was purged with nitrogen and heated at 80° C. overnight. After cooling, the mixture was partitioned between ethyl acetate and brine. The organic layer was washed with brine, dried (MgSO$_4$), filtered, and concentrated. The residue was purified by silica gel column chromatography (10-20% gradient ethyl acetate in heptane) to provide the title compound. MS (ESI$^+$) m/z 603 (M+H)$^+$.

Example 127H tert-butyl 4-(8-fluoro-5-methyl-1,3,4,5-tetrahydro-1, 5,12-triazabenzo[4,5]cycloocta[1,2,3-cd]inden-2-yl)-5,6-dihydropyridine-1(2H)-carboxylate A mixture of Example 127G (3.1 g, 5.14 mmol), 2.5 N NaOH aqueous solution (20.57 mL, 51.4 mmol) and methanol (20 mL) was heated at 90° C. overnight. After cooling, water was added and the formed solid was collected by filtration, washed with water, dried (MgSO$_4$), and filtered to provide the title compound. MS (ESI$^+$) m/z 449 (M+H)$^+$.

Example 127I 8-fluoro-5-methyl-2-(1,2,3,6-tetrahydropyridin-4-yl)-1,3,4,5-tetrahydro-1,5,12-triazabenzo[4,5]cycloocta[1,2,3-cd]indene To a solution of Example 127H (2 g, 4.46 mmol) in a 1:2 mixture of dioxane/methylene chloride (30 mL) was added a 4N solution of hydrogen chloride in dioxane (11.15 mL, 44.6 mmol). The reaction mixture was stirred at room temperature for 30 minutes and was partitioned between methylene chloride and aqueous NaHCO$_3$ solution. The organic phase was washed with brine, dried over magnesium sulfate, filtered and concentrated to provide the title compound. $^1$H NMR (400 MHz, DMSO-$d_6$) δ 2.21-2.26 (m, 1H), 2.33-2.41 (m, 1H), 2.56 (s, 3H), 2.78-2.85 (m, 2H), 2.87-2.97 (m, 3H), 3.22-3.41 (m, 4H), 6.00 (s, 1H), 6.89 (d, J=4.88 Hz, 1H), 7.31 (d, J=8.54 Hz, 2H), 7.51-7.54 (m, 1H), 8.16 (d, J=4.88 Hz, 1H), 11.33 (s, 1H). MS (ESI$^+$) m/z 349 (M+H)$^+$.

Example 128

8-fluoro-5-methyl-2-[1-(methylsulfonyl)-1,2,3,6-tetrahydropyridin-4-yl]-1,3,4,5-tetrahydro-1,5,12-triazabenzo[4,5]cycloocta[1,2,3-cd]indene To a suspension of Example 127 (100 mg, 0.287 mmol) in methylene chloride (6 mL) was added triethylamine (0.16 mL, 1.148 mmol) and methanesulfonyl chloride (49.3 mg, 0.431 mmol). This solution was stirred at room temperature for 3 hours. The formed solid material was collected by filtration, washed with methylene chloride and dried in vacuo to provide the title compound. $^1$H NMR (400 MHz, DMSO-$d_6$) δ 2.34-2.42 (m, 1H), 2.57 (s, 3H), 2.78-2.85 (m, 3H), 2.92-2.98 (m, 1H), 2.96 (s, 3H), 3.37-3.41 (m, 1H), 3.89-3.91 (m, 2H), 6.02 (s, 1H), 6.93 (d, J=5.19 Hz, 1H), 7.30-7.35 (m, 2H), 7.54 (dd, J=8.54, 5.49 Hz, 1H), 8.19 (d, J=4.88 Hz, 1H), 11.45 (s, 1H). MS (ESI$^+$) m/z 427 (M+H)$^+$.

Example 129

2-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]-N,N-dimethylacetamide To a suspension of Example 127 (200 mg, 0.574 mmol) in anhydrous N,N-dimethylformamide (6 mL) was added triethylamine (0.480 mL, 3.44 mmol) and 2-chloro-N,N-dimethylacetamide (84 mg, 0.689 mmol). The mixture was heated at 70° C. for 3 hours. After cooling, the mixture was partitioned between ethyl acetate and brine. The organic phase was washed with brine and concentrated. The residue was separated by flash chromatography on silica gel (Teledyne CombiFlash Rf, 10-20% gradient CH$_3$OH in 2:1 ethyl acetate/hexane) to provide the title compound. $^1$H NMR (400 MHz, DMSO-$d_6$) δ 2.35-2.39 (m, 1H), 2.56 (s, 3H), 2.68-2.73 (m, 2H), 2.80-2.83 (m, 4H), 2.93 (dd, J=9.15, 3.97 Hz, 1H), 3.03 (s, 2H), 3.20 (d, J=2.44 Hz, 2H), 3.28 (s, 3H), 3.33 (s, 3H), 5.96 (s, 1H), 6.90 (d, J=4.88 Hz, 1H), 7.32 (t, J=8.24 Hz, 2H), 7.53 (dd, J=8.70, 5.34 Hz, 1H), 8.17 (d, J=4.88 Hz, 1H), 11.35 (s, 1H). MS (ESI$^+$) m/z 434 (M+H)$^+$.

Example 130

{trans-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid The title compound was prepared as described in Example 124C, substituting Example 124B for Example 124A to provide the title compound. $^1$H NMR (400 MHz, CD$_3$OD) δ 1.08 (q, J=12.31 Hz, 2H), 1.53-1.70 (m, 4H), 1.87 (d, J=11.90 Hz, 2H), 2.12-2.27 (m, 4H), 2.85 (s, 3H), 2.97-3.06 (m, 2H), 3.19-3.29 (m, 2H), 3.71-3.77 (m, 1H), 3.89-4.03 (m, 2H), 5.94 (s, 1H), 7.44-7.50 (m, 1H), 7.72 (d, J=5.49 Hz, 1H), 7.99 (s, 1H), 8.42 (d, J=5.49 Hz, 1H), 11.11 (s, 1H), 12.76 (s, 1H). MS (ESI$^+$) m/z 475 (M+H)$^+$.

Example 131

9,10-difluoro-7-methyl-5-[1-(methylsulfonyl)-1,2,3,6-tetrahydropyridin-4-yl]-6,7-dihydro-4H-3,4,7-triazadibenzo[cd,f]azulene The title compound was prepared as the trifluoroacetic acid salt essentially as described in Example 11, substituting Example 144K for Example 9. $^1$H NMR (400 MHz, DMSO-$d_6$) δ 2.73 (q, J=4.5 Hz, 2H), 2.94 (s, 3H), 2.98 (s, 3H), 3.42 (t, J=5.7 Hz, 2H), 3.97 (d, J=8.4 Hz, 2H), 4.19 (s, 2H), 5.88-5.99 (m, 1H), 7.32 (dd, J=13.2, 7.5 Hz, 1H), 7.41 (d, J=5.6 Hz, 1H), 8.00 (dd, J=12.4, 9.2 Hz, 1H), 8.28 (d, J=5.5 Hz, 1H). MS (ESI$^+$) m/z 431 (M+1).

Example 132

2-[4-(9,10-difluoro-7-methyl-6,7-dihydro-4H-3,4,7-triazadibenzo[cd,f]azulen-5-yl)-3,6-dihydropyridin-1(2H)-yl]-N,N-dimethylacetamide The title compound was prepared as the trifluoroacetic acid salt essentially as described in Example 12, substituting Example 144K for Example 1. $^1$H NMR (400 MHz, DMSO-$d_6$) δ 2.95 (d, J=2.0 Hz, 6H), 2.97 (s, 3H), 3.38 (d, J=13.2 Hz, 1H), 3.64 (m, 1H), 3.97 (s, 2H), 4.11 (s, 2H), 4.20 (s, 2H), 4.38 (s, 2H), 5.85 (t, J=3.1 Hz, 1H), 7.33 (dd, J=13.2, 7.6 Hz, 1H), 7.39 (d, J=5.5 Hz, 1H), 8.00 (dd, J=12.5, 9.2 Hz, 1H), 8.29 (d, J=5.3 Hz, 1H). MS (ESI$^+$) m/z 438 (M+1).

Example 133 methyl{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate To a suspension of Example 144K (200 mg, 0.57 mmol) and methyl 2-(4-oxocyclohexyl)acetate (145 mg, 0.85 mmol) in a mixture of methanol (5 mL) and dichloromethane (5 mL) was added acetic acid (204 mg, 3.41 mmol). The mixture was stirred at room temperature for 10 minutes. The solid material dissolved. MP-Cyanoborohydride (Biotage, 2.44 mmol/g, 1 g) was added. The suspension was stirred at room temperature overnight. The reaction mixture was filtered. The filtrate was concentrated and separated by flash chromatography on silica gel (Teledyne CombiFlash Rf, 0-15% of 3% NH$_4$OH/CH$_3$OH in 2/1 ethyl acetate/hexane). The slower-eluting fractions (more polar fraction) were collected to provide the title compound. $^1$H NMR (400 MHz, DMSO-$d_6$) δ 0.93-1.08 (m, 2H), 1.21-1.36 (m, 2H), 1.80 (ddd, J=32.5, 12.3, 4.8 Hz, 4H), 2.20 (d, J=6.9 Hz, 2H), 2.32 (ddd, J=15.9, 7.8, 3.6 Hz, 1H), 2.47-2.58 (m, 3H), 2.72 (t, J=5.6 Hz, 2H), 2.92 (s, 3H), 3.24-3.35 (m, 2H), 3.59 (s, 3H), 4.15 (s, 2H), 5.87 (d, J=3.2 Hz, 1H), 7.22-7.32 (m, 2H), 7.93 (dd, J=12.5, 9.3 Hz, 1H), 8.20 (d, J=5.2 Hz, 1H). MS (ESI$^+$) m/z 507 (M+1).

Example 134 methyl{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate A suspension of Example 144K (200 mg, 0.57 mmol) and methyl 2-(4-oxocyclohexyl)acetate (145 mg, 0.85 mmol) in a mixture of methanol (5 mL) and methylene chloride (5 mL) was added acetic acid (204 mg, 3.41 mmol). The mixture was stirred at room temperature for 10 minutes. The solid material went into solution. MP-Cyanoborohydride (Biotage, 2.44 mmol/g, 1 g) was added. The suspension was stirred at room temperature overnight. The reaction mixture was filtered. The filtrate was concentrated and the crude material was separated by flash chromatography on silica gel (Teledyne CombiFlash Rf, 0-15% of 3% NH$_4$OH/CH$_3$OH in 2/1 ethyl acetate/hexane). The faster-eluting fractions (less polar fraction) were collected to provide the title compound. $^1$H NMR (400 MHz, DMSO-d$_6$) δ 1.37-1.62 (m, 7H), 1.71 (q, J=7.2 Hz, 2H), 1.98 (d, J=8.5 Hz, 1H), 2.30 (d, J=7.3 Hz, 2H), 2.58 (m, 2H), 2.69 (q, J=5.1, 4.5 Hz, 2H), 2.92 (s, 3H), 3.23 (d, J=3.3 Hz, 2H), 3.59 (s, 3H), 4.17 (s, 2H), 5.91 (d, J=3.7 Hz, 1H), 7.19-7.35 (m, 2H), 7.93 (dd, J=12.6, 9.3 Hz, 1H), 8.20 (d, J=5.2 Hz, 1H). MS (ESI$^+$) m/z 507 (M+1).

Example 135

7-methyl-5-(1,2,3,6-tetrahydropyridin-4-yl)-6,7-dihydro-4H-3,4,7,8-tetraazadibenzo[cd,f]azulene Example 135A 4-bromo-1-(phenylsulfonyl)-1H-pyrrolo[2,3-b]pyridine To a solution of 4-bromo-1H-pyrrolo[2,3-b]pyridine (15 g, 76 mmol) in N,N-dimethylformamide (300 mL) was added NaH (95%, 3.96 g, 99 mmol) at 0° C. The mixture was allowed to warm up to room temperature and was stirred for another 30 minutes. Benzenesulfonyl chloride (11.78 mL, 91 mmol) was added. After stirring at room temperature for 16 hours, the reaction mixture was quenched with aqueous NaHCO$_3$ solution and was extracted with ethyl acetate (three times with 450 mL). The combined organic layers were washed with water, dried over MgSO$_4$, and filtered. The filtrate was concentrated and the residue was separated by flash chromatography on silica gel (Teledyne CombiFlash Rf, 5% of ethyl acetate in dichloromethane) to provide the title compound. MS (ESI$^+$) m/z 337 (M+1).

Example 135B 4-bromo-2-iodo-1-(phenylsulfonyl)-1H-pyrrolo[2,3-b]pyridine

To a −78° C. solution of Example 135A (250 mg, 0.741 mmol) in 10 mL tetrahydrofuran was added lithium diisopropylamide (2.0M solution in tetrahydrofuran, 0.556 mL, 1.112 mmol) slowly over the course of 5 minutes. The resulting solution was stirred at the same temperature for 30 minutes after which iodine (376 mg, 1.483 mmol) in 5 mL of tetrahydrofuran was slowly added over 10 minutes. The reaction was stirred at −78° C. for 2.5 hours, and was quenched by addition of 1M aqueous sodium thiosulfate solution. The mixture was extracted with dichloromethane. The combined organic layers were washed with brine, dried over MgSO$_4$, filtered, and concentrated to give the title compound. MS (ESI$^+$) m/z 462 (M+1).

Example 135C tert-butyl 4-(4-bromo-1-(phenylsulfonyl)-1H-pyrrolo[2,3-b]pyridin-2-yl)-5,6-dihydropyridine-1(2H)-carboxylate A mixture of Example 135B (260.0 mg, 0.561 mmol), tert-butyl 4-(4,4,5,5-tetramethyl-1,3,2-dioxaborolan-2-yl)-5,6-dihydropyridine-1(2H)-carboxylate (191 mg, 0.618 mmol), Pd(Ph$_3$P)$_4$ (32.4 mg, 0.028 mmol), and saturated sodium bicarbonate solution (2 mL, 0.561 mmol) in N,N-dimethylformamide (8 mL) was purged with nitrogen and heated at 80° C. for 4 hours. The mixture was partitioned between ethyl acetate and brine. The organic layer was washed with brine, dried over MgSO$_4$, and filtered. The filtrate was concentrated and the residue was separated by flash chromatography on silica gel (Teledyne CombiFlash Rf, 40% to 100% ethyl acetate in hexane) to provide the title compound. MS (ESI$^+$) m/z 306 (M+1).

Example 135D tert-butyl 4-(4-bromo-1H-pyrrolo[2,3-b]pyridin-2-yl)-5,6-dihydropyridine-1(2H)-carboxylate A mixture of Example 135C (3.00 g, 5.63 mmol) and 20% sodium hydroxide in water (2.5 mL, 5.63 mmol) in dioxane (35 mL) was heated at 90° C. for 6 hours. The solvent was evaporated. The residue was partitioned between ethyl acetate and water. The organic layer was washed with brine, dried over MgSO$_4$, and filtered. The filtrate was concentrated to about 10 mL. The solid material was filtered, washed with ethyl acetate and dried to provide the title compound. MS (ESI$^+$) m/z 378 (M+1).

Example 135E tert-butyl 4-(4-(2-(methylamino)pyridin-3-yl)-1H-pyrrolo[2,3-b]pyridin-2-yl)-5,6-dihydropyridine-1(2H)-carboxylate A mixture of Example 135D (170 mg, 0.45 mmol), N-methyl-3-(4,4,5,5-tetramethyl-1,3,2-dioxaborolan-2-yl)pyridin-2-amine (105 mg, 0.45 mmol), bis(triphenylphosphine) palladium(II) chloride (31 mg, 0.045 mmol), tricyclohexylphosphine (13 mg, 0.045 mmol) and cesium carbonate (443 mg, 1.34 mmol) in a round bottom flask was purged with nitrogen. Dioxane (10 mL) was added and the mixture was heated at 100° C. overnight. After cooling, the mixture was triturated with dichloromethane (200 mL) and filtered. The filtrate was concentrated and the residue was separated by flash chromatography on silica gel (Teledyne CombiFlash Rf, 40% to 100% ethyl acetate in hexane) to provide the title compound. MS (ESI$^+$) m/z 406 (M+1).

Example 135F tert-butyl 4-(4-methyl-3,4-dihydro-1H-1,4,5,11-tetraazadibenzo[cd,f]azulen-2-yl)-5,6-dihydropyridine-1(2H)-carboxylate The title compound was prepared essentially as described in Example 1 G, substituting Example 135E for Example 1F. MS (ESI$^+$) m/z 418 (M+1).

Example 135G 7-methyl-5-(1,2,3,6-tetrahydropyridin-4-yl)-6,7-dihydro-4H-3,4,7,8-tetraazadibenzo[cd,f]azulene A solution of Example 135F (200 mg, 0.48 mmol) in methylene chloride (5 mL) was treated with trifluoroacetic acid (1 mL) at room temperature for 1 hour. The volatiles were removed, and the residue was purified by reverse phase HPLC (Zorbax, C-18, 250×2.54 column, Mobile phase A: 0.1% TFA in H₂O; B: 0.1% TFA in CH₃CN; 0-100% gradient) to provide the title compound as the TFA salt. This material was dissolved in a mixture of acetonitrile and methylene chloride and treated with 2 N HCl in ether. Removal of the volatiles provided the title product as the HCl salt. ¹H NMR (400 MHz, DMSO-$d_6$) δ 2.77-2.90 (m, 2H), 3.10 (s, 3H), 3.40 (dq, J=7.6, 4.8 Hz, 2H), 3.88 (d, J=4.9 Hz, 2H), 4.33 (s, 2H), 5.95 (d, J=3.1 Hz, 1H), 7.08-7.25 (m, 1H), 7.38 (d, J=5.3 Hz, 1H), 8.31 (d, J=5.3 Hz, 1H), 8.38 (d, J=6.1 Hz, 2H). MS (ESI⁺) m/z 318 (M+1).

Example 136

{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid A solution of Example 134 (140 mg, 0.27 mmol) in dioxane (10 mL) was treated with a solution of NaOH (33 mg, 1.3 mmol) in 1 mL of water. The mixture was stirred at 60° C. overnight. The reaction mixture was concentrated and the residue was purified by reverse phase HPLC (Zorbax, C-18, 250×2.54 column, Mobile phase A: 0.1% TFA in H₂O; B: 0.1% TFA in CH₃CN; 0-100% gradient) to provide the title compound as TFA salt. The material was dissolved in a mixture of methylene chloride and acetonitrile and treated with HCl in ether. Concentration of the mixture provided the title compound as HCl salt. ¹H NMR (400 MHz, DMSO-$d_6$) δ 1.57 (dq, J=14.0, 9.7, 7.1 Hz, 2H), 1.75 (dd, J=17.4, 7.7 Hz, 4H), 1.96 (t, J=14.7 Hz, 2H), 2.03-2.19 (m, 2H), 2.35 (d, J=7.6 Hz, 2H), 2.97 (s, 3H), 3.01 (d, J=10.2 Hz, 2H), 3.10-3.32 (m, 2H), 3.79 (d, J=12.1 Hz, 2H), 4.08-4.40 (m, 2H), 5.89 (d, J=3.9 Hz, 1H), 7.42 (dd, J=13.1, 7.4 Hz, 1H), 7.58 (d, J=5.9 Hz, 1H), 8.11 (dd, J=12.4, 9.1 Hz, 1H), 8.35 (d, J=5.8 Hz, 1H). MS (ESI⁺) m/z 493 (M+1).

Example 137

2-[4-(9,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone The title was prepared compound as the HCl salt essentially as described in Example 50, substituting azetidin-3-ol for dimethylamine and Example 145 for Example 41E. ¹H NMR (400 MHz, DMSO-$d_6$) δ 2.97 (s, 3H), 2.99-3.06 (m, 3H), 3.48 (m, 1H), 3.70 (ddd, J=21.8, 8.3, 4.1 Hz, 2H), 3.92-4.02 (m, 1H), 4.10 (d, J=19.6 Hz, 2H), 4.19 (d, J=4.5 Hz, 2H), 4.24-4.34 (m, 2H), 4.35-4.44 (m, 1H), 4.54 (ddt, J=9.1, 6.7, 3.3 Hz, 1H), 5.95 (t, J=3.2 Hz, 1H), 7.53 (s, 1H), 7.72 (d, J=6.2 Hz, 1H), 8.19 (dd, J=12.3, 9.0 Hz, 1H), 8.38 (d, J=6.1 Hz, 1H). MS (ESI⁺) m/z 466 (M+1).

Example 138

7-methyl-5-[1-(methylsulfonyl)-1,2,3,6-tetrahydropyridin-4-yl]-6,7-dihydro-4H-3,4,7,8-tetraazadibenzo[cd,f]azulene The title compound was prepared as the HCl salt essentially as described in Example 11, substituting Example 135G for Example 9. ¹H NMR (400 MHz, DMSO-$d_6$) δ 2.79 (q, J=5.2, 4.6 Hz, 2H), 3.00 (s, 3H), 3.20 (s, 3H), 3.44 (t, J=5.7 Hz, 2H), 3.99 (q, J=2.8 Hz, 2H), 4.46 (s, 2H), 6.10 (d, J=3.5 Hz, 1H), 7.28 (dd, J=7.8, 4.8 Hz, 1H), 7.61 (d, J=5.9 Hz, 1H), 8.35 (d, J=5.8 Hz, 1H), 8.44 (dd, J=5.0, 1.6 Hz, 1H), 8.63 (d, J=7.7 Hz, 1H). MS (ESI⁺) m/z 396 (M+1).

Example 139

N-methyl-4-(7-methyl-6,7-dihydro-4H-3,4,7,8-tetraazadibenzo[cd,f]azulen-5-yl)-3,6-dihydropyridine-1(2H)-carboxamide The title compound was prepared as the HCl salt essentially as described in Example 13, substituting Example 135G for Example 1. ¹H NMR (400 MHz, DMSO-$d_6$) δ 2.60 (s, 3H), 2.66 (m, 2H), 3.23 (s, 3H), 3.58 (t, J=5.5 Hz, 2H), 4.10 (q, J=2.8 Hz, 2H), 4.49 (s, 2H), 6.15 (t, J=3.1 Hz, 1H), 7.33 (dd, J=7.8, 4.9 Hz, 1H), 7.70 (d, J=6.2 Hz, 1H), 8.36 (d, J=6.0 Hz, 1H), 8.47 (dd, J=4.9, 1.6 Hz, 1H), 8.72 (dd, J=8.1, 1.7 Hz, 1H). MS (ESI⁺) m/z 375 (M+1).

Example 140

{3-[4-(10-fluoro-7-methyl-6,7-dihydro-4H-3,4,7-triazadibenzo[cd,f]azulen-5-yl)-3,6-dihydropyridin-1(2H)-yl]cyclobutyl}acetic acid The title compound was prepared as described in Example 124, substituting methyl 2-(3-oxocyclobutyl)acetate for methyl 2-(4-oxocyclohexyl)acetate in Example 124A. ¹H NMR (400 MHz, CD₃OD) δ 1.89-1.97 (m, 2H), 2.27-2.42 (m, 6H), 2.77-2.82 (m, 2H), 2.89 (s, 3H), 4.15 (s, 2H), 5.84 (s, 1H), 7.23-7.36 (m, 3H), 7.70 (dd, J=10.38, 2.75 Hz, 2H), 8.26 (d, J=5.19 Hz, 2H), 11.62 (s, 2H). MS (ESI⁺) m/z 447 (M+H)⁺.

Example 141 trans-4-[4-(10-fluoro-7-methyl-6,7-dihydro-4H-3,4,7-triazadibenzo[cd,f]azulen-5-yl)-3,6-dihydropyridin-1(2H)-yl]cyclohexanecarboxylic acid The title compound was prepared as described in Example 124, substituting ethyl 4-oxocyclohexanecarboxylate for methyl 2-(4-oxocyclohexyl)acetate in Example 124A. ¹H NMR (400 MHz, CD₃OD) δ 1.35-1.48 (m, 2H), 1.54-1.70 (m, 2H), 2.06 (d, J=10.07 Hz, 2H), 2.19-2.30 (m, 3H), 2.86 (s, 3H), 3.00-3.05 (m, 2H), 3.21-3.39 (m, 3H), 3.73 (d, J=10.99 Hz, 1H), 3.90-4.02 (m, 2H), 4.45-4.60 (m, 2H), 5.94 (s, 1H), 7.43-7.50 (m, 1H), 7.70 (d, J=5.49 Hz, 1H), 7.98 (s, 1H), 8.42 (d, J=5.49 Hz, 1H), 11.13 (s, 1H), 12.71 (s, 1H). MS (ESI⁺) m/z 461 (M+H)⁺.

Example 142

(6S)-6-ethyl-10-fluoro-7-methyl-5-(1,2,3,6-tetrahydropyridin-4-yl)-6,7-dihydro-4H-3,4,7-triazadibenzo[cd,f]azulene

Example 142A (S)-tert-butyl 4-(3-ethyl-7-fluoro-4-methyl-3,4-dihydro-1H-1,4,11-triazadibenzo[cd,f]azulen-2-yl)-5,6-dihydropyridine-1(2H)-carboxylate Example 8 was separated by preparative SFC on a THAR/Waters SFC 80 system (ChiralPak IA column, 5-50% gradient CH₃OH in CO₂). The faster eluting fraction was concentrated to provide the title compound. MS (ESI⁺) m/z 463 (M+H)⁺.

Example 142B (R)-tert-butyl 4-(3-ethyl-7-fluoro-4-methyl-3,4-dihydro-1H-1,4,11-triazadibenzo[cd,f]azulen-2-yl)-5,6-dihydropyridine-1(2H)-carboxylate Example 8 was separated by preparative SFC on a THAR/Waters SFC 80 system (ChiralPak IA column, 5-50% gradient $CH_3OH$ in $CO_2$). The slower eluting fraction was concentrated to provide the title compound. MS ($ESI^+$) m/z 463 $(M+H)^+$.

Example 142C (6S)-6-ethyl-10-fluoro-7-methyl-5-(1,2,3,6-tetrahydropyridin-4-yl)-6,7-dihydro-4H-3,4,7-triazadibenzo[cd,f]azulene A solution of Example 142A (2 g, 4.32 mmol) in methylene chloride (20 mL) was treated with TFA (5 mL) for 2 hours, and concentrated. The residue was partitioned between ethyl acetate and diluted aqueous NaOH solution. The organic phase was washed with water and concentrated to provide the title compound. $^1H$ NMR (400 MHz, DMSO-$d_6$) δ 0.85 (t, J=7.17 Hz, 3H), 1.23-1.30 (m, 1H), 1.35-1.44 (m, 1H), 2.37-2.44 (m, 1H), 2.49-2.55 (m, 1H), 2.86-2.88 (m, 3H), 2.90-2.99 (m, 2H), 3.45 (d, J=2.44 Hz, 2H), 4.28 (dd, J=9.16, 5.19 Hz, 1H), 6.11 (s, 1H), 7.19-7.28 (m, 2H), 7.32 (d, J=5.49 Hz, 1H), 7.76 (dd, J=10.83, 2.90 Hz, 1H), 8.19 (d, J=5.49 Hz, 1H), 11.39 (s, 1H). MS ($ESI^+$) m/z 363 $(M+H)^+$.

Example 143

(6R)-6-ethyl-10-fluoro-7-methyl-5-(1,2,3,6-tetrahydropyridin-4-yl)-6,7-dihydro-4H-3,4,7-triazadibenzo[cd,f]azulene The title compound was prepared as described in Example 142C, substituting Example 142B for Example 142A. $^1H$ NMR (400 MHz, DMSO-$d_6$) δ 0.85 (t, J=7.17 Hz, 3H), 1.24-1.30 (m, 1H), 1.36-1.44 (m, 1H), 2.38-2.43 (m, 1H), 2.50-2.54 (m, 1H), 2.86 (s, 3H), 2.89-2.93 (m, 1H), 2.94-3.00 (m, 1H), 3.45 (d, J=2.14 Hz, 2H), 4.26-4.29 (m, 1H), 6.11 (s, 1H), 7.20-7.28 (m, 2H), 7.32 (d, J=5.49 Hz, 1H), 7.76 (dd, J=10.83, 2.90 Hz, 1H), 8.20 (d, J=5.49 Hz, 1H), 11.40 (s, 1H). MS ($ESI^+$) m/z 363 $(M+H)^+$.

Example 144

9,10-difluoro-7-methyl-5-(1,2,3,6-tetrahydropyridin-4-yl)-6,7-dihydro-4H-3,4,7-triazadibenzo[cd,f]azulene

Example 144A tert-butyl(2-bromo-4,5-difluorophenyl)carbamate

To a solution of 2-bromo-4,5-difluoroaniline (25.28 g, 122 mmol) in tetrahydrofuran (200 mL) was added di-tert-butyl dicarbonate (150 mL, 300 mmol) and 4-dimethylaminopyridine (2.97 g, 24.31 mmol) at room temperature. The solution was stirred at ambient temperature overnight, and concentrated. The residue was partitioned between ethyl acetate and brine. The organic phase was washed with brine, dried over $MgSO_4$, filtered and concentrated to provide the title compound. MS ($ESI^+$) m/z 308 (M+1)

Example 144B tert-butyl(2-bromo-4,5-difluorophenyl)(methyl)carbamate

To a solution of Example 144A (12.37 g, 40.1 mmol) in anhydrous N,N-dimethylformamide (100 mL) was added cesium carbonate (19.62 g, 60.2 mmol) and iodomethane (5.02 mL, 80 mmol) at room temperature. The reaction mixture was stirred at room temperature for 4 hours, and was partitioned between ethyl acetate and brine. The organic phase was washed with brine, dried over $MgSO_4$ and filtered. The filtrate was concentrated and the residue was separated by flash chromatography on silica gel (Teledyne CombiFlash Rf, 40% to 100% ethyl acetate in hexane) to provide the title compound. MS ($ESI^+$) m/z 322 (M+1).

Example 144C 2-bromo-4,5-difluoro-N-methylaniline

To a solution of Example 144B (29.5 g, 92 mmol) in dichloromethane (200 mL) was added trifluoroacetic acid (141 mL, 1831 mmol). The reaction mixture was stirred at room temperature for 2 hours and concentrated. The residue was partitioned between ethyl acetate and brine. The organic phase was washed with brine, dried with $MgSO_4$, filtered, and concentrated. The filtrate was concentrated and the residue was separated by flash chromatography on silica gel (Teledyne CombiFlash Rf, 40% to 100% ethyl acetate in hexane) to provide the title compound. MS ($ESI^+$) m/z 222 (M+1).

Example 144D 4,5-difluoro-N-methyl-2-(4,4,5,5-tetramethyl-1,3,2-dioxaborolan-2-yl)aniline A 1000 mL round bottom flask under argon containing Example 144C (18.31 g, 82 mmol) was evacuated under high vacuum for 30 minutes. The flask was backfilled with argon and potassium acetate (24.28 g, 247 mmol), bis(pinacolato)diboron (25.1 g, 99 mmol) and anhydrous N,N-dimethylformamide (500 mL), were added successively. Argon was bubbled through with stirring for 60 minutes using a gas dispersion tube, then $PdCl_2$(dppf)-$CH_2Cl_2$ adduct (3.37 g, 4.12 mmol) was added and bubbling was continued for another 20 minutes. A vigreux column was attached and the mixture was heated to 83° C. and stirred overnight under argon. Heptane was added and the mixture was filtered through a diatomaceous earth plug. The filtrate was concentrated and the crude product was used immediately in next reaction. MS ($ESI^+$) m/z 270 (M+1).

Example 144E 4,5-difluoro-N-methyl-2-(1H-pyrrolo[2,3-b]pyridin-4-yl)aniline

To a 1000 mL round bottom flask with crude Example 144D (22.07 g, 82 mmol) was added potassium phosphate (32.6 g, 154 mmol) in 50 mL of water, dioxane (300 mL), and 4-bromo-1H-pyrrolo[2,3-b]pyridine (10.10 g, 51.3 mmol). To the reaction was added {1,3-bis(2,6-diisopropylphenyl)imidazole-2-ylidene}chloro {3-phenylallyl}palladium(II) (1.660 g, 2.56 mmol) and the mixture was heated to 90° C. overnight. The reaction was cooled to room temperature and filtered through a diatomaceous earth plug. The mixture was diluted with ethyl acetate and washed with water. The organic phase was concentrated to give the crude residue which was dissolved in 200 mL ethyl acetate. Mercaptosilica gel (10 g) was added and the mixture was stirred for 30 minutes. This mixture was then filtered through a 1 inch silica plug and concentrated. The residue was purified by flash column chromatography on silica gel (40% to 100% ethyl acetate in hexane) to give the title compound. MS (ESI$^+$) m/z 260 (M+1).

Example 144F 6,7-difluoro-4-methyl-3,4-dihydro-1H-1,4,11-triazadibenzo[cd,f]azulene A 250 mL round bottom flask containing Example 144E (5 g, 19.29 mmol) was charged with paraformaldehyde (2.90 g, 96 mmol) and acetic acid (64.3 mL) and the mixture was stirred at room temperature overnight. The reaction was diluted with dichloromethane and extracted with aqueous NaHCO$_3$ solution. The organic phase was dried over MgSO$_4$, filtered and concentrated to give the title compound. MS (ESI$^+$) m/z 272 (M+1).

Example 144G 6,7-difluoro-4-methyl-1-tosyl-3,4-dihydro-1H-1,4,11-triazadibenzo[cd,f]azulene To a 500 mL round bottom flask containing Example 144F (8.1 g, 29.9 mmol) under argon was added anhydrous N,N-dimethylformamide (100 mL) and sodium hydride (2.389 g, 59.7 mmol). The reaction mixture was stirred at room temperature for 30 minutes. Toluenesulfonyl chloride (11.39 g, 59.7 mmol) was added and the mixture was stirred overnight. The reaction was diluted with ethyl acetate and washed with water. The organic phase was concentrated to give the crude residue which was purified by flash column chromatography on silica gel (10% to 100% ethyl acetate in hexane) to provide the title compound. MS (ESI$^+$) m/z 426. (M+1).

Example 144H 6,7-difluoro-2-iodo-4-methyl-1-tosyl-3,4-dihydro-1H-1,4,11-triazadibenzo[cd,f]azulene To a 500 mL round bottom flask with Example 144G (9.43 g, 22.16 mmol) under N$_2$, was added anhydrous tetrahydrofuran (111 mL). The reaction was cooled to −78° C. and lithium diisopropylamide (16.62 mL, 33.2 mmol) as a tetrahydrofuran solution was added at once. The mixture was stirred for 15 minutes and then added iodine (11.25 g, 44.3 mmol) as a solid. The reaction was stirred another 15 min at −78° C. The reaction was diluted with ethyl acetate and washed with water and Na$_2$S$_2$O$_3$ aqueous solution. The organic phase was concentrated to give the title compound. MS (ESI$^+$) m/z 552 (M+1).

Example 144I 6,7-difluoro-2-iodo-4-methyl-3,4-dihydro-1H-1,4,11-triazadibenzo[cd,f]azulene In a 1000 mL round bottom flask with Example 144H (12.2 g, 22.13 mmol) was added dioxane (200 mL) and sodium hydroxide (44.3 mL, 221 mmol). The flask was fitted with a vigreux column and the mixture was stirred at 90° C. for 4 hours. The reaction was cooled to room temperature, poured onto 300 mL water and filtered. The solid product was washed with water and dried over oven. MS (ESI$^+$) m/z 398 (M+1).

Example 144J tert-butyl 4-(6,7-difluoro-4-methyl-3,4-dihydro-1H-1,4,11-triazadibenzo[cd,f]azulen-2-yl)-5,6-dihydropyridine-1(2H)-carboxylate The title compound was prepared essentially as described in Example 1D, substituting Example 144I for Example 1C. LC/MS (ESI$^+$) m/z 452 (M+H)$^+$.

Example 144K 9,10-difluoro-7-methyl-5-(1,2,3,6-tetrahydropyridin-4-yl)-6,7-dihydro-4H-3,4,7-triazadibenzo[cd,f]azulene The title compound was prepared as the trifluoroacetic acid salt essentially as described in Example 1H, substituting Example 144J for Example 1D. $^1$H NMR (500 MHz, DMSO-d$_6$) δ 2.81 (dt, J=7.4, 3.9 Hz, 2H), 2.93 (s, 3H), 3.38 (dt, J=7.2, 3.7 Hz, 2H), 3.82-3.92 (m, 2H), 4.18 (s, 2H), 5.81-5.93 (m, 1H), 7.32 (dd, J=13.2, 7.5 Hz, 1H), 7.38 (d, J=5.4 Hz, 1H), 7.99 (dd, J=12.4, 9.2 Hz, 1H), 8.30 (d, J=5.4 Hz, 1H). MS (ESI$^+$) m/z 353 (M+1).

Example 145

[4-(9,10-difluoro-7-methyl-6,7-dihydro-4H-3,4,7-triazadibenzo[cd,f]azulen-5-yl)-3,6-dihydropyridin-1(2H)-yl]acetic acid The title compound was prepared as the trifluoroacetic acid salt essentially as described in Example 16A and 16B, substituting Example 144 for Example 1. $^1$H NMR (400 MHz, DMSO-d$_6$) δ 2.90 (d, J=9.9 Hz, 2H), 2.94 (s, 3H), 3.57 (s, 2H), 3.97-4.13 (m, 2H), 4.19 (s, 2H), 4.25 (s, 2H), 5.85 (d, J=3.6 Hz, 1H), 7.32 (dd, J=13.3, 7.6 Hz, 1H), 7.37 (d, J=5.4 Hz, 1H), 7.99 (dd, J=12.4, 9.2 Hz, 1H), 8.29 (d, J=5.3 Hz, 1H). MS (ESI$^+$) m/z 411 (M+1).

Example 146

{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid The title compound was prepared as the HCl salt essentially as described in Example 136, substituting Example 133 for Example 134. $^1$H NMR (400 MHz, DMSO-d$_6$) δ 0.98-1.17 (m, 2H), 1.49-1.75 (m, 2H), 1.85 (d, J=12.5 Hz, 2H), 2.10-2.20 (m, 2H), 2.25 (d, J=6.9 Hz, 2H), 2.97 (s, 3H), 3.03 (ddd, J=17.9, 8.9, 5.2 Hz, 2H), 3.14-3.30 (m, 2H), 3.72 (d, J=12.0 Hz, 2H), 3.95 (s, 2H), 4.20 (d, J=15.5 Hz, 1H), 4.31-4.40 (m, 1H), 5.90 (d, J=4.0 Hz, 1H), 7.44 (dd, J=12.5, 7.3 Hz, 1H), 7.64 (d, J=6.0 Hz, 1H), 8.14 (dd, J=12.3, 9.1 Hz, 1H), 8.36 (d, J=5.9 Hz, 1H). MS (ESI$^+$) m/z 493 (M+1).

Example 147

2-[4-(9,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone The title compound was prepared as the HCl salt essentially as described in Example 50, substituting (S)-pyrrolidin- 2-ylmethanol for dimethylamine and Example 145 for Example 41E. $^1$H NMR (400 MHz, DMSO-d$_6$) δ 1.61-2.12 (m, 4H), 2.64-2.80 (m, 2H), 2.97 (s, 3H), 2.99-3.09 (m, 4H), 3.32-3.57 (m, 4H), 3.95-4.23 (m, 2H), 4.24-4.55 (m, 3H), 5.94 (d, J=12.3 Hz, 1H), 7.52 (dt, J=11.9, 7.5 Hz, 1H), 7.72 (d, J=6.1 Hz, 1H), 8.19 (dd, J=12.3, 9.0 Hz, 1H), 8.38 (d, J=6.1 Hz, 1H). MS (ESI$^+$) m/z 494 (M+1).

Example 148

2-[4-(9,10-difluoro-7-methyl-6,7-dihydro-4H-3,4,7-triazadibenzo[cd,f]azulen-5-yl)-3,6-dihydropyridin-1 (2H)-yl]-N-(3-hydroxycyclobutyl)-N-methylacetamide The title compound was prepared as the HCl salt essentially as described in Example 50, substituting 3-(methylamino)cyclobutanol for dimethylamine and Example 145 for Example 41E. $^1$H NMR (400 MHz, DMSO-d$_6$) δ 1.97-2.20 (m, 2H), 2.35-2.46 (m, 1H), 2.94 (d, J=7.2 Hz, 3H), 2.97 (s, 3H), 2.99-3.07 (m, 2H), 3.47 (m, 1H), 3.60-3.73 (m, 1H), 3.83 (dt, J=20.0, 7.0 Hz, 2H), 4.06 (m, 1H), 4.14 (s, 1H), 4.30 (m, 1H), 4.31-4.43 (m, 2H), 4.48 (s, 2H), 5.95 (t, J=3.7 Hz, 1H), 7.55 (d, J=13.0 Hz, 1H), 7.72 (d, J=6.3 Hz, 1H), 8.19 (dd, J=12.3, 9.0 Hz, 1H), 8.38 (d, J=6.1 Hz, 1H). MS (ESI$^+$) m/z 494 (M+1).

Example 149

N,N-dimethyl-2-[4-(7-methyl-6,7-dihydro-4H-3,4,7, 8-tetraazadibenzo[cd,f]azulen-5-yl)-3,6-dihydropyridin-1(2H)-yl]acetamide The title compound was prepared as the HCl salt essentially as described in Example 12, substituting Example 135F for Example 1. $^1$H NMR (400 MHz, DMSO-d$_6$) δ 2.94 (s, 3H), 3.00 (s, 3H), 3.01-3.10 (m, 2H), 3.25 (s, 3H), 3.50 (d, J=10.5 Hz, 1H), 3.64-3.74 (m, 1H), 3.98-4.22 (m, 2H), 4.42-4.54 (m, 4H), 6.03 (d, J=3.8 Hz, 1H), 7.33 (dd, J=7.8, 5.0 Hz, 1H), 7.68 (d, J=6.1 Hz, 1H), 8.39 (d, J=6.0 Hz, 1H), 8.47 (dd, J=5.0, 1.7 Hz, 1H), 8.71 (dd, J=8.0, 1.8 Hz, 1H). MS (ESI$^+$) m/z 403 (M+1).

Example 150 trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid Example 150A trans-ethyl 4-(4-(6,7-difluoro-4-methyl-3,4-dihydro-1H-1,4,11-triazadibenzo[cd,f]azulen-2-yl)-5,6-dihydropyridin-1(2H)-yl)cyclohexanecarboxylate To a suspension of Example 144K (250 mg, 0.71 mmol) and ethyl 4-oxocyclohexanecarboxylate (181 mg, 1.01 mmol) in a mixture of methanol (5 mL) and methylene chloride (5 mL) was added acetic acid (255 mg, 4.26 mmol). The mixture was stirred at room temperature for 10 minutes. MP-Cyanoborohydride (Biotage, 2.44 mmol/g, 1.7 g) was then added. The suspension was stirred at room temperature overnight. The reaction mixture was filtered. The filtrate was concentrated and the residue was separated by flash chromatography on silica gel (Teledyne CombiFlash Rf, 0-15% 3% NH$_4$OH/CH$_3$OH in 2/1 ethyl acetate/hexane). Slower-diluting fractions (more polar fractions) were collected to provide the title compound. MS (ESI$^+$) m/z 507 (M+1).

Example 150B trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid The title compound was prepared as the HCl salt essentially as described in Example 136, substituting Example 150A for Example 134. $^1$H NMR (400 MHz, DMSO-d$_6$) δ 1.34-1.48 (m, 1H), 1.60 (dddd, J=27.2, 23.3, 12.8, 6.6 Hz, 3H), 1.96-2.11 (m, 1H), 2.10-2.35 (m, 3H), 2.64 (q, J=3.6 Hz, 1H), 2.97 (s, 3H), 3.02 (m, 2H), 3.12-3.37 (m, 2H), 3.70 (ddd, J=11.6, 8.0, 4.3 Hz, 1H), 3.96 (d, J=8.5 Hz, 2H), 4.20 (d, J=15.4 Hz, 1H), 4.34 (dd, J=15.4, 5.7 Hz, 1H), 5.90 (q, J=3.6 Hz, 1H), 7.29-7.54 (m, 1H), 7.62 (d, J=6.0 Hz, 1H), 8.12 (dd, J=12.3, 9.1 Hz, 1H), 8.36 (d, J=5.9 Hz, 1H). MS (ESI$^+$) m/z 479 (M+1).

Example 151

(8aR)-7-(10-fluoro-7-methyl-6,7-dihydro-4H-3,4,7-triazadibenzo[cd,f]azulen-5-yl)-1,5,6,8a-tetrahydro [1,3]oxazolo[3,4-a]pyridin-3-one The title compound was prepared using the conditions described in Example 125E, substituting Example 144I with Example 43A. $^1$H NMR (400 MHz, DMSO-d$_6$) δ 11.59 (s, 1H), 8.26 (d, J=5.2 Hz, 1H), 7.70 (dd, J=10.5, 2.9 Hz, 1H), 7.37-7.19 (m, 3H), 5.91 (s, 1H), 4.69-4.63 (m, 1H), 4.55 (t, J=8.6 Hz, 1H), 4.20-4.09 (m, 3H), 3.86 (dd, J=13.5, 6.5 Hz, 1H), 3.24 (ddd, J=13.4, 11.5, 4.8 Hz, 1H), 2.89 (s, 3H), 2.72-2.60 (m, 1H), 2.56-2.48 (m, 1H). MS (ESI$^+$) m/z 391.2 (M+H)$^+$.

Example 152

(8aS)-7-(10-fluoro-7-methyl-6,7-dihydro-4H-3,4,7-triazadibenzo[cd,f]azulen-5-yl)-1,5,6,8a-tetrahydro [1,3]oxazolo[3,4-a]pyridin-3-one Example 152A (S)-7-(4,4,5,5-tetramethyl-1,3,2-dioxaborolan-2-yl)-5,6-dihydro-1H-oxazolo[3,4-a]pyridin-3(8aH)-one The title compound was prepared as described in Example 125A-D, substituting (S)-tert-butyl(1-hydroxybut-3-en-2-yl) carbamate for (R)-tert-butyl(1-hydroxybut-3-en-2-yl)carbamate in Example 125A. MS (ESI$^+$) m/z 266.1 (M+H)$^+$.

Example 152B (8aS)-7-(10-fluoro-7-methyl-6,7-dihydro-4H-3,4,7-triazadibenzo[cd,f]azulen-5-yl)-1,5,6,8a-tetrahydro [1,3]oxazolo[3,4-a]pyridin-3-one The title compound was prepared using the conditions described in Example 125E, substituting Example 125D with Example 152A and Example 144I with Example 43A. $^1$H NMR (400 MHz, DMSO-d$_6$) δ 11.59 (s, 1H), 8.26 (d, J=5.2 Hz, 1H), 7.70 (dd, J=10.5, 3.0 Hz, 1H), 7.36-7.20 (m, 3H), 5.91 (s, 1H), 4.70-4.62 (m, 1H), 4.55 (t, J=8.6 Hz, 1H), 4.22-4.09 (m, 3H), 3.85 (dd, J=13.4, 6.4 Hz, 1H), 3.24 (ddd, J=13.4, 11.5, 4.8 Hz, 1H), 2.89 (s, 3H), 2.73-2.60 (m, 1H), 2.56-2.48 (m, 1H). MS (ESI+) m/z 391.2 (M+H)+.

Example 153

(8aR)-7-(10-fluoro-7-methyl-6,7-dihydro-4H-3,4,7-triazadibenzo[cd,f]azulen-5-yl)-1,5,8,8a-tetrahydro [1,3]oxazolo[3,4-a]pyridin-3-one Example 153A (R)-tert-butyl(1-hydroxypent-4-yn-2-yl)carbamate An oven-dried, nitrogen-flushed 3-neck 500 mL round bottom flask equipped with a pressure-equalizing addition funnel was charged with LiAlH$_4$ (1N in tetrahydrofuran, 46.9 ml, 46.9 mmol), and the flask was chilled in an ice-water bath. A solution of (R)—N-Boc-propargylglycine (5.0 g, 23.45 mmol) in tetrahydrofuran (100 ml) was then added dropwise through the funnel, controlling the addition so that the bubbling was not too vigorous. The reaction was allowed to come to room temperature and was stirred overnight, and chilled in an ice bath. Saturated aqueous NaHCO$_3$ solution (15 mL) was added dropwise over about 0.5 hours. The resulting suspension was diluted with water (~25 mL) and filtered through diatomaceous earth, rinsing with ether. The filtrate was transferred to a separatory funnel and the layers were separated. The organic phase was washed with saturated Rochelle's salt, water and brine then dried (Na$_2$SO$_4$), filtered and concentrated to give the title compound, which was used without further purification.

Example 153B (R)-4-(prop-2-yn-1-yl)oxazolidin-2-one

The title compound was prepared as described in Example 125A, substituting Example 153A for (R)-tert-butyl(1-hydroxybut-3-en-2-yl)carbamate. MS (ESI+) m/z 142.9 (M+NH$_4$)+.

Example 153C (R)-3-allyl-4-(prop-2-yn-1-yl)oxazolidin-2-one

To an ice-cooled suspension of Example 153B (1 g, 7.99 mmol) and Cs$_2$CO$_3$ (3.91 g, 11.99 mmol) in N,N-dimethylformamide (10 mL) was added dropwise allyl bromide (1.06 g, 8.79 mmol), and the reaction was stirred at room temperature overnight. The reaction mixture was partitioned between water (100 mL) and ethyl acetate (3×40 mL). The organic extracts were dried (Na$_2$SO$_4$), filtered, and concentrated to give the title compound which was used without further purification. MS (ESI+) m/z 166.0 (M+H)+.

Example 153D (R)-7-(4,4,5,5-tetramethyl-1,3,2-dioxaborolan-2-yl)-8,8a-dihydro-1H-oxazolo[3,4-a]pyridin-3(5H)-one The product was prepared using the procedures previously described for Example 125C-D, substituting Example 153C for Example 125B in Example 125C. MS (ESI+) m/z 266.1 (M+H)+.

Example 153E (8aR)-7-(10-fluoro-7-methyl-6,7-dihydro-4H-3,4,7-triazadibenzo[cd,f]azulen-5-yl)-1,5,8,8a-tetrahydro [1,3]oxazolo[3,4-a]pyridin-3-one The title compound was prepared using the conditions described in Example 125E, substituting Example 125D with Example 153D and Example 144I with Example 43A. $^1$H NMR (400 MHz, DMSO-d$_6$) δ 11.58 (s, 1H), 8.25 (d, J=5.2 Hz, 1H), 7.70 (dd, J=10.5, 3.0 Hz, 1H), 7.35-7.20 (m, 3H), 5.96-5.92 (m, 1H), 4.56 (t, J=8.2 Hz, 1H), 4.26-4.11 (m, 4H), 4.03-3.94 (m, 1H), 3.89 (dd, J=19.3, 2.3 Hz, 1H), 2.89 (s, 3H), 2.81 (d, J=14.0 Hz, 1H), 2.62-2.52 (m, 1H). MS (ESI+) m/z 391.2 (M+H)+.

Example 154

[(2R)-4-(10-fluoro-7-methyl-6,7-dihydro-4H-3,4,7-triazadibenzo[cd,f]azulen-5-yl)-1,2,5,6-tetrahydropyridin-2-yl]methanol The title compound was prepared using the conditions described in Example 126, substituting Example 151 for Example 125E. $^1$H NMR (400 MHz, CD$_3$OD) δ 8.51 (d, J=6.3 Hz, 1H), 8.04 (dd, J=9.8, 2.9 Hz, 1H), 7.94 (d, J=6.4 Hz, 1H), 7.86 (dd, J=9.0, 4.9 Hz, 1H), 7.50 (ddd, J=9.1, 7.3, 2.9 Hz, 1H), 6.02 (d, J=2.0 Hz, 1H), 4.81-4.70 (m, 2H), 4.33-4.25 (m, 1H), 4.02 (dd, J=11.7, 4.0 Hz, 1H), 3.87 (dd, J=11.7, 7.3 Hz, 1H), 3.71 (dt, J=12.6, 4.9 Hz, 1H), 3.55-3.46 (m, 1H), 3.05 (s, 3H), 3.11-2.91 (m, 2H). MS (ESI+) m/z 365.2 (M+H)+.

Example 155

[(2S)-4-(10-fluoro-7-methyl-6,7-dihydro-4H-3,4,7-triazadibenzo[cd,f]azulen-5-yl)-1,2,5,6-tetrahydropyridin-2-yl]methanol The title compound was prepared using the conditions described in Example 126, substituting Example 152B for Example 125E. $^1$H NMR (400 MHz, CD$_3$OD) δ 8.51 (d, J=6.3 Hz, 1H), 8.04 (dd, J=9.8, 2.9 Hz, 1H), 7.94 (d, J=6.4 Hz, 1H), 7.85 (dd, J=9.0, 4.9 Hz, 1H), 7.49 (ddd, J=9.2, 7.3, 2.9 Hz, 1H), 6.02 (d, J=1.9 Hz, 1H), 4.79-4.69 (m, 2H), 4.33-4.25 (m, 1H), 4.02 (dd, J=11.7, 4.0 Hz, 1H), 3.87 (dd, J=11.7, 7.3 Hz, 1H), 3.71 (dt, J=12.6, 4.9 Hz, 1H), 3.55-3.46 (m, 1H), 3.05 (s, 3H), 3.10-2.91 (m, 2H). MS (ESI+) m/z 365.1 (M+H)+.

Example 156

[(2R)-4-(10-fluoro-7-methyl-6,7-dihydro-4H-3,4,7-triazadibenzo[cd,f]azulen-5-yl)-1,2,3,6-tetrahydropyridin-2-yl]methanol The title compound was prepared using the conditions described in Example 126, substituting Example 153E for Example 125E. $^1$H NMR (400 MHz, CD$_3$OD) δ 8.45 (d, J=6.3 Hz, 1H), 7.97 (dd, J=9.8, 2.8 Hz, 1H), 7.86 (d, J=6.3 Hz, 1H), 7.72 (dd, J=9.0, 5.0 Hz, 1H), 7.48-7.41 (m, 1H), 6.09 (s, 1H), 4.61 (s, 2H), 4.08-4.02 (m, 2H), 4.00 (dd, J=11.8, 3.6 Hz, 1H), 3.80 (dd, J=11.8, 6.2 Hz, 1H), 3.69 (ddd, J=11.0, 7.4, 4.6 Hz, 1H), 3.04 (s, 3H), 2.92 (d, J=6.3 Hz, 2H). MS (ESI+) m/z 365.1 (M+H)+.

Example 157

2-[4-(9,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide The title compound was prepared as the trifluoroacetic acid salt essentially as described in Example 50, substituting 2-(methylamino)ethanol for dimethylamine and Example 145 for Example 41E. $^1$H NMR (400 MHz, CD$_3$OD) δ 3.00 (s, 3H), 3.04 (s, 1H), 3.06 (s, 3H), 3.10 (s, 1H), 3.47 (t, J=4.9 Hz, 1H), 3.60 (t, J=5.5 Hz, 1H), 3.67 (s, 2H), 3.75 (t, J=5.1 Hz, 2H), 4.15 (d, J=11.8 Hz, 2H), 4.27 (d, J=2.5 Hz, 2H), 4.40 (s, 1H), 4.50 (s, 1H), 5.75-6.09 (m, 1H), 7.26 (dd, J=12.8, 7.4 Hz, 1H), 7.47 (d, J=5.8 Hz, 1H), 7.90 (dd, J=12.1, 9.0 Hz, 1H), 8.29 (d, J=5.8 Hz, 1H). MS (ESI$^+$) m/z 468 (M+1).

Example 158

7-methyl-5-(1,2,3,6-tetrahydropyridin-4-yl)-6,7-dihydro-4H-3,4,7-triazadibenzo[cd,f]azulene

Example 158A

N-methyl-2-(1H-pyrrolo[2,3-b]pyridin-4-yl)aniline

A 1000 mL round bottom flask containing N-methyl-2-(4,4,5,5-tetramethyl-1,3,2-dioxaborolan-2-yl)aniline (18.88 g, 81 mmol) was charged with 4-bromo-1H-pyrrolo[2,3-b]pyridine (11.40 g, 57.9 mmol), potassium phosphate (36.8 g, 174 mmol) and phenylallylchloro[1,3-bis(diisopropylphenyl)-2-imidazol-2-ylidene]palladium (II) (1.873 g, 2.89 mmol) under argon. To this was added a mixture of dioxane (400 mL) and water (100 mL) that had been degassed with argon for 30 minutes. The mixture was purged with nitrogen again, and heated at 80° C. overnight under nitrogen. The reaction mixture was cooled to ambient temperature and partitioned between ethyl acetate (750 mL) and 50% brine (1000 mL). The organic layers were dried over sodium sulfate, filtered and concentrated. The crude residue was dissolved in a minimum of methylene chloride, diluted with an equal volume of heptane and was purified on a Teledyne CombiFlash RF chromatography system on a silica gel Gold Rf cartridge (330 g) eluted with a 5-30% 3:1 ethyl acetate/ethanol in heptane to give the title compound. MS (ESI$^+$) m/z 224 (M+1).

Example 158B 4-methyl-3,4-dihydro-1H-1,4,11-triazadibenzo[cd,f]azulene

The title compound was prepared essentially as described in Example 144F, substituting Example 158A for Example 144E. MS (ESI$^+$) m/z 236 (M+1).

Example 158C 4-methyl-1-tosyl-3,4-dihydro-1H-1,4,11-triazadibenzo[cd,f]azulene The title compound was prepared essentially as described in Example 144G, substituting Example 158B for Example 144F. MS (ESI$^+$) m/z 389 (M+1).

Example 158D 2-iodo-4-methyl-1-tosyl-3,4-dihydro-1H-1,4,11-triazadibenzo[cd,f]azulene The title compound was prepared essentially as described in Example 144H, substituting Example 158C for Example 144G. MS (ESI$^+$) m/z 389 (M+1).

Example 158E 2-iodo-4-methyl-3,4-dihydro-1H-1,4,11-triazadibenzo[cd,f]azulene The title compound was prepared essentially as described in Example 144 I, substituting Example 158D for Example 144H. MS (ESI$^+$) m/z 362 (M+1).

Example 158F tert-butyl 4-(4-methyl-3,4-dihydro-1H-1,4,11-triazadibenzo[cd,f]azulen-2-yl)-5,6-dihydropyridine-1(2H)-carboxylate The title compound was prepared essentially as described in Example 144J, substituting Example 158E for Example 144I. MS (ESI$^+$) m/z 417 (M+1).

Example 158G 7-methyl-5-(1,2,3,6-tetrahydropyridin-4-yl)-6,7-dihydro-4H-3,4,7-triazadibenzo[cd,f]azulene The title compound was prepared essentially as described in Example 1H, substituting Example 158F for Example 1G. $^1$H NMR (400 MHz, DMSO-d$_6$) δ 2.53 (d, J=3.9 Hz, 2H), 2.93 (s, 3H), 2.99 (t, J=5.7 Hz, 2H), 3.50 (q, J=2.9 Hz, 2H), 4.16 (s, 2H), 5.89 (p, J=1.9 Hz, 1H), 7.09-7.20 (m, 1H), 7.24-7.30 (m, 2H), 7.40 (ddd, J=8.5, 7.3, 1.6 Hz, 1H), 7.88 (dd, J=7.9, 1.6 Hz, 1H), 8.21 (d, J=5.2 Hz, 1H). MS (ESI$^+$) m/z 315 (M+1).

Example 159

1-fluoro-7-methyl-5-(1,2,3,6-tetrahydropyridin-4-yl)-6,7-dihydro-4H-3,4,7-triazadibenzo[cd,f]azulene

Example 159A 2-(5-fluoro-1H-pyrrolo[2,3-b]pyridin-4-yl)-N-methylaniline

The title compound was prepared essentially as described in Example 158A, substituting 4-chloro-5-fluoro-1H-pyrrolo[2,3-b]pyridine for 4-bromo-1H-pyrrolo[2,3-b]pyridine. MS (ESI$^+$) m/z 242 (M+1).

Example 159B 9-fluoro-4-methyl-3,4-dihydro-1H-1,4,11-triazadibenzo[cd,f]azulene The title compound was prepared essentially as described in Example 144F, substituting Example 159A for Example 144E. MS (ESI$^+$) m/z 254 (M+1).

Example 159C 9-fluoro-4-methyl-1-tosyl-3,4-dihydro-1H-1,4,11-triazadibenzo[cd,f]azulene The title compound was prepared essentially as described in Example 144G, substituting Example 159B for Example 144F. MS (ESI$^+$) m/z 408 (M+1).

Example 159D 2-iodo-4-methyl-1-tosyl-3,4-dihydro-1H-1,4,11-triazadibenzo[cd,f]azulene The title compound was prepared essentially as described in Example 144H, substituting Example 159C for Example 144G. MS (ESI$^+$) m/z 534 (M+1).

Example 159E 2-iodo-4-methyl-3,4-dihydro-1H-1,4,11-triazadibenzo[cd,f]azulene The title compound was prepared essentially as described in Example 144I, substituting Example 159D for Example 144H. MS (ESI$^+$) m/z 380 (M+1).

Example 159F tert-butyl 4-(9-fluoro-4-methyl-3,4-dihydro-1H-1,4,11-triazadibenzo[cd,f]azulen-2-yl)-5,6-dihydropyridine-1(2H)-carboxylate The title compound was prepared essentially as described in Example 144J, substituting Example 159E for Example 144I. MS (ESI$^+$) m/z 435 (M+1).

Example 159G 1-fluoro-7-methyl-5-(1,2,3,6-tetrahydropyridin-4-yl)-6,7-dihydro-4H-3,4,7-triazadibenzo[cd,f]azulene The title compound was prepared essentially as described in Example 1H, substituting Example 159F for Example 1G. $^1$H NMR (400 MHz, DMSO-d$_6$) δ 2.84 (s, 3H), 3.36 (t, J=6.3 Hz, 2H), 3.83 (d, J=5.2 Hz, 2H), 4.25 (s, 2H), 4.54 (s, 2H), 5.91 (s, 1H), 7.43-7.78 (m, 2H), 8.11 (s, 1H), 8.41 (d, J=4.8 Hz, 1H), 9.55 (s, 1H). MS (ESI$^+$) m/z 335 (M+1).

Example 160

7-methyl-5-[1-(methylsulfonyl)-1,2,3,6-tetrahydropyridin-4-yl]-6,7-dihydro-4H-3,4,7-triazadibenzo[cd,f]azulene The title compound was prepared as the trifluoroacetic acid salt essentially as described in Example 11, substituting Example 158G for Example 9. $^1$H NMR (400 MHz, DMSO-d$_6$) δ 2.67-2.79 (m, 2H), 2.97 (s, 4H), 2.98 (s, 3H), 3.43 (t, J=5.7 Hz, 2H), 3.97 (q, J=2.9 Hz, 2H), 4.29 (s, 2H), 5.89-6.03 (m, 1H), 7.27 (t, J=7.5 Hz, 1H), 7.38 (d, J=8.1 Hz, 1H), 7.44-7.53 (m, 2H), 7.99 (dd, J=8.1, 1.6 Hz, 1H), 8.33 (d, J=5.6 Hz, 1H). MS (ESI$^+$) m/z 395 (M+1).

Example 161

1-fluoro-7-methyl-5-[1-(methylsulfonyl)-1,2,3,6-tetrahydropyridin-4-yl]-6,7-dihydro-4H-3,4,7-triazadibenzo[cd,f]azulene The title compound was prepared as the trifluoroacetic acid salt essentially as described in Example 11, substituting Example 159G for Example 9. $^1$H NMR (400 MHz, CD$_3$OD) δ 2.74 (d, J=29.6 Hz, 2H), 2.95 (s, 3H), 3.09 (s, 3H), 3.56 (t, J=5.5 Hz, 2H), 4.06 (q, J=2.8 Hz, 2H), 4.80 (s, 2H), 5.98 (td, J=3.4, 1.8 Hz, 1H), 7.62-7.72 (m, 2H), 7.75 (dd, J=7.4, 2.0 Hz, 1H), 8.28 (dt, J=7.1, 2.5 Hz, 1H), 8.36 (d, J=4.9 Hz, 1H). MS (ESI$^+$) m/z 413 (M+1).

Example 162

N,N-dimethyl-2-[4-(7-methyl-6,7-dihydro-4H-3,4,7-triazadibenzo[cd,f]azulen-5-yl)-3,6-dihydropyridin-1(2H)-yl]acetamide The title compound was prepared as the trifluoroacetic acid salt essentially as described in Example 12, substituting Example 158G for Example 1. $^1$H NMR (400 MHz, CD$_3$OD) δ 3.04 (s, 3H), 3.05 (s, 3H), 3.07 (s, 3H), 3.31 (dt, J=3.4, 1.6 Hz, 2H), 3.69 (s, 2H), 4.18 (s, 2H), 4.41 (s, 2H), 4.46 (s, 2H), 5.96-6.08 (m, 1H), 7.33-7.43 (m, 1H), 7.51 (dd, J=8.3, 1.2 Hz, 1H), 7.61 (ddd, J=8.6, 7.2, 1.5 Hz, 1H), 7.74 (d, J=6.3 Hz, 1H), 8.10 (dd, J=8.0, 1.5 Hz, 1H), 8.36 (d, J=6.2 Hz, 1H). MS (ESI$^+$) m/z 402 (M+1).

Example 163

2-[4-(1-fluoro-7-methyl-6,7-dihydro-4H-3,4,7-triazadibenzo[cd,f]azulen-5-yl)-3,6-dihydropyridin-1(2H)-yl]-N,N-dimethylacetamide The title compound was prepared as the trifluoroacetic acid salt essentially as described in Example 12, substituting Example 159G for Example 1. $^1$H NMR (400 MHz, CD$_3$OD) δ 3.02 (s, 3H), 3.04 (d, J=3.4 Hz, 6H), 3.67 (m, 2H), 4.06-4.25 (m, 2H), 4.39 (s, 2H), 4.71 (s, 2H), 4.87 (s, 15H), 5.92 (t, J=3.4 Hz, 1H), 7.55 (t, J=7.6 Hz, 1H), 7.63 (t, J=7.7 Hz, 1H), 7.73 (d, J=8.1 Hz, 1H), 8.21 (d, J=7.8 Hz, 1H), 8.35 (d, J=4.9 Hz, 1H). MS (ESI$^+$) m/z 420 (M+1).

Example 164

3-[4-(10-fluoro-4,6-dihydro-7-oxa-3,4-diazadibenzo[cd,f]azulen-5-yl)-3,6-dihydropyridin-1(2H)-yl]propane-1,2-diol To a mixture of Example 14J (80.0 mg, 0.203 mmol) and triethylamine (0.062 mL, 0.446 mmol) in dichloromethane (1.5 mL) and CH$_3$OH (1.5 mL) was added acetic acid (0.058 mL, 1.015 mmol), 2,3-dihydroxypropanal (36.6 mg, 0.406 mmol) and MP-CNBH$_3$ (2.49 mmol/g, Biotage, 326 mg). The reaction mixture was heated at 40° C. for 3 hours. The solid material was filtered and rinsed with dichloromethane and CH$_3$OH. The filtrate was concentrated and purified by reverse-phase HPLC performed on a Zorbax RX-C18 column using a gradient of 15-100% methanol in 0.1% aqueous trifluoroacetic acid at a flow rate of 15 mL/minute to provide the product as a trifluoroacetic acid salt. The salt was flushed through a 5 g SCX column eluting with 2M NH₃ in CH₃OH to provide the title compound as a free base. ¹H NMR (400 MHz, pyridine-d5) δ 12.88 (s, 1H), 8.63 (d, J=5.2 Hz, 1H), 7.93 (dd, J=10.1, 3.1 Hz, 1H), 7.51 (d, J=5.2 Hz, 1H), 7.39 (dd, J=8.9, 5.2 Hz, 1H), 7.26-7.17 (m, 1H), 5.96 (d, J=3.5 Hz, 1H), 5.34 (s, 2H), 4.44 (p, J=5.7 Hz, 1H), 4.20-4.04 (m, 2H), 3.64-3.44 (m, 2H), 3.03-2.74 (m, 6H). MS (ESI) m/z 396.0 (M+H)⁺.

Example 165

{4-[4-(10-fluoro-4,6-dihydro-7-oxa-3,4-diaza-dibenzo[cd,f]azulen-5-yl)-3,6-dihydropyridin-1(2H)-yl]cyclohexyl}acetic acid Example 165A methyl 2-(4-(4-(7-fluoro-1,3-dihydro-4-oxa-1,11-diazadibenzo[cd,f]azulen-2-yl)-5,6-dihydropyridin-1(2H)-yl)cyclohexyl)acetate To a mixture of Example 14J (0.150 g, 0.380 mmol) and triethylamine (0.117 mL, 0.837 mmol) in dichloromethane (2 mL) and CH₃OH (2 mL) was added acetic acid (0.109 mL, 1.902 mmol), methyl 2-(4-oxocyclohexyl)acetate (0.122 mL, 0.761 mmol) and MP-CNBH₃ (2.49 mmol/g, Biotage, 582 mg). The reaction mixture was heated at 40° C. for 3 hours. The solid material was filtered and rinsed with dichloromethane and CH₃OH. The filtrate was concentrated. The residue was partitioned between ethyl acetate and saturated aqueous sodium bicarbonate. The suspension in the aqueous layer was extracted with dichloromethane. The combined organic layers were dried over anhydrous sodium sulfate, filtered and concentrated until most of the solvent was removed. The suspension was filtered and washed with cold ethyl acetate to give the title compound. The filtrate was purified on a 12 g column using the ISCO Companion flash system eluting with dichloromethane/CH₃OH/NH₄OH (18:1:0.1 to 12:1:0.1) to give more title compound. MS (ESI) m/z 476.0 (M+H)⁺.

Example 165B

{4-[4-(10-fluoro-4,6-dihydro-7-oxa-3,4-diaza-dibenzo[cd,f]azulen-5-yl)-3,6-dihydropyridin-1(2H)-yl]cyclohexyl}acetic acid A mixture of Example 165A (0.094 g, 0.198 mmol) and lithium hydroxide (9.47 mg, 0.395 mmol) in tetrahydrofuran (3 ml), CH₃OH (1.2 ml), and water (0.9 ml) was stirred overnight. The reaction mixture was concentrated and purified by reverse-phase HPLC on a Zorbax RX-C18 column (250×21.2 mm, 7 µm particle size) using a gradient of 10-95% acetonitrile in 0.1% aqueous trifluoroacetic acid to provide the title compound as a trifluoroacetic acid salt. ¹H NMR (400 MHz, CD₃OD) δ 8.39 (bs, 1H), 7.79 (dd, J=9.8, 3.0 Hz, 1H), 7.60 (d, J=5.0 Hz, 1H), 7.33-7.15 (m, 2H), 5.91 (t, J=3.1 Hz, 1H), 5.27 (d, J=6.7 Hz, 2H), 4.16-4.02 (m, 2H), 3.94-3.78 (m, 1H), 3.48-3.34 (m, 2H), 3.02 (bs, 2H), 2.45 (d, J=7.7 Hz, 1H), 2.31-2.20 (m, 3H), 2.09-1.98 (m, 2H), 1.91-1.61 (m, 4H), 1.22 (qd, J=13.0, 3.2 Hz, 1H). MS (ESI) m/z 462.1 (M+H)⁺.

Example 166 trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid Example 166A 7,9-difluoro-2-iodo-4-methyl-3,4-dihydro-1H-1,4,11-triazadibenzo[cd,f]azulene The title compound was prepared as described in Example 144E-I, substituting Example 1A for Example 144D and 4-chloro-5-fluoro-1H-pyrrolo[2,3-b]pyridine for 4-bromo-1H-pyrrolo[2,3-b]pyridine in Example 144E. MS (ESI⁺) m/z 397 (M+H)⁺.

Example 166B trans-ethyl 4-aminocyclohexanecarboxylate

Trans-4-aminocyclohexanecarboxylic acid hydrochloric acid (10 g, 55.7 mmol) was suspended in absolute ethanol (159 mL). Concentrated HCl (8.35 mL, 100 mmol) was added. The mixture was heated at 60° C. for 3 days, and concentrated. More ethanol and acetonitrile were added and the mixture was concentrated to provide the title compound as the HCl salt. MS (DCI) m/z 172 (M+H)⁺.

Example 166C trans-ethyl 4-(4-oxopiperidin-1-yl)cyclohexanecarboxylate

Example 166B (9.89 g, 47.6 mmol) was suspended in ethanol (100 mL) and water (10 mL). Potassium carbonate (13.16 g, 95 mmol) was added and the mixture was heated to reflux. To the refluxing suspension was added a solution of 1-ethyl-1-methyl-4-oxopiperidin-1-ium, iodide anion (19.22 g, 71.4 mmol) in water (33.3 mL) over 30 minutes. The reaction mixture was stirred at the same temperature for 40 minutes and was concentrated. The residue was partitioned between water and methylene chloride. The aqueous phase was extracted with methylene chloride and the combined organics were dried over sodium sulfate, filtered and concentrated. The residue was separated by flash chromatography on silica gel (Teledyne CombiFlash Rf, 0-30% acetone in methylene chloride) to provide the title compound. MS (DCI) m/z 254 (M+H)⁺.

Example 166D trans-ethyl 4-(4-(((trifluoromethyl)sulfonyl)oxy)-5,6-dihydropyridin-1(2H)-yl)cyclohexanecarboxylate Example 166C (8.86 g, 35.0 mmol) was dissolved in tetrahydrofuran (100 mL) under nitrogen and the solution was chilled in a dry ice-acetone bath for 15 minutes before adding dropwise lithium bis(trimethylsilyl)amide (1N in hexanes, 36.7 mL, 36.7 mmol) over 10 minutes. The mixture was stirred at −78° C. for 1 hour, and a solution of 1,1,1-trifluoro-N-phenyl-N-((trifluoromethyl)sulfonyl)methanesulfonamide (13.12 g, 36.7 mmol) in tetrahydrofuran (25 mL) was added dropwise over 10 minutes. The reaction was stirred at −78° C. for 30 minutes and allowed to warm to room temperature for 1 hour. The reaction was quenched with water (100 mL) and extracted with ethyl acetate (3×100 mL). The organic extracts were dried (Na₂SO₄), filtered, and concentrated. The residue was separated by flash chromatography on silica gel (Teledyne CombiFlash Rf, 0-20% acetone in heptane) to provide the title compound. MS (ESI⁺) m/z 386 (M+H)⁺.

Example 166E trans-ethyl 4-(4-(7,9-difluoro-4-methyl-3,4-dihydro-1H-1,4,11-triazadibenzo[cd,f]azulen-2-yl)-5,6-dihydropyridin-1(2H)-yl)cyclohexanecarboxylate A mixture of Example 166D (374 mg, 0.969 mmol), bis(pinacolato)diboron (246 mg, 0.969 mmol), potassium acetate (259 mg, 2.64 mmol) and PdCl₂(dppf)-CH₂Cl₂ (36 mg, 0.044 mmol) was dried under high vacuum for 30 minutes. Anhydrous dioxane (6 mL) was added. This mixture was purged with nitrogen and heated at 75° C. for 1 hour. After cooling, Example 166A (350 mg, 0.881 mmol), sodium carbonate (2 M solution, 1.76 mL, 3.53 mmol) and PdCl₂(dppf)-CH₂Cl₂ (36 mg, 0.044 mmol) were added. The mixture was purged with nitrogen again and heated at 75° C. overnight. After cooling, the reaction mixture was partitioned between ethyl acetate and brine. The organic phase was concentrated. The residue was separated by flash chromatography (5-20% gradient CH₃OH containing 3% NH₄OH in 2:1 ethyl acetate/heptane) to provide the title compound. MS (ESI⁺) m/z 507 (M+H)⁺.

Example 166F trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid To a solution of Example 166E (152 mg, 0.300 mmol) in a mixture of tetrahydrofuran (4 mL) and methanol (2 mL) was added lithium hydroxide monohydrate (25 mg, 0.6 mmol) in water (4 mL). The solution was stirred at room temperature for 4 hours, and was concentrated. The residue was suspended in a mixture of acetonitrile and water and treated with TFA. The formed solution was separated by HPLC (Zorbax, C-18, 250×2.54 column, Mobile phase A: 0.1% TFA in H₂O; B: 0.1% TFA in CH₃CN; 0-100% gradient) to provide the title compound as TFA salt. The TFA salt was converted into the HCl salt by dissolving the salt in a mixture of acetonitrile and methylene chloride and treating with HCl in ether. Evaporation of the volatiles provided the title compound as a HCl salt. ¹H NMR (400 MHz, DMSO-d₆) δ 1.35-1.45 (m, 2H), 1.55-1.68 (m, 2H), 2.03-2.09 (m, 2H), 2.19-2.29 (m, 3H), 2.86 (s, 3H), 2.96-3.03 (m, 1H), 3.22-3.34 (m, 2H), 3.66-3.75 (m, 1H), 3.87-3.99 (m, 2H), 4.36-4.57 (m, 2H), 5.89 (s, 1H), 7.48 (s, 1H), 7.82 (s, 1H), 8.40 (d, J=4.58 Hz, 1H), 11.06 (s, 1H), 12.25 (s, 1H). MS (ESI⁺) m/z 479 (M+H)⁺.

Example 167

{trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexyl}acetic acid The title compound as the HCl salt was prepared as described in Example 124, substituting Example 47 for Example 1 in Example 124A and Example 124B for Example 124A in Example 124C. ¹H NMR (500 MHz, DMSO-d₆) δ 1.03-1.12 (m, 2H), 1.52-1.70 (m, 3H), 1.83-1.90 (m, 2H), 2.13-2.25 (m, 4H), 2.86 (s, 3H), 2.94-3.05 (m, 1H), 3.19-3.28 (m, 2H), 3.69-3.75 (m, 1H), 3.90-4.01 (m, 2H), 4.39-4.58 (m, 2H), 5.88 (s, 1H), 7.48 (s, 1H), 7.84 (s, 1H), 8.40 (d, J=4.27 Hz, 1H), 11.00 (s, 1H), 12.26 (s, 1H). MS (ESI⁺) m/z 493 (M+H)⁺.

Example 168

2-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}-N,N-dimethylacetamide The title compound was prepared as described in Example 129, substituting Example 142 for Example 127. ¹H NMR (400 MHz, DMSO-d₆) δ 0.84 (t, J=7.32 Hz, 3H), 1.22-1.29 (m, 2H), 1.35-1.42 (m, 1H), 2.56-2.64 (m, 1H), 2.67-2.73 (m, 1H), 2.86 (s, 3H), 2.87 (s, 3H), 3.03 (s, 3H), 3.30-3.37 (m, 2H), 3.42-3.49 (m, 2H), 4.25-4.30 (m, 1H), 6.07 (s, 1H), 7.19-7.28 (m, 2H), 7.33 (d, J=5.49 Hz, 1H), 7.76 (dd, J=10.68, 2.75 Hz, 1H), 8.21 (d, J=5.19 Hz, 1H), 11.43 (s, 1H). MS (ESI⁺) m/z 448 (M+H)⁺.

Example 169

{trans-4-[4-(7-methyl-6,7-dihydro-4H-3,4,7-triazadibenzo[cd,f]azulen-5-yl)-3,6-dihydropyridin-1(2H)-yl]cyclohexyl}acetic acid Example 169A trans methyl 2-(4-(4-(4-methyl-3,4-dihydro-1H-1,4,11-triazadibenzo[cd,f]azulen-2-yl)-5,6-dihydropyridin-1(2H)-yl)cyclohexyl)acetate The title compound was prepared essentially as described in Example 133, substituting Example 158G for Example 144K. MS (ESI⁺) m/z 471 (M+1).

Example 169B

{trans-4-[4-(7-methyl-6,7-dihydro-4H-3,4,7-triazadibenzo[cd,f]azulen-5-yl)-3,6-dihydropyridin-1(2H)-yl]cyclohexyl}acetic acid The title compound was prepared as the trifluoroacetic acid salt essentially as described in Example 136, substituting Example 169A for Example 134. ¹H NMR (400 MHz, CD₃OD) δ 1.23 (qd, J=13.2, 3.4 Hz, 2H), 1.69 (d, J=13.2 Hz, 2H), 1.76-1.92 (m, 1H), 2.05 (d, J=13.8 Hz, 2H), 2.25 (d, J=6.9 Hz, 3H), 3.03 (s, 5H), 3.36 (d, J=13.6 Hz, 2H), 3.92 (d, J=48.7 Hz, 1H), 4.10 (d, J=3.7 Hz, 2H), 4.38 (s, 2H), 5.99 (d, J=3.7 Hz, 1H), 7.34 (t, J=7.6 Hz, 1H), 7.46 (d, J=8.1 Hz, 1H), 7.57 (td, J=7.8, 7.3, 1.6 Hz, 1H), 7.66 (d, J=6.0 Hz, 1H), 8.06 (dd, J=8.0, 1.6 Hz, 1H), 8.33 (d, J=6.0 Hz, 1H). MS (ESI⁺) m/z 457 (M+1).

Example 170

{cis-4-[4-(7-methyl-6,7-dihydro-4H-3,4,7-triazadibenzo[cd,f]azulen-5-yl)-3,6-dihydropyridin-1(2H)-yl]cyclohexyl}acetic acid

Example 170A cismethyl 2-(4-(4-(4-methyl-3,4-dihydro-1H-1,4,11-triazadibenzo[cd,f]azulen-2-yl)-5,6-dihydropyridin-1(2H)-yl)cyclohexyl)acetate The title compound as the faster-eluting fraction (less polar fraction) was prepared essentially as described in Example 133, substituting Example 158G for Example 144K. MS (ESI$^+$) m/z 471 (M+1).

Example 170B

{cis-4-[4-(7-methyl-6,7-dihydro-4H-3,4,7-triazadibenzo[cd,f]azulen-5-yl)-3,6-dihydropyridin-1(2H)-yl]cyclohexyl}acetic acid The title compound was prepared as the trifluoroacetic acid salt essentially as described in Example 136, substituting 170A in place of Example 134. $^1$H NMR (400 MHz, CD$_3$OD) δ 1.63-1.91 (m, 6H), 2.02 (s, 2H), 2.30 (dd, J=8.5, 4.3 Hz, 1H), 2.41-2.54 (m, 2H), 3.05 (s, 5H), 3.41 (dd, J=11.5, 7.4 Hz, 2H), 3.92 (d, J=13.3 Hz, 1H), 4.11 (s, 2H), 4.42 (s, 2H), 6.02 (t, J=3.5 Hz, 1H), 7.30-7.41 (m, 1H), 7.41-7.52 (m, 1H), 7.54-7.64 (m, 1H), 7.71 (d, J=6.2 Hz, 1H), 8.08 (dd, J=8.0, 1.5 Hz, 1H), 8.35 (d, J=6.2 Hz, 1H). MS (ESI$^+$) m/z 457 (M+1).

Example 171 trans-4-[4-(7-methyl-6,7-dihydro-4H-3,4,7-triazadibenzo[cd,f]azulen-5-yl)-3,6-dihydropyridin-1(2H)-yl]cyclohexanecarboxylic acid

Example 171A trans-ethyl 4-(4-(4-methyl-3,4-dihydro-1H-1,4,11-triazadibenzo[cd,f]azulen-2-yl)-5,6-dihydropyridin-1(2H)-yl)cyclohexanecarboxylate The title compound was prepared essentially as described in Example 150A, using the slower-diluting fraction (more polar fraction) and substituting Example 158G for Example 144K. MS (ESI$^+$) m/z 471 (M+1).

Example 171B trans-4-[4-(7-methyl-6,7-dihydro-4H-3,4,7-triazadibenzo[cd,f]azulen-5-yl)-3,6-dihydropyridin-1(2H)-yl]cyclohexanecarboxylic acid The title compound was prepared as the trifluoroacetic acid salt essentially as described in Example 136, substituting Example 171A for Example 134. $^1$H NMR (400 MHz, CD$_3$OD) δ 1.56-1.94 (m, 4H), 2.13 (m, 2H), 2.38 (d, J=13.3 Hz, 2H), 2.75 (dt, J=4.7, 2.3 Hz, 1H), 2.99 (m, 1H), 3.02 (m, 1H), 3.05 (s, 3H), 3.35-3.53 (m, 2H), 3.78 (d, J=38.5 Hz, 1H), 4.10 (d, J=7.3 Hz, 2H), 4.42 (d, J=3.8 Hz, 2H), 5.91-6.07 (m, 1H), 7.37 (t, J=7.5 Hz, 1H), 7.48 (d, J=8.2 Hz, 1H), 7.59 (td, J=7.7, 7.1, 1.5 Hz, 1H), 7.71 (d, J=6.2 Hz, 1H), 8.08 (dd, J=7.9, 1.6 Hz, 1H), 8.35 (d, J=6.2 Hz, 1H). MS (ESI$^+$) m/z 443 (M+1).

Example 172

4-[4-(7-methyl-6,7-dihydro-4H-3,4,7-triazadibenzo[cd,f]azulen-5-yl)-3,6-dihydropyridin-1(2H)-yl]cyclohexanecarboxylic acid

Example 172A ethyl 4-(4-(4-methyl-3,4-dihydro-1H-1,4,11-triazadibenzo[cd,f]azulen-2-yl)-5,6-dihydropyridin-1(2H)-yl)cyclohexanecarboxylate The title compound was prepared as a cis/trans mixture as described in Example 150A, substituting Example 158G for Example 144K. MS (ESI$^+$) m/z 471 (M+1).

Example 172B

4-[4-(7-methyl-6,7-dihydro-4H-3,4,7-triazadibenzo[cd,f]azulen-5-yl)-3,6-dihydropyridin-1(2H)-yl]cyclohexanecarboxylic acid The title compound was prepared essentially as described in Example 136, substituting Example 172A for Example 134. $^1$H NMR (400 MHz, CD$_3$OD) δ 1.55-1.86 (m, 4H), 2.13 (d, J=11.2 Hz, 1H), 2.20-2.33 (m, 3H), 2.36 (m, 1H), 3.04 (d, J=1.6 Hz, 5H), 3.43 (ddt, J=11.9, 8.4, 3.6 Hz, 1H), 3.69 (s, 1H), 3.85 (s, 1H), 4.10 (d, J=6.7 Hz, 2H), 4.41 (d, J=3.7 Hz, 2H), 5.97-6.05 (m, 1H), 7.36 (t, J=7.6 Hz, 1H), 7.48 (d, J=8.2 Hz, 1H), 7.55-7.62 (m, 1H), 7.70 (d, J=6.2 Hz, 1H), 8.08 (dd, J=8.1, 1.5 Hz, 1H), 8.34 (d, J=6.2 Hz, 1H). MS (ESI$^+$) m/z 443 (M+1).

Example 173

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetonitrile

Example 173A 2-cyano-2-(4-oxocyclohexylidene)acetic acid

A solution of 1,4-dioxaspiro[4.5]decan-8-one (7.00 g, 44.8 mmol), tert-butyl 2-cyanoacetate (6.96 g, 49.3 mmol), ammonium acetate (0.28 g) and acetic acid (1.4 mL) in toluene (90 ml) was refluxed using Dean-Stark water separator to isolate water formed for 48 hours. The reaction mixture was washed twice with water, dried over Na$_2$SO$_4$, filtered, and concentrated in vacuo. To the crude material was added 140 ml of a 2% aqueous sulfuric acid solution and the mixture was refluxed for 1 hour. The reaction mixture was then cooled to room temperature and filtered to provide the title compound. $^1$H NMR (400 MHz, DMSO-d$_6$) δ 2.36-2.55 (m, 4H), 3.04 (dd, J=7.6, 5.8 Hz, 2H), 3.30 (d, J=13.6 Hz, 2H).

Example 173B

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetonitrile A solution of Example 1 (100 mg, 0.299 mmol) in dichloromethane (2 mL) and methanol (2 mL) was treated with Example 173A (69.7 mg, 0.389 mmol) and acetic acid (71.8 mg, 1.196 mmol). The reaction mixture was stirred at room temperature for 10 minutes. MP-CNBH$_3$ (546 mg, 1.196 mmol) was then added and the reaction mixture was stirred at room temperature for 3 days. The solid material was filtered off and rinsed with a mixture of dichloromethane and methanol (1/1). The filtrate was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile: 0.1% trifluoroacetic acid in water to provide the title compound as bis-trifluoroacetic acid salt. $^1$H NMR (400 MHz, Pyridine-d$_5$) δ 1.50-2.39 (m, 8H), 2.83 (s, 3H), 2.93-3.34 (m, 5H), 3.81 (d, J=3.4 Hz, 2H), 4.22 (s, 2H), 5.52 (s, 1H), 5.92 (d, J=3.7 Hz, 1H), 7.07-7.21 (m, 2H), 7.30 (d, J=5.2 Hz, 1H), 7.74 (dd, J=10.4, 3.0 Hz, 1H), 8.48 (d, J=5.2 Hz, 1H), 12.66 (s, 1H). MS (ESI) m/e 454.2 (M+H)$^+$.

Example 174 methyl 2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoate

Example 174A methyl 2-(4-oxocyclohexylidene)propanoate

A mixture of methyl 2-(triphenylphosphoranylidene)propanoate (2.5 g, 7.18 mmol) and cyclohexane-1,4-dione (1.609 g, 14.35 mmol) in toluene (25 mL) was stirred at 100° C. overnight and then concentrated in vacuo. The residue was triturated with a mixture of hexanes (100 mL) and ethyl acetate (100 mL), and filtered. The filtrate was concentrated in vacuo and the residue was purified by flash chromatography on Analogix IntelliFlash$^{280}$ eluting with 0 to 50% ethyl acetate/hexanes to provide the title compound. $^1$H NMR (400 MHz, DMSO-d$_6$) δ 1.85 (p, J=1.5 Hz, 3H), 2.27-2.35 (m, 2H), 2.41 (dd, J=8.0, 5.8 Hz, 2H), 2.55-2.65 (m, 2H), 2.81-2.90 (m, 2H), 3.66 (s, 3H).

Example 174B methyl 2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoate The title compound, as the bis-trifluoroacetic acid salt, was prepared as described in Example 173B, substituting Example 174A for Example 173A. $^1$H NMR (400 MHz, Pyridine-d$_5$) δ 1.62-2.11 (m, 4H), 1.88 (s, 3H), 2.25-2.42 (m, 2H), 2.70 (dd, J=13.7, 3.3 Hz, 1H), 3.00 (s, 3H), 3.19-3.61 (m, 6H), 3.73 (s, 3H), 4.09 (d, J=3.4 Hz, 2H), 4.36 (s, 2H), 6.05 (d, J=3.2 Hz, 1H), 7.20-7.34 (m, 2H), 7.44 (d, J=5.2 Hz, 1H), 7.88 (dd, J=10.3, 2.9 Hz, 2H), 8.63 (d, J=5.1 Hz, 1H), 12.83 (s, 1H). MS (ESI$^+$) m/z 501.1 (M+H)$^+$.

Example 175 tert-butyl{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetate

Example 175A tert-butyl 2-(4-oxocyclohexylidene)acetate

The title compound was prepared as described in Example 174A, substituting tert-butyl 2-(triphenylphosphoranylidene)acetate for methyl 2-(triphenylphosphoranylidene)propanoate. $^1$H NMR (400 MHz, DMSO-d$_6$) δ 1.43 (s, 9H), 2.38 (dt, J=10.3, 6.9 Hz, 4H), 2.62 (td, J=6.8, 1.4 Hz, 2H), 3.05 (td, J=7.1, 1.7 Hz, 2H), 5.75 (p, J=1.5 Hz, 1H).

Example 175B tert-butyl{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetate The title compound was prepared as the bis-trifluoroacetic acid salt as described in Example 173B, substituting Example 175A for Example 173A. $^1$H NMR (400 MHz, Pyridine-d$_5$) δ 1.53 (s, 9H), 1.59-2.41 (m, 8H), 2.97 (s, 3H), 3.17 (s, 2H), 3.20-3.41 (m, 2H), 3.91 (d, J=3.9 Hz, 2H), 4.13 (d, J=14.3 Hz, 1H), 4.36 (s, 2H), 5.71 (d, J=1.6 Hz, 1H), 6.07 (d, J=3.2 Hz, 1H), 7.18-7.34 (m, 2H), 7.44 (d, J=5.2 Hz, 1H), 7.89 (dd, J=10.4, 3.0 Hz, 1H), 8.62 (d, J=5.2 Hz, 1H), 12.79 (s, 1H). MS (ESI$^+$) m/z 529.1 (M+H)$^+$.

Example 176

2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoic acid To a solution of Example 174B (110 mg, 0.151 mmol) in a mixture of tetrahydrofuran (1 mL) and methanol (0.5 mL) was added LiOH (1M aqueous solution, 453 μL, 0.453 mmol). This mixture was heated at 65° C. for 5 hours. After cooling, the reaction was neutralized with 1M aqueous hydrochloride acid. The formed solid was collected by filtration, washed with water and hexanes, and dried in vacuo to provide the title compound. $^1$H NMR (400 MHz, Pyridine-d$_5$) δ 1.51-2.22 (m, 8H), 2.12 (s, 3H), 2.74 (d, J=13.3 Hz, 1H), 2.93 (s, 3H), 2.95-3.15 (m, 3H), 3.53-3.79 (m, 3H), 4.38 (s, 2H), 6.11 (d, J=3.4 Hz, 1H), 7.27 (td, J=8.3, 7.6, 4.2 Hz, 2H), 7.44 (d, J=5.3 Hz, 1H), 7.89 (dd, J=10.4, 3.0 Hz, 1H), 8.62 (d, J=5.2 Hz, 1H), 12.78 (s, 1H). MS (ESI$^+$) m/z 487.1 (M+H)$^+$.

Example 177

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetic acid A mixture of Example 175B (90 mg, 0.119 mmol) in 1:1 dichloromethane/trifluoroacetic acid (0.6 mL) was stirred at room temperature for 3 hours. The reaction mixture was concentrated in vacuo to provide the title compound as bis-trifluroacetic acid salt. $^1$H NMR (400 MHz, Pyridine-d$_5$) δ 1.68-2.43 (m, 8H), 2.99 (s, 3H), 3.18-3.61 (m, 4H), 4.05 (d, J=3.7 Hz, 2H), 4.32-4.47 (m, 3H), 5.93-6.15 (m, 2H), 7.15-7.32 (m, 2H), 7.44 (d, J=5.2 Hz, 1H), 7.88 (dd, J=10.4, 3.0 Hz, 1H), 8.63 (d, J=5.2 Hz, 1H), 12.82 (s, 1H). MS (ESI$^+$) m/z 473.1 (M+H)$^+$.

Example 178

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylethanesulfonamide To a suspension of Example 1 (200 mg, 0.598 mmol) in N,N-dimethylformamide (5 mL) was added triethylamine (0.1 mL, 0.718 mmol) and N,N-dimethylethenesulfonamide (97 mg, 0.718 mmol). The reaction mixture was stirred at room temperature for 2 weeks, and partitioned between ethyl acetate and brine. The organic phase was washed with brine and concentrated. The residue was separated by flash chromatography on silica gel (Teledyne CombiFlash Rf, 10-20% gradient CH₃OH in 2:1 ethyl acetate/heptane) to provide the title compound. $^1$H NMR (400 MHz, DMSO-d$_6$) δ 2.60-2.64 (m, 2H), 2.72 (t, J=5.49 Hz, 2H), 2.80 (s, 6H), 2.81-2.84 (m, 1H), 2.88 (s, 3H), 3.22 (d, J=2.14 Hz, 2H), 3.29-3.32 (m, 1H), 4.13 (s, 2H), 5.85 (s, 1H), 7.20-7.32 (m, 3H), 7.69 (dd, J=10.53, 2.90 Hz, 1H), 8.23 (d, J=5.19 Hz, 1H), 11.50 (s, 1H). MS (ESI$^+$) m/z 470 (M+H)$^+$.

Example 179

2-[4-(10-fluoro-7-methyl-6,7-dihydro-4H-3,4,7-triazadibenzo[cd,f]azulen-5-yl)-3,6-dihydropyridin-1(2H)-yl]ethanesulfonamide The title compound was prepared as described in Example 178, substituting ethenesulfonamide for N,N-dimethylethenesulfonamide. $^1$H NMR (400 MHz, DMSO-d$_6$) δ 2.60-2.63 (m, 2H), 2.70 (t, J=5.34 Hz, 2H), 2.85-2.88 (m, 1H), 2.88 (s, 3H), 3.20-3.28 (m, 4H), 4.14 (s, 2H), 5.86 (s, 1H), 6.83 (s, 1H), 7.21-7.33 (m, 3H), 7.69 (dd, J=10.53, 2.90 Hz, 1H), 8.23 (d, J=5.19 Hz, 1H), 11.48 (s, 1H). MS (ESI$^+$) m/z 442 (M+H)$^+$.

Example 180

{trans-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid

Example 180A trans-methyl 2-(4-(4-(9-fluoro-4-methyl-3,4-dihydro-1H-1,4,11-triazadibenzo[cd,f]azulen-2-yl)-5,6-dihydropyridin-1(2H)-yl)cyclohexyl)acetate The title compound (slower-diluting/more polar isomer) was prepared essentially as described in Example 133, substituting Example 159G for Example 144K. MS (ESI$^+$) m/z 489 (M+1).

Example 180B

{trans-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid The title compound was prepared as the bis-trifluoroacetic acid salt essentially as described in Example 136, substituting Example 180A for Example 134. $^1$H NMR (400 MHz, DMSO-d$_6$) δ 0.97-1.18 (m, 2H), 1.41-1.77 (m, 3H), 1.77-1.97 (m, 2H), 2.14 (t, J=9.4 Hz, 5H), 2.93 (s, 3H), 3.11-3.36 (m, 2H), 3.50-3.85 (m, 2H), 3.99 (d, J=5.0 Hz, 2H), 4.11 (s, 2H), 5.84 (d, J=3.6 Hz, 1H), 7.21 (t, J=7.5 Hz, 1H), 7.38 (d, J=8.1 Hz, 1H), 7.40-7.57 (m, 1H), 7.89 (ddd, J=7.9, 3.9, 1.6 Hz, 1H), 8.29 (d, J=4.9 Hz, 1H). MS (ESI$^+$) m/z 475.

Example 181 trans-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid

Example 181A trans-ethyl 4-(4-(9-fluoro-4-methyl-3,4-dihydro-1H-1,4,11-triazadibenzo[cd,f]azulen-2-yl)-5,6-dihydropyridin-1(2H)-yl)cyclohexanecarboxylate The title compound (slower-diluting/more polar isomer) was prepared essentially as described in Example 150A, substituting Example 159G for Example 144K. MS (ESI$^+$) m/z 489 (M+1).

Example 181B trans-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid The title compound was prepared essentially as described in Example 136, substituting Example 181A for Example 134. $^1$H NMR (400 MHz, DMSO-d$_6$) δ 1.19-1.41 (m, 2H), 1.41-1.54 (m, 1H), 1.54-1.69 (m, 2H), 1.87 (d, J=10.5 Hz, 1H), 1.97 (dt, J=10.7, 4.8 Hz, 2H), 2.09-2.41 (m, 1H), 2.42-2.60 (m, 4H), 2.70 (dt, J=13.8, 5.5 Hz, 2H), 2.92 (s, 3H), 3.15-3.33 (m, 2H), 4.07 (d, J=3.8 Hz, 2H), 5.85 (dd, J=8.8, 4.3 Hz, 1H), 7.18 (t, J=7.5 Hz, 1H), 7.34 (d, J=8.2 Hz, 1H), 7.38-7.49 (m, 1H), 7.87 (ddd, J=7.9, 3.9, 1.6 Hz, 1H), 8.20 (d, J=5.0 Hz, 1H). MS (ESI$^+$) m/z 461 (M+1).

Example 182

{cis-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid

Example 182A cis-methyl 24(4-(4-(9-fluoro-4-methyl-3,4-dihydro-1H-1,4,11-triazadibenzo[cd,f]azulen-2-yl)-5,6-dihydropyridin-1(2H)-yl)cyclohexyl)acetate The title compound (faster-diluting/less polar isomer) was prepared essentially as described in Example 133, substituting Example 159G for Example 144K. MS (ESI$^+$) m/z 489 (M+1).

Example 182B

{cis-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid The title compound was prepared as the bis-trifluoroacetic acid salt essentially as described in Example 136, substituting Example 182A for Example 134. $^1$H NMR (400 MHz, DMSO-d$_6$) δ 1.67 (ddd, J=37.7, 26.8, 13.4 Hz, 7H), 1.81-1.98 (m, 2H), 2.14 (dq, J=7.9, 3.8 Hz, 1H), 2.34 (d, J=7.5 Hz, 2H), 2.93 (s, 3H), 3.14-3.37 (m, 3H), 3.81 (d, J=12.2 Hz, 1H), 3.94-4.08 (m, 2H), 4.12 (s, 2H), 5.85 (d, J=4.2 Hz, 1H), 7.21 (t, J=7.4 Hz, 1H), 7.38 (d, J=8.1 Hz, 1H), 7.46 (t, J=7.7 Hz, 1H), 7.89 (dd, J=8.2, 3.7 Hz, 1H), 8.29 (d, J=4.8 Hz, 1H). MS (ESI$^+$) m/z 475 (M+1).

Example 183 cis-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid

Example 183A cis-ethyl 4-(4-(9-fluoro-4-methyl-3,4-dihydro-1H-1,4,11-triazadibenzo[cd,f]azulen-2-yl)-5,6-dihydropyridin-1(2H)-yl)cyclohexanecarboxylate The title compound (faster-diluting/less polar isomer) was prepared essentially as described in Example 150A, substituting Example 159G for Example 144K. MS (ESI$^+$) m/z 489 (M+1).

Example 183B cis-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid The title compound was prepared as the bis-trifluoroacetic acid salt essentially as described in Example 136, substituting Example 183A for Example 134. $^1$H NMR (400 MHz, DMSO-d$_6$) δ 1.40-1.76 (m, 4H), 1.93-2.22 (m, 4H), 2.64 (d, J=4.4 Hz, 1H), 2.93 (s, 5H), 3.16-3.38 (m, 2H), 3.60-3.81 (m, 1H), 3.99 (d, J=15.9 Hz, 2H), 4.13 (s, 2H), 5.83 (d, J=4.3 Hz, 1H), 7.15-7.28 (m, 1H), 7.40 (d, J=8.1 Hz, 1H), 7.47 (td, J=7.6, 7.1, 1.5 Hz, 1H), 7.90 (ddd, J=7.9, 3.8, 1.6 Hz, 1H), 8.29 (d, J=4.9 Hz, 1H). MS (ESI$^+$) m/z 461 (M+1).

Example 184

{4-[4-(10-fluoro-7-methyl-6,7-dihydro-4H-3,4,7-triazadibenzo[cd,f]azulen-5-yl)-2,3,6,7-tetrahydro-1H-azepin-1-yl]cyclohexylidene}acetic acid

Example 184A tert-butyl 2-(4-(4-(7-fluoro-4-methyl-3,4-dihydro-1H-1,4,11-triazadibenzo[cd,f]azulen-2-yl)-2,3,6,7-tetrahydro-1H-azepin-1-yl)cyclohexylidene)acetate The title compound was prepared as described in Example 175, substituting Example 87F for Example 1. MS (ESI$^+$) m/z 543 (M+H)$^+$.

Example 184B

{4-[4-(10-fluoro-7-methyl-6,7-dihydro-4H-3,4,7-triazadibenzo[cd,f]azulen-5-yl)-2,3,6,7-tetrahydro-1H-azepin-1-yl]cyclohexylidene}acetic acid The title compound was prepared as described in Example 177, substituting Example 184A for Example 175B. $^1$H NMR (400 MHz, DMSO-d$_6$) δ 1.61 (dd, J=27.3, 13.4 Hz, 2H), 1.96 (t, J=13.9 Hz, 1H), 2.16-2.44 (m, 4H), 2.68 (d, J=17.2 Hz, 1H), 2.85 (s, 3H), 2.97 (q, J=16.4, 13.6 Hz, 2H), 3.27 (q, J=16.4, 11.6 Hz, 4H), 3.80-4.00 (m, 2H) 4.39 (s, 3H), 5.66 (s, 1H), 5.96 (s, 1H), 7.29-7.57 (m, 1H), 7.66 (s, 1H), 7.78-8.17 (m, 2H), 8.37 (s, 1H), 11.19 (s, 1H), 12.52 (s, 1H). MS (ESI$^+$) m/z 487 (M+H)$^+$.

Example 185

2-{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}-2-methylpropanoic acid A solution of Example 1 (84 mg, 0.25 mmol) in a mixture of dichloromethane (1 mL) and methanol (1 mL) was treated with 2-methyl-2-(4-oxocyclohexyl)propanoic acid (59.9 mg, 0.325 mmol) and acetic acid (60.1 mg, 1.0 mmol) at room temperature for 10 minutes. MP-CNBH$_3$ (456 mg, 1.000 mmol) was added and the reaction mixture was stirred at room temperature for 24 hours. The solid material was filtered off and rinsed with 1/1 dichloromethane/methanol. The filtrate was concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile: 0.1% trifluoroacetic acid in water to provide the crude product. The product was further purified by silica gel thin layer chromatography eluting with dichloromethane/methanol (10/1) to provide the title compound. $^1$H NMR (400 MHz, pyridine-d$_5$) δ 1.17-1.82 (m, 8H), 1.33 (s, 6H), 1.97-2.38 (m, 4H), 2.77 (t, J=5.4 Hz, 2H), 2.89 (s, 3H), 3.35 (s, 2H), 4.38 (s, 2H), 6.15 (d, J=3.6 Hz, 1H), 7.21-7.33 (m, 2H), 7.43 (d, J=5.3 Hz, 1H), 7.88 (dd, J=10.4, 3.0 Hz, 1H), 8.61 (d, J=5.2 Hz, 1H), 12.68 (s, 1H). MS (ESI) m/e 503.2 (M+H)$^+$.

Example 186 methyl cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylate To a suspension of Example 142 (200 mg, 0.552 mmol) and methyl 3-oxocyclobutanecarboxylate (106 mg, 0.828 mmol) in a mixture of methanol (4 mL) and methylene chloride (4 mL) was added acetic acid (0.2 mL, 3.31 mmol) and the mixture was stirred at room temperature for 10 minutes. MP-Cyanoborohydride (Biotage, 2.19 mmol/g, 1 g) was then added. The suspension was stirred at room temperature for 3 days. Solid material was filtered off, and the filtrate was concentrated. The residue was separated by flash chromatography on silica gel (Teledyne CombiFlash Rf, 5-20% gradient CH$_3$OH in 2/1 ethyl acetate/heptane) to provide the title compound as a major product. The cis-configuration was determined by NOE experiment. $^1$H NMR (500 MHz, DMSO-d$_6$) δ 0.92 (t, J=7.32 Hz, 3H), 1.36-1.44 (m, 1H), 1.48-1.55 (m, 1H), 2.27-2.34 (m, 2H), 2.41-2.47 (m, 2H), 2.62-2.79 (m, 3H), 2.86-2.96 (m, 2H), 2.93 (s, 3H), 3.15-3.19 (m, 1H), 3.25-3.30 (m, 1H), 3.70 (s, 3H), 4.33 (dd, J=9.77, 4.88 Hz, 1H), 6.11 (s, 1H), 7.05-7.09 (m, 1H), 7.20-7.23 (m, 1H), 7.27 (d, J=5.80 Hz, 1H), 7.61-7.64 (m, 1H), 8.25 (d, J=5.19 Hz, 1H), 11.34 (s, 1H). MS (ESI$^+$) m/z 475 (M+H)$^+$.

Example 187 cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid A solution of Example 186 (160 mg, 0.337 mmol) in a mixture of tetrahydrofuran (4 mL) and methanol (2 mL) was added lithium hydroxide monohydrate (28.3 mg, 0.674 mmol) in water (4 mL). The solution was stirred at room temperature overnight, and concentrated. The residue was suspended in a mixture of acetonitrile and water, treated with TFA and separated by reverse phase HPLC (Zorbax, C-18, 250×2.54 column, Mobile phase A: 0.1% TFA in H$_2$O; B: 0.1% TFA in CH$_3$CN; 0-100% gradient) to provide the title compound as TFA salt. The TFA salt was dissolved in a mixture of acetonitrile and methylene chloride, and treated with HCl in ether (2 M solution). Concentration of the mixture provided the title compound as HCl salt. $^1$H NMR (400 MHz, DMSO-d$_6$) δ 0.82-0.87 (m, 3H), 1.23-1.32 (m, 1H), 1.55-1.64 (m, 1H), 2.49-2.60 (m, 4H), 2.81-3.00 (m, 6H), 3.11-3.16 (m, 1H), 3.58 (t, J=11.60 Hz, 1H), 3.70-3.81 (m, 2H), 4.00-4.08 (m, 1H), 4.59-4.62 (m, 1H), 6.18 (d, J=10.38 Hz, 1H), 7.46-7.51 (m, 1H), 7.76 (d, J=5.80 Hz, 1H), 8.08 (d, J=9.46 Hz, 1H), 8.38-8.43 (m, 1H), 11.39 (s, 1H), 12.74 (s, 1H). MS (ESI$^+$) m/z 461 (M+H)$^+$.

Example 188 cis-3-[4-(8-fluoro-5-methyl-1,3,4,5-tetrahydro-1,5, 12-triazabenzo[4,5]cycloocta[1,2,3-cd]inden-2-yl)-3, 6-dihydropyridin-1(2H)-yl]cyclobutanecarboxylic acid The title compound was prepared as described in Example 186 and 187, substituting Example 127 for Example 142 in Example 186. $^1$H NMR (400 MHz, DMSO-d$_6$) δ 1.99-2.08 (m, 2H), 2.30-2.44 (m, 3H), 2.53-2.57 (m, 1H), 2.62 (s, 3H), 2.72-2.89 (m, 6H), 2.94-3.02 (m, 1H), 3.04-3.07 (m, 2H), 6.01 (s, 1H), 6.96 (d, J=4.88 Hz, 1H), 7.35-7.41 (m, 2H), 7.58 (dd, J=8.70, 5.65 Hz, 1H), 8.22 (d, J=4.88 Hz, 1H), 11.40 (s, 1H). MS (ESI$^+$) m/z 447 (M+H)$^+$.

Example 189 trans-3-{4-[(6S)-6-ethyl-10-fluoro-7-methyl-6,7-dihydro-4H-3,4,7-triazadibenzo[cd,f]azulen-5-yl]-3, 6-dihydropyridin-1(2H)-yl}cyclobutanecarboxylic acid Example 189A trans-methyl 3-(4-((S)-3-ethyl-7-fluoro-4-methyl-3, 4-dihydro-1H-1,4,11-triazadibenzo[cd,f]azulen-2-yl)-5,6-dihydropyridin-1(2H)-yl)cyclobutanecarboxylate To a suspension of Example 142 (200 mg, 0.552 mmol) and methyl 3-oxocyclobutanecarboxylate (106 mg, 0.828 mmol) in a mixture of methanol (4 mL) and methylene chloride (4 mL) was added acetic acid (0.2 mL, 3.31 mmol) and the mixture was stirred at room temperature for 10 minutes. MP-Cyanoborohydride (Biotage, 2.19 mmol/g, 1 g) was then added. The suspension was stirred at room temperature for 3 days. Solid material was filtered off, and the filtrate was concentrated. The residue was separated by flash chromatography on silica gel (Teledyne CombiFlash Rf, 5-20% gradient CH$_3$OH in 2/1 ethyl acetate/heptane) to provide the title compound as a minor product. The trans-configuration was determined by NOE experiment. MS (ESI$^+$) m/z 475 (M+H)$^+$.

Example 189B trans-3-{4-[(6S)-6-ethyl-10-fluoro-7-methyl-6,7-dihydro-4H-3,4,7-triazadibenzo[cd,f]azulen-5-yl]-3, 6-dihydropyridin-1(2H)-yl}cyclobutanecarboxylic acid The title compound was prepared as the HCl salt as described in 187, substituting Example 189A for Example 186. $^1$H NMR (400 MHz, DMSO-d$_6$) δ 0.81-0.87 (m, 3H), 1.23-1.33 (m, 1H), 1.57-1.64 (m, 1H), 2.08 (s, 2H), 2.42-2.52 (m, 2H), 2.77-2.92 (m, 4H), 2.96-3.14 (m, 3H), 3.54-3.60 (m, 1H), 3.68-3.76 (m, 1H), 3.95-4.06 (m, 2H), 6.18 (d, J=20.14 Hz, 1H), 7.50 (s, 1H), 7.77 (d, J=5.80 Hz, 1H), 8.08 (s, 1H), 8.41 (dd, J=5.49, 3.05 Hz, 1H), 11.90 (s, 1H), 12.77 (s, 1H). MS (ESI$^+$) m/z 461 (M+H)$^+$.

Example 190 trans-3-[4-(8-fluoro-5-methyl-1,3,4,5-tetrahydro-1,5, 12-triazabenzo[4,5]cycloocta[1,2,3-cd]inden-2-yl)-3, 6-dihydropyridin-1(2H)-yl]cyclobutanecarboxylic acid The title compound was prepared as the HCl salt as described in 189, substituting Example 127 for Example 142 in Example 189A. $^1$H NMR (400 MHz, DMSO-d$_6$) δ 2.44-2.49 (m, 1H), 2.79 (m, 3H), 2.98 (s, 3H), 2.98-3.14 (m, 4H), 3.31-3.56 (m, 4H), 3.64-3.71 (m, 1H), 3.89-3.99 (m, 2H), 6.06 (s, 1H), 7.31 (d, J=5.49 Hz, 1H), 7.54-7.61 (m, 3H), 7.92-7.97 (m, 1H), 8.41 (s, 1H), 12.61 (s, 1H). MS (ESI$^+$) m/z 447 (M+H)$^+$.

Example 191 cyano{4-[4-(10-fluoro-7-methyl-6,7-dihydro-4H-3,4, 7-triazadibenzo[cd,f]azulen-5-yl)-3,6-dihydropyridin-1(2H)-yl]cyclohexyl}acetic acid Example 191A tert-butyl 2-cyano-2-(4-oxocyclohexylidene)acetate A solution of 1,4-dioxaspiro[4.5]decan-8-one (5 g, 32.0 mmol), tert-butyl 2-cyanoacetate (4.97 g, 35.2 mmol), ammonium acetate (0.2 g) and acetic acid (1.0 mL) in toluene (75 ml) was refluxed using Dean-Stark water separator to isolate water formed for 16 hours. After cooling, the reaction mixture was washed twice with water, dried over Na$_2$SO$_4$, filtered, and concentrated in vacuo. The crude material (4.18 g, 14.96 mmol) was treated with acetic acid (80% in water, 42.8 mL, 599 mmol) at 65° C. overnight. The reaction mixture was concentrated in vacuo and the residue was purified by flash chromatography on Analogix IntelliFlash$^{280}$ eluting with 5 to 100% ethyl acetate/hexanes to give the title compound. $^1$H NMR (501 MHz, CDCl$_3$) δ 1.54 (s, 9H), 2.49-2.62 (m, 4H), 3.05-3.16 (m, 2H), 3.37 (t, J=7.0 Hz, 2H).

Example 191B tert-butyl 2-cyano-2-(4-(4-(7-fluoro-4-methyl-3,4-dihydro-1H-1,4,11-triazadibenzo[cd,f]azulen-2-yl)-5,6-dihydropyridin-1(2H)-yl)cyclohexyl)acetate The title compound as the bis-trifluoroacetic acid salt was prepared as described in Example 173B, substituting Example 191A for Example 173A. LC-MS 555.9 (M+H)$^+$.

Example 191C cyano{4-[4-(10-fluoro-7-methyl-6,7-dihydro-4H-3,4, 7-triazadibenzo[cd,f]azulen-5-yl)-3,6-dihydropyridin-1(2H)-yl]cyclohexyl}acetic acid A mixture of Example 191B (~0.151 mmol) in 1:1 dichloromethane/trifluoroacetic acid (0.6 mL) was stirred at room temperature for 2 hours. The mixture was then concentrated in vacuo and the residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to provide the title compound as bis-trifluoroacetic acid salt. $^1$H NMR (400 MHz, Pyridine-d$_5$) δ 1.43-2.65 (m, 10H), 2.88-3.05 (m, 3H), 3.10-3.55 (m, 5H), 3.94 (s, 1H), 4.13 (d, J=4.6 Hz, 1H), 4.28-4.40 (m, 2H), 6.07 (dt, J=16.0, 3.4 Hz, 1H), 7.22-7.32 (m, 2H), 7.44 (d, J=5.2 Hz, 1H), 7.77-7.93 (m, 1H), 8.62 (d, J=5.2 Hz, 1H), 12.82 (s, 1H). MS (ESI) m/e 500.2 (M+H)$^+$.

Example 192

{3-[4-(1,10-difluoro-7-methyl-6,7-dihydro-4H-3,4,7-triazadibenzo[cd,f]azulen-5-yl)-3,6-dihydropyridin-1(2H)-yl]cyclobutyl}acetic acid A suspension of Example 48 (120 mg, 0.34 mmol) and methyl 2-(3-oxocyclobutyl)acetate (73 mg, 0.51 mmol) in a mixture of methanol (2 mL) and methylene chloride (2 mL) was added acetic acid (204 mg, 3.41 mmol) and the mixture was stirred at room temperature for 10 minutes. All solid material went into solution. MP-Cyanoborohydride (Biotage, 2.44 mmol/g, 1 g) was added. The suspension was stirred at room temperature overnight. The reaction mixture was filtered. The filtrate was concentrated and the residue was separated by flash chromatography on silica gel (Teledyne CombiFlash Rf 0-15% 3% NH$_4$OH/CH$_3$OH in 2/1 ethyl acetate/hexane) to provide an intermediate. The material was dissolved in a mixture of tetrahydrofuran (10 mL) and methanol (5 mL), and treated with lithium hydroxide monohydrate (175 mg, 4.3 mmol) in water (10 mL) at room temperature overnight. The reaction was concentrated and the residue was purified by reverse-phase HPLC on a Zorbax RX-C18 column using a gradient of 15% to 100% methanol/0.1% aqueous trifluoroacetic acid to provide the title compound as trifluoroacetic acid salt. The trifluoroacetic acid salt was dissolved in a mixture of methylene chloride and methanol and treated with HCl in diethyl ether. Concentration of the mixture provided the title compound as a HCl salt. $^1$H NMR (400 MHz, DMSO-d$_6$) δ 1.92-2.12 (m, 2H), 2.30-2.55 (m, 5H), 2.89 (s, 3H), 3.08-3.19 (m, 1H), 3.54-3.63 (m, 2H), 3.65-3.76 (m, 2H), 4.03 (d, J=50.4 Hz, 4H), 5.83 (d, J=4.2 Hz, 1H), 7.27-7.45 (m, 2H), 7.66 (dt, J=10.6, 2.8 Hz, 1H), 8.31 (d, J=4.9 Hz, 1H). MS (ESI$^+$) m/z 465 (M+1).

Example 193

3-[4-(1,10-difluoro-7-methyl-6,7-dihydro-4H-3,4,7-triazadibenzo[cd,f]azulen-5-yl)-3,6-dihydropyridin-1(2H)-yl]cyclobutanecarboxylic acid The title compound was prepared as the bis-trifluoroacetic acid salt essentially as described in Example 192, substituting methyl 3-oxocyclobutanecarboxylate for methyl 2-(3-oxocyclobutyl)acetate. $^1$H NMR (400 MHz, DMSO-d$_6$) δ 2.37-2.68 (m, 4H), 2.89 (s, 3H), 2.90-3.08 (m, 2H), 3.16 (ddt, J=14.3, 10.0, 4.1 Hz, 1H), 3.65 (s, 2H), 3.72 (d, J=31.2 Hz, 2H), 3.97 (s, 1H), 4.10 (s, 2H), 5.77-5.91 (m, 1H), 7.33 (td, J=9.0, 8.5, 3.0 Hz, 1H), 7.41 (dd, J=9.1, 5.5 Hz, 1H), 7.67 (dt, J=10.5, 2.8 Hz, 1H), 8.32 (d, J=4.9 Hz, 1H). MS (ESI$^+$) m/z 451 (M+1).

Biological Examples

CDK9 Enzyme Protocol

CDK9 enzyme activities were measured using LANCE ULight TR-FRET kinase assay reagents (PerkinElmer, Waltham, Mass.). Compounds were diluted in 100% DMSO then diluted with 1:10 in serine/threonine kinase assay buffer containing 20 mM HEPES, 10 mM MgCl$_2$, 100 mM Na$_3$VO$_4$, and 0.0075% Triton X-100. Equal volume of the compound dilutions was added to a final reaction mixture containing LANCE detection buffer (PerkinElmer CR97-100), 100 nM ULight MBP (PerkinElmer TRF0109M), 1000 µM ATP, and CDK9/Cyclin T1 (Carna Biosciences 04-110). The kinase reaction was carried out for 1 hour before addition of stopping buffer to a final of 20 mM EDTA and 0.5 nM of LANCE Ultra Europium anti-phospho-MBP antibody (PerkinElmer TRF0201M) in LANCE detection buffer. The reaction was incubated for 1 hour and the signal was read in Envision in TR-FRET mode (excitation at 320 nm and emission at 615/665 nm). The results are reported in Table 1.

Cell Viability Protocol

The cell viability assay was performed using H929 cells. Cells were seeded in 96-well plates at 10,000 cells/well and, after overnight incubation, treated with compounds in a dose response of 3-fold dilutions from 10 µM to 0.005 µM (10 mL/well, 0.1% final DMSO concentration). After 24 hours at 37° C., cell viability was measured using Cell TiterGlo reagent (Promega) with a luminescence reader. The results are reported in Table 1.

TABLE 1

| EXAMPLE | CDK9/Cyclin T1 IC$_{50}$ (µM) | Cell Viability H929 IC$_{50}$ (µM) |
|---|---|---|
| 1 | 0.021 | 0.04 |
| 2 | 0.23 | 0.94 |
| 3 | 0.047 | 0.59 |
| 4 | 0.025 | 0.15 |
| 5 | 0.062 | 0.73 |
| 6 | 0.34 | 2.1 |
| 7 | 0.8 | 3.3 |
| 8 | 1.4 | ND |
| 9 | 0.048 | 0.01 |
| 10 | 0.23 | 0.36 |
| 11 | 0.12 | 0.032 |
| 12 | 0.051 | 0.042 |
| 13 | 0.03 | 0.093 |
| 14 | 0.02 | 0.18 |
| 15 | 0.094 | 0.59 |
| 16 | 0.061 | 0.22 |
| 17 | 0.07 | 0.009 |
| 18 | 0.044 | 0.16 |
| 19 | 0.048 | 0.008 |
| 20 | 0.11 | 0.047 |
| 21 | 0.4 | 0.46 |
| 22 | 2.8 | ND |
| 23 | 0.15 | ND |
| 24 | 0.04 | 0.027 |
| 25 | 0.022 | 0.065 |
| 26 | 0.093 | 0.15 |
| 27 | 0.091 | 0.21 |
| 28 | 0.15 | 0.025 |
| 29 | 0.046 | 0.094 |
| 30 | 0.1 | 0.1 |
| 31 | 0.086 | 0.07 |
| 32 | 0.056 | 0.17 |
| 33 | 0.54 | 0.15 |
| 34 | 0.12 | 0.092 |
| 35 | 0.061 | 0.091 |
| 36 | 0.064 | 0.025 |
| 37 | 0.16 | 0.29 |
| 38 | 0.091 | 0.27 |
| 39 | 0.13 | 0.099 |
| 40 | 0.081 | 0.32 |
| 41 | 0.15 | 1.1 |
| 42 | 0.048 | 0.079 |
| 43 | 0.066 | 0.23 |
| 44 | 0.13 | 0.49 |

TABLE 1-continued

| EXAMPLE | CDK9/Cyclin T1 IC$_{50}$ (μM) | Cell Viability H929 IC$_{50}$ (μM) |
|---|---|---|
| 45 | 0.11 | 0.83 |
| 46 | 3.3 | >10 |
| 47 | 0.15 | 9.8 |
| 48 | 0.027 | 0.02 |
| 49 | 0.78 | 0.78 |
| 50 | 0.12 | 0.96 |
| 51 | 0.11 | 0.47 |
| 52 | 0.063 | 0.15 |
| 53 | 0.057 | 0.047 |
| 54 | 0.063 | 0.092 |
| 55 | 0.16 | 0.15 |
| 56 | 0.096 | 0.68 |
| 57 | 0.2 | 2.2 |
| 58 | 0.17 | 1.4 |
| 59 | 0.088 | 0.19 |
| 60 | 0.075 | 0.32 |
| 61 | 0.4 | 1.2 |
| 62 | 0.046 | 0.15 |
| 63 | 0.038 | 0.09 |
| 64 | 0.062 | 0.094 |
| 65 | 0.1 | 0.14 |
| 66 | 0.044 | 0.01 |
| 67 | 0.048 | 0.13 |
| 68 | 0.038 | 0.13 |
| 69 | 0.08 | 0.095 |
| 70 | 0.086 | 0.005 |
| 71 | 0.1 | 0.021 |
| 72 | 0.079 | 0.021 |
| 73 | 0.052 | 0.02 |
| 74 | 0.089 | 0.021 |
| 75 | 0.051 | 0.008 |
| 76 | 0.041 | 0.022 |
| 77 | 0.046 | 0.078 |
| 78 | 0.062 | 0.03 |
| 79 | 0.072 | 0.049 |
| 80 | 0.097 | 0.19 |
| 81 | 0.068 | 0.79 |
| 82 | 0.1 | 4.7 |
| 83 | 0.14 | 0.14 |
| 84 | 0.094 | 0.18 |
| 85 | 0.099 | 0.25 |
| 86 | 0.043 | 0.094 |
| 87 | 0.09 | 0.1 |
| 88 | 0.15 | 0.15 |
| 89 | 0.12 | 0.23 |
| 90 | 0.17 | 1.9 |
| 91 | 0.18 | 0.22 |
| 92 | 0.42 | 1.2 |
| 93 | 0.046 | 0.11 |
| 94 | 0.1 | 0.091 |
| 95 | 0.13 | 1.2 |
| 96 | 0.18 | 0.68 |
| 97 | 0.42 | 0.58 |
| 98 | 0.073 | 0.15 |
| 99 | 0.4 | 2.6 |
| 100 | 0.083 | 1.2 |
| 101 | 0.11 | 0.091 |
| 102 | 0.044 | 0.623 |
| 103 | 0.086 | 0.051 |
| 104 | 0.057 | 0.065 |
| 105 | 0.098 | 0.19 |
| 106 | 0.066 | 0.13 |
| 107 | 0.11 | 0.11 |
| 108 | 0.11 | 1.2 |
| 109 | 0.043 | 0.010 |
| 110 | 0.045 | 0.014 |
| 111 | 1.6 | 5.5 |
| 112 | 0.24 | ND |
| 113 | 0.65 | 2.7 |
| 114 | 0.87 | 3.4 |
| 115 | 0.95 | 2.6 |
| 116 | 0.89 | 1.7 |
| 117 | 0.96 | 2.4 |
| 118 | 1.2 | 2.6 |
| 119 | 1.3 | 2.4 |
| 120 | 0.48 | 2.1 |
| 121 | 0.16 | 1.1 |
| 122 | 0.42 | 1.4 |
| 123 | 0.54 | 3.1 |
| 124 | 0.048 | 0.088 |
| 125 | 0.054 | 0.30 |
| 126 | 0.058 | 0.039 |
| 127 | 0.026 | 0.10 |
| 128 | 0.078 | 0.15 |
| 129 | 0.067 | 0.13 |
| 130 | 0.064 | 0.070 |
| 131 | 0.036 | 0.079 |
| 132 | 0.040 | 0.014 |
| 133 | 0.058 | ND |
| 134 | 0.047 | 0.31 |
| 135 | 0.063 | 0.076 |
| 136 | 0.058 | 0.021 |
| 137 | 0.052 | 0.045 |
| 138 | 0.069 | 0.18 |
| 139 | 0.094 | 0.18 |
| 140 | 0.042 | 0.058 |
| 141 | 0.051 | 0.030 |
| 142 | 0.030 | 0.005 |
| 143 | 0.417 | 0.582 |
| 144 | 0.029 | 0.007 |
| 145 | 0.042 | 0.18 |
| 146 | 0.082 | 0.032 |
| 147 | 0.045 | 0.006 |
| 148 | 0.053 | 0.025 |
| 149 | 0.11 | 0.16 |
| 150 | 0.057 | 0.028 |
| 151 | 0.037 | 0.19 |
| 152 | 0.041 | 0.66 |
| 153 | 0.066 | 0.60 |
| 154 | 0.028 | 0.056 |
| 155 | 0.041 | 0.039 |
| 156 | 0.030 | 0.022 |
| 157 | 0.046 | 0.010 |
| 158 | 0.096 | 0.020 |
| 159 | 0.034 | 0.008 |
| 160 | 0.085 | 0.094 |
| 161 | 0.040 | 0.065 |
| 162 | 0.115 | 0.021 |
| 163 | 0.056 | 0.007 |
| 164 | 0.13 | 0.27 |
| 165 | 0.39 | 0.97 |
| 166 | 0.075 | 0.008 |
| 167 | 0.067 | 0.010 |
| 168 | 0.060 | 0.008 |
| 169 | 0.090 | ND |
| 170 | 0.11 | ND |
| 171 | 0.15 | ND |
| 172 | 0.12 | ND |
| 173 | 0.045 | 0.068 |
| 174 | 0.057 | 0.12 |
| 175 | 0.12 | 0.49 |
| 176 | 0.084 | ND |
| 177 | 0.058 | 0.12 |
| 178 | 0.025 | 0.040 |
| 179 | 0.024 | 0.064 |
| 180 | 0.073 | 0.011 |
| 181 | 0.063 | 0.012 |
| 182 | 0.071 | 0.010 |
| 183 | 0.080 | 0.014 |
| 184 | 0.13 | 0.19 |
| 185 | 0.13 | 0.16 |
| 186 | 0.064 | 0.013 |
| 187 | 0.11 | 0.015 |
| 188 | 0.15 | 0.29 |
| 189 | 0.11 | 0.006 |
| 190 | 0.16 | 0.19 |
| 191 | 0.088 | 0.44 |
| 192 | 0.079 | 0.027 |
| 193 | 0.076 | 0.011 |

ND = not determined

What is claimed is:

1. A compound of Formula (Ia), or a pharmaceutically acceptable salt thereof,

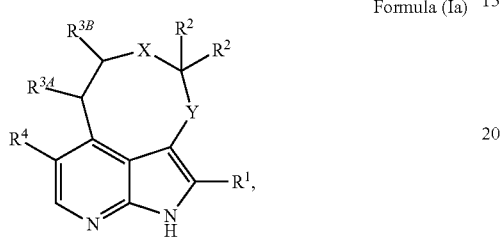

Formula (Ia)

wherein
X is O or $NR^{2A}$;
Y is $C(R^2)_2$ or is absent;
$R^1$ is selected from the group consisting of cycloalkyl, cycloalkenyl, aryl, heteroaryl, heterocycloalkyl, and heterocycloalkenyl; wherein the $R^1$ cycloalkyl, cycloalkenyl, aryl, heteroaryl, heterocycloalkyl, and heterocycloalkenyl are optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHSO_2R^5$, $NR^5SO_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $SO_2NHC(O)OR^5$, $C(O)H$, $C(O)OH$, (O), OH, CN, $NO_2$, F, Cl, Br and I;
$R^2$, at each occurrence, is independently selected from the group consisting of hydrogen, $C_1$-$C_4$ alkyl, cycloalkyl, cycloalkenyl, heteroaryl, heterocycloalkyl, heterocycloalkenyl, C(O)OH, and $C(O)OR^{2B}$; wherein each $R^2$ cycloalkyl, cycloalkenyl, heteroaryl, heterocycloalkyl, and heterocycloalkenyl is optionally substituted with one or more substituents independently selected from the group consisting $C_1$-$C_8$ alkyl, $C_2$-$C_6$ alkenyl, and $C_2$-$C_6$ alkynyl;
$R^{2A}$ is hydrogen or $C_1$-$C_4$ alkyl; wherein the $R^{2A}$ $C_1$-$C_4$ alkyl is optionally substituted with one or more substituents independently selected from the group consisting of cycloalkyl, cycloalkenyl, heterocycloalkyl, heterocycloalkenyl, $C_1$-$C_6$ alkoxy, OH, CN, F, Cl, Br and I;
$R^{2B}$ is $C_1$-$C_4$ alkyl;
$R^{3A}$ and $R^{3B}$, taken together, form $R^3$;
$R^3$ is selected from the group consisting of phenyl and pyridinyl; wherein the $R^3$ phenyl and pyridinyl are optionally substituted with one or more substituents independently selected from the group consisting of $C_1$-$C_6$ alkyl, $C_2$-$C_6$ alkenyl, $C_2$-$C_6$ alkynyl, $NH_2$, C(O)H, C(O)OH, OH, CN, $NO_2$, F, Cl, Br and I;
$R^4$ is selected from the group consisting of hydrogen, $C_1$-$C_4$ alkyl, $C_1$-$C_4$ alkoxy, CN, F, Cl, Br, and I;
$R^5$, at each occurrence, is independently selected from the group consisting of $C_1$-$C_8$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^5 C_1$-$C_8$ alkyl, $C_2$-$C_6$ alkenyl, and $C_2$-$C_6$ alkynyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHSO_2R^6$, $NR^6SO_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, OH, CN, $NO_2$, F, Cl, Br and I; wherein each $R^5$ aryl, cycloalkyl, cycloalkenyl, heteroaryl, heterocycloalkyl, and heterocycloalkenyl is optionally substituted with one or more substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHSO_2R^7$, $NR^7SO_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, (O), OH, CN, $NO_2$, F, Cl, Br and I;
$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of aryl, heteroaryl, cycloalkyl, cycloalkenyl, heterocycyloalkyl, heterocycloalkenyl, $NH_2$, C(O)H, C(O)OH, OH, CN, $NO_2$, F, Cl, Br and I; wherein each $R^6$ aryl, cycloalkyl, cycloalkenyl, heteroaryl, heterocycloalkyl, and heterocycloalkenyl is optionally substituted with one or more substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHSO_2R^8$, $NR^8SO_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, C(O)H, C(O)OH, (O), OH, CN, $NO_2$, F, Cl, Br and I;
$R^7$, at each occurrence, is independently selected from the group consisting of $C_1$-$C_6$ alkyl, $C_2$-$C_6$ alkenyl, and $C_2$-$C_6$ alkynyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $OR^9$, $SR^9$, $S(O)R^9$, $SO_2R^9$, $C(O)R^9$, $CO(O)R^9$, $OC(O)R^9$, $OC(O)OR^9$, $NH_2$, C(O)H, C(O)OH, OH, CN, $NO_2$, F, Cl, Br and I;
$R^8$, at each occurrence, is independently selected from the group consisting of $C_1$-$C_6$ alkyl, $C_2$-$C_6$ alkenyl, and $C_2$-$C_6$ alkynyl; wherein each $R^8$ $C_1$-$C_6$ alkyl, C₂-C₆ alkenyl, and C₂-C₆ alkynyl is optionally substituted with one or more substituents independently selected from the group consisting of NH₂, C(O)H, C(O)OH, OH, CN, NO₂, F, Cl, Br and I; and R⁹, at each occurrence, is independently selected from the group consisting of C₁-C₆ alkyl, C₂-C₆ alkenyl, and C₂-C₆ alkynyl.

2. The compound of claim 1, or a pharmaceutically acceptable salt thereof, wherein Y is absent.

3. The compound of claim 2, or a pharmaceutically acceptable salt thereof, wherein X is NR²ᴬ.

4. The compound of claim 3, or a pharmaceutically acceptable salt thereof, wherein R⁴ is selected from the group consisting of hydrogen, F, Cl, Br, and I.

5. The compound of claim 3, or a pharmaceutically acceptable salt thereof, wherein R³ is phenyl; wherein the R³ phenyl is optionally substituted with one or more substituents independently selected from the group consisting of C₁-C₆ alkyl, C₂-C₆ alkenyl, C₁-C₆ alkynyl, NH₂, C(O)H, C(O)OH, OH, CN, NO₂, F, Cl, Br and I.

6. The compound of claim 3, or a pharmaceutically acceptable salt thereof, wherein R³ is phenyl; wherein the R³ phenyl is substituted with one F.

7. The compound of claim 3, or a pharmaceutically acceptable salt thereof, wherein R¹ is selected from the group consisting of cycloalkyl, cycloalkenyl, aryl, heteroaryl, heterocycloalkyl, and heterocycloalkenyl; wherein the R¹ cycloalkyl, cycloalkenyl, aryl, heteroaryl, heterocycloalkyl, and heterocycloalkenyl are optionally substituted with one or more substituents independently selected from the group consisting of R⁵, SO₂R⁵, C(O)R⁵, CO(O)R⁵, NH₂, NHR⁵, C(O)NHR⁵, C(O)N(R⁵)₂, SO₂NHC(O)OR⁵, C(O)OH, F, Cl, Br and I.

8. The compound of claim 1, selected from the group consisting of:

10-fluoro-7-methyl-5-(1,2,3,6-tetrahydropyridin-4-yl)-6,7-dihydro-4H-3,4,7-triazadibenzo[cd,f]azulene;

tert-butyl 4-(10-fluoro-7-methyl-6,7-dihydro-4H-3,4,7-triazadibenzo[cd,f]azulen-5-yl)-3,6-dihydropyridine-1(2H)-carboxylate;

ethyl{[4-(10-fluoro-7-methyl-6,7-dihydro-4H-3,4,7-triazadibenzo[cd,f]azulen-5-yl)-3,6-dihydropyridin-1(2H)-yl]sulfonyl}carbamate;

10-fluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-6,7-dihydro-4H-3,4,7-triazadibenzo[cd,f]azulene;

10-fluoro-5-[1-(methylsulfonyl)-1,2,3,6-tetrahydropyridin-4-yl]-7-propyl-6,7-dihydro-4H-3,4,7-triazadibenzo[cd,f]azulene;

10-fluoro-5-[1-(methylsulfonyl)-1,2,3,6-tetrahydropyridin-4-yl]-7-(tetrahydro-2H-pyran-4-ylmethyl)-6,7-dihydro-4H-3,4,7-triazadibenzo[cd,f]azulene;

tert-butyl 4-(6-ethyl-10-fluoro-7-methyl-6,7-dihydro-4H-3,4,7-triazadibenzo[cd,f]azulen-5-yl)-3,6-dihydropyridine-1(2H)-carboxylate;

6-ethyl-10-fluoro-7-methyl-5-(1,2,3,6-tetrahydropyridin-4-yl)-6,7-dihydro-4H-3,4,7-triazadibenzo[cd,f]azulene dihydrochloride;

10-fluoro-7-methyl-6-(1-methyl-1H-pyrazol-4-yl)-5-(1,2,3,6-tetrahydropyridin-4-yl)-6,7-dihydro-4H-3,4,7-triazadibenzo[cd,f]azulene;

6-ethyl-10-fluoro-7-methyl-5-[1-(methylsulfonyl)-1,2,3,6-tetrahydropyridin-4-yl]-6,7-dihydro-4H-3,4,7-triazadibenzo[cd,f]azulene;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;

4-(10-fluoro-7-methyl-6,7-dihydro-4H-3,4,7-triazadibenzo[cd,f]azulen-5-yl)-N-methyl-3,6-dihydropyridine-1(2H)-carboxamide;

10-fluoro-5-(1,2,3,6-tetrahydropyridin-4-yl)-4,6-dihydro-7-oxa-3,4-diazadibenzo[cd,f]azulene;

10-fluoro-5-[1-(methylsulfonyl)-1,2,3,6-tetrahydropyridin-4-yl]-4,6-dihydro-7-oxa-3,4-diazadibenzo[cd,f]azulene;

[4-(10-fluoro-7-methyl-6,7-dihydro-4H-3,4,7-triazadibenzo[cd,f]azulen-5-yl)-3,6-dihydropyridin-1(2H)-yl]acetic acid dihydrochloride;

2-[4-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(10-fluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

10-fluoro-6,7-dimethyl-5-[1-(methylsulfonyl)-1,2,3,6-tetrahydropyridin-4-yl]-6,7-dihydro-4H-3,4,7-triazadibenzo[cd,f]azulene;

10-fluoro-7-methyl-5-(piperidin-4-yl)-6,7-dihydro-4H-3,4,7-triazadibenzo[cd,f]azulene;

tert-butyl[4-(10-fluoro-7-methyl-6,7-dihydro-4H-3,4,7-triazadibenzo[cd,f]azulen-5-yl)piperidin-1-yl]acetate;

[4-(10-fluoro-7-methyl-6,7-dihydro-4H-3,4,7-triazadibenzo[cd,f]azulen-5-yl)piperidin-1-yl]acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-N-methyl-2-oxo ethanesulfonamide;

2-[4-(10-fluoro-7-methyl-6,7-dihydro-4H-3,4,7-triazadibenzo[cd,f]azulen-5-yl)piperidin-1-yl]-1-[(2S)-2-(hydroxymethyl)pyrrolidin-1-yl]ethanone;

2-[4-(10-fluoro-7-methyl-6,7-dihydro-4H-3,4,7-triazadibenzo[cd,f]azulen-5-yl)piperidin-1-yl]-N-(2-hydroxyethyl)-N-methylacetamide;

ethyl 10-fluoro-7-methyl-5-(1,2,3,6-tetrahydropyridin-4-yl)-6,7-dihydro-4H-3,4,7-triazadibenzo[cd,f]azulene-6-carboxylate;

N-[4-(10-fluoro-7-methyl-6,7-dihydro-4H-3,4,7-triazadibenzo[cd,f]azulen-5-yl)cyclohex-3-en-1-yl]-D-valine;

N-[4-(10-fluoro-7-methyl-6,7-dihydro-4H-3,4,7-triazadibenzo[cd,f]azulen-5-yl)cyclohex-3-en-1-yl]-L-alanine;

N-[4-(10-fluoro-7-methyl-6,7-dihydro-4H-3,4,7-triazadibenzo[cd,f]azulen-5-yl)cyclohex-3-en-1-yl]glycine;

(2S)-{[4-(10-fluoro-7-methyl-6,7-dihydro-4H-3,4,7-triazadibenzo[cd,f]azulen-5-yl)cyclohex-3-en-1-yl]amino}(phenyl)acetic acid;

10-fluoro-7-methyl-5-(1,2,3,6-tetrahydropyridin-4-yl)-6,7-dihydro-4H-3,4,7-triazadibenzo[cd,f]azulene-6-carboxylic acid;

N-[4-(10-fluoro-7-methyl-6,7-dihydro-4H-3,4,7-triazadibenzo[cd,f]azulen-5-yl)cyclohex-3-en-1-yl]-L-valine;

N-[4-(10-fluoro-7-methyl-6,7-dihydro-4H-3,4,7-triazadibenzo[cd,f]azulen-5-yl)cyclohex-3-en-1-yl]-L-phenylalanine;

N-[4-(10-fluoro-7-methyl-6,7-dihydro-4H-3,4,7-triazadibenzo[cd,f]azulen-5-yl)cyclohex-3-en-1-yl]-3-methyl-L-valine;

1-[4-(10-fluoro-7-methyl-6,7-dihydro-4H-3,4,7-triazadibenzo[cd,f]azulen-5-yl)cyclohex-3-en-1-yl]-L-proline;

N-[4-(10-fluoro-7-methyl-6,7-dihydro-4H-3,4,7-triazadibenzo[cd,f]azulen-5-yl)cyclohex-3-en-1-yl]-L-serine;

N-[4-(10-fluoro-7-methyl-6,7-dihydro-4H-3,4,7-triazadibenzo[cd,f]azulen-5-yl)cyclohex-3-en-1-yl]-L-norvaline;

N-[4-(10-fluoro-7-methyl-6,7-dihydro-4H-3,4,7-triazadibenzo[cd,f]azulen-5-yl)cyclohex-3-en-1-yl]-L-tyrosine;

4-(10-fluoro-7-methyl-6,7-dihydro-4H-3,4,7-triazadibenzo[cd,f]azulen-5-yl)cyclohex-3-ene-1-carboxylic acid;

2-[4-(10-fluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

10-fluoro-7-methyl-5-[4-(methylsulfonyl)phenyl]-6,7-dihydro-4H-3,4,7-triazadibenzo[cd,f]azulene;

10-fluoro-7-methyl-5-(pyridin-4-yl)-6,7-dihydro-4H-3,4,7-triazadibenzo[cd,f]azulene;

10-fluoro-7-methyl-5-[6-(methylsulfonyl)pyridin-3-yl]-6,7-dihydro-4H-3,4,7-triazadibenzo[cd,f]azulene;

5-(10-fluoro-7-methyl-6,7-dihydro-4H-3,4,7-triazadibenzo[cd,f]azulen-5-yl)pyrimidin-2-amine;

4-(10-fluoro-7-methyl-6,7-dihydro-4H-3,4,7-triazadibenzo[cd,f]azulen-5-yl)benzoic acid;

1,10-difluoro-7-methyl-5-(1,2,3,6-tetrahydropyridin-4-yl)-6,7-dihydro-4H-3,4,7-triazadibenzo[cd,f]azulene;

tert-butyl 4-(1,10-difluoro-7-methyl-6,7-dihydro-4H-3,4,7-triazadibenzo[cd,f]azulen-5-yl)-3,6-dihydropyridine-1(2H)-carboxylate;

4-(10-fluoro-7-methyl-6,7-dihydro-4H-3,4,7-triazadibenzo[cd,f]azulen-5-yl)-N,N-dimethylcyclohex-3-ene-1-carboxamide;

[4-(10-fluoro-7-methyl-6,7-dihydro-4H-3,4,7-triazadibenzo[cd,f]azulen-5-yl)cyclohex-3-en-1-yl](3-hydroxyazetidin-1-yl)methanone;

4-(10-fluoro-7-methyl-6,7-dihydro-4H-3,4,7-triazadibenzo[cd,f]azulen-5-yl)-N-methylcyclohex-3-ene-1-carboxamide;

2-[4-(10-fluoro-7-methyl-6,7-dihydro-4H-3,4,7-triazadibenzo[cd,f]azulen-5-yl)-3,6-dihydropyridin-1(2H)-yl]-N,N-bis(2-hydroxyethyl)acetamide;

1-(3,3-difluoroazetidin-1-yl)-2-[4-(10-fluoro-7-methyl-6,7-dihydro-4H-3,4,7-triazadibenzo[cd,f]azulen-5-yl)-3,6-dihydropyridin-1(2H)-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N,N-dimethylacetamide;

10-fluoro-7-methyl-5-[(1R,5S)-8-(methylsulfonyl)-8-azabicyclo[3.2.1]oct-2-en-3-yl]-6,7-dihydro-4H-3,4,7-triazadibenzo[cd,f]azulene;

(1R,5S)-3-(10-fluoro-7-methyl-6,7-dihydro-4H-3,4,7-triazadibenzo[cd,f]azulen-5-yl)-N-methyl-8-azabicyclo[3.2.1]oct-2-ene-8-carboxamide;

[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]acetic acid;

10-fluoro-5-(1,2,3,3a,4,6a-hexahydrocyclopenta[c]pyrrol-5-yl)-7-methyl-6,7-dihydro-4H-3,4,7-triazadibenzo[cd,f]azulene;

10-fluoro-7-methyl-5-(pyridin-3-yl)-6,7-dihydro-4H-3,4,7-triazadibenzo[cd,f]azulene;

ethyl 4-(10-fluoro-7-methyl-6,7-dihydro-4H-3,4,7-triazadibenzo[cd,f]azulen-5-yl)cyclohex-3-ene-1-carboxylate;

5-[(1R,5S)-8-azabicyclo[3.2.1]oct-2-en-3-yl]-10-fluoro-7-methyl-6,7-dihydro-4H-3,4,7-triazadibenzo[cd,f]azulene;

N-(2,3-dihydroxypropyl)-2-[4-(10-fluoro-7-methyl-6,7-dihydro-4H-3,4,7-triazadibenzo[cd,f]azulen-5-yl)-3,6-dihydropyridin-1(2H)-yl]-N-methylacetamide;

2-[4-(10-fluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

tert-butyl[4-(1,10-difluoro-7-methyl-6,7-dihydro-4H-3,4,7-triazadibenzo[cd,f]azulen-5-yl)-3,6-dihydropyridin-1(2H)-yl]acetate;

2-[4-(1,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;

[4-(1,10-difluoro-7-methyl-6,7-dihydro-4H-3,4,7-triazadibenzo[cd,f]azulen-5-yl)-3,6-dihydropyridin-1(2H)-yl]acetic acid;

1,10-difluoro-7-methyl-5-[1-(methylsulfonyl)-1,2,3,6-tetrahydropyridin-4-yl]-6,7-dihydro-4H-3,4,7-triazadibenzo[cd,f]azulene;

10-fluoro-5-{2-[(2-methoxyethyl)sulfonyl]-1,2,3,3a,4,6a-hexahydrocyclopenta[c]pyrrol-5-yl}-7-methyl-6,7-dihydro-4H-3,4,7-triazadibenzo[cd,f]azulene;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;

2-[4-(1,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(3S)-3-hydroxypyrrolidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[3-(hydroxymethyl)azetidin-1-yl]ethanone;

2-[4-(1,10-difluoro-7-methyl-6,7-dihydro-4H-3,4,7-triazadibenzo[cd,f]azulen-5-yl)-3,6-dihydropyridin-1(2H)-yl]-1-[(2R)-2-(hydroxymethyl)pyrrolidin-1-yl]ethanone;

5-(10-fluoro-7-methyl-6,7-dihydro-4H-3,4,7-triazadibenzo[cd,f]azulen-5-yl)-N-methyl-3,3a,4,6a-tetrahydrocyclopenta[c]pyrrole-2(1H)-carboxamide;

2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N,N-dimethylacetamide;

10-fluoro-7-methyl-5-[2-(methylsulfonyl)-1,2,3,3a,4,6a-hexahydrocyclopenta[c]pyrrol-5-yl]-6,7-dihydro-4H-3,4,7-triazadibenzo[cd,f]azulene;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-[(2S)-2-(hydroxymethyl)pyrrolidin-1-yl]ethanone;

2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-1-(3-hydroxyazetidin-1-yl)ethanone;
[4-(10-fluoro-7-methyl-6,7-dihydro-4H-3,4,7-triazadibenzo[cd,f]azulen-5-yl)phenyl]acetic acid;
[3-(10-fluoro-7-methyl-6,7-dihydro-4H-3,4,7-triazadibenzo[cd,f]azulen-5-yl)phenyl]acetic acid;
N-(2,3-dihydroxypropyl)-2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-methylacetamide;
2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-1-(3-hydroxyazetidin-1-yl)ethanone;
N-(2,3-dihydroxypropyl)-2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-methylacetamide;
2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(2-hydroxyethyl)-N-methylacetamide;
10-fluoro-7-methyl-5-(2,3,6,7-tetrahydro-1H-azepin-4-yl)-6,7-dihydro-4H-3,4,7-triazadibenzo[cd,f]azulene;
2-[4-(10-fluoro-7-methyl-6,7-dihydro-4H-3,4,7-triazadibenzo[cd,f]azulen-5-yl)-2,3,6,7-tetrahydro-1H-azepin-1-yl]-N,N-dimethylacetamide;
10-fluoro-7-methyl-5-[1-(methylsulfonyl)-2,3,6,7-tetrahydro-1H-azepin-4-yl]-6,7-dihydro-4H-3,4,7-triazadibenzo[cd,f]azulene;
[4-(10-fluoro-7-methyl-6,7-dihydro-4H-3,4,7-triazadibenzo[cd,f]azulen-5-yl)-2,3,6,7-tetrahydro-1H-azepin-1-yl]acetic acid;
2-[4-(10-fluoro-7-methyl-6,7-dihydro-4H-3,4,7-triazadibenzo[cd,f]azulen-5-yl)-2,3,6,7-tetrahydro-1H-azepin-1-yl]-1-(3-hydroxyazetidin-1-yl)ethanone;
5-(3,3-dimethyl-1,2,3,6-tetrahydropyridin-4-yl)-10-fluoro-7-methyl-6,7-dihydro-4H-3,4,7-triazadibenzo[cd,f]azulene;
10-fluoro-7-methyl-5-(1,2,5,6-tetrahydropyridin-3-yl)-6,7-dihydro-4H-3,4,7-triazadibenzo[cd,f]azulene;
2-[5-(10-fluoro-7-methyl-6,7-dihydro-4H-3,4,7-triazadibenzo[cd,f]azulen-5-yl)-3,3a,4,6a-tetrahydrocyclopenta[c]pyrrol-2(1H)-yl]-N-(3-hydroxycyclobutyl)-N-methylacetamide;
10-fluoro-7-methyl-5-[1-(methylsulfonyl)-1,2,5,6-tetrahydropyridin-3-yl]-6,7-dihydro-4H-3,4,7-triazadibenzo[cd,f]azulene;
5-(10-fluoro-7-methyl-6,7-dihydro-4H-3,4,7-triazadibenzo[cd,f]azulen-5-yl)-N-methyl-3,6-dihydropyridine-1(2H)-carboxamide;
2-[5-(10-fluoro-7-methyl-6,7-dihydro-4H-3,4,7-triazadibenzo[cd,f]azulen-5-yl)-3,6-dihydropyridin-1(2H)-yl]-N,N-dimethylacetamide;
2-[(1R,5S)-3-(10-fluoro-7-methyl-6,7-dihydro-4H-3,4,7-triazadibenzo[cd,f]azulen-5-yl)-8-azabicyclo[3.2.1]oct-2-en-8-yl]-N-(3-hydroxycyclobutyl)-N-methylacetamide;
10-fluoro-7-methyl-5-[9-(methylsulfonyl)-9-azabicyclo[3.3.1]non-2-en-3-yl]-6,7-dihydro-4H-3,4,7-triazadibenzo[cd,f]azulene;
3-(10-fluoro-7-methyl-6,7-dihydro-4H-3,4,7-triazadibenzo[cd,f]azulen-5-yl)-N-methyl-9-azabicyclo[3.3.1]non-2-ene-9-carboxamide;
2-[3-(10-fluoro-7-methyl-6,7-dihydro-4H-3,4,7-triazadibenzo[cd,f]azulen-5-yl)-9-azabicyclo[3.3.1]non-2-en-9-yl]-N,N-dimethylacetamide;
3-[3-(10-fluoro-7-methyl-6,7-dihydro-4H-3,4,7-triazadibenzo[cd,f]azulen-5-yl)-9-azabicyclo[3.3.1]non-2-en-9-yl]-3-oxopropanenitrile;
2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(2-hydroxyethyl)-N-methylacetamide;
2-[3-(10-fluoro-7-methyl-6,7-dihydro-4H-3,4,7-triazadibenzo[cd,f]azulen-5-yl)-9-azabicyclo[3.3.1]non-2-en-9-yl]-1-[(2S)-2-(hydroxymethyl)pyrrolidin-1-yl]ethanone;
2-[3-(10-fluoro-7-methyl-6,7-dihydro-4H-3,4,7-triazadibenzo[cd,f]azulen-5-yl)-9-azabicyclo[3.3.1]non-2-en-9-yl]-1-(3-hydroxyazetidin-1-yl)ethanone;
2-[3-(10-fluoro-7-methyl-6,7-dihydro-4H-3,4,7-triazadibenzo[cd,f]azulen-5-yl)-9-azabicyclo[3.3.1]non-2-en-9-yl]-N-(3-hydroxycyclobutyl)-N-methylacetamide;
N-(2,3-dihydroxypropyl)-2-[3-(10-fluoro-7-methyl-6,7-dihydro-4H-3,4,7-triazadibenzo[cd,f]azulen-5-yl)-9-azabicyclo[3.3.1]non-2-en-9-yl]-N-methylacetamide;
[3-(10-fluoro-7-methyl-6,7-dihydro-4H-3,4,7-triazadibenzo[cd,f]azulen-5-yl)-9-azabicyclo[3.3.1]non-2-en-9-yl]acetic acid;
2-[4-(1,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;
2-[4-(1,10-difluoro-7-methyl-6,7-dihydro-4H-3,4,7-triazadibenzo[cd,f]azulen-5-yl)-3,6-dihydropyridin-1(2H)-yl]-N-(2,3-dihydroxypropyl)-N-methylacetamide;
[4-(10-fluoro-7-methyl-6,7-dihydro-4H-3,4,7-triazadibenzo[cd,f]azulen-5-yl)-3,3-dimethyl-3,6-dihydropyridin-1(2H)-yl]acetic acid;
[5-(10-fluoro-7-methyl-6,7-dihydro-4H-3,4,7-triazadibenzo[cd,f]azulen-5-yl)-3,6-dihydropyridin-1(2H)-yl]acetic acid;
5-[3,3-dimethyl-1-(methylsulfonyl)-1,2,3,6-tetrahydropyridin-4-yl]-10-fluoro-7-methyl-6,7-dihydro-4H-3,4,7-triazadibenzo[cd,f]azulene;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N,N-dimethylacetamide;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-[(2S)-2-(hydroxymethyl)pyrrolidin-1-yl]ethanone;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(2-hydroxyethyl)-N-methylacetamide;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-1-(3-hydroxyazetidin-1-yl)ethanone;
2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-(3-hydroxycyclobutyl)-N-methylacetamide;
N-(2,3-dihydroxypropyl)-2-[4-(10-fluoro-7-methyl-6,7-dihydro-4H-3,4,7-triazadibenzo[cd,f]azulen-5-yl)-3,3-dimethyl-3,6-dihydropyridin-1(2H)-yl]-N-methylacetamide;

2-[5-(10-fluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;
2-[5-(10-fluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;
2-[5-(10-fluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;
N-(2,3-dihydroxypropyl)-2-[5-(10-fluoro-7-methyl-6,7-dihydro-4H-3,4,7-triazadibenzo[cd,f]azulen-5-yl)-3,6-dihydropyridin-1(2H)-yl]-N-methylacetamide;
{cis-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;
(8aR)-7-(9,10-difluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;
[(2R)-4-(9,10-difluoro-7-methyl-6,7-dihydro-4H-3,4,7-triazadibenzo[cd,f]azulen-5-yl)-1,2,5,6-tetrahydropyridin-2-yl]methanol;
8-fluoro-5-methyl-2-(1,2,3,6-tetrahydropyridin-4-yl)-1,3,4,5-tetrahydro-1,5,12-triazabenzo[4,5]cycloocta[1,2,3-cd]indene;
8-fluoro-5-methyl-2-[1-(methylsulfonyl)-1,2,3,6-tetrahydropyridin-4-yl]-1,3,4,5-tetrahydro-1,5,12-triazabenzo[4,5]cycloocta[1,2,3-cd]indene;
2-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]-N,N-dimethylacetamide;
{trans-4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;
9,10-difluoro-7-methyl-5-[1-(methylsulfonyl)-1,2,3,6-tetrahydropyridin-4-yl]-6,7-dihydro-4H-3,4,7-triazadibenzo[cd,f]azulene;
2-[4-(9,10-difluoro-7-methyl-6,7-dihydro-4H-3,4,7-triazadibenzo[cd,f]azulen-5-yl)-3,6-dihydropyridin-1(2H)-yl]-N,N-dimethylacetamide;
methyl{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;
methyl{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetate;
7-methyl-5-(1,2,3,6-tetrahydropyridin-4-yl)-6,7-dihydro-4H-3,4,7,8-tetraazadibenzo[cd,f]azulene;
{cis-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;
2-[4-(9,10-difluoro-7-methyl-6,7-dihydro-4H-3,4,7-triazadibenzo[cd,f]azulen-5-yl)-3,6-dihydropyridin-1(2H)-yl]-1-(3-hydroxyazetidin-1-yl)ethanone;
7-methyl-5-[1-(methylsulfonyl)-1,2,3,6-tetrahydropyridin-4-yl]-6,7-dihydro-4H-3,4,7,8-tetraazadibenzo[cd,f]azulene;
N-methyl-4-(7-methyl-6,7-dihydro-4H-3,4,7,8-tetraazadibenzo[cd,f]azulen-5-yl)-3,6-dihydropyridine-1(2H)-carboxamide;
{3-[4-(10-fluoro-7-methyl-6,7-dihydro-4H-3,4,7-triazadibenzo[cd,f]azulen-5-yl)-3,6-dihydropyridin-1(2H)-yl]cyclobutyl}acetic acid;
trans-4-[4-(10-fluoro-7-methyl-6,7-dihydro-4H-3,4,7-triazadibenzo[cd,f]azulen-5-yl)-3,6-dihydropyridin-1(2H)-yl]cyclohexanecarboxylic acid;
(6S)-6-ethyl-10-fluoro-7-methyl-5-(1,2,3,6-tetrahydropyridin-4-yl)-6,7-dihydro-4H-3,4,7-triazadibenzo[cd,f]azulene;
(6R)-6-ethyl-10-fluoro-7-methyl-5-(1,2,3,6-tetrahydropyridin-4-yl)-6,7-dihydro-4H-3,4,7-triazadibenzo[cd,f]azulene;
9,10-difluoro-7-methyl-5-(1,2,3,6-tetrahydropyridin-4-yl)-6,7-dihydro-4H-3,4,7-triazadibenzo[cd,f]azulene;
[4-(9,10-difluoro-7-methyl-6,7-dihydro-4H-3,4,7-triazadibenzo[cd,f]azulen-5-yl)-3,6-dihydropyridin-1(2H)-yl]acetic acid;
{trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;
2-[4-(9,10-difluoro-7-methyl-6,7-dihydro-4H-3,4,7-triazadibenzo[cd,f]azulen-5-yl)-3,6-dihydropyridin-1(2H)-yl]-1-[(2S)-2-(hydroxymethyl)pyrrolidin-1-yl]ethanone;
2-[4-(9,10-difluoro-7-methyl-6,7-dihydro-4H-3,4,7-triazadibenzo[cd,f]azulen-5-yl)-3,6-dihydropyridin-1(2H)-yl]-N-(3-hydroxycyclobutyl)-N-methylacetamide;
N,N-dimethyl-2-[4-(7-methyl-6,7-dihydro-4H-3,4,7,8-tetraazadibenzo[cd,f]azulen-5-yl)-3,6-dihydropyridin-1(2H)-yl]acetamide;
trans-4-[4-(9,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;
(8aR)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;
(8aS)-7-(10-fluoro-7-methyl-6,7-dihydro-4H-3,4,7-triazadibenzo[cd,f]azulen-5-yl)-1,5,6,8a-tetrahydro[1,3]oxazolo[3,4-a]pyridin-3-one;
(8aR)-7-(10-fluoro-7-methyl-6,7-dihydro-4H-3,4,7-triazadibenzo[cd,f]azulen-5-yl)-1,5,8,8a-tetrahydro[1,3]oxazolo[3,4-a]pyridin-3-one;
[(2R)-4-(10-fluoro-7-methyl-6,7-dihydro-4H-3,4,7-triazadibenzo[cd,f]azulen-5-yl)-1,2,5,6-tetrahydropyridin-2-yl]methanol;
[(2S)-4-(10-fluoro-7-methyl-6,7-dihydro-4H-3,4,7-triazadibenzo[cd,f]azulen-5-yl)-1,2,5,6-tetrahydropyridin-2-yl]methanol;
[(2R)-4-(10-fluoro-7-methyl-6,7-dihydro-4H-3,4,7-triazadibenzo[cd,f]azulen-5-yl)-1,2,3,6-tetrahydropyridin-2-yl]methanol;
2-[4-(9,10-difluoro-7-methyl-6,7-dihydro-4H-3,4,7-triazadibenzo[cd,f]azulen-5-yl)-3,6-dihydropyridin-1(2H)-yl]-N-(2-hydroxyethyl)-N-methylacetamide;
7-methyl-5-(1,2,3,6-tetrahydropyridin-4-yl)-6,7-dihydro-4H-3,4,7-triazadibenzo[cd,f]azulene;
1-fluoro-7-methyl-5-(1,2,3,6-tetrahydropyridin-4-yl)-6,7-dihydro-4H-3,4,7-triazadibenzo[cd,f]azulene;
7-methyl-5-[1-(methylsulfonyl)-1,2,3,6-tetrahydropyridin-4-yl]-6,7-dihydro-4H-3,4,7-triazadibenzo[cd,f]azulene;
1-fluoro-7-methyl-5-[1-(methylsulfonyl)-1,2,3,6-tetrahydropyridin-4-yl]-6,7-dihydro-4H-3,4,7-triazadibenzo[cd,f]azulene;
N,N-dimethyl-2-[4-(7-methyl-6,7-dihydro-4H-3,4,7-triazadibenzo[cd,f]azulen-5-yl)-3,6-dihydropyridin-1(2H)-yl]acetamide;
2-[4-(1-fluoro-7-methyl-6,7-dihydro-4H-3,4,7-triazadibenzo[cd,f]azulen-5-yl)-3,6-dihydropyridin-1(2H)-yl]-N,N-dimethylacetamide;

3-[4-(10-fluoro-4,6-dihydro-7-oxa-3,4-diazadibenzo[cd,f]azulen-5-yl)-3,6-dihydropyridin-1(2H)-yl]propane-1,2-diol;

{4-[4-(10-fluoro-4,6-dihydro-7-oxa-3,4-diazadibenzo[cd,f]azulen-5-yl)-3,6-dihydropyridin-1(2H)-yl]cyclohexyl}acetic acid;

trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexanecarboxylic acid;

{trans-4-[4-(1,10-difluoro-7-methyl-6,7-dihydro-4H-3,4,7-triazadibenzo[cd,f]azulen-5-yl)-3,6-dihydropyridin-1(2H)-yl]cyclohexyl}acetic acid;

2-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}-N,N-dimethylacetamide;

{trans-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

{cis-4-[4-(7-methyl-6,7-dihydro-4H-3,4,7-triazadibenzo[cd,f]azulen-5-yl)-3,6-dihydropyridin-1(2H)-yl]cyclohexyl}acetic acid;

trans-4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

4-[4-(7-methyl-6,7-dihydro-4H-3,4,7-triazadibenzo[cd,f]azulen-5-yl)-3,6-dihydropyridin-1(2H)-yl]cyclohexanecarboxylic acid;

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetonitrile;

methyl 2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoate;

tert-butyl{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetate;

2-{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}propanoic acid;

{4-[4-(10-fluoro-7-methyl-6,7-dihydro-4H-3,4,7-triazadibenzo[cd,f]azulen-5-yl)-3,6-dihydropyridin-1(2H)-yl]cyclohexylidene}acetic acid;

2-[4-(10-fluoro-7-methyl-6,7-dihydro-4H-3,4,7-triazadibenzo[cd,f]azulen-5-yl)-3,6-dihydropyridin-1(2H)-yl]-N,N-dimethylethanesulfonamide;

2-[4-(10-fluoro-7-methyl-6,7-dihydro-4H-3,4,7-triazadibenzo[cd,f]azulen-5-yl)-3,6-dihydropyridin-1(2H)-yl]ethanesulfonamide;

{trans-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;

trans-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

{cis-4-[4-(1-fluoro-7-methyl-6,7-dihydro-4H-3,4,7-triazadibenzo[cd,f]azulen-5-yl)-3,6-dihydropyridin-1(2H)-yl]cyclohexyl}acetic acid;

cis-4-[4-(1-fluoro-7-methyl-6,7-dihydro-4H-3,4,7-triazadibenzo[cd,f]azulen-5-yl)-3,6-dihydropyridin-1(2H)-yl]cyclohexanecarboxylic acid;

{4-[4-(10-fluoro-7-methyl-6,7-dihydro-4H-3,4,7-triazadibenzo[cd,f]azulen-5-yl)-2,3,6,7-tetrahydro-1H-azepin-1-yl]cyclohexylidene}acetic acid;

2-{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}-2-methylpropanoic acid;

methyl cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylate;

cis-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;

cis-3-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]cyclobutanecarboxylic acid;

trans-3-{4-[(6S)-6-ethyl-10-fluoro-7-methyl-6,7-dihydro-4H-3,4,7-triazadibenzo[cd,f]azulen-5-yl]-3,6-dihydropyridin-1(2H)-yl}cyclobutanecarboxylic acid;

trans-3-[4-(8-fluoro-5-methyl-1,3,4,5-tetrahydro-1,5,12-triazabenzo[4,5]cycloocta[1,2,3-cd]inden-2-yl)-3,6-dihydropyridin-1(2H)-yl]cyclobutanecarboxylic acid;

cyano{4-[4-(10-fluoro-7-methyl-6,7-dihydro-4H-3,4,7-triazadibenzo[cd,f]azulen-5-yl)-3,6-dihydropyridin-1(2H)-yl]cyclohexyl}acetic acid;

{3-[4-(1,10-difluoro-7-methyl-6,7-dihydro-4H-3,4,7-triazadibenzo[cd,f]azulen-5-yl)-3,6-dihydropyridin-1(2H)-yl]cyclobutyl}acetic acid;

3-[4-(1,10-difluoro-7-methyl-6,7-dihydro-4H-3,4,7-triazadibenzo[cd,f]azulen-5-yl)-3,6-dihydropyridin-1(2H)-yl]cyclobutanecarboxylic acid; and pharmaceutically acceptable salts thereof.

9. A pharmaceutical composition comprising a pharmaceutically acceptable exicipient and a therapeutically effective amount of a compound of claim 1 or a pharmaceutically acceptable salt thereof.

\* \* \* \* \*